US007547532B2

(12) United States Patent
Urade et al.

(10) Patent No.: US 7,547,532 B2
(45) Date of Patent: Jun. 16, 2009

(54) THREE-DIMENSIONAL STRUCTURE OF PROSTAGLANDIN D SYNTHASE AND UTILIZATION THEREOF

(75) Inventors: Yoshihiro Urade, Kyoto (JP); Osamu Hayaishi, Kyoto (JP); Tsuyoshi Inoue, Toyonaka (JP); Yasushi Kai, Toyonaka (JP); Yousuke Okano, Mino (JP); Shigehiro Kinugasa, Itabashi-ku (JP); Hiroyoshi Matsumura, Ibaraki (JP); Daisuke Irikura, Mino (JP); Masaki Yamamoto, Ako-gun (JP); Takashi Kumasaka, Yokohama (JP); Masashi Miyano, Ibo-gun (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 361 days.

(21) Appl. No.: 10/495,218

(22) PCT Filed: Sep. 27, 2002

(86) PCT No.: PCT/JP02/09994

§ 371 (c)(1),
(2), (4) Date: Jul. 13, 2004

(87) PCT Pub. No.: WO03/042381

PCT Pub. Date: May 22, 2003

(65) Prior Publication Data

US 2005/0255576 A1    Nov. 17, 2005

(30) Foreign Application Priority Data

Nov. 12, 2001    (JP)    ............................. 2001-346035

(51) Int. Cl.
*C12N 9/00*    (2006.01)
*C12N 9/02*    (2006.01)

(52) U.S. Cl. ...................................... 435/183; 435/189

(58) Field of Classification Search ................. 435/183; 424/94.1
See application file for complete search history.

(56) References Cited

FOREIGN PATENT DOCUMENTS

JP            9-322773        12/1997

OTHER PUBLICATIONS

Vormann, J. Magnesium: Nutrition and Metabolism. Molecular Aspects of Medicine. 2003. vol. 24, pp. 27-37.*
Machine translation into English of JP 09-322773, Dec. 16, 1997.*
Giege et al. Crystallogenesis of Biological Macromolecules: Facts and Perspectives, Acta Cryst. D., 1994, D50:339-350.*
Weber, P.C. Overview of Crystallization Methods. Methods in Enzymology. 1997. vol. 276, pp. 13-22.*
Drenth, "Principles of Protein X-Ray Crystallography", 2nd Edition, 1999 Springer-Verlag New York Inc., Chapter 1, p. 1-21.*
Cudney R. Protein Crystallization and Dumb Luck. The Rigaku Journal. 1999. vol. 16, No. 1, pp. 1-7.*
McPherson, A. Current Approaches to Macromolecular Crystallization. European Journal of Biochemistry. 1990. vol. 189, pp. 1-23.*
Meister, A., Methods for the Selective Modification of Glutathione Metabolism and Study of Glutathione Transport. Methods in Enzymology. 1985. vol. 113, pp. 571-585.*
Derewenda et al. Entropy and Surface Engineering in Protein Crystallization. Acta Crystallographica Section D. 2006. vol. D62, pp. 116-124.*
Ngo et al., in The Protein Folding Problem and Tertiary Structure Prediction, 1994, Merz et al. (ed.), Birkhauser, Boston, MA, pp. 433 and 492-495.*
Branden et al., "Introduction to Protein Structure Second Edition", Garland Publishing Inc., New York, 1999.*
Drenth, "Principles of X-ray Crystallography," Springer, New York, 1995.*
Kierzek et al., Biophys Chem 91:1-20, 2001.*
Human Recombinant PGDS commercially available from Cayman Chemical, Retrieved from the Internet <URL:http://www.caymanchem.com/app/template/Product.vm/catalog/100 06593/a/z>.*
T. Inoue et al., "First Determination of the Inhibitor Complex Structure of Human Hematopoietic Prostaglandin D Synthase", J. Biochem., vol. 135, pp. 279-283, 2004.
T. Inoue et al., "Mechanism of Metal Activation of Human Hematopoietic Prostaglandin D Synthase", Nature Structural Biology, Advance online publication, Mar. 3, 2003.
Y. Kanaoka et al:, "Cloning and Crystal structure of hematopoietic prostaglandin D synthase" Cell, vol. 90, No. 6, pp. 1085-1095, 1997.
N. Matsushita et al., "Pharmacological studies on the novel antiallergic drug HQL-79: II. Elucidation of mechanisms for antiallergic and antiasthmatic effects", Japanese Journal of Pharmacology, vol. 78, No. 1, pp. 11-22, Sep. 1998.
S. M. Aziz et al., "Intrinsic microbicidal activity and pulmonary hypertension in isolated newborn piglet lungs", Pediatric Research, vol. 34, No. 1, pp. 32-37, 1993.
M. Hawkins et al., "Analogs of endoperoxide precursors of prostaglandins: failure to affect body temperature when injected into primary and secondary central temperature controls", Prostaglandins, vol. 13, No. 2, pp. 209-218, 1977.
E. Pinzar et al., "Structural basis of hematopoietic prostaglandin D synthase activity elucidated by site-directed mutagenesis", J. Biol. Chem., vol. 275, No. 40, pp. 31239-31244, 2000.
N. Matsushita, "Prostaglandin D Gosei Koso Sogaiyaku Allergy-sei Zensoku Chiryoyaku toshite no Kanosei", Protein, Nucleic Acid and Enzyme, vol. 45, No. 6, pp. 1072-1076, 2000.

* cited by examiner

*Primary Examiner*—Suzanne M. Noakes
*Assistant Examiner*—Jae W Lee
(74) *Attorney, Agent, or Firm*—Wenderoth, Lind & ponack, L.L.P.

(57) ABSTRACT

A method of designing an anti-allergic agent, sleep controlling agent, anti-obestic agent and remedy for brain injury acting via the inhibition of biosynthesis of prostaglandin $D_2$. Crystal of a complex of human origin hematopoietic prostaglandin D synthase, glutathione, and a substrate analog or an inhibitor, etc are prepared and the three-dimensional structural coordinate of each atom in the complex is determined by X-ray crystal analysis.

1 Claim, 6 Drawing Sheets

THREE-DIMENSIONAL STRUCTURE OF PROSTAGLANDIN D SYNTHASE AND UTILIZATION THEREOF

This application is a U.S. national stage of International Application No. PCT/JP02/09994 filed Sep. 27, 2002.

This application is a U.S. National Stage of International Application No. PCT/JP02/09994 filed Sep. 27, 2002.

BACKGROUND OF THE INVENTION

The present invention relates to three-dimensional structures' of hematopoietic prostaglandin D synthase (which may refer to as "PGDS" hereinafter), and a method for designing PGDS inhibitor using the three-dimensional structures.

Prostaglandin $D_2$ ($PGD_2$) is synthesized in vivo by PGDS from prostaglandin $H_2$ ($PGH_2$). There are two types of PGDS, i.e., brain-type PGDS and hematopoietic PGDS. Hematopoietic PGDS absolutely requires glutathione for enzymatic reactions while brain-type PGDS also causes enzymatic reactions in the presence of thiol reagents other than glutathione.

$PGD_2$ is synthesized in the central nervous system by brain-type PGDS, and has functions of sleep induction, thermodepression, inhibition of secretion of corpus luteum hormone and control of responses to pain and odor. $PGD_2$ is synthesized in peripheral tissue by hematopoietic PGDS, and is known to have physiological functions including dilation of peripheral blood vessels, bronchoconstruction, and inhibition of platelet coagulation. It also acts as an allergic mediator released from mast cells (Lewis, R. A., Soter, N. A., Diamond, P. T., Austen, K. F., Oates, J. A. & Roberts, L. J. Prostaglandin $D_2$ generation after activation of rat and human mast cells with anti-IgE. J. Immunol., 129, 1627-1631 (1982)). It has been reported that allergic reaction is significantly reduced in knockout mouse lacking prostaglandin $D_2$ receptor protein (DP receptor) (Matsuoka, T., Hirata, M., Tanaka, H., Takahashi, Y., Murata, T., Kabashima, K., Sugimito, Y., Kobayashi, T., Ushikubi, F., Aze, Y., Yoshida, N., Honda, Y., Nagai, H. & Narumiya, S. Prostaglandin $D_2$ as a mediator of allergic asthma. Science, 287, 2013-2017 (2000)). There is another prostaglandin $D_2$ receptor (CRTH receptor) in Th2 lymphocytes, eosinophils, and basophils involved in allergic reactions, which promotes chemotaxis of those inflammatory cells (Hirai, H., Tanaka, K., Yoshie, O., Ogawa, K., Kenmotsu, K., Takamori, Y., Ichimasa, M., Sugamura, K., Nakamura, M., Takano, S., and Nagata, K., Prostaglandin D2 selectively induces chemotaxis in T helper type 2 cells, eosinophils and basophils via seven-transmembrane receptor CRTH2, J. Exp. Med., 193, 255-261 (2001)). The synthesis of prostaglandin $D_2$ in mast cells (Urade, Y., Ujihara, M., Horiguchi, Y., Igarashi, M., Nagata, A., Ikai, K. and Hayaishi, O. Mast cells contain spleen-type prostaglandin D synthase, J. Biol. Chem., 265, 371-375 (1990)) and human Th2 lymphocytes (Tanaka, K., Ogawa, K., Sugamura, K., Nakamura, M., Takano, S, and Nagata, K., Differential production of prostaglandin D2 by human helper T cell subsets, J. Immunol., 164, 2277-2280 (2000)) is made by hematopoietic PGDS.

If a compound capable of inhibiting the enzymatic activity of PGDS is discovered, it would become possible to control $PGD_2$ synthesis to obtain anti-allergic agents, sleep control agents and anti-obesity agents.

Recently, attempts to design medicines from the three dimensional structure of proteins have been made. However, no one has succeeded in determining the three dimensional structure of human hematopoietic PGDS. It is hence difficult to design an inhibitor of human hematopoietic PGDS from the three dimensional structure thereof. It is an object of the present invention to clarify the three dimensional structure of human hematopoietic PGDS to provide a method for designing an inhibitor of human hematopoietic PGDS using the three dimensional structure.

SUMMARY OF THE INVENTION

The inventors has succeeded in preparing crystals of complexes of human hematopoietic PGDS (which has as metal ion calcium ion (referred to as "calcium type" hereinafter) or magnesium ion (referred to as "magnesium type" hereinafter)), glutathione (GSH) which is a cofactor of PGDS, and analog of prostaglandin $H_2$ ($PGH_2$) which is a substrate of PGDS or several types of inhibitor of PGDS. The inventors have succeeded in clarifying the three dimensional structures of these complexes with crystallography techniques using X-ray diffraction methods for the first time.

The present invention is related to a complex of human calcium type hematopoietic PGDS having an amino acid sequence of SEQ. ID NO 1 and glutathione which has a three dimensional structure represented by the structural coordinates in Table 1.

The present invention is related to a complex of human magnesium type hematopoietic PGDS having an amino acid sequence of SEQ. ID NO 1 and glutathione which has a three dimensional structure represented by the structural coordinates in Table 2.

The present invention is related to a complex of human calcium type hematopoietic PGDS having an amino acid sequence of SEQ. ID NO 1, glutathione and 9,11-dideoxy-9 α,11α methanoepoxyprostaglandin $F_{2\alpha}$ (referred to as "U46" hereinafter) which has a three dimensional structure represented by the structural coordinates in Table 3.

U46 is represented by the formula:

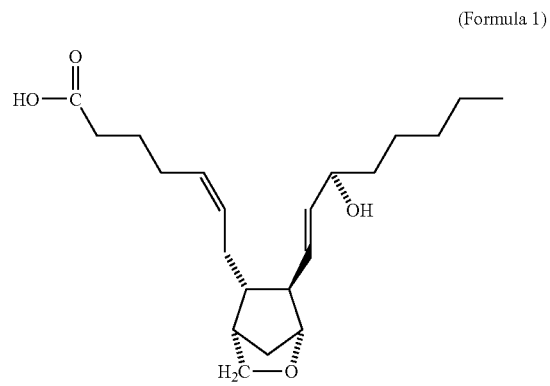

(Formula 1)

and is an analog of prostaglandin $H_2$ ($PGH_2$) which is a substrate of PGDS.

The present invention is related to a complex of human magnesium type hematopoietic PGDS having an amino acid sequence of SEQ. ID NO 1, glutathione and U46 which has a three dimensional structure represented by the structural coordinates in Table 4.

The present invention is related to a complex of human calcium type hematopoietic PGDS having an amino acid sequence of SEQ. ID NO 1, glutathione and 9,11-dideoxy-9 α,11α epoxymetanoprostaglandin $F_{2\alpha}$ (referred to as "U44" hereinafter) which has a three dimensional structure represented by the structural coordinates in Table 5.

U44 is represented by the formula:

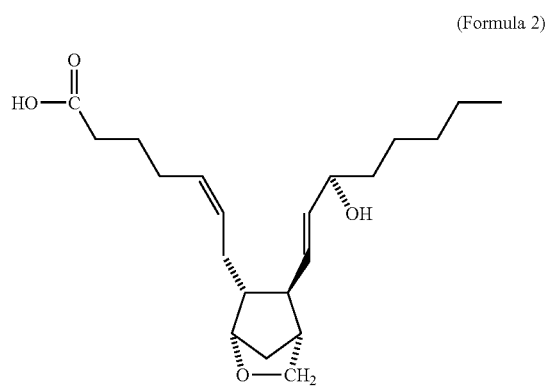

(Formula 2)

and is an analog of prostaglandin $H_2$ which is a substrate of PGDS.

The present invention is related to a complex of human magnesium type hematopoietic PGDS having an amino acid sequence of SEQ. ID NO 1, glutathione and U44 which has a three dimensional structure represented by the structural coordinates in Table 6.

The present invention is related to a complex of human calcium type hematopoietic PGDS having an amino acid sequence of SEQ. ID NO 1, glutathione and Cibacron Blue (trademark) (1-amino-4-{4-[4-chloro-6-(2-sulfo-phenylamino)-[1,3,5]triazine-2-ylmethyl]-3-sulfo-phenylamino}-9,10-dioxo-9,10-dihydroanthracene-2-sulfonic acid) which has a three dimensional structure represented by the structural coordinates in Table 7.

Cibacron Blue™ is represented by the formula:

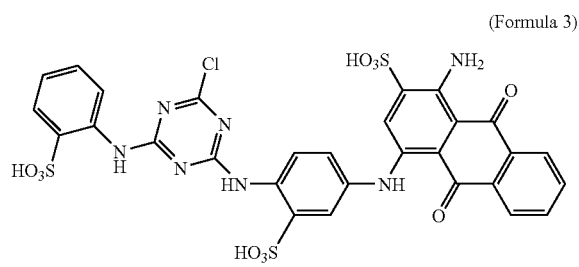

(Formula 3)

and is known as an inhibitor of PGDS (Thomson, A. M., Meyer, D. J. & Hayes, J. D. Sequence, catalytic properties and expression of chicken glutathione-dependent prostaglandin $D_2$ synthase, a novel class Sigma glutathione S-transferase. Biochem. J., 333, 317-325 (1998)).

The present invention is related to a complex of human magnesium type hematopoietic PGDS having an amino acid sequence of SEQ. ID NO 1, glutathione and 4-benzhydryloxy-1-{3-(1H-tetrazol-5-yl)-propyl}piperidine (referred to as "HQL-79" hereinafter) which has a three dimensional structures represented by the structural coordinates in Table 8.

HQL-79 is represented by the formula:

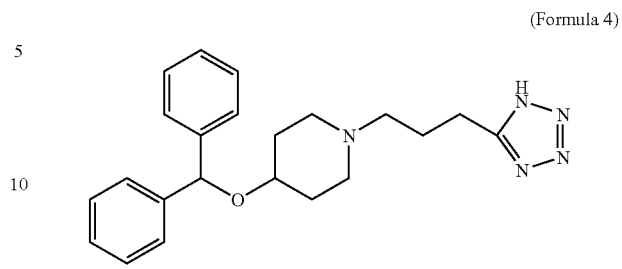

(Formula 4)

and is known to have anti-allergic activity (Matsushita N, Hizue M, Aritake K, Hayashi K, Takada A, Mitsui K, Hayashi M, Hirotsu I, Kimura Y, Tani T and Nakajima H, Pharmacological studies on the novel anti-allergic drug HQL-79: I. Anti-allergic and anti-asthmatic effects in various experimental models. Japanese Journal of Pharmacology, 78, 1-10 (1998)).

The present invention is further related to use of at least one structural coordinates selected from the group consisting of the structural coordinates represented in Tables 1-8 in selecting a compound for inhibiting human hematopoietic PGDS.

The present invention is related to a method for selecting an inhibitor of human hematopoietic PGDS, comprising steps of:

(a) providing at least one structural coordinates selected from the group consisting of the structural coordinates represented in Tables 1-8 which characterizes an active site of human hematopoietic PGDS;

(b) providing steric structure of a candidate compound; and (c) fitting the candidate compound to the active site of human hematopoietic PGDS to select the inhibitor.

The amino acid residues involved in the active site of human hematopoietic PGDS are Tyr8, Phe9, Asn10, Met11, Arg12, Gly13, Arg14, Ala15, Glu16, Leu17, Trp39, Pro40, Glu41, Ile42, Lys43, Gly49, Lys50, Ile51, Pro52, Ile53, His 62, Gln63, Ser64, Leu65, Asp93, Thr94, Leu95, Asp96, Asp97, Phe98, Met99, Ser100, Cys101, Phe102, Phe103, Trp104, Ala105, Glu106, Lys107, Lys108, Gln109, Asp110, Val111, Lys112, Glu113, Gln114, Met115, Phe116, Tyr152, Trp153, Glu154, Ile155, Leu156, Ser157, Thr158, Thr159, Leu160, Leu161, Val162, Phe163, Thr197, Lys198, and Leu199.

The term "fit" means that a candidate compound is optimized in energy and configuration to the active site of human hematopoietic PGDS. A compound is selected in such a manner that the contact area of a candidate compound with human hematopoietic PGDS is maximum when the compound binds to the active site of human hematopoietic PGDS, and that the binding mode between the compound and the active site of human hematopoietic PGDS is maximum.

Preferably, it is confirmed that the thus selected inhibitor inhibits PGDS by contacting the inhibitor with hematopoietic PGDS in the presence of prostaglandin $H_2$.

In addition, the inhibitor is confirmed whether it has at least one biological activity selected from the group consisting of anti-allergic activity, sleep control activity, anti-obesity activity and brain wound healing activity.

(calcium type) and glutathione. PGDS forms a dimer, and there is a metal ion-binding site in the center of the dimer.

Figure 2:
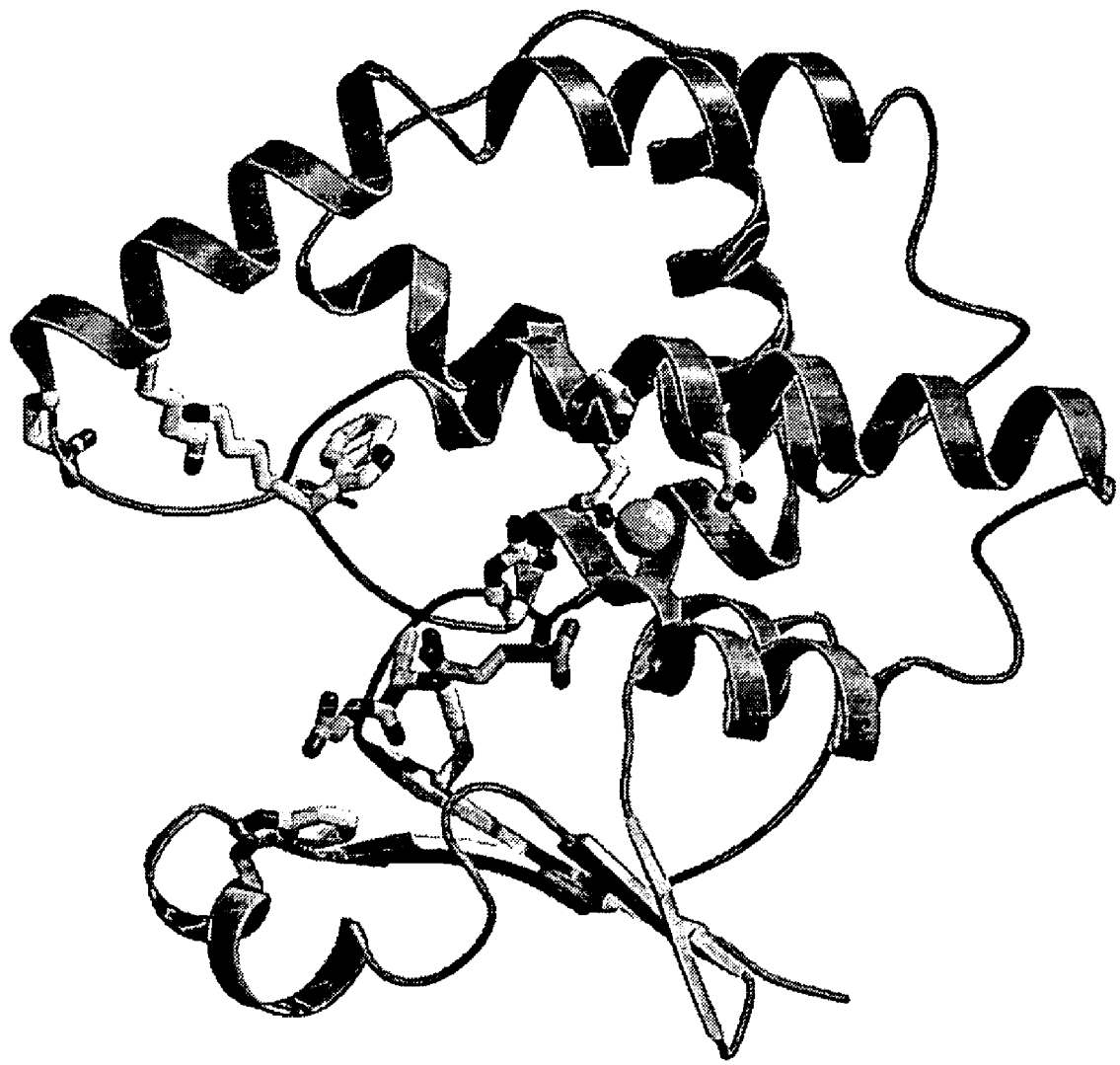

FIG. 2 shows PGDS monomer structure viewed from the side of the monomer.

Figure 3:
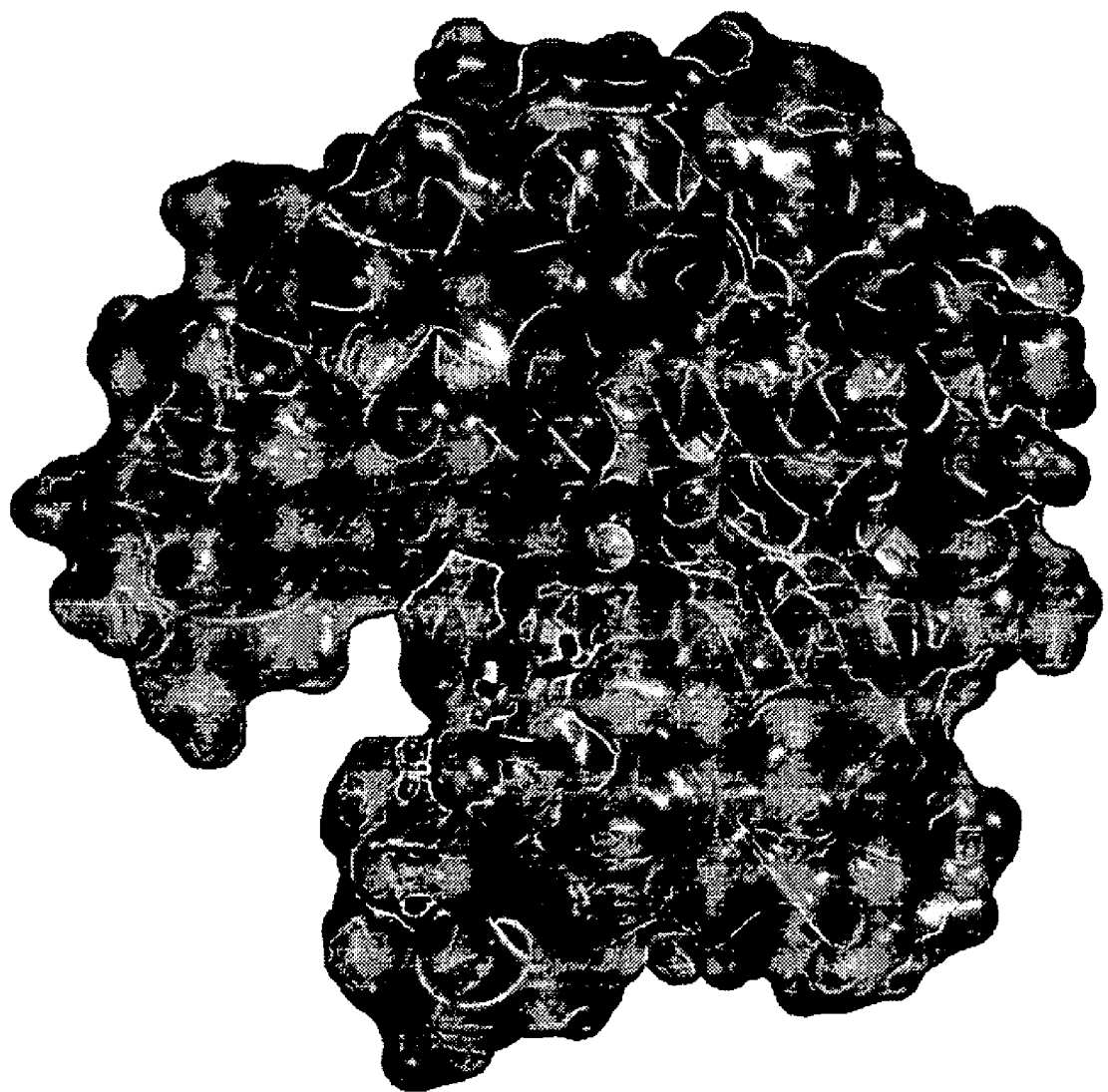

FIG. 3 shows a surface structure of PGDS viewed from the same direction as in FIG. 2.

Figure 4:
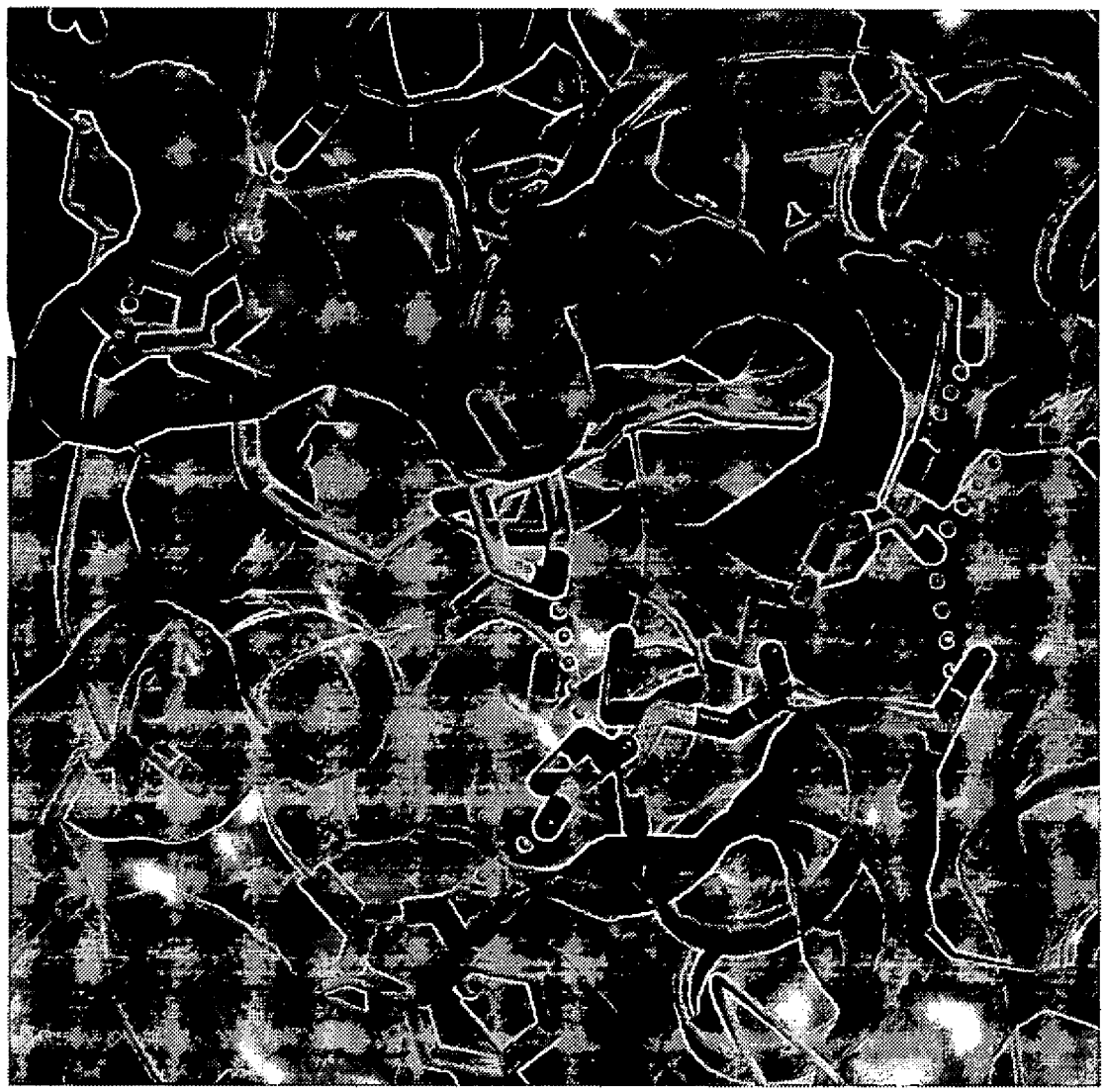
Figure 5:

FIG. 4 is an enlarged view of surface structure of PGDS complexed with calcium, glutathione, and U46. Oxygen atom of cyclopentane ring of U46 forms hydrogen bond with glutathione FIG. 5 shows the three-dimensional structure of PGDS complexed with calcium, glutathione and U44. The alpha chain of the substrate analogue is surrounded by Lys107, Lys112 and Lys198 of PGDS which are basic amino acid residues. The residues form salt-bridge with carboxylate of the α chain. In magnesium-type PGDS, similar three-dimensional structure is observed.

Figure 6:
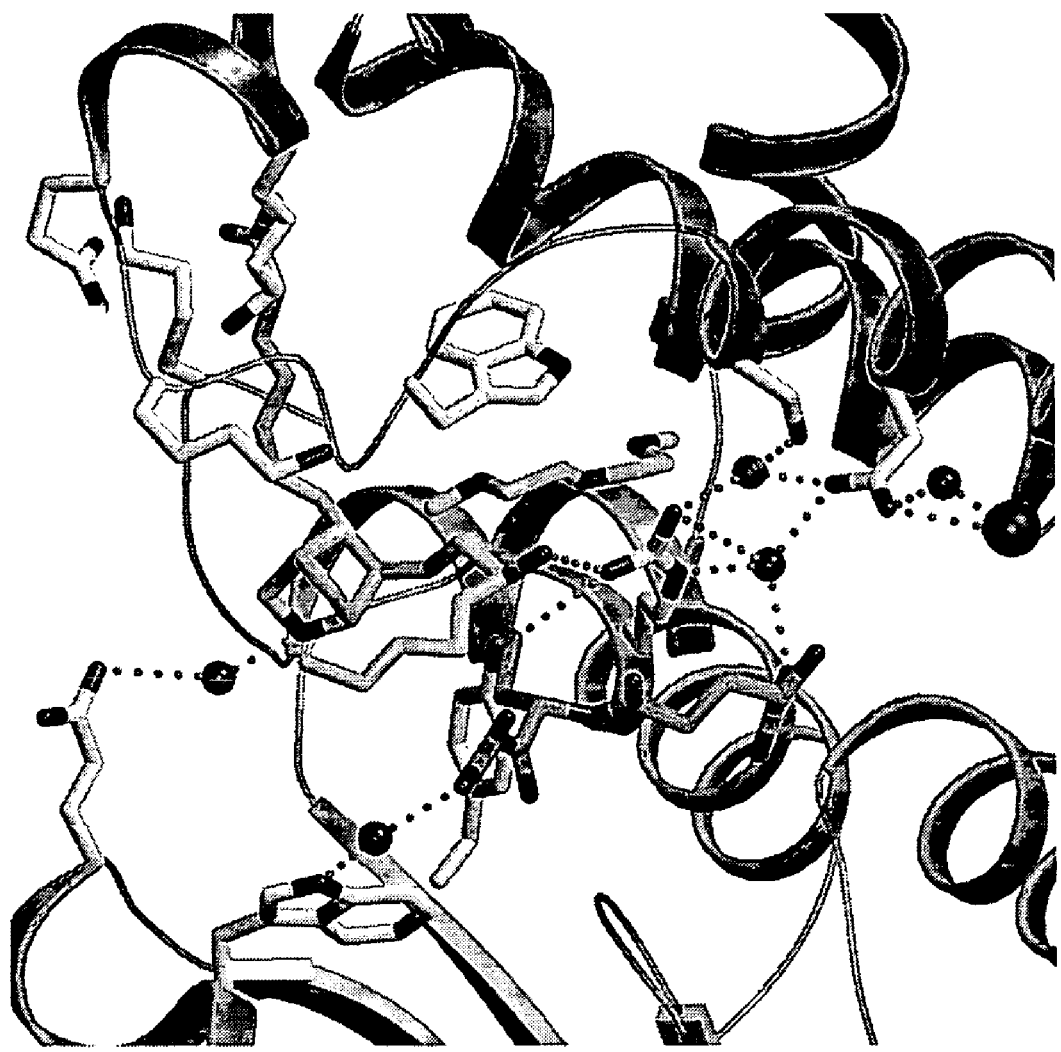

FIG. 6 shows three dimensional structure of PGDS complexed with magnesium, glutathione and U46.

DETAILED DESCRIPTION OF THE PREFERRED EMBODIMENTS (1) Human Hematopoietic Prostaglandin D Synthase The amino acid sequence of human hematopoietic prostaglandin D synthase is known. The method for preparing it is also disclosed (Japanese Patent Kokai No. 322773/1997). Although it is possible to obtain the enzyme from human tissue, it is convenient to prepare it using recombinant techniques.

For example, an expression plasmid (pT7-7hPGDS) which comprises cDNA encoding human hematopoietic prostaglandin D synthase having amino acid sequence of SEQ. ID. NO. 1 under the control of T7 polymerase gene promoter is constructed (Japanese Patent Kokai No. 322773/1997). *Escherichia coli* BL21 (DE-3) is transformed with the expression plasmid using modified calcium chloride method (Inoue, et al., Gene 96:23-28 (1990)). *Escherichia coli* pYK1 transformed with the expression plasmid is deposited under accession number FERM BP-5489 in National Institute of Advanced Industrial Science and Technology.

*Escherichia coli* pYK1 is cultured in LB medium (containing 50 µg/ml of ampicillin) at 37° C. overnight. IPTG (isopropylthio-β-D-galactoside) is then added to final concentration of 0.4 mM and *Escherichia coli* pYK1 is further cultured for additional 4 to 6 hours.

After the completion of cultivation, the bacteria is fractured by ultrasonication and centrifuged at 13,000 rpm at 4° C. for 15 minutes to remove precipitates. Fractionation is effected with ammonium sulfate. Fraction of 40% to 60% saturation of ammonium sulfate is obtained and dialyzed against 50 mM sodium phosphate buffer. The dialyzed solution is applied to Glutathione Sephalose 4B column and purified by affinity chromatography.

(II) Crystal of Human Hematopoietic Prostaglandin D Synthase Complex

Crystallization of a protein utilizes depositing a protein under specific conditions as a crystal when the protein is switched from dissolving conditions to non-dissolving conditions by adding a precipitating agent to a solution of the protein of interest, or by reducing the amount of solution by vaporizing solvent.

The inventors have found that human hematopoietic PGDS complex is successfully crystallized with the hanging drop vapor diffusion method. The hanging drop vapor diffusion method is a method wherein a mixed solution of protein solution with a precipitating solution is hanged up on a glass plate using surface tension and the solution is enclosed with another precipitating solution having a higher concentration in a sealed space to form a crystal of the protein. Due to vapor diffusion, the concentration of the precipitating agent is gradually increased to obtain a crystal. When a large crystal is required, a crystal obtained in a first crystallization and having a size of about 0.01 mm is selected and re-crystallized again with a macro-seeding method (Stura, E. A. & Wilson, L. A. Applications of the streak seeding technique in protein crystallization. J. of Crystal Growth, 110, 270-282 (1991).) to obtain a crystal having size of about 0.3×0.3×1.5 mm, which is proper for X-ray diffraction experiments.

The conditions for preparing eight human hematopoietic PGDS complexes are described hereinafter.

(1) Complex of human hematopoietic PGDS with calcium and Glutathione

Composition:

|   |   | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|   | dithiothreitol | 5 mM | 10 mM |
|   | Calcium chloride | 2.5 mM | 5 mM |
|   | Dioxane | 1% | 2% |
| Protein | PGDS | 5 mg/mL | — |

Temperature: 20° C., pH: 8.4

(2) Complex of human hematopoietic PGDS with magnesium and glutathione

Composition:

|   |   | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|   | dithiothreitol | 5 mM | 10 mM |
|   | Magnesium chloride | 2.5 mM | 5 mM |
|   | Dioxane | 1% | 2% |
| Protein | PGDS | 5 mg/mL | — |

Temperature: 20° C., pH: 8.4

(3) Complex of human hematopoietic PGDS with calcium, glutathione and 9,11-dideoxy-9α,11α-methanoepoxyprostaglandine $F_{2\alpha}$ (U46)

Composition:

|   |   | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|   | dithiothreitol | 5 mM | 10 mM |

|  |  | Internal Sol. | External Sol. |
|---|---|---|---|
|  | Calcium chloride | 2.5 mM | 5 mM |
|  | Dioxane | 1% | 2% |
|  | U46 | 10 mM | — |
| Protein | PGDS | 5 mg/mL | — |

Temperature: 20° C., pH: 8.4

(4) Complex of human hematopoietic PGDS with magnesium, glutathione and 9,11-dideoxy-9α,11α-methanoepoxyprostaglandine $F_{2\alpha}$ (U46)

Composition:

|  |  | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|  | dithiothreitol | 5 mM | 10 mM |
|  | Magnesium chloride | 2.5 mM | 5 mM |
|  | Dioxane | 1% | 2% |
|  | U46 | 10 mM | — |
| Protein | PGDS | 5 mg/mL | — |

Temperature: 20° C., pH: 8.4

(5) Complex of human hematopoietic PGDS with calcium, Glutathione and 9,11-dideoxy-9α,11α-epoxymethanoprostaglandine $F_{2\alpha}$ (U44)

Composition:

|  |  | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|  | dithiothreitol | 5 mM | 10 mM |
|  | Calcium chloride | 2.5 mM | 5 mM |
|  | Dioxane | 1% | 2% |
|  | U46 | 5 mM | — |
| Protein | PGDS | 5 mg/mL | — |

Temperature: 20° C., pH: 8.4

(6) Complex of human hematopoietic PGDS with magnesium, glutathione and 9,11-dideoxy-9α,11α-epoxymethanoprostaglandine $F_{2\alpha}$ (U44)

Composition:

|  |  | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|  | dithiothreitol | 5 mM | 10 mM |
|  | Magnecium chloride | 2.5 mM | 5 mM |
|  | Dioxane | 1% | 2% |
|  | U44 | 5 mM | — |
| Protein | PGDS | 5 mg/mL | — |

Temperature: 20° C., pH: 8.4

(7) Complex of human hematopoietic PGDS with calcium, glutathione and Cibacron Blue (trademark) (1-amino-4-{4-[4-chloro-6-(2-sulfo-phenylamino)-[1,3,5]triazine-2-ylmethyl]-3-sulfo-phenylamino}-9,10-dioxo-9,10-dihydro-anthracene-2-sulfonic acid)

Composition:

|  |  | Internal Sol. | External Sol. |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|  | dithiothreitol | 5 mM | 10 mM |
|  | Calcium chloride | 2.5 mM | 5 mM |
|  | Dioxane | 1% | 2% |
|  | Cibacron Blue | 1 mM | — |
| Protein | PGDS | 5 mg/mL | — |

Temperature: 20° C., pH: 8.4

(8) Complex of human hematopoietic PGDS with calcium, glutathione and 4-benzhydryloxy-1-{3-(1H-tetrazol-5-yl)-propyl}piperidine (HQL-79)

Composition:

|  |  | Internal Sol. | External Sol |
|---|---|---|---|
| Precipitating agent | PEG 6000 | 14% | 16% |
| Buffer | Tris buffer | 50 mM | 100 mM |
| Admixture | Glutathione | 5 mM | 10 mM |
|  | dithiothreitol | 5 mM | 10 mM |
|  | Calcium chloride | 2.5 mM | 5 mM |
|  | Dioxane | 1% | 2% |
|  | HQL-79 | saturated | — |
| Protein | PGDS | 5 mg/mL | — |

Temperature: 20° C., pH: 8.4

(III) Three-Dimensional Coordinate of Human Hematopoietic PGDS Complex

Three-dimensional structure of human hematopoietic PGDS complex was clarified using X-ray crystallography from the crystal of human hematopoietic PGDS complex obtained from (II).

Data collection was carried out for a mercury derivative crystal of human hematopoietic PGDS of the calcium type in SPring-8 RIKEN beam line BL45XD in consideration of the anomalous dispersion effect. Data collection was carried out using synchrotron radiation lights of three wavelengths of 1.009 Å, 1.04 Å and 1.10 Å to calculate eight positions of mercury from the analysis of the Patterson function. The position was precisely determined using the program MLPHARE (Otwinowski, Z. in Proceedings of CCP4 Study Weekend, Isomorphous Replacement and Anomalous Scattering, edited by Sawyer, L., Issacs, N., and Bailey, S. [Science and Engineering Research Council (England) Daresbury Lab., Warrington, U.K.], pp. 80-86 (1993)) to obtain electron density of the enzyme. An enzyme model was constructed on a graphics workstation to obtain a highly accurate enzyme model of human hematopoietic PGDS of the calcium type using the refinement program CNS (Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. & Warren, G. L. Crystallography & NMR system: A new software suite for macromolecular structure determination. Acta Cryst., D54, 905-921 (1998)).

The other structural model was obtained in high accuracy with the program CNS using the calcium type model firstly obtained as the search model.

Crystallographic data obtained for the crystals prepared in (II)(1) to (II)(8) are as follows:

| | Crystal | | | |
|---|---|---|---|---|
| | (1) | (2) | (3) | (4) |
| Space group | P2$_1$ | P2$_1$ | P2$_1$ | P1 |
| Resolution (Å) | 37.3-1.8 | 30.9-1.7 | 37.3-2.0 | 33.8-1.2 |
| No. of water molecules | 1089 | 983 | 744 | 1587 |
| R$_{cryst}$ (%) | 19.3 | 21.0 | 20.6 | 18.0 |
| R$_{free}$ (%) | 22.6 | 24.1 | 25.2 | 19.1 |
| R.m.s.deviation of | | | | |
| bond length (Å) | 0.005 | 0.006 | 0.006 | 0.006 |
| Bond angles (deg.) | 1.1 | 1.0 | 1.0 | 1.2 |
| dihedral angles (deg.) | 20.3 | 20.1 | 20.2 | 20.6 |
| Average B (Å$^2$) | 18.7 | 24.5 | 18.2 | 14.9 |
| Average B of GSH (Å$^2$) | 17.7 | 27.2 | 20.8 | 10.0 |

| | Crystal | | | |
|---|---|---|---|---|
| | (5) | (6) | (7) | (8) |
| Space group | P2$_1$ | P2$_1$ | P2$_1$ | P1 |
| Resolution(Å) | 37.4-1.8 | 29.0-2.0 | 91.6-2.1 | 500-1.45 |
| No. of water molecules | 858 | 1639 | 858 | 1398 |
| R$_{cryst}$ (%) | 21.2 | 17.8 | 20.3 | 19.2 |
| R$_{free}$ (%) | 24.7 | 23.0 | 25.7 | 20.7 |
| R.m.s.deviation of | | | | |
| bond length (Å) | 0.006 | 0.006 | 0.007 | 0.012 |
| Bond angles (deg.) | 1.0 | 1.1 | 1.1 | 1.3 |
| dihedral angles (deg.) | 20.4 | 20.6 | 20.1 | 20.1 |
| Average B (Å$^2$) | 22.8 | 19.5 | 22.4 | 14.4 |
| Average B of GSH (Å$^2$) | 23.6 | 15.1 | 44.8 | 11.6 |

Table 1 represents the structural coordinates of the complex of human hematopoietic PGDS with calcium and glutathione; Table 2 represents the structural coordinates of the complex of human hematopoietic PGDS with magnesium and glutathione; Table 3 represents the structural coordinates of the complex of human hematopoietic PGDS with calcium, glutathione and 9,11-dideoxy-9α,11α-methanoepoxyprostaglandine F$_{2α}$ (U46); Table 4 represents the structural coordinates of the complex of human hematopoietic PGDS with magnesium, glutathione and 9,11-dideoxy-9α,11α-methanoepoxyprostaglandine F$_{2α}$ (U46); Table 5 represents the structural coordinates of the complex of human hematopoietic PGDS with calcium, glutathione and 9,11-dideoxy-9α, 11α-epoxymethanoprostaglandine F$_{2α}$ (U44); Table 6 represents the structural coordinates of the complex of human hematopoietic PGDS with calcium, glutathione and 9,11-dideoxy-9α,11α-epoxymethanoprostaglandine F$_{2α}$ (U44); Table 7 represents the structural coordinates of the complex of human hematopoietic PGDS with calcium, glutathione and Cibacron Blue (trademark); Table 8 represents the structural coordinates of the complex of human hematopoietic PGDS with magnesium, glutathione and 4-benzhydryloxy-1-{3-(1H-tetrazol-5-yl)-propyl}piperidine (HQL-79).

Each table represents three-dimensional structural coordinates according to the format of Protein Data Bank (rcsb.org/pdb/, USA). "ATOM" at the first column indicates that the row describes atom coordinates; the second column indicates the atom number; the third column indicates the atom type in the amino acid residue or the like, for example, carbonyl carbon atom is represented by C, and carbonyl oxygen atom is represented by O; the fourth column indicates the amino acid residue or the like; the fifth column indicates the class of molecule; the sixth column indicates the amino acid number; the seventh, eighth, and ninth columns indicate coordinates of the atom (in Å for X-axis, Y-axis, and Z-axis directions in the order); the tenth column indicates the occupancy of the atom (in the present invention 1.00 for all atoms); and the eleventh column indicates the temperature factor of the atom. The twelfth column indicates the class of molecule like the fifth column.

Figure 1:
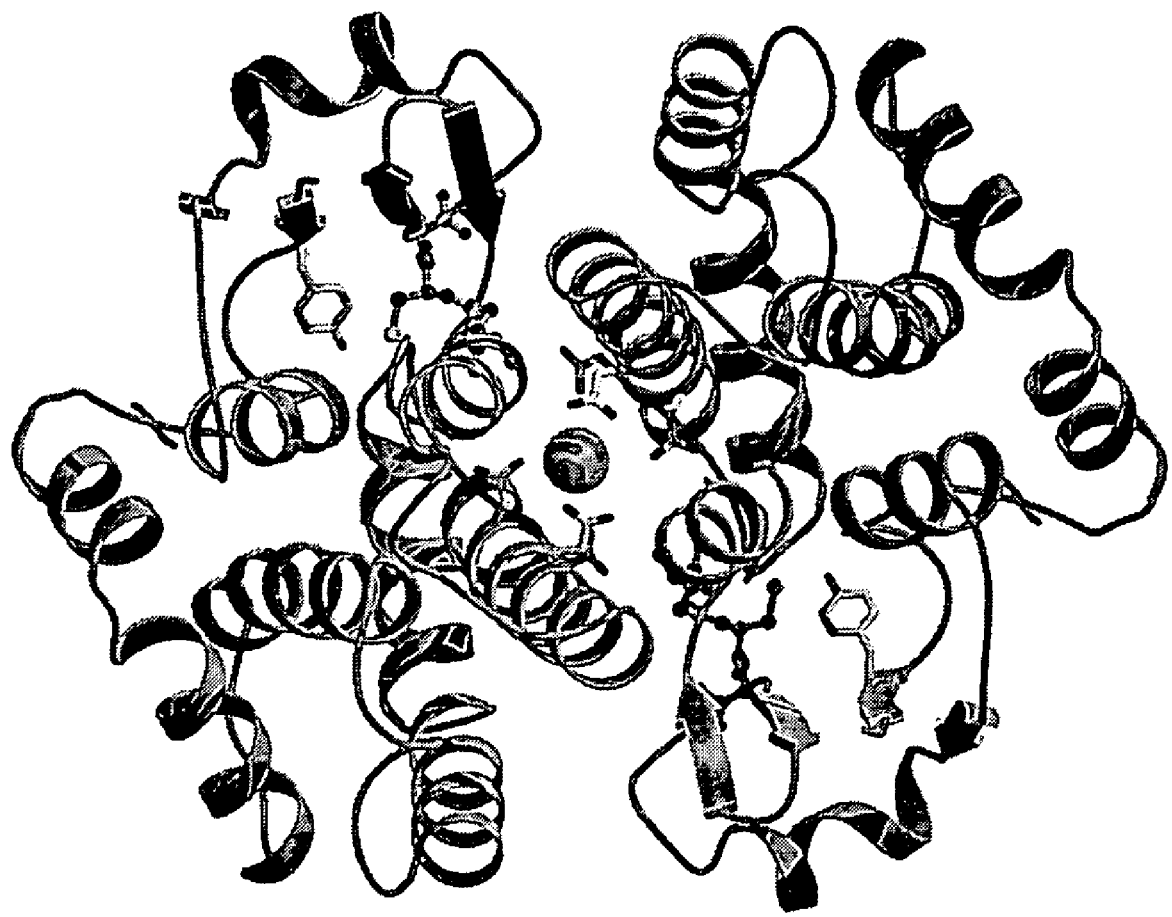
FIG. 1 shows the three-dimensional structure of a complex of human hematopoietic prostaglandin D synthase (PGDS)

(IV) Three-Dimensional Structure and Binding Site of Human Hematopoietic PGDS Complex (1) Complex of Human Hematopoietic PGDS with Calcium and Glutathione Prostaglandin D synthase form a dimer and calcium ion exists in the center of the dimer (see FIG. 1). Calcium has no influence on the glutathione binding, but increases the reaction rate of PGDS enzyme. Glutathione binds to Tyr8, Arg14, Trp39, Gly49, Lys50, Ile51, Pro52, Gln63 and Ser64 of PGDS.

(2) Complex of Human Hematopoietic PGDS with Magnesium and Glutathione

In accordance with the change of metal ion in the center of the dimer from calcium ion to magnesium ion, coordination structure of water molecule to the metal ion is significantly changed. Magnesium increases the affinity of glutathione to PGDS by more than 3 times.

(3) Complex of Human Hematopoietic PGDS with Calcium, Glutathione and 9,11-dideoxy-9α,11α-methanoepoxyprostaglandine F$_{2α}$ (U46)

In the complex, there exists calcium ion in the center of the dimer as in (1). In addition, substrate analog, U46, binds to PGDS. U46 binds to Tyr8, Gly3, Arg14, Gln36, Trp104, Gln36, Trp104, Gln109, Lys112, Tyr152, Lys198, and Leu199 of PGDS, and GSH. Carboxyl group of U46 is hydrogen bonded to either of Gln109, Lys112, or Lys198 of PGDS. Oxygen atom at C11 site of U46 is positioned at 4.6 Å from S atom of GSH. The ω chain of U46 approaches Tyr152 existing in the deepest portion of substrate binding site to van der Waals contact distance.

(4) Complex of Human Hematopoietic PGDS with Magnesium, Glutathione and 9,11-dideoxy-9α,11α-methanoepoxyprostaglandine F$_{2α}$ (U46)

The structure of the complex differs from that of (3) in that magnesium ion exists in the center of the dimer. Although the α chain of U46 is positioned near Gln109, Lys112 and Lys198 of PGDS, it is not hydrogen bonded but is in van der Waals contact. Oxygen atom at 11 site of U46 is hydrogen bonded to Gln36 of PGDS through water molecule. The OH group in the ω chain of U46 is hydrogen bonded to rotated Arg14 and the ω chain is out of the pocket. Ether which is a solvent for U46 binds at the aperture between Trp104 of PGDS and U46 molecule.

(5) Complex of Human Hematopoietic PGDS with Calcium, glutathione and 9,11-dideoxy-9α,11α-epoxymethanoprostaglandine $F_{2\alpha}$ (U44)

The complex differs from that of (1) to (4) in that a substrate analog U44 binds to PGDS. In the calcium-binding structure, although the binding site of U44 is the same as that of U46, the manner of hydrogen bonding differs. Although they are both in the calcium-binding form, being different from U46, α-chain of U44 is hydrogen bonded with to all of Gln109, Lys112, and Lys198 of PGDS, and oxygen atom at 9 site is hydrogen bonded through water to Gln36. The α-chain of U44 is about 5 Å apart from back Tyr152, differing from the structure of (3).

(6) Complex of Human Hematopoietic PGDS with Magnesium, Glutathione and 9,11-dideoxy-9α,11α-epoxymethanoprostaglandine $F_{2\alpha}$ (U44)

Although this complex is identical with (5) in that they are complexes with substrate analog U44, it is different from (5) in that the metal ion positioned in the center of dimer is magnesium ion.

(7) Complex of Human Hematopoietic PGDS with Calcium, Glutathione and Cibacron Blue (Trade Mark)

The complex differs from the above six structures in that it is a complex with an inhibitor Cibacron Blue. Metal ion in the center of the dimer is calcium. Cibacron Blue binds to Phe9, Gly10, Gly13, Arg14, Gln36, Met99, Ser100, Trp104, Glu106, Lys107, Gln109, Lys112, Tyr152, Cys156, Lys198, and Leu199 of PGDS, and GSH (8) Complex of Human Hematopoietic PGDS with Magnesium, Glutathione and 4-benzhydryloxy-1-{3-(1H-tetrazol-5-yl)-propyl}piperidine (HQL-79)

The complex is different from (1) to (6) in that it is a complex with an inhibitor HQL-79, and an inhibitor different from (7) is used. Magnesium ion is bonded in the center of the dimer. Induce-fit phenomenon is caused due to the binding of HQL-79, and space group is changed from $P2_1$ to $P1_1$. HQL-79 binds to Tyr8, Phe9, Arg14, Met99, Phe102, Trp104, Tyr152, Ile155, Thr159, Phe163, and Leu199 of PGDS and GSH.

(V) Use of Three Dimensional Coordinates for Preparing Inhibitor of Human Hematopoietic Prostaglandin D Synthase A compound capable of inhibiting human hematopoietic PGDS can be selected using three-dimensional coordinates of Tables 1 to 8.

The present invention is related to a method for selecting an inhibitor of human hematopoietic PGDS, comprising steps of:

(a) providing at least one of these structural coordinates selected from the group consisting of the structural coordinates represented in Tables 1-8 which characterizes an active site feature of human hematopoietic PGDS;

(b) providing steric structure of a candidate compound; and (c) fitting the candidate compound to the active site of human hematopoietic PGDS to select the inhibitor.

The amino acid residues involved in the active site of human hematopoietic PGDS are Tyr8, Phe9, Asn10, Met11, Arg12, Gly13, Arg14, Ala15, Glu16, Leu17, Trp39, Pro40, Glu41, Ile42, Lys43, Gly49, Lys50, Ile51, Pro52, Ile53, His 62, Gln63, Ser64, Leu65, Asp93, Thr94, Leu95, Asp96, Asp97, Phe98, Met99, Ser100, Cys101, Phe102, Phe103, Trp104, Ala105, Glu106, Lys107, Lys108, Gln109, Asp110, Val111, Lys112, Glu113, Gln114, Met115, Phe116, Tyr152, Trp153, Glu154, Ile155, Leu156, Ser157, Thr158, Thr159, Leu160, Leu161, Val162, Phe163, Thr197, Lys198, and Leu19

Based on the three-dimensional structure information, commercially available compounds are one by one minimized in energy using various programs so that the binding to the active site of the enzyme occurs in the most appropriate orientation. This procedure is automatically effected for all commercially available compounds to compare free energy to select compounds which readily bind to the active site of the enzyme. A compound thus obtained is used as basic backbone, and more stable derivative is designed to synthesize more stable compound in order to develop a new inhibitor of the enzyme.

It is preferred to design inhibitors using a computer. For example, Indigo 2, a workstation supplied by Silicon Graphics, Inc., is suitable as a computer used for designing inhibitors. However, the computer is not limited to this one, and any computer may be used so long as it is capable of running an appropriate program. Likewise, there is no particular limitation on the computer storage medium. For example, Insight II, a computer program commercially available from Accelrys, Inc. may be used as a program for designing. In particular, the programs Ludi or DOCK, a module of Insight II specially prepared for such purposes, may be used alone or in combination to facilitate identification, searching, evaluation, or designing.

In designing of inhibitor, there are conceptually two steps. The first step is to find a compound which serves as a starting point for drug design, known for those skilled in the art as a lead compound. The next step is optimization of the lead compound wherein compounds having better properties as medicines, for example, having better activity, having better pharmacokinetics, or having less toxicities and side effects are sought starting from the lead compound.

The step in which a lead compound is found using the structure coordinates of the PGDS complex provided by the present invention is achieved, for example, using a database in a computer into which structures of plural compounds have been entered, by a method in which interactions between three-dimensional structures of a compound in the database and PGDS are sorted out in a visual manner one after another, or by a method in which amplitudes of binding energy are calculated one after another using a computer and compounds which stably bind to PGDS are found from the database. Although it is preferred that the database of compound's structures contains determined three-dimensional structure coordinates entered therein, for low molecular weight compounds, it does not have to be a database of three-dimensional structure coordinates, because such low molecular weight compounds may change their conformations relatively freely, and also because three-dimensional structure coordinates for each conformation can be derived by calculations in a relatively short time. In the latter cases, information for chemical covalent bonds of low molecular weight compounds are entered into the database.

Specifically, in the visual method, PGDS complexes are firstly displayed on a computer screen according to the structure coordinates of the present invention. In this step, although a three-dimensional representation may be made on the computer screen using, for example, Crystal Eye as described above, visual examinations can also be achieved without using such a three-dimensional representation.

Chemical interactions to be considered include electrostatic interactions, hydrophobic interactions, hydrogen bonding, van der Waals interactions, and the like. Thus, the structure should be comprehensively examined whether it is favorable for interactions, for example, so that functional groups which tend to bear negative charges such as carboxyl groups, nitro groups, and halogens interact with amino acid residues in PGDS having positive charge such as lysine, arginine, and histidine, so that functional groups which tend to bear positive charge such as amino, imino, and guanidyl groups interact with amino acid residues in PGDS having negative charge such as glutamic acid and aspartic acid, so that hydrophobic functional groups such as aliphatic groups and aromatic groups interact with hydrophobic amino acid residues such as alanine, leucine, isoleucine, valine, proline, phenylalanine, tryptophan and methionine, so that functional groups involved in hydrogen bonding such as hydroxyl and amide groups can form hydrogen bonds with backbone or side chain portions of PGDS, so that binding between the compound and PGDS causes no steric hindrance, and so that empty spaces are filled to minimize such empty spaces and maximize van der Waals interactions. Thus, electrostatic interactions, hydrophobic interactions, van der Waals interactions, hydrogen bonding, and other factors are visually and comprehensively considered to finally determine whether or not the compound is suitable as a lead compound.

In the method of energy evaluation with a computer, the energy of binding between a compound and PGDS is determined by molecular force field calculations. Such calculations are applied to each compound in the database to find compounds which may serve as a lead compound capable of stable binding. As a molecular force field used in the calculations, for example, CVFF, AMBER force field optimized for proteins, which is contained in DISCOVER module of Insight II program may be used. In addition, some computer programs like Ludi in Insight II can automatically output candidates for lead compound when three-dimensional structure coordinates of interacting amino acid residues in a protein molecule are given, and such programs may also be applied to the method of present invention.

Furthermore, the visual examinations and the examination considering energy are not strictly sorted out from each other, and both techniques may be used in combination as appropriate.

The next step, in which optimization of the lead compound is conducted using the structure coordinates of the PGDS complex is used for the purpose of, where a lead compound which binds to PGDS has already been found by the above method or separately found in an experimental manner, optimizing the lead compound to obtain a better compound such as a compound having higher biological activities as an inhibitor or a compound having a structure favorable for oral administration as a medicine. It becomes possible only after a precise picture of chemical bonding between the lead compound and PGDS has been elucidated to directly find a site which is not optimal for interactions between the lead compound and PGDS and to design a new compound having an optimal functional group at that site, thereby enabling to design a more optimized compound.

For visual examinations with a computer, a model of the complex between the lead compound and PGDS is firstly displayed on a computer screen by entering the three-dimensional structure coordinates of the lead compound and the structure coordinates of PGDS provided by the present invention into a computer on which a computer program expressing three-dimensional coordinates of molecules runs or into a storage medium of the computer. In this step, although a three-dimensional representation may be made on the computer screen using, for example, Crystal Eye as described above, visual examinations can also be achieved without using such a three-dimensional representation. It is a logical to design a compound to modify the lead compound so as to yield a compound more favorably interacting with PGDS or a compound having better pharmacokinetics while retaining such interactions.

Chemical interactions to be considered are the same as those in the step to find a lead compound, and a new compound having better properties as an inhibitor is finally designed starting from the lead compound.

In the method by energy evaluation with a computer, the energy of binding between a new compound designed from the lead compound and PGDS is determined by molecular force field calculations to judge the validity of the design. In addition, it is also possible to use a method in which other molecules such as solvent molecules are additionally included in the model and the free energy is determined using molecular dynamics to derive a compound capable of stable binding. As a molecular force field used in the calculations, for example, CVFF, AMBER force field optimized for proteins, which is contained in DISCOVER module of Insight II program may be used.

Furthermore, the visual examinations and the method by energy evaluations may be used in combination as appropriate.

After a candidate compound for inhibition of hematopoietic PGDS is thus selected, the selected compound is contacted with the enzyme in the presence of the substrate (prostaglandin $H_2$) to confirm the compound can inhibit the enzymatic activity (Shimizu, T., Yamamoto, S., and Hayaishi, O. (1979). Purification and properties of prostaglandin D synthase from rat brain. J. Biol. Chem. 254, 5222-5228). The measurement of enzymatic activity is, for example, carried out as follows: The substrate $[1-{}^{14}C]$prostaglandin(PG)$H_2$ is prepared by reacting $[1-{}^{14}C]$arachidonic acid with cyclooxygenase. Since $PGH_2$ is easily decomposed in aqueous solution (half-life: about 5 minutes), it is dried and stored at a low temperature ($-80°$ C.). The enzymatic reaction is carried out by injecting with microsyringe 1 µl of $PGH_2$ solution (acetone or nonvolatile diethleneglycohol solution) to 50 µl of 0.1 M phosphate buffer (pH 7.5) containing 1 mM glutathione and the enzyme. After the reaction is effected for 30–60 seconds, the reaction is quenched by adding 300 µl of ice-cooled ether/methanol/0.1M citric acid mixture (20:4:1 v/v/v), and the substrate and the reaction product are extracted with ether under acidic condition. Anhydrous sodium sulfate is then added to the reaction solution to remove water. An aliquot (about 50 µl) of organic layer is applied on silica gel thin layer in a cool room (about 4° C.) and silica gel thin layer chromatography (development solvent: ether/methanol/acetic acid (9:2:0.1)) is carried out in a freezer ($-20°$ C.). After the development, radioactivity of $PGD_2$ fraction and other fraction are measured and the enzyme activity is calculated from the ratio of conversion to $PGD_2$.

Alternatively, enzyme reaction is carried out using commercially available non-labeled $PGH_2$. After the reaction, $PGH_2$ is decomposed to 12(S)-hydroxy-8,10-trans-5-cis-heptadecatrienolic acid with the treatment by $FeCl_2$ before quantifying with reverse phase HPLC using 11-β-$PGE_2$ as an internal standard or commercially available ELISA to quantify $PGD_2$.

Since an inhibitor of hematopoietic PGDS can be an anti-allergic agent, a sleep control agent, an anti-obesity agent, and brain wound healing agent, pharmacological activity of the inhibitor is measured as each medicine.

A method for measuring pharmacological activity as an anti-allergic agent is described in Fugner A, Bechtel W. D., Kuhn, F. J. and Mierau, J. In vitro and in vivo studies of the non-sedating antihistamine epinastine. Arzneimittelforschung, 38, 1446-1453 (1988); Kamei, C., Izushi, K., Adachi, Y., Shimazawa, M. and Tasaka, K. Inhibitory effect of epinastine on the type II-IV allergic reactions in mice, rats and guinea pigs. Arzneimittelforschung, 41, 1150-1153 (1991). Activity of an anti-allergic agent is measured as follows: Candidate prostaglandin D synthase inhibitors are administered to an animal or cells. Allergic reactions in animals or the production of prostaglandin $D_2$ from cells is then measured to evaluate the activity of the candidate compound. Alternatively, for example, any allergen is administered to animal before a candidate compound for prostaglandin D synthase inhibitor is administered and systemic allergic reaction of the animal is observed to evaluate efficacy of the candidate compound. Alternatively, for example, any allergen is administered to an animal to put the animal in an allergic condition. Cells are collected from the animal, and the candidate compound of prostaglandin D synthase inhibitor is added to the cells in vitro. The amount of prostaglandin $D_2$ caused by the stimulation of the cells with allergen is measured to evaluate of efficacy of the candidate compound.

A method for measuring pharmacological activity as sleep control agent is described in Huang, Z.-H., Qu, W.-M., Li, W.-D., Mochizuki, T., Eguchi, N., Watanabe, T., Urade, Y. & Hayaishi, O. Arousal effect f orexin A depends on activation of the histaminergic system. Proc. Natl. Acad. Sci. USA, 98, 9965-9970 (2001). For example, the activity is measured as follows: When prostaglandin D synthase inhibitor is administered in ventricle of the brain of a mouse, significant sleep disturbance occurs. On the other hand, when prostaglandin $D_2$ is administered in the ventricle of the brain of a mouse, sleep is induced. Accordingly, the candidate compound of prostaglandin D synthase inhibitor is administered to an animal and the sleep condition is observed to evaluate the medical efficacy of the candidate compound. The measurement of the sleep condition of animal is, for example, carried out by measuring brain wave, electromyogram, activity, feeding and water-drinking amount, temperature, etc. from time to time.

A method for measuring pharmacological activity as anti-obesity agent is described in Ikeda H, Taketomi S, Sugiyama Y, Shimura Y, Sohda T, Meguro K & Fujita T. Effects of pioglitazone on glucose and lipid metabolism in normal and insulin resistant animals. Arzneimittelforschung, 40, 156-162 (1990) and Sohda T, Mizuno K, Momose Y, Ikeda H, Fujita T & Meguro K. Studies on anti-diabetic agents. 11. Novel thiazolidinedione derivatives as potent hypoglycemic and hypolipidemic agents. J. Med. Chem., 35, 2617-2626 (1992).

The measurement of pharmacological activity as anti-obesity agent is carried out as follows: The Prostaglandin D synthase inhibitor candidate is administered to an animal and the activity of the candidate compound is measured by measuring the obesity of the animal. For example, high fatty food is given to an animal and the candidate compound of prostaglandin D synthase inhibitor is then administered to the animal. The Obesity condition of animal is, for example, estimated by measuring body weight, active mass, feeding amount, fat weight, biochemical value in blood, etc. from time to time.

The measurement of activity of brain wound healing agent in individual is carried out as follows: Medical efficacy of the candidate compound is measured by administering the candidate compound of prostaglandin D synthase inhibitor to an animal and then measuring the degree of brain wound healing. For example, it is measured by administering the candidate compound of prostaglandin D synthase inhibitor to a traumatic cerebral cortex wound (Stab wound) model (Salhia B et al, Brain Res., 888:87-97, 2000; Asahi M., et al., J. Neurosci., 21:7724-7732, 2001; Garcia de Yebenes E., et al., J. Neurochem., 73:812-1999). The measurement of brain wound healing is effected by measuring for example, amount of behavior, immunohistochemical staining, amount of expressed gene.

TABLE 1

Three-dimensional structural coordinate of the complex of human hematopoietic PGDS (SEQ ID NO: 1) with calcium and glutathione

| ATOM | 4966 | N | TYR | A | 8 | −2.182 | −4.051 | 33.067 | 1.00 | 13.69 | A |
|------|------|-----|-----|---|----|--------|---------|--------|------|-------|---|
| ATOM | 4967 | CA | TYR | A | 8 | −0.772 | −4.337 | 33.302 | 1.00 | 13.75 | A |
| ATOM | 4968 | CB | TYR | A | 8 | 0.013 | −3.029 | 33.442 | 1.00 | 12.77 | A |
| ATOM | 4969 | CG | TYR | A | 8 | 1.519 | −3.203 | 33.467 | 1.00 | 11.97 | A |
| ATOM | 4970 | CD1 | TYR | A | 8 | 2.186 | −3.810 | 32.407 | 1.00 | 11.66 | A |
| ATOM | 4971 | CE1 | TYR | A | 8 | 3.576 | −3.936 | 32.403 | 1.00 | 11.17 | A |
| ATOM | 4972 | CD2 | TYR | A | 8 | 2.279 | −2.725 | 34.535 | 1.00 | 11.40 | A |
| ATOM | 4973 | CE2 | TYR | A | 8 | 3.666 | −2.843 | 34.545 | 1.00 | 11.23 | A |
| ATOM | 4974 | CZ | TYR | A | 8 | 4.307 | −3.447 | 33.475 | 1.00 | 11.71 | A |
| ATOM | 4975 | OH | TYR | A | 8 | 5.680 | −3.555 | 33.475 | 1.00 | 12.03 | A |
| ATOM | 4976 | C | TYR | A | 8 | −0.651 | −5.143 | 34.588 | 1.00 | 14.05 | A |
| ATOM | 4977 | O | TYR | A | 8 | −1.650 | −5.413 | 35.253 | 1.00 | 14.34 | A |
| ATOM | 4978 | N | PHE | A | 9 | 0.569 | −5.539 | 34.932 | 1.00 | 14.40 | A |
| ATOM | 4979 | CA | PHE | A | 9 | 0.793 | −6.283 | 36.165 | 1.00 | 15.06 | A |
| ATOM | 4980 | CB | PHE | A | 9 | 2.198 | −6.887 | 36.177 | 1.00 | 15.16 | A |
| ATOM | 4981 | CG | PHE | A | 9 | 2.369 | −8.046 | 35.234 | 1.00 | 16.21 | A |
| ATOM | 4982 | CD1 | PHE | A | 9 | 3.275 | −7.974 | 34.180 | 1.00 | 16.15 | A |
| ATOM | 4983 | CD2 | PHE | A | 9 | 1.633 | −9.214 | 35.406 | 1.00 | 16.28 | A |
| ATOM | 4984 | CE1 | PHE | A | 9 | 3.450 | −9.050 | 33.307 | 1.00 | 16.56 | A |
| ATOM | 4985 | CE2 | PHE | A | 9 | 1.797 | −10.299 | 34.540 | 1.00 | 16.94 | A |
| ATOM | 4986 | CZ | PHE | A | 9 | 2.708 | −10.215 | 33.490 | 1.00 | 16.76 | A |
| ATOM | 4987 | C | PHE | A | 9 | 0.644 | −5.318 | 37.339 | 1.00 | 15.24 | A |
| ATOM | 4988 | O | PHE | A | 9 | 0.482 | −4.111 | 37.139 | 1.00 | 14.55 | A |
| ATOM | 4989 | N | ASN | A | 10 | 0.692 | −5.847 | 38.559 | 1.00 | 15.45 | A |
| ATOM | 4990 | CA | ASN | A | 10 | 0.577 | −5.003 | 39.742 | 1.00 | 15.61 | A |
| ATOM | 4991 | CB | ASN | A | 10 | −0.020 | −5.775 | 40.925 | 1.00 | 16.21 | A |
| ATOM | 4992 | CG | ASN | A | 10 | −0.106 | −4.926 | 42.189 | 1.00 | 16.84 | A |

TABLE 1-continued

Three-dimensional structural coordinate of the complex of
human hematopoietic PGDS (SEQ ID NO: 1) with calcium and glutathione

| ATOM | 4993 | OD1 | ASN | A | 10 | −0.304 | −3.707 | 42.124 | 1.00 | 17.30 | A |
|---|---|---|---|---|---|---|---|---|---|---|---|
| ATOM | 4994 | ND2 | ASN | A | 10 | 0.032 | −5.566 | 43.344 | 1.00 | 17.59 | A |
| ATOM | 4995 | C | ASN | A | 10 | 1.940 | −4.458 | 40.125 | 1.00 | 15.68 | A |
| ATOM | 4996 | O | ASN | A | 10 | 2.594 | −4.955 | 41.040 | 1.00 | 15.31 | A |
| ATOM | 4997 | N | MET | A | 11 | 2.371 | −3.438 | 39.396 | 1.00 | 15.55 | A |
| ATOM | 4998 | CA | MET | A | 11 | 3.644 | −2.784 | 39.650 | 1.00 | 15.24 | A |
| ATOM | 4999 | CB | MET | A | 11 | 4.823 | −3.726 | 39.351 | 1.00 | 17.25 | A |
| ATOM | 5000 | CG | MET | A | 11 | 4.880 | −4.298 | 37.949 | 1.00 | 19.23 | A |
| ATOM | 5001 | SD | MET | A | 11 | 6.385 | −5.318 | 37.662 | 1.00 | 22.67 | A |
| ATOM | 5002 | CE | MET | A | 11 | 5.752 | −6.968 | 37.938 | 1.00 | 21.71 | A |
| ATOM | 5003 | C | MET | A | 11 | 3.705 | −1.543 | 38.772 | 1.00 | 14.23 | A |
| ATOM | 5004 | O | MET | A | 11 | 2.864 | −1.363 | 37.894 | 1.00 | 13.37 | A |
| ATOM | 5005 | N | ARG | A | 12 | 4.671 | −0.669 | 39.031 | 1.00 | 13.48 | A |
| ATOM | 5006 | CA | ARG | A | 12 | 4.804 | 0.537 | 38.227 | 1.00 | 12.43 | A |
| ATOM | 5007 | CB | ARG | A | 12 | 5.841 | 1.480 | 38.844 | 1.00 | 12.14 | A |
| ATOM | 5008 | CG | ARG | A | 12 | 5.472 | 1.978 | 40.246 | 1.00 | 12.08 | A |
| ATOM | 5009 | CD | ARG | A | 12 | 6.475 | 3.012 | 40.757 | 1.00 | 11.93 | A |
| ATOM | 5010 | NE | ARG | A | 12 | 7.833 | 2.474 | 40.769 | 1.00 | 12.08 | A |
| ATOM | 5011 | CZ | ARG | A | 12 | 8.301 | 1.623 | 41.680 | 1.00 | 12.27 | A |
| ATOM | 5012 | NH1 | ARG | A | 12 | 7.520 | 1.210 | 42.671 | 1.00 | 12.04 | A |
| ATOM | 5013 | NH2 | ARG | A | 12 | 9.550 | 1.174 | 41.589 | 1.00 | 11.83 | A |
| ATOM | 5014 | C | ARG | A | 12 | 5.232 | 0.080 | 36.838 | 1.00 | 12.15 | A |
| ATOM | 5015 | O | ARG | A | 12 | 4.517 | 0.285 | 35.858 | 1.00 | 12.05 | A |
| ATOM | 5016 | N | GLY | A | 13 | 6.393 | −0.563 | 36.770 | 1.00 | 12.02 | A |
| ATOM | 5017 | CA | GLY | A | 13 | 6.898 | −1.068 | 35.509 | 1.00 | 11.77 | A |
| ATOM | 5018 | C | GLY | A | 13 | 6.769 | −0.128 | 34.328 | 1.00 | 11.54 | A |
| ATOM | 5019 | O | GLY | A | 13 | 6.967 | 1.080 | 34.449 | 1.00 | 11.13 | A |
| ATOM | 5020 | N | ARG | A | 14 | 6.418 | −0.702 | 33.183 | 1.00 | 11.75 | A |
| ATOM | 5021 | CA | ARG | A | 14 | 6.277 | 0.040 | 31.939 | 1.00 | 11.78 | A |
| ATOM | 5022 | CB | ARG | A | 14 | 6.507 | −0.912 | 30.766 | 1.00 | 12.75 | A |
| ATOM | 5023 | CG | ARG | A | 14 | 7.908 | −1.488 | 30.767 | 1.00 | 14.50 | A |
| ATOM | 5024 | CD | ARG | A | 14 | 8.186 | −2.373 | 29.566 | 1.00 | 15.97 | A |
| ATOM | 5025 | NE | ARG | A | 14 | 9.622 | −2.433 | 29.307 | 1.00 | 18.20 | A |
| ATOM | 5026 | CZ | ARG | A | 14 | 10.303 | −1.488 | 28.666 | 1.00 | 19.33 | A |
| ATOM | 5027 | NH1 | ARG | A | 14 | 9.678 | −0.413 | 28.202 | 1.00 | 19.36 | A |
| ATOM | 5028 | NH2 | ARG | A | 14 | 11.613 | −1.603 | 28.516 | 1.00 | 20.58 | A |
| ATOM | 5029 | C | ARG | A | 14 | 4.945 | 0.753 | 31.770 | 1.00 | 11.74 | A |
| ATOM | 5030 | O | ARG | A | 14 | 4.748 | 1.488 | 30.801 | 1.00 | 11.56 | A |
| ATOM | 5031 | N | ALA | A | 15 | 4.031 | 0.548 | 32.709 | 1.00 | 11.10 | A |
| ATOM | 5032 | CA | ALA | A | 15 | 2.728 | 1.191 | 32.618 | 1.00 | 10.68 | A |
| ATOM | 5033 | CB | ALA | A | 15 | 1.644 | 0.237 | 33.111 | 1.00 | 10.84 | A |
| ATOM | 5034 | C | ALA | A | 15 | 2.665 | 2.492 | 33.400 | 1.00 | 10.23 | A |
| ATOM | 5035 | O | ALA | A | 15 | 1.789 | 3.322 | 33.157 | 1.00 | 10.48 | A |
| ATOM | 5036 | N | GLU | A | 16 | 3.600 | 2.679 | 34.327 | 1.00 | 9.72 | A |
| ATOM | 5037 | CA | GLU | A | 16 | 3.618 | 3.870 | 35.169 | 1.00 | 9.10 | A |
| ATOM | 5038 | CB | GLU | A | 16 | 4.808 | 3.809 | 36.132 | 1.00 | 9.10 | A |
| ATOM | 5039 | CG | GLU | A | 16 | 4.692 | 4.729 | 37.336 | 1.00 | 9.09 | A |
| ATOM | 5040 | CD | GLU | A | 16 | 3.527 | 4.369 | 38.243 | 1.00 | 9.08 | A |
| ATOM | 5041 | OE1 | GLU | A | 16 | 2.920 | 3.291 | 38.061 | 1.00 | 9.56 | A |
| ATOM | 5042 | OE2 | GLU | A | 16 | 3.218 | 5.163 | 39.150 | 1.00 | 9.58 | A |
| ATOM | 5043 | C | GLU | A | 16 | 3.646 | 5.194 | 34.409 | 1.00 | 9.31 | A |
| ATOM | 5044 | O | GLU | A | 16 | 3.032 | 6.170 | 34.837 | 1.00 | 8.78 | A |
| ATOM | 5045 | N | ILE | A | 17 | 4.361 | 5.237 | 33.288 | 1.00 | 9.01 | A |
| ATOM | 5046 | CA | ILE | A | 17 | 4.435 | 6.471 | 32.517 | 1.00 | 8.95 | A |
| ATOM | 5047 | CB | ILE | A | 17 | 5.388 | 6.335 | 31.303 | 1.00 | 9.06 | A |
| ATOM | 5048 | CG2 | ILE | A | 17 | 4.929 | 5.211 | 30.385 | 1.00 | 8.42 | A |
| ATOM | 5049 | CG1 | ILE | A | 17 | 5.449 | 7.658 | 30.531 | 1.00 | 8.92 | A |
| ATOM | 5050 | CD1 | ILE | A | 17 | 5.944 | 8.827 | 31.354 | 1.00 | 9.68 | A |
| ATOM | 5051 | C | ILE | A | 17 | 3.038 | 6.861 | 32.044 | 1.00 | 9.27 | A |
| ATOM | 5052 | O | ILE | A | 17 | 2.701 | 8.044 | 31.989 | 1.00 | 9.18 | A |
| ATOM | 5242 | N | TRP | A | 39 | −2.568 | −14.235 | 33.625 | 1.00 | 32.11 | A |
| ATOM | 5243 | CA | TRP | A | 39 | −1.844 | −13.679 | 32.486 | 1.00 | 31.66 | A |
| ATOM | 5244 | CB | TRP | A | 39 | −0.384 | −13.406 | 32.876 | 1.00 | 30.89 | A |
| ATOM | 5245 | CG | TRP | A | 39 | 0.496 | −12.996 | 31.726 | 1.00 | 30.01 | A |
| ATOM | 5246 | CD2 | TRP | A | 39 | 0.197 | −12.029 | 30.710 | 1.00 | 29.51 | A |
| ATOM | 5247 | CE2 | TRP | A | 39 | 1.310 | −11.981 | 29.840 | 1.00 | 29.33 | A |
| ATOM | 5248 | CE3 | TRP | A | 39 | −0.901 | −11.197 | 30.449 | 1.00 | 29.25 | A |
| ATOM | 5249 | CD1 | TRP | A | 39 | 1.741 | −13.478 | 31.440 | 1.00 | 29.80 | A |
| ATOM | 5250 | NE1 | TRP | A | 39 | 2.237 | −12.875 | 30.308 | 1.00 | 29.45 | A |
| ATOM | 5251 | CZ2 | TRP | A | 39 | 1.356 | −11.136 | 28.726 | 1.00 | 29.02 | A |
| ATOM | 5252 | CZ3 | TRP | A | 39 | −0.854 | −10.356 | 29.340 | 1.00 | 28.91 | A |
| ATOM | 5253 | CH2 | TRP | A | 39 | 0.269 | −10.333 | 28.493 | 1.00 | 28.96 | A |
| ATOM | 5254 | C | TRP | A | 39 | −1.892 | −14.593 | 31.255 | 1.00 | 31.85 | A |
| ATOM | 5255 | O | TRP | A | 39 | −2.215 | −14.142 | 30.156 | 1.00 | 31.82 | A |
| ATOM | 5256 | N | PRO | A | 40 | −1.571 | −15.888 | 31.424 | 1.00 | 31.95 | A |
| ATOM | 5257 | CD | PRO | A | 40 | −1.187 | −16.569 | 32.675 | 1.00 | 32.13 | A |

TABLE 1-continued

Three-dimensional structural coordinate of the complex of
human hematopoietic PGDS (SEQ ID NO: 1) with calcium and glutathione

| ATOM | 5258 | CA | PRO | A | 40 | −1.586 | −16.839 | 30.306 | 1.00 | 32.00 | A |
|---|---|---|---|---|---|---|---|---|---|---|---|
| ATOM | 5259 | CB | PRO | A | 40 | −1.477 | −18.186 | 31.007 | 1.00 | 32.11 | A |
| ATOM | 5260 | CG | PRO | A | 40 | −0.591 | −17.866 | 32.170 | 1.00 | 31.99 | A |
| ATOM | 5261 | C | PRO | A | 40 | −2.830 | −16.740 | 29.427 | 1.00 | 31.94 | A |
| ATOM | 5262 | O | PRO | A | 40 | −2.734 | −16.751 | 28.200 | 1.00 | 32.11 | A |
| ATOM | 5263 | N | GLU | A | 41 | −3.995 | −16.645 | 30.060 | 1.00 | 31.73 | A |
| ATOM | 5264 | CA | GLU | A | 41 | −5.258 | −16.542 | 29.338 | 1.00 | 31.51 | A |
| ATOM | 5265 | CB | GLU | A | 41 | −6.433 | −16.620 | 30.319 | 1.00 | 32.22 | A |
| ATOM | 5266 | CG | GLU | A | 41 | −7.807 | −16.488 | 29.668 | 1.00 | 33.37 | A |
| ATOM | 5267 | CD | GLU | A | 41 | −8.272 | −17.772 | 29.001 | 1.00 | 34.21 | A |
| ATOM | 5268 | OE1 | GLU | A | 41 | −7.544 | −18.301 | 28.131 | 1.00 | 34.63 | A |
| ATOM | 5269 | OE2 | GLU | A | 41 | −9.374 | −18.251 | 29.351 | 1.00 | 34.59 | A |
| ATOM | 5270 | C | GLU | A | 41 | −5.344 | −15.236 | 28.550 | 1.00 | 30.86 | A |
| ATOM | 5271 | O | GLU | A | 41 | −5.612 | −15.240 | 27.347 | 1.00 | 30.86 | A |
| ATOM | 5272 | N | ILE | A | 42 | −5.116 | −14.122 | 29.239 | 1.00 | 29.82 | A |
| ATOM | 5273 | CA | ILE | A | 42 | −5.174 | −12.797 | 28.624 | 1.00 | 28.89 | A |
| ATOM | 5274 | CB | ILE | A | 42 | −4.914 | −11.697 | 29.673 | 1.00 | 29.12 | A |
| ATOM | 5275 | CG2 | ILE | A | 42 | −4.936 | −10.323 | 29.011 | 1.00 | 29.10 | A |
| ATOM | 5276 | CG1 | ILE | A | 42 | −5.973 | −11.780 | 30.776 | 1.00 | 29.24 | A |
| ATOM | 5277 | CD1 | ILE | A | 42 | −5.692 | −10.894 | 31.969 | 1.00 | 29.54 | A |
| ATOM | 5278 | C | ILE | A | 42 | −4.162 | −12.637 | 27.492 | 1.00 | 28.04 | A |
| ATOM | 5279 | O | ILE | A | 42 | −4.476 | −12.078 | 26.442 | 1.00 | 27.96 | A |
| ATOM | 5280 | N | LYS | A | 43 | −2.949 | −13.128 | 27.718 | 1.00 | 27.12 | A |
| ATOM | 5281 | CA | LYS | A | 43 | −1.877 | −13.041 | 26.733 | 1.00 | 26.46 | A |
| ATOM | 5282 | CB | LYS | A | 43 | −0.644 | −13.791 | 27.243 | 1.00 | 26.21 | A |
| ATOM | 5283 | CG | LYS | A | 43 | 0.542 | −13.791 | 26.286 | 1.00 | 26.04 | A |
| ATOM | 5284 | CD | LYS | A | 43 | 1.639 | −14.723 | 26.785 | 1.00 | 25.92 | A |
| ATOM | 5285 | CE | LYS | A | 43 | 2.864 | −14.705 | 25.878 | 1.00 | 26.04 | A |
| ATOM | 5286 | NZ | LYS | A | 43 | 3.565 | −13.389 | 25.888 | 1.00 | 25.88 | A |
| ATOM | 5287 | C | LYS | A | 43 | −2.282 | −13.599 | 25.371 | 1.00 | 26.05 | A |
| ATOM | 5288 | O | LYS | A | 43 | −1.989 | −13.002 | 24.333 | 1.00 | 25.81 | A |
| ATOM | 5328 | N | GLY | A | 49 | 0.690 | −10.284 | 22.410 | 1.00 | 14.48 | A |
| ATOM | 5329 | CA | GLY | A | 49 | 0.907 | −10.936 | 23.690 | 1.00 | 14.19 | A |
| ATOM | 5330 | C | GLY | A | 49 | 1.776 | −10.250 | 24.725 | 1.00 | 14.00 | A |
| ATOM | 5331 | O | GLY | A | 49 | 2.495 | −10.913 | 25.474 | 1.00 | 13.78 | A |
| ATOM | 5332 | N | LYS | A | 50 | 1.702 | −8.928 | 24.792 | 1.00 | 13.70 | A |
| ATOM | 5333 | CA | LYS | A | 50 | 2.505 | −8.180 | 25.749 | 1.00 | 13.72 | A |
| ATOM | 5334 | CB | LYS | A | 50 | 3.703 | −7.544 | 25.032 | 1.00 | 14.43 | A |
| ATOM | 5335 | CG | LYS | A | 50 | 4.612 | −8.550 | 24.344 | 1.00 | 15.06 | A |
| ATOM | 5336 | CD | LYS | A | 50 | 5.479 | −9.277 | 25.357 | 1.00 | 15.66 | A |
| ATOM | 5337 | CE | LYS | A | 50 | 6.250 | −10.411 | 24.705 | 1.00 | 16.36 | A |
| ATOM | 5338 | NZ | LYS | A | 50 | 6.972 | −9.943 | 23.493 | 1.00 | 16.93 | A |
| ATOM | 5339 | C | LYS | A | 50 | 1.689 | −7.085 | 26.416 | 1.00 | 13.59 | A |
| ATOM | 5340 | O | LYS | A | 50 | 0.670 | −6.644 | 25.888 | 1.00 | 13.10 | A |
| ATOM | 5341 | N | ILE | A | 51 | 2.142 | −6.661 | 27.588 | 1.00 | 13.34 | A |
| ATOM | 5342 | CA | ILE | A | 51 | 1.484 | −5.588 | 28.305 | 1.00 | 13.51 | A |
| ATOM | 5343 | CB | ILE | A | 51 | 0.720 | −6.100 | 29.544 | 1.00 | 14.11 | A |
| ATOM | 5344 | CG2 | ILE | A | 51 | −0.628 | −6.656 | 29.113 | 1.00 | 14.02 | A |
| ATOM | 5345 | CG1 | ILE | A | 51 | 1.563 | −7.135 | 30.299 | 1.00 | 14.40 | A |
| ATOM | 5346 | CD1 | ILE | A | 51 | 0.909 | −7.639 | 31.571 | 1.00 | 15.17 | A |
| ATOM | 5347 | C | ILE | A | 51 | 2.543 | −4.578 | 28.724 | 1.00 | 13.35 | A |
| ATOM | 5348 | O | ILE | A | 51 | 3.731 | −4.892 | 28.769 | 1.00 | 13.56 | A |
| ATOM | 5349 | N | PRO | A | 52 | 2.122 | −3.355 | 29.061 | 1.00 | 13.08 | A |
| ATOM | 5350 | CD | PRO | A | 52 | 3.043 | −2.244 | 29.369 | 1.00 | 13.17 | A |
| ATOM | 5351 | CA | PRO | A | 52 | 0.732 | −2.892 | 29.086 | 1.00 | 12.94 | A |
| ATOM | 5352 | CB | PRO | A | 52 | 0.838 | −1.561 | 29.813 | 1.00 | 12.82 | A |
| ATOM | 5353 | CG | PRO | A | 52 | 2.132 | −1.022 | 29.259 | 1.00 | 13.02 | A |
| ATOM | 5354 | C | PRO | A | 52 | 0.017 | −2.716 | 27.749 | 1.00 | 12.81 | A |
| ATOM | 5355 | O | PRO | A | 52 | 0.625 | −2.677 | 26.677 | 1.00 | 12.35 | A |
| ATOM | 5356 | N | ILE | A | 53 | −1.300 | −2.611 | 27.846 | 1.00 | 12.88 | A |
| ATOM | 5357 | CA | ILE | A | 53 | −2.140 | −2.343 | 26.697 | 1.00 | 13.33 | A |
| ATOM | 5358 | CB | ILE | A | 53 | −2.916 | −3.585 | 26.200 | 1.00 | 13.90 | A |
| ATOM | 5359 | CG2 | ILE | A | 53 | −1.950 | −4.591 | 25.585 | 1.00 | 14.50 | A |
| ATOM | 5360 | CG1 | ILE | A | 53 | −3.736 | −4.186 | 27.339 | 1.00 | 14.62 | A |
| ATOM | 5361 | CD1 | ILE | A | 53 | −4.703 | −5.260 | 26.878 | 1.00 | 15.26 | A |
| ATOM | 5362 | C | ILE | A | 53 | −3.132 | −1.312 | 27.213 | 1.00 | 13.08 | A |
| ATOM | 5363 | O | ILE | A | 53 | −3.373 | −1.222 | 28.421 | 1.00 | 13.05 | A |
| ATOM | 5423 | N | HIS | A | 62 | −1.221 | −0.970 | 22.034 | 1.00 | 11.06 | A |
| ATOM | 5424 | CA | HIS | A | 62 | −0.137 | −1.598 | 22.788 | 1.00 | 10.38 | A |
| ATOM | 5425 | CB | HIS | A | 62 | 0.135 | −3.029 | 22.287 | 1.00 | 10.67 | A |
| ATOM | 5426 | CG | HIS | A | 62 | 0.735 | −3.103 | 20.917 | 1.00 | 11.13 | A |
| ATOM | 5427 | CD2 | HIS | A | 62 | 1.972 | −3.468 | 20.504 | 1.00 | 10.67 | A |
| ATOM | 5428 | ND1 | HIS | A | 62 | 0.027 | −2.801 | 19.773 | 1.00 | 11.52 | A |
| ATOM | 5429 | CE1 | HIS | A | 62 | 0.800 | −2.978 | 18.718 | 1.00 | 11.13 | A |
| ATOM | 5430 | NE2 | HIS | A | 62 | 1.987 | −3.383 | 19.134 | 1.00 | 12.00 | A |
| ATOM | 5431 | C | HIS | A | 62 | 1.136 | −0.748 | 22.707 | 1.00 | 9.83 | A |

TABLE 1-continued

Three-dimensional structural coordinate of the complex of
human hematopoietic PGDS (SEQ ID NO: 1) with calcium and glutathione

| ATOM | 5432 | O   | HIS | A | 62 | 1.162  | 0.263  | 22.007 | 1.00 | 9.03  | A |
|------|------|-----|-----|---|----|--------|--------|--------|------|-------|---|
| ATOM | 5433 | N   | GLN | A | 63 | 2.169  | −1.173 | 23.436 | 1.00 | 9.33  | A |
| ATOM | 5434 | CA  | GLN | A | 63 | 3.456  | −0.486 | 23.515 | 1.00 | 8.74  | A |
| ATOM | 5435 | CB  | GLN | A | 63 | 4.009  | −0.166 | 22.119 | 1.00 | 8.90  | A |
| ATOM | 5436 | CG  | GLN | A | 63 | 4.690  | −1.358 | 21.414 | 1.00 | 8.45  | A |
| ATOM | 5437 | CD  | GLN | A | 63 | 6.016  | −1.771 | 22.058 | 1.00 | 9.03  | A |
| ATOM | 5438 | OE1 | GLN | A | 63 | 6.588  | −1.032 | 22.858 | 1.00 | 7.87  | A |
| ATOM | 5439 | NE2 | GLN | A | 63 | 6.513  | −2.954 | 21.691 | 1.00 | 8.38  | A |
| ATOM | 5440 | C   | GLN | A | 63 | 3.316  | 0.778  | 24.362 | 1.00 | 8.66  | A |
| ATOM | 5441 | O   | GLN | A | 63 | 2.739  | 1.783  | 23.938 | 1.00 | 7.74  | A |
| ATOM | 5442 | N   | SER | A | 64 | 3.855  | 0.704  | 25.574 | 1.00 | 8.31  | A |
| ATOM | 5443 | CA  | SER | A | 64 | 3.766  | 1.789  | 26.543 | 1.00 | 8.33  | A |
| ATOM | 5444 | CB  | SER | A | 64 | 4.595  | 1.446  | 27.787 | 1.00 | 8.01  | A |
| ATOM | 5445 | OG  | SER | A | 64 | 5.978  | 1.416  | 27.493 | 1.00 | 7.87  | A |
| ATOM | 5446 | C   | SER | A | 64 | 4.153  | 3.172  | 26.040 | 1.00 | 8.36  | A |
| ATOM | 5447 | O   | SER | A | 64 | 3.435  | 4.133  | 26.290 | 1.00 | 8.26  | A |
| ATOM | 5448 | N   | LEU | A | 65 | 5.274  | 3.287  | 25.333 | 1.00 | 8.41  | A |
| ATOM | 5449 | CA  | LEU | A | 65 | 5.708  | 4.601  | 24.866 | 1.00 | 8.36  | A |
| ATOM | 5450 | CB  | LEU | A | 65 | 7.197  | 4.568  | 24.514 | 1.00 | 8.81  | A |
| ATOM | 5451 | CG  | LEU | A | 65 | 8.082  | 4.104  | 25.687 | 1.00 | 9.51  | A |
| ATOM | 5452 | CD1 | LEU | A | 65 | 9.553  | 4.275  | 25.322 | 1.00 | 10.70 | A |
| ATOM | 5453 | CD2 | LEU | A | 65 | 7.763  | 4.915  | 26.941 | 1.00 | 9.59  | A |
| ATOM | 5454 | C   | LEU | A | 65 | 4.867  | 5.102  | 23.691 | 1.00 | 8.52  | A |
| ATOM | 5455 | O   | LEU | A | 65 | 4.659  | 6.308  | 23.540 | 1.00 | 8.38  | A |
| ATOM | 5662 | N   | ASP | A | 93 | 13.380 | 7.412  | 24.678 | 1.00 | 8.42  | A |
| ATOM | 5663 | CA  | ASP | A | 93 | 13.975 | 6.203  | 24.118 | 1.00 | 9.01  | A |
| ATOM | 5664 | CB  | ASP | A | 93 | 14.076 | 6.291  | 22.584 | 1.00 | 9.85  | A |
| ATOM | 5665 | CG  | ASP | A | 93 | 12.788 | 5.838  | 21.886 | 1.00 | 11.05 | A |
| ATOM | 5666 | OD1 | ASP | A | 93 | 12.750 | 5.784  | 20.630 | 1.00 | 11.80 | A |
| ATOM | 5667 | OD2 | ASP | A | 93 | 11.809 | 5.531  | 22.605 | 1.00 | 11.10 | A |
| ATOM | 5668 | C   | ASP | A | 93 | 15.344 | 5.869  | 24.740 | 1.00 | 8.95  | A |
| ATOM | 5669 | O   | ASP | A | 93 | 15.656 | 4.696  | 24.951 | 1.00 | 9.47  | A |
| ATOM | 5670 | N   | THR | A | 94 | 16.156 | 6.881  | 25.036 | 1.00 | 8.96  | A |
| ATOM | 5671 | CA  | THR | A | 94 | 17.462 | 6.638  | 25.661 | 1.00 | 8.70  | A |
| ATOM | 5672 | CB  | THR | A | 94 | 18.240 | 7.965  | 25.849 | 1.00 | 9.08  | A |
| ATOM | 5673 | OG1 | THR | A | 94 | 18.678 | 8.430  | 24.568 | 1.00 | 8.81  | A |
| ATOM | 5674 | CG2 | THR | A | 94 | 19.462 | 7.778  | 26.759 | 1.00 | 8.34  | A |
| ATOM | 5675 | C   | THR | A | 94 | 17.264 | 5.948  | 27.017 | 1.00 | 9.09  | A |
| ATOM | 5676 | O   | THR | A | 94 | 17.967 | 4.987  | 27.347 | 1.00 | 8.99  | A |
| ATOM | 5677 | N   | LEU | A | 95 | 16.302 | 6.442  | 27.792 | 1.00 | 8.65  | A |
| ATOM | 5678 | CA  | LEU | A | 95 | 15.996 | 5.867  | 29.094 | 1.00 | 9.14  | A |
| ATOM | 5679 | CB  | LEU | A | 95 | 14.965 | 6.725  | 29.838 | 1.00 | 9.16  | A |
| ATOM | 5680 | CG  | LEU | A | 95 | 15.454 | 8.091  | 30.320 | 1.00 | 9.32  | A |
| ATOM | 5681 | CD1 | LEU | A | 95 | 14.308 | 8.874  | 30.967 | 1.00 | 9.37  | A |
| ATOM | 5682 | CD2 | LEU | A | 95 | 16.580 | 7.876  | 31.328 | 1.00 | 9.77  | A |
| ATOM | 5683 | C   | LEU | A | 95 | 15.462 | 4.452  | 28.934 | 1.00 | 9.18  | A |
| ATOM | 5684 | O   | LEU | A | 95 | 15.891 | 3.539  | 29.634 | 1.00 | 8.68  | A |
| ATOM | 5685 | N   | ASP | A | 96 | 14.529 | 4.272  | 28.003 | 1.00 | 9.39  | A |
| ATOM | 5686 | CA  | ASP | A | 96 | 13.950 | 2.960  | 27.759 | 1.00 | 9.93  | A |
| ATOM | 5687 | CB  | ASP | A | 96 | 12.878 | 3.058  | 26.668 | 1.00 | 11.27 | A |
| ATOM | 5688 | CG  | ASP | A | 96 | 12.035 | 1.796  | 26.564 | 1.00 | 12.51 | A |
| ATOM | 5689 | OD1 | ASP | A | 96 | 11.700 | 1.220  | 27.616 | 1.00 | 14.48 | A |
| ATOM | 5690 | OD2 | ASP | A | 96 | 11.698 | 1.382  | 25.444 | 1.00 | 13.59 | A |
| ATOM | 5691 | C   | ASP | A | 96 | 15.051 | 1.981  | 27.354 | 1.00 | 9.66  | A |
| ATOM | 5692 | O   | ASP | A | 96 | 15.094 | 0.854  | 27.845 | 1.00 | 9.47  | A |
| ATOM | 5693 | N   | ASP | A | 97 | 15.951 | 2.419  | 26.476 | 1.00 | 9.43  | A |
| ATOM | 5694 | CA  | ASP | A | 97 | 17.054 | 1.567  | 26.034 | 1.00 | 9.98  | A |
| ATOM | 5695 | CB  | ASP | A | 97 | 18.033 | 2.334  | 25.134 | 1.00 | 9.49  | A |
| ATOM | 5696 | CG  | ASP | A | 97 | 17.466 | 2.650  | 23.760 | 1.00 | 10.73 | A |
| ATOM | 5697 | OD1 | ASP | A | 97 | 18.142 | 3.390  | 23.013 | 1.00 | 10.05 | A |
| ATOM | 5698 | OD2 | ASP | A | 97 | 16.365 | 2.164  | 23.425 | 1.00 | 10.69 | A |
| ATOM | 5699 | C   | ASP | A | 97 | 17.845 | 1.038  | 27.230 | 1.00 | 10.11 | A |
| ATOM | 5700 | O   | ASP | A | 97 | 18.159 | −0.150 | 27.296 | 1.00 | 10.03 | A |
| ATOM | 5701 | N   | PHE | A | 98 | 18.185 | 1.923  | 28.164 | 1.00 | 10.63 | A |
| ATOM | 5702 | CA  | PHE | A | 98 | 18.965 | 1.507  | 29.325 | 1.00 | 11.09 | A |
| ATOM | 5703 | CB  | PHE | A | 98 | 19.440 | 2.717  | 30.134 | 1.00 | 11.78 | A |
| ATOM | 5704 | CG  | PHE | A | 98 | 20.383 | 2.358  | 31.255 | 1.00 | 12.44 | A |
| ATOM | 5705 | CD1 | PHE | A | 98 | 21.628 | 1.793  | 30.983 | 1.00 | 12.99 | A |
| ATOM | 5706 | CD2 | PHE | A | 98 | 20.016 | 2.555  | 32.579 | 1.00 | 12.82 | A |
| ATOM | 5707 | CE1 | PHE | A | 98 | 22.494 | 1.425  | 32.022 | 1.00 | 13.35 | A |
| ATOM | 5708 | CE2 | PHE | A | 98 | 20.869 | 2.193  | 33.623 | 1.00 | 13.21 | A |
| ATOM | 5709 | CZ  | PHE | A | 98 | 22.109 | 1.627  | 33.343 | 1.00 | 13.21 | A |
| ATOM | 5710 | C   | PHE | A | 98 | 18.181 | 0.565  | 30.231 | 1.00 | 11.33 | A |
| ATOM | 5711 | O   | PHE | A | 98 | 18.683 | −0.494 | 30.616 | 1.00 | 11.57 | A |
| ATOM | 5712 | N   | MET | A | 99 | 16.951 | 0.944  | 30.568 | 1.00 | 11.37 | A |
| ATOM | 5713 | CA  | MET | A | 99 | 16.125 | 0.113  | 31.429 | 1.00 | 12.06 | A |

TABLE 1-continued

Three-dimensional structural coordinate of the complex of
human hematopoietic PGDS (SEQ ID NO: 1) with calcium and glutathione

| ATOM | 5714 | CB | MET | A | 99 | 14.782 | 0.796 | 31.715 | 1.00 | 12.55 | A |
| --- | --- | --- | --- | --- | --- | --- | --- | --- | --- | --- | --- |
| ATOM | 5715 | CG | MET | A | 99 | 14.894 | 2.142 | 32.413 | 1.00 | 13.10 | A |
| ATOM | 5716 | SD | MET | A | 99 | 15.806 | 2.070 | 33.972 | 1.00 | 14.07 | A |
| ATOM | 5717 | CE | MET | A | 99 | 14.630 | 1.211 | 35.020 | 1.00 | 14.27 | A |
| ATOM | 5718 | C | MET | A | 99 | 15.877 | −1.260 | 30.812 | 1.00 | 12.60 | A |
| ATOM | 5719 | O | MET | A | 99 | 15.754 | −2.253 | 31.528 | 1.00 | 12.65 | A |
| ATOM | 5720 | N | SER | A | 100 | 15.807 | −1.316 | 29.484 | 1.00 | 12.96 | A |
| ATOM | 5721 | CA | SER | A | 100 | 15.567 | −2.576 | 28.784 | 1.00 | 13.81 | A |
| ATOM | 5722 | CB | SER | A | 100 | 15.121 | −2.302 | 27.344 | 1.00 | 14.23 | A |
| ATOM | 5723 | OG | SER | A | 100 | 13.828 | −1.725 | 27.328 | 1.00 | 15.92 | A |
| ATOM | 5724 | C | SER | A | 100 | 16.789 | −3.494 | 28.785 | 1.00 | 14.13 | A |
| ATOM | 5725 | O | SER | A | 100 | 16.669 | −4.686 | 28.507 | 1.00 | 14.04 | A |
| ATOM | 5726 | N | CYS | A | 101 | 17.959 | −2.938 | 29.097 | 1.00 | 14.67 | A |
| ATOM | 5727 | CA | CYS | A | 101 | 19.187 | −3.723 | 29.152 | 1.00 | 15.64 | A |
| ATOM | 5728 | CB | CYS | A | 101 | 20.415 | −2.812 | 29.235 | 1.00 | 16.10 | A |
| ATOM | 5729 | SG | CYS | A | 101 | 20.893 | −2.013 | 27.701 | 1.00 | 17.92 | A |
| ATOM | 5730 | C | CYS | A | 101 | 19.197 | −4.670 | 30.350 | 1.00 | 15.85 | A |
| ATOM | 5731 | O | CYS | A | 101 | 19.926 | −5.662 | 30.350 | 1.00 | 15.88 | A |
| ATOM | 5732 | N | PHE | A | 102 | 18.404 | −4.361 | 31.373 | 1.00 | 15.73 | A |
| ATOM | 5733 | CA | PHE | A | 102 | 18.343 | −5.214 | 32.562 | 1.00 | 15.76 | A |
| ATOM | 5734 | CB | PHE | A | 102 | 17.748 | −4.462 | 33.754 | 1.00 | 15.27 | A |
| ATOM | 5735 | CG | PHE | A | 102 | 18.613 | −3.348 | 34.258 | 1.00 | 15.10 | A |
| ATOM | 5736 | CD1 | PHE | A | 102 | 18.642 | −2.125 | 33.600 | 1.00 | 14.99 | A |
| ATOM | 5737 | CD2 | PHE | A | 102 | 19.414 | −3.527 | 35.380 | 1.00 | 14.73 | A |
| ATOM | 5738 | CE1 | PHE | A | 102 | 19.457 | −1.092 | 34.050 | 1.00 | 15.09 | A |
| ATOM | 5739 | CE2 | PHE | A | 102 | 20.237 | −2.500 | 35.841 | 1.00 | 14.94 | A |
| ATOM | 5740 | CZ | PHE | A | 102 | 20.256 | −1.280 | 35.174 | 1.00 | 14.83 | A |
| ATOM | 5741 | C | PHE | A | 102 | 17.505 | −6.455 | 32.295 | 1.00 | 16.19 | A |
| ATOM | 5742 | O | PHE | A | 102 | 16.415 | −6.366 | 31.728 | 1.00 | 15.63 | A |
| ATOM | 5743 | N | PRO | A | 103 | 18.009 | −7.632 | 32.699 | 1.00 | 16.76 | A |
| ATOM | 5744 | CD | PRO | A | 103 | 19.356 | −7.845 | 33.260 | 1.00 | 17.02 | A |
| ATOM | 5745 | CA | PRO | A | 103 | 17.319 | −8.914 | 32.512 | 1.00 | 17.47 | A |
| ATOM | 5746 | CB | PRO | A | 103 | 18.456 | −9.923 | 32.609 | 1.00 | 17.20 | A |
| ATOM | 5747 | CG | PRO | A | 103 | 19.315 | −9.315 | 33.668 | 1.00 | 17.07 | A |
| ATOM | 5748 | C | PRO | A | 103 | 16.246 | −9.145 | 33.577 | 1.00 | 18.16 | A |
| ATOM | 5749 | O | PRO | A | 103 | 16.363 | −10.043 | 34.418 | 1.00 | 18.22 | A |
| ATOM | 5750 | N | TRP | A | 104 | 15.197 | −8.331 | 33.525 | 1.00 | 18.78 | A |
| ATOM | 5751 | CA | TRP | A | 104 | 14.099 | −8.414 | 34.482 | 1.00 | 19.84 | A |
| ATOM | 5752 | CB | TRP | A | 104 | 13.017 | −7.381 | 34.141 | 1.00 | 18.95 | A |
| ATOM | 5753 | CG | TRP | A | 104 | 13.517 | −5.971 | 34.076 | 1.00 | 18.24 | A |
| ATOM | 5754 | CD2 | TRP | A | 104 | 13.896 | −5.144 | 35.182 | 1.00 | 17.79 | A |
| ATOM | 5755 | CE2 | TRP | A | 104 | 14.321 | −3.906 | 34.652 | 1.00 | 17.69 | A |
| ATOM | 5756 | CE3 | TRP | A | 104 | 13.921 | −5.329 | 36.572 | 1.00 | 17.54 | A |
| ATOM | 5757 | CD1 | TRP | A | 104 | 13.720 | −5.224 | 32.951 | 1.00 | 17.72 | A |
| ATOM | 5758 | NE1 | TRP | A | 104 | 14.201 | −3.981 | 33.289 | 1.00 | 17.64 | A |
| ATOM | 5759 | CZ2 | TRP | A | 104 | 14.765 | −2.856 | 35.463 | 1.00 | 17.79 | A |
| ATOM | 5760 | CZ3 | TRP | A | 104 | 14.363 | −4.282 | 37.379 | 1.00 | 17.58 | A |
| ATOM | 5761 | CH2 | TRP | A | 104 | 14.778 | −3.064 | 36.820 | 1.00 | 17.48 | A |
| ATOM | 5762 | C | TRP | A | 104 | 13.449 | −9.790 | 34.572 | 1.00 | 20.99 | A |
| ATOM | 5763 | O | TRP | A | 104 | 13.031 | −10.207 | 35.650 | 1.00 | 21.33 | A |
| ATOM | 5764 | N | ALA | A | 105 | 13.359 | −10.493 | 33.447 | 1.00 | 22.46 | A |
| ATOM | 5765 | CA | ALA | A | 105 | 12.720 | −11.807 | 33.434 | 1.00 | 23.88 | A |
| ATOM | 5766 | CB | ALA | A | 105 | 11.878 | −11.961 | 32.169 | 1.00 | 23.69 | A |
| ATOM | 5767 | C | ALA | A | 105 | 13.685 | −12.982 | 33.565 | 1.00 | 24.90 | A |
| ATOM | 5768 | O | ALA | A | 105 | 13.262 | −14.136 | 33.576 | 1.00 | 25.13 | A |
| ATOM | 5769 | N | GLU | A | 106 | 14.976 | −12.686 | 33.675 | 1.00 | 26.10 | A |
| ATOM | 5770 | CA | GLU | A | 106 | 15.996 | −13.721 | 33.803 | 1.00 | 27.43 | A |
| ATOM | 5771 | CB | GLU | A | 106 | 17.388 | −13.083 | 33.790 | 1.00 | 27.61 | A |
| ATOM | 5772 | CG | GLU | A | 106 | 18.550 | −14.065 | 33.842 | 1.00 | 28.16 | A |
| ATOM | 5773 | CD | GLU | A | 106 | 18.455 | −15.144 | 32.775 | 1.00 | 28.35 | A |
| ATOM | 5774 | OE1 | GLU | A | 106 | 17.850 | −16.200 | 33.045 | 1.00 | 28.68 | A |
| ATOM | 5775 | OE2 | GLU | A | 106 | 18.973 | −14.931 | 31.662 | 1.00 | 28.90 | A |
| ATOM | 5776 | C | GLU | A | 106 | 15.823 | −14.543 | 35.077 | 1.00 | 28.31 | A |
| ATOM | 5777 | O | GLU | A | 106 | 15.898 | −14.010 | 36.185 | 1.00 | 28.41 | A |
| ATOM | 5778 | N | LYS | A | 107 | 15.591 | −15.842 | 34.908 | 1.00 | 29.48 | A |
| ATOM | 5779 | CA | LYS | A | 107 | 15.420 | −16.754 | 36.038 | 1.00 | 30.63 | A |
| ATOM | 5780 | CB | LYS | A | 107 | 14.695 | −18.028 | 35.594 | 1.00 | 31.06 | A |
| ATOM | 5781 | CG | LYS | A | 107 | 13.187 | −18.016 | 35.779 | 1.00 | 31.97 | A |
| ATOM | 5782 | CD | LYS | A | 107 | 12.495 | −17.030 | 34.864 | 1.00 | 32.92 | A |
| ATOM | 5783 | CE | LYS | A | 107 | 10.983 | −17.201 | 34.945 | 1.00 | 33.65 | A |
| ATOM | 5784 | NZ | LYS | A | 107 | 10.485 | −17.067 | 36.346 | 1.00 | 34.05 | A |
| ATOM | 5785 | C | LYS | A | 107 | 16.775 | −17.133 | 36.630 | 1.00 | 31.06 | A |
| ATOM | 5786 | O | LYS | A | 107 | 16.874 | −17.465 | 37.810 | 1.00 | 31.19 | A |
| ATOM | 5787 | N | LYS | A | 108 | 17.810 | −17.094 | 35.796 | 1.00 | 31.69 | A |
| ATOM | 5788 | CA | LYS | A | 108 | 19.163 | −17.421 | 36.231 | 1.00 | 32.35 | A |
| ATOM | 5789 | CB | LYS | A | 108 | 20.082 | −17.563 | 35.017 | 1.00 | 32.50 | A |

TABLE 1-continued

Three-dimensional structural coordinate of the complex of
human hematopoietic PGDS (SEQ ID NO: 1) with calcium and glutathione

| ATOM | 5790 | CG | LYS | A | 108 | 19.634 | −18.632 | 34.033 | 1.00 | 32.81 | A |
|------|------|-----|-----|---|-----|--------|---------|--------|------|-------|---|
| ATOM | 5791 | CD | LYS | A | 108 | 20.454 | −18.602 | 32.757 | 1.00 | 33.35 | A |
| ATOM | 5792 | CE | LYS | A | 108 | 19.977 | −19.664 | 31.777 | 1.00 | 33.34 | A |
| ATOM | 5793 | NZ | LYS | A | 108 | 20.660 | −19.552 | 30.454 | 1.00 | 33.69 | A |
| ATOM | 5794 | C | LYS | A | 108 | 19.668 | −16.305 | 37.143 | 1.00 | 32.68 | A |
| ATOM | 5795 | O | LYS | A | 108 | 20.180 | −15.288 | 36.675 | 1.00 | 32.69 | A |
| ATOM | 5796 | N | GLN | A | 109 | 19.518 | −16.510 | 38.447 | 1.00 | 33.05 | A |
| ATOM | 5797 | CA | GLN | A | 109 | 19.923 | −15.529 | 39.443 | 1.00 | 33.40 | A |
| ATOM | 5798 | CB | GLN | A | 109 | 19.719 | −16.101 | 40.846 | 1.00 | 34.05 | A |
| ATOM | 5799 | CG | GLN | A | 109 | 18.943 | −15.175 | 41.763 | 1.00 | 34.95 | A |
| ATOM | 5800 | CD | GLN | A | 109 | 17.561 | −14.854 | 41.223 | 1.00 | 35.27 | A |
| ATOM | 5801 | OE1 | GLN | A | 109 | 16.934 | −13.878 | 41.633 | 1.00 | 35.73 | A |
| ATOM | 5802 | NE2 | GLN | A | 109 | 17.077 | −15.682 | 40.301 | 1.00 | 35.62 | A |
| ATOM | 5803 | C | GLN | A | 109 | 21.360 | −15.042 | 39.293 | 1.00 | 33.21 | A |
| ATOM | 5804 | O | GLN | A | 109 | 21.619 | −13.842 | 39.374 | 1.00 | 33.28 | A |
| ATOM | 5805 | N | ASP | A | 110 | 22.290 | −15.966 | 39.078 | 1.00 | 32.78 | A |
| ATOM | 5806 | CA | ASP | A | 110 | 23.692 | −15.597 | 38.927 | 1.00 | 32.30 | A |
| ATOM | 5807 | CB | ASP | A | 110 | 24.569 | −16.852 | 38.841 | 1.00 | 32.93 | A |
| ATOM | 5808 | CG | ASP | A | 110 | 24.303 | −17.670 | 37.592 | 1.00 | 33.42 | A |
| ATOM | 5809 | OD1 | ASP | A | 110 | 23.137 | −18.065 | 37.371 | 1.00 | 33.92 | A |
| ATOM | 5810 | OD2 | ASP | A | 110 | 25.263 | −17.921 | 36.832 | 1.00 | 33.95 | A |
| ATOM | 5811 | C | ASP | A | 110 | 23.891 | −14.734 | 37.684 | 1.00 | 31.55 | A |
| ATOM | 5812 | O | ASP | A | 110 | 24.641 | −13.759 | 37.708 | 1.00 | 31.47 | A |
| ATOM | 5813 | N | VAL | A | 111 | 23.211 | −15.096 | 36.600 | 1.00 | 30.50 | A |
| ATOM | 5814 | CA | VAL | A | 111 | 23.310 | −14.352 | 35.350 | 1.00 | 29.55 | A |
| ATOM | 5815 | CB | VAL | A | 111 | 22.661 | −15.130 | 34.188 | 1.00 | 29.61 | A |
| ATOM | 5816 | CG1 | VAL | A | 111 | 22.743 | −14.322 | 32.907 | 1.00 | 29.78 | A |
| ATOM | 5817 | CG2 | VAL | A | 111 | 23.353 | −16.469 | 34.017 | 1.00 | 29.84 | A |
| ATOM | 5818 | C | VAL | A | 111 | 22.613 | −13.000 | 35.485 | 1.00 | 28.61 | A |
| ATOM | 5819 | O | VAL | A | 111 | 23.069 | −11.995 | 34.939 | 1.00 | 28.38 | A |
| ATOM | 5820 | N | LYS | A | 112 | 21.509 | −12.986 | 36.224 | 1.00 | 27.55 | A |
| ATOM | 5821 | CA | LYS | A | 112 | 20.746 | −11.763 | 36.435 | 1.00 | 26.48 | A |
| ATOM | 5822 | CB | LYS | A | 112 | 19.414 | −12.083 | 37.117 | 1.00 | 26.47 | A |
| ATOM | 5823 | CG | LYS | A | 112 | 18.452 | −10.907 | 37.177 | 1.00 | 25.94 | A |
| ATOM | 5824 | CD | LYS | A | 112 | 17.173 | −11.278 | 37.904 | 1.00 | 26.05 | A |
| ATOM | 5825 | CE | LYS | A | 112 | 16.181 | −10.125 | 37.906 | 1.00 | 25.77 | A |
| ATOM | 5826 | NZ | LYS | A | 112 | 14.951 | −10.457 | 38.676 | 1.00 | 25.64 | A |
| ATOM | 5827 | C | LYS | A | 112 | 21.523 | −10.765 | 37.287 | 1.00 | 26.12 | A |
| ATOM | 5828 | O | LYS | A | 112 | 21.631 | −9.589 | 36.941 | 1.00 | 25.60 | A |
| ATOM | 5829 | N | GLU | A | 113 | 22.062 | −11.243 | 38.404 | 1.00 | 25.24 | A |
| ATOM | 5830 | CA | GLU | A | 113 | 22.818 | −10.393 | 39.314 | 1.00 | 25.10 | A |
| ATOM | 5831 | CB | GLU | A | 113 | 23.128 | −11.159 | 40.605 | 1.00 | 25.39 | A |
| ATOM | 5832 | CG | GLU | A | 113 | 23.862 | −10.347 | 41.669 | 1.00 | 25.63 | A |
| ATOM | 5833 | CD | GLU | A | 113 | 23.026 | −9.213 | 42.248 | 1.00 | 25.83 | A |
| ATOM | 5834 | OE1 | GLU | A | 113 | 23.522 | −8.525 | 43.170 | 1.00 | 25.56 | A |
| ATOM | 5835 | OE2 | GLU | A | 113 | 21.880 | −9.008 | 41.786 | 1.00 | 25.58 | A |
| ATOM | 5836 | C | GLU | A | 113 | 24.113 | −9.891 | 38.676 | 1.00 | 24.67 | A |
| ATOM | 5837 | O | GLU | A | 113 | 24.578 | −8.791 | 38.975 | 1.00 | 24.33 | A |
| ATOM | 5838 | N | GLN | A | 114 | 24.689 | −10.702 | 37.796 | 1.00 | 24.42 | A |
| ATOM | 5839 | CA | GLN | A | 114 | 25.926 | −10.341 | 37.116 | 1.00 | 24.24 | A |
| ATOM | 5840 | CB | GLN | A | 114 | 26.438 | −11.538 | 36.308 | 1.00 | 24.91 | A |
| ATOM | 5841 | CG | GLN | A | 114 | 27.868 | −11.417 | 35.789 | 1.00 | 25.97 | A |
| ATOM | 5842 | CD | GLN | A | 114 | 28.030 | −10.372 | 34.700 | 1.00 | 26.74 | A |
| ATOM | 5843 | OE1 | GLN | A | 114 | 27.278 | −10.353 | 33.723 | 1.00 | 26.88 | A |
| ATOM | 5844 | NE2 | GLN | A | 114 | 29.026 | −9.502 | 34.856 | 1.00 | 27.12 | A |
| ATOM | 5845 | C | GLN | A | 114 | 25.685 | −9.148 | 36.193 | 1.00 | 23.68 | A |
| ATOM | 5846 | O | GLN | A | 114 | 26.465 | −8.194 | 36.180 | 1.00 | 23.45 | A |
| ATOM | 5847 | N | MET | A | 115 | 24.598 | −9.196 | 35.429 | 1.00 | 22.98 | A |
| ATOM | 5848 | CA | MET | A | 115 | 24.284 | −8.113 | 34.503 | 1.00 | 22.57 | A |
| ATOM | 5849 | CB | MET | A | 115 | 23.229 | −8.566 | 33.489 | 1.00 | 24.00 | A |
| ATOM | 5850 | CG | MET | A | 115 | 22.980 | −7.560 | 32.371 | 1.00 | 25.61 | A |
| ATOM | 5851 | SD | MET | A | 115 | 24.507 | −6.939 | 31.592 | 1.00 | 28.29 | A |
| ATOM | 5852 | CE | MET | A | 115 | 24.966 | −8.333 | 30.583 | 1.00 | 27.44 | A |
| ATOM | 5853 | C | MET | A | 115 | 23.815 | −6.855 | 35.228 | 1.00 | 21.47 | A |
| ATOM | 5854 | O | MET | A | 115 | 24.191 | −5.747 | 34.851 | 1.00 | 20.89 | A |
| ATOM | 5855 | N | PHE | A | 116 | 22.998 | −7.025 | 36.265 | 1.00 | 20.55 | A |
| ATOM | 5856 | CA | PHE | A | 116 | 22.515 | −5.882 | 37.033 | 1.00 | 19.83 | A |
| ATOM | 5857 | CB | PHE | A | 116 | 21.626 | −6.334 | 38.195 | 1.00 | 19.24 | A |
| ATOM | 5858 | CG | PHE | A | 116 | 20.154 | −6.260 | 37.901 | 1.00 | 18.22 | A |
| ATOM | 5859 | CD1 | PHE | A | 116 | 19.554 | −7.163 | 37.030 | 1.00 | 17.96 | A |
| ATOM | 5860 | CD2 | PHE | A | 116 | 19.368 | −5.284 | 38.501 | 1.00 | 17.91 | A |
| ATOM | 5861 | CE1 | PHE | A | 116 | 18.186 | −7.096 | 36.761 | 1.00 | 17.74 | A |
| ATOM | 5862 | CE2 | PHE | A | 116 | 18.001 | −5.205 | 38.241 | 1.00 | 17.75 | A |
| ATOM | 5863 | CZ | PHE | A | 116 | 17.409 | −6.114 | 37.368 | 1.00 | 17.62 | A |
| ATOM | 5864 | C | PHE | A | 116 | 23.701 | −5.110 | 37.593 | 1.00 | 20.07 | A |
| ATOM | 5865 | O | PHE | A | 116 | 23.789 | −3.891 | 37.450 | 1.00 | 19.59 | A |

TABLE 1-continued

Three-dimensional structural coordinate of the complex of
human hematopoietic PGDS (SEQ ID NO: 1) with calcium and glutathione

| ATOM | 6152 | N   | TYR | A | 152 | 9.211  | 10.332 | 32.716 | 1.00 | 8.70  | A |
|------|------|-----|-----|---|-----|--------|--------|--------|------|-------|---|
| ATOM | 6153 | CA  | TYR | A | 152 | 9.897  | 9.070  | 32.511 | 1.00 | 8.91  | A |
| ATOM | 6154 | CB  | TYR | A | 152 | 10.120 | 8.824  | 31.021 | 1.00 | 9.31  | A |
| ATOM | 6155 | CG  | TYR | A | 152 | 10.158 | 7.355  | 30.660 | 1.00 | 10.11 | A |
| ATOM | 6156 | CD1 | TYR | A | 152 | 9.197  | 6.466  | 31.160 | 1.00 | 10.35 | A |
| ATOM | 6157 | CE1 | TYR | A | 152 | 9.215  | 5.109  | 30.811 | 1.00 | 10.49 | A |
| ATOM | 6158 | CD2 | TYR | A | 152 | 11.137 | 6.854  | 29.804 | 1.00 | 10.28 | A |
| ATOM | 6159 | CE2 | TYR | A | 152 | 11.160 | 5.505  | 29.448 | 1.00 | 10.37 | A |
| ATOM | 6160 | CZ  | TYR | A | 152 | 10.206 | 4.642  | 29.950 | 1.00 | 10.60 | A |
| ATOM | 6161 | OH  | TYR | A | 152 | 10.245 | 3.314  | 29.587 | 1.00 | 10.57 | A |
| ATOM | 6162 | C   | TYR | A | 152 | 11.211 | 9.033  | 33.272 | 1.00 | 9.20  | A |
| ATOM | 6163 | O   | TYR | A | 152 | 11.622 | 7.982  | 33.759 | 1.00 | 9.19  | A |
| ATOM | 6164 | N   | TRP | A | 153 | 11.869 | 10.180 | 33.386 | 1.00 | 9.22  | A |
| ATOM | 6165 | CA  | TRP | A | 153 | 13.113 | 10.224 | 34.135 | 1.00 | 9.64  | A |
| ATOM | 6166 | CB  | TRP | A | 153 | 13.752 | 11.613 | 34.067 | 1.00 | 10.03 | A |
| ATOM | 6167 | CG  | TRP | A | 153 | 14.748 | 11.836 | 35.157 | 1.00 | 10.79 | A |
| ATOM | 6168 | CD2 | TRP | A | 153 | 15.900 | 11.033 | 35.441 | 1.00 | 11.30 | A |
| ATOM | 6169 | CE2 | TRP | A | 153 | 16.521 | 11.583 | 36.585 | 1.00 | 11.43 | A |
| ATOM | 6170 | CE3 | TRP | A | 153 | 16.467 | 9.899  | 34.841 | 1.00 | 11.63 | A |
| ATOM | 6171 | CD1 | TRP | A | 153 | 14.717 | 12.816 | 36.111 | 1.00 | 10.88 | A |
| ATOM | 6172 | NE1 | TRP | A | 153 | 15.780 | 12.669 | 36.974 | 1.00 | 11.27 | A |
| ATOM | 6173 | CZ2 | TRP | A | 153 | 17.682 | 11.040 | 37.142 | 1.00 | 11.66 | A |
| ATOM | 6174 | CZ3 | TRP | A | 153 | 17.629 | 9.354  | 35.398 | 1.00 | 12.00 | A |
| ATOM | 6175 | CH2 | TRP | A | 153 | 18.221 | 9.931  | 36.539 | 1.00 | 11.19 | A |
| ATOM | 6176 | C   | TRP | A | 153 | 12.836 | 9.867  | 35.593 | 1.00 | 9.64  | A |
| ATOM | 6177 | O   | TRP | A | 153 | 13.518 | 9.022  | 36.175 | 1.00 | 9.85  | A |
| ATOM | 6178 | N   | GLU | A | 154 | 11.827 | 10.504 | 36.177 | 1.00 | 9.88  | A |
| ATOM | 6179 | CA  | GLU | A | 154 | 11.491 | 10.260 | 37.570 | 1.00 | 9.73  | A |
| ATOM | 6180 | CB  | GLU | A | 154 | 10.379 | 11.222 | 38.007 | 1.00 | 10.24 | A |
| ATOM | 6181 | CG  | GLU | A | 154 | 10.187 | 11.310 | 39.509 | 1.00 | 11.28 | A |
| ATOM | 6182 | CD  | GLU | A | 154 | 9.315  | 10.199 | 40.035 | 1.00 | 11.50 | A |
| ATOM | 6183 | OE1 | GLU | A | 154 | 9.291  | 9.987  | 41.267 | 1.00 | 12.33 | A |
| ATOM | 6184 | OE2 | GLU | A | 154 | 8.645  | 9.543  | 39.207 | 1.00 | 12.17 | A |
| ATOM | 6185 | C   | GLU | A | 154 | 11.081 | 8.802  | 37.785 | 1.00 | 9.53  | A |
| ATOM | 6186 | O   | GLU | A | 154 | 11.468 | 8.180  | 38.776 | 1.00 | 9.12  | A |
| ATOM | 6187 | N   | ILE | A | 155 | 10.320 | 8.257  | 36.837 | 1.00 | 8.98  | A |
| ATOM | 6188 | CA  | ILE | A | 155 | 9.870  | 6.875  | 36.904 | 1.00 | 8.87  | A |
| ATOM | 6189 | CB  | ILE | A | 155 | 8.810  | 6.599  | 35.815 | 1.00 | 8.72  | A |
| ATOM | 6190 | CG2 | ILE | A | 155 | 8.550  | 5.097  | 35.683 | 1.00 | 9.06  | A |
| ATOM | 6191 | CG1 | ILE | A | 155 | 7.524  | 7.354  | 36.173 | 1.00 | 8.74  | A |
| ATOM | 6192 | CD1 | ILE | A | 155 | 6.467  | 7.383  | 35.064 | 1.00 | 8.73  | A |
| ATOM | 6193 | C   | ILE | A | 155 | 11.035 | 5.888  | 36.782 | 1.00 | 9.35  | A |
| ATOM | 6194 | O   | ILE | A | 155 | 11.180 | 4.986  | 37.609 | 1.00 | 9.36  | A |
| ATOM | 6195 | N   | CYS | A | 156 | 11.873 | 6.063  | 35.766 | 1.00 | 9.31  | A |
| ATOM | 6196 | CA  | CYS | A | 156 | 13.012 | 5.175  | 35.589 | 1.00 | 10.15 | A |
| ATOM | 6197 | CB  | CYS | A | 156 | 13.734 | 5.471  | 34.269 | 1.00 | 10.37 | A |
| ATOM | 6198 | SG  | CYS | A | 156 | 12.770 | 5.037  | 32.774 | 1.00 | 11.81 | A |
| ATOM | 6199 | C   | CYS | A | 156 | 14.008 | 5.280  | 36.741 | 1.00 | 10.50 | A |
| ATOM | 6200 | O   | CYS | A | 156 | 14.480 | 4.262  | 37.247 | 1.00 | 10.92 | A |
| ATOM | 6201 | N   | SER | A | 157 | 14.325 | 6.499  | 37.163 | 1.00 | 10.75 | A |
| ATOM | 6202 | CA  | SER | A | 157 | 15.291 | 6.680  | 38.246 | 1.00 | 10.88 | A |
| ATOM | 6203 | CB  | SER | A | 157 | 15.633 | 8.167  | 38.431 | 1.00 | 11.09 | A |
| ATOM | 6204 | OG  | SER | A | 157 | 14.501 | 8.948  | 38.749 | 1.00 | 11.29 | A |
| ATOM | 6205 | C   | SER | A | 157 | 14.813 | 6.073  | 39.565 | 1.00 | 11.31 | A |
| ATOM | 6206 | O   | SER | A | 157 | 15.618 | 5.576  | 40.357 | 1.00 | 11.45 | A |
| ATOM | 6207 | N   | THR | A | 158 | 13.506 | 6.113  | 39.799 | 1.00 | 11.14 | A |
| ATOM | 6208 | CA  | THR | A | 158 | 12.932 | 5.538  | 41.008 | 1.00 | 11.46 | A |
| ATOM | 6209 | CB  | THR | A | 158 | 11.396 | 5.654  | 40.996 | 1.00 | 10.96 | A |
| ATOM | 6210 | OG1 | THR | A | 158 | 11.028 | 7.026  | 41.168 | 1.00 | 11.35 | A |
| ATOM | 6211 | CG2 | THR | A | 158 | 10.775 | 4.806  | 42.114 | 1.00 | 10.93 | A |
| ATOM | 6212 | C   | THR | A | 158 | 13.310 | 4.059  | 41.104 | 1.00 | 11.75 | A |
| ATOM | 6213 | O   | THR | A | 158 | 13.749 | 3.588  | 42.151 | 1.00 | 11.75 | A |
| ATOM | 6214 | N   | THR | A | 159 | 13.139 | 3.328  | 40.006 | 1.00 | 11.91 | A |
| ATOM | 6215 | CA  | THR | A | 159 | 13.470 | 1.910  | 40.002 | 1.00 | 12.52 | A |
| ATOM | 6216 | CB  | THR | A | 159 | 12.884 | 1.205  | 38.760 | 1.00 | 12.63 | A |
| ATOM | 6217 | OG1 | THR | A | 159 | 11.455 | 1.252  | 38.832 | 1.00 | 12.91 | A |
| ATOM | 6218 | CG2 | THR | A | 159 | 13.327 | −0.263 | 38.705 | 1.00 | 12.73 | A |
| ATOM | 6219 | C   | THR | A | 159 | 14.978 | 1.666  | 40.084 | 1.00 | 12.45 | A |
| ATOM | 6220 | O   | THR | A | 159 | 15.424 | 0.723  | 40.739 | 1.00 | 12.48 | A |
| ATOM | 6221 | N   | LEU | A | 160 | 15.767 | 2.516  | 39.436 | 1.00 | 12.52 | A |
| ATOM | 6222 | CA  | LEU | A | 160 | 17.215 | 2.356  | 39.490 | 1.00 | 12.72 | A |
| ATOM | 6223 | CB  | LEU | A | 160 | 17.908 | 3.355  | 38.555 | 1.00 | 12.33 | A |
| ATOM | 6224 | CG  | LEU | A | 160 | 17.690 | 3.148  | 37.047 | 1.00 | 13.04 | A |
| ATOM | 6225 | CD1 | LEU | A | 160 | 18.367 | 4.267  | 36.268 | 1.00 | 12.38 | A |
| ATOM | 6226 | CD2 | LEU | A | 160 | 18.247 | 1.793  | 36.629 | 1.00 | 12.53 | A |
| ATOM | 6227 | C   | LEU | A | 160 | 17.716 | 2.563  | 40.922 | 1.00 | 12.87 | A |

TABLE 1-continued

Three-dimensional structural coordinate of the complex of
human hematopoietic PGDS (SEQ ID NO: 1) with calcium and glutathione

| ATOM | 6228 | O | LEU | A | 160 | 18.607 | 1.850 | 41.380 | 1.00 | 13.07 | A |
|---|---|---|---|---|---|---|---|---|---|---|---|
| ATOM | 6229 | N | LEU | A | 161 | 17.130 | 3.528 | 41.628 | 1.00 | 13.22 | A |
| ATOM | 6230 | CA | LEU | A | 161 | 17.530 | 3.828 | 43.000 | 1.00 | 13.77 | A |
| ATOM | 6231 | CB | LEU | A | 161 | 16.833 | 5.102 | 43.490 | 1.00 | 13.77 | A |
| ATOM | 6232 | CG | LEU | A | 161 | 17.314 | 6.417 | 42.863 | 1.00 | 13.80 | A |
| ATOM | 6233 | CD1 | LEU | A | 161 | 16.371 | 7.552 | 43.241 | 1.00 | 13.46 | A |
| ATOM | 6234 | CD2 | LEU | A | 161 | 18.736 | 6.723 | 43.329 | 1.00 | 13.49 | A |
| ATOM | 6235 | C | LEU | A | 161 | 17.252 | 2.684 | 43.967 | 1.00 | 14.34 | A |
| ATOM | 6236 | O | LEU | A | 161 | 17.839 | 2.619 | 45.050 | 1.00 | 14.37 | A |
| ATOM | 6237 | N | VAL | A | 162 | 16.350 | 1.792 | 43.578 | 1.00 | 14.42 | A |
| ATOM | 6238 | CA | VAL | A | 162 | 16.019 | 0.639 | 44.404 | 1.00 | 15.39 | A |
| ATOM | 6239 | CB | VAL | A | 162 | 14.826 | −0.146 | 43.813 | 1.00 | 15.43 | A |
| ATOM | 6240 | CG1 | VAL | A | 162 | 14.643 | −1.467 | 44.565 | 1.00 | 15.56 | A |
| ATOM | 6241 | CG2 | VAL | A | 162 | 13.559 | 0.698 | 43.910 | 1.00 | 15.37 | A |
| ATOM | 6242 | C | VAL | A | 162 | 17.232 | −0.289 | 44.493 | 1.00 | 16.01 | A |
| ATOM | 6243 | O | VAL | A | 162 | 17.490 | −0.899 | 45.535 | 1.00 | 16.21 | A |
| ATOM | 6244 | N | PHE | A | 163 | 17.982 | −0.381 | 43.399 | 1.00 | 16.34 | A |
| ATOM | 6245 | CA | PHE | A | 163 | 19.160 | −1.237 | 43.354 | 1.00 | 17.20 | A |
| ATOM | 6246 | CB | PHE | A | 163 | 19.218 | −1.999 | 42.026 | 1.00 | 17.31 | A |
| ATOM | 6247 | CG | PHE | A | 163 | 17.979 | −2.791 | 41.729 | 1.00 | 18.00 | A |
| ATOM | 6248 | CD1 | PHE | A | 163 | 16.865 | −2.177 | 41.173 | 1.00 | 18.03 | A |
| ATOM | 6249 | CD2 | PHE | A | 163 | 17.917 | −4.149 | 42.029 | 1.00 | 18.06 | A |
| ATOM | 6250 | CE1 | PHE | A | 163 | 15.704 | −2.900 | 40.922 | 1.00 | 18.23 | A |
| ATOM | 6251 | CE2 | PHE | A | 163 | 16.757 | −4.884 | 41.782 | 1.00 | 18.01 | A |
| ATOM | 6252 | CZ | PHE | A | 163 | 15.649 | −4.258 | 41.227 | 1.00 | 18.18 | A |
| ATOM | 6253 | C | PHE | A | 163 | 20.470 | −0.482 | 43.553 | 1.00 | 17.48 | A |
| ATOM | 6254 | O | PHE | A | 163 | 21.473 | −1.078 | 43.937 | 1.00 | 17.90 | A |
| ATOM | 6528 | N | THR | A | 197 | 4.591 | −0.941 | 45.453 | 1.00 | 17.89 | A |
| ATOM | 6529 | CA | THR | A | 197 | 5.221 | −2.157 | 44.953 | 1.00 | 17.58 | A |
| ATOM | 6530 | CB | THR | A | 197 | 4.623 | −2.571 | 43.592 | 1.00 | 17.29 | A |
| ATOM | 6531 | OG1 | THR | A | 197 | 4.796 | −1.501 | 42.652 | 1.00 | 17.06 | A |
| ATOM | 6532 | CG2 | THR | A | 197 | 3.135 | −2.881 | 43.732 | 1.00 | 17.03 | A |
| ATOM | 6533 | C | THR | A | 197 | 6.712 | −1.903 | 44.780 | 1.00 | 17.29 | A |
| ATOM | 6534 | O | THR | A | 197 | 7.139 | −0.757 | 44.661 | 1.00 | 17.19 | A |
| ATOM | 6535 | N | LYS | A | 198 | 7.507 | −2.967 | 44.775 | 1.00 | 17.12 | A |
| ATOM | 6536 | CA | LYS | A | 198 | 8.948 | −2.813 | 44.620 | 1.00 | 17.28 | A |
| ATOM | 6537 | CB | LYS | A | 198 | 9.647 | −4.168 | 44.727 | 1.00 | 17.40 | A |
| ATOM | 6538 | CG | LYS | A | 198 | 11.159 | −4.088 | 44.582 | 1.00 | 17.55 | A |
| ATOM | 6539 | CD | LYS | A | 198 | 11.792 | −5.459 | 44.688 | 1.00 | 17.80 | A |
| ATOM | 6540 | CE | LYS | A | 198 | 13.304 | −5.355 | 44.747 | 1.00 | 17.96 | A |
| ATOM | 6541 | NZ | LYS | A | 198 | 13.944 | −6.692 | 44.918 | 1.00 | 19.01 | A |
| ATOM | 6542 | C | LYS | A | 198 | 9.292 | −2.172 | 43.280 | 1.00 | 17.06 | A |
| ATOM | 6543 | O | LYS | A | 198 | 9.996 | −1.163 | 43.225 | 1.00 | 16.95 | A |
| ATOM | 6544 | N | LEU | A | 199 | 8.783 | −2.762 | 42.205 | 1.00 | 17.25 | A |
| ATOM | 6545 | CA | LEU | A | 199 | 9.049 | −2.271 | 40.860 | 1.00 | 17.51 | A |
| ATOM | 6546 | CB | LEU | A | 199 | 9.557 | −3.420 | 39.987 | 1.00 | 18.10 | A |
| ATOM | 6547 | CG | LEU | A | 199 | 10.722 | −4.239 | 40.550 | 1.00 | 18.31 | A |
| ATOM | 6548 | CD1 | LEU | A | 199 | 11.046 | −5.365 | 39.591 | 1.00 | 18.98 | A |
| ATOM | 6549 | CD2 | LEU | A | 199 | 11.941 | −3.350 | 40.768 | 1.00 | 18.60 | A |
| ATOM | 6550 | C | LEU | A | 199 | 7.804 | −1.655 | 40.228 | 1.00 | 17.54 | A |
| ATOM | 6551 | O | LEU | A | 199 | 6.789 | −1.503 | 40.943 | 1.00 | 17.46 | A |
| ATOM | 6552 | OXT | LEU | A | 199 | 7.864 | −1.331 | 39.025 | 1.00 | 17.38 | A |
| ATOM | 6613 | N1 | GSH | H | 200 | 8.267 | −2.783 | 25.084 | 1.00 | 18.14 | H |
| ATOM | 6614 | CA1 | GSH | H | 200 | 6.892 | −3.012 | 25.512 | 1.00 | 18.05 | H |
| ATOM | 6615 | C1 | GSH | H | 200 | 6.253 | −1.716 | 26.049 | 1.00 | 17.74 | H |
| ATOM | 6616 | O11 | GSH | H | 200 | 6.974 | −0.743 | 26.300 | 1.00 | 17.76 | H |
| ATOM | 6617 | O12 | GSH | H | 200 | 4.957 | −1.770 | 26.305 | 1.00 | 17.69 | H |
| ATOM | 6618 | CB1 | GSH | H | 200 | 6.915 | −4.033 | 26.658 | 1.00 | 18.51 | H |
| ATOM | 6619 | CG1 | GSH | H | 200 | 6.911 | −5.492 | 26.184 | 1.00 | 19.29 | H |
| ATOM | 6620 | CD1 | GSH | H | 200 | 7.126 | −6.355 | 27.445 | 1.00 | 18.72 | H |
| ATOM | 6621 | OE1 | GSH | H | 200 | 8.184 | −6.947 | 27.593 | 1.00 | 19.64 | H |
| ATOM | 6622 | N2 | GSH | H | 200 | 6.110 | −6.407 | 28.322 | 1.00 | 18.69 | H |
| ATOM | 6623 | CA2 | GSH | H | 200 | 6.216 | −7.299 | 29.489 | 1.00 | 18.57 | H |
| ATOM | 6624 | C2 | GSH | H | 200 | 5.273 | −8.489 | 29.291 | 1.00 | 19.14 | H |
| ATOM | 6625 | O2 | GSH | H | 200 | 4.151 | −8.358 | 28.784 | 1.00 | 19.07 | H |
| ATOM | 6626 | CB2 | GSH | H | 200 | 5.800 | −6.596 | 30.799 | 1.00 | 18.29 | H |
| ATOM | 6627 | SG2 | GSH | H | 200 | 7.094 | −5.503 | 31.467 | 1.00 | 17.57 | H |
| ATOM | 6628 | N3 | GSH | H | 200 | 5.713 | −9.677 | 29.767 | 1.00 | 19.66 | H |
| ATOM | 6629 | CA3 | GSH | H | 200 | 4.866 | −10.887 | 29.805 | 1.00 | 20.05 | H |
| ATOM | 6630 | C3 | GSH | H | 200 | 5.256 | −11.824 | 28.677 | 1.00 | 20.59 | H |
| ATOM | 6631 | O31 | GSH | H | 200 | 4.643 | −12.911 | 28.623 | 1.00 | 20.61 | H |
| ATOM | 6632 | O32 | GSH | H | 200 | 6.164 | −11.461 | 27.881 | 1.00 | 20.69 | H |
| ATOM | 6633 | CA + 2 | CA2 | M | 900 | 12.319 | 1.399 | 22.690 | 1.00 | 23.39 | M |
| ATOM | 6700 | OH2 | WAT | S | 68 | 14.121 | 2.911 | 22.047 | 1.00 | 14.43 | S |
| ATOM | 6701 | OH2 | WAT | S | 69 | 10.382 | 0.015 | 22.374 | 1.00 | 17.83 | S |
| ATOM | 6702 | OH2 | WAT | S | 70 | 6.835 | 1.587 | 23.510 | 1.00 | 10.00 | S |

TABLE 1-continued

Three-dimensional structural coordinate of the complex of
human hematopoietic PGDS (SEQ ID NO: 1) with calcium and glutathione

| ATOM | 6703 | OH2 | WAT | S | 71 | 9.084 | 0.596 | 24.637 | 1.00 | 20.95 | S |
|---|---|---|---|---|---|---|---|---|---|---|---|
| ATOM | 6704 | OH2 | WAT | S | 72 | 7.464 | 2.364 | 29.866 | 1.00 | 18.58 | S |
| ATOM | 6705 | OH2 | WAT | S | 73 | 6.627 | 3.292 | 32.747 | 1.00 | 10.51 | S |
| ATOM | 6706 | OH2 | WAT | S | 74 | 10.027 | −0.425 | 37.514 | 1.00 | 16.92 | S |
| ATOM | 6707 | OH2 | WAT | S | 75 | 8.932 | 1.748 | 36.205 | 1.00 | 14.34 | S |
| ATOM | 6708 | OH2 | WAT | S | 76 | 9.214 | 3.513 | 38.532 | 1.00 | 18.39 | S |
| ATOM | 6736 | OH2 | WAT | S | 106 | 8.886 | −7.534 | 20.205 | 1.00 | 13.51 | S |
| ATOM | 6737 | OH2 | WAT | S | 107 | 3.110 | −4.937 | 22.720 | 1.00 | 12.05 | S |
| ATOM | 6738 | OH2 | WAT | S | 108 | 0.868 | −6.588 | 23.134 | 1.00 | 10.94 | S |
| ATOM | 6739 | OH2 | WAT | S | 109 | 5.765 | −8.770 | 20.668 | 1.00 | 22.48 | S |
| ATOM | 6740 | OH2 | WAT | S | 110 | 7.826 | −6.141 | 22.398 | 1.00 | 11.14 | S |
| ATOM | 6741 | OH2 | WAT | S | 111 | 5.382 | −6.173 | 21.467 | 1.00 | 10.04 | S |
| ATOM | 6742 | OH2 | WAT | S | 112 | 13.216 | −1.032 | 21.636 | 1.00 | 18.10 | S |
| ATOM | 6744 | OH2 | WAT | S | 114 | 17.856 | −1.808 | 25.058 | 1.00 | 20.41 | S |
| ATOM | 6760 | OH2 | WAT | S | 130 | 3.197 | −14.232 | 20.833 | 1.00 | 51.90 | S |
| ATOM | 6991 | OH2 | WAT | S | 374 | 1.473 | 2.207 | 40.356 | 1.00 | 10.67 | S |
| ATOM | 6992 | OH2 | WAT | S | 375 | 4.951 | 1.805 | 44.037 | 1.00 | 15.41 | S |
| ATOM | 7014 | OH2 | WAT | S | 399 | −1.260 | −6.795 | 21.531 | 1.00 | 15.82 | S |
| ATOM | 7015 | OH2 | WAT | S | 400 | −2.774 | −4.748 | 20.376 | 1.00 | 27.99 | S |
| ATOM | 7018 | OH2 | WAT | S | 403 | 2.577 | 0.177 | 41.980 | 1.00 | 13.62 | S |
| ATOM | 7019 | OH2 | WAT | S | 404 | 0.564 | −8.538 | 39.036 | 1.00 | 23.05 | S |
| ATOM | 7020 | OH2 | WAT | S | 405 | 8.238 | −9.999 | 31.265 | 1.00 | 29.66 | S |
| ATOM | 7040 | OH2 | WAT | S | 426 | 11.203 | 0.001 | 32.951 | 1.00 | 36.44 | S |
| ATOM | 7041 | OH2 | WAT | S | 428 | 15.066 | −17.180 | 32.416 | 1.00 | 31.37 | S |
| ATOM | 7042 | OH2 | WAT | S | 429 | 10.965 | −7.436 | 30.782 | 1.00 | 46.48 | S |
| ATOM | 7053 | OH2 | WAT | S | 443 | −2.454 | −1.326 | 35.257 | 1.00 | 9.90 | S |
| ATOM | 7075 | OH2 | WAT | S | 476 | 9.258 | −15.961 | 22.392 | 1.00 | 35.74 | S |
| ATOM | 7079 | OH2 | WAT | S | 484 | 18.667 | −6.199 | 25.509 | 1.00 | 51.86 | S |
| ATOM | 7181 | OH2 | WAT | S | 609 | 14.259 | 0.633 | 24.144 | 1.00 | 13.45 | S |
| ATOM | 7185 | OH2 | WAT | S | 616 | 6.184 | −5.556 | 45.296 | 1.00 | 23.90 | S |
| ATOM | 7186 | OH2 | WAT | S | 617 | 8.234 | −7.048 | 46.247 | 1.00 | 26.45 | S |
| ATOM | 7201 | OH2 | WAT | S | 637 | 8.943 | −7.562 | 24.594 | 1.00 | 21.20 | S |
| ATOM | 7202 | OH2 | WAT | S | 638 | 10.718 | −9.017 | 21.394 | 1.00 | 20.69 | S |
| ATOM | 7203 | OH2 | WAT | S | 639 | 6.772 | −12.758 | 20.621 | 1.00 | 31.01 | S |
| ATOM | 7204 | OH2 | WAT | S | 640 | 4.298 | −12.631 | 22.679 | 1.00 | 44.61 | S |
| ATOM | 7205 | OH2 | WAT | S | 642 | 11.438 | −5.078 | 25.419 | 1.00 | 41.38 | S |
| ATOM | 7215 | OH2 | WAT | S | 657 | 2.956 | −3.352 | 25.272 | 1.00 | 13.15 | S |
| ATOM | 7232 | OH2 | WAT | S | 690 | 14.369 | −9.780 | 30.964 | 1.00 | 44.36 | S |
| ATOM | 7233 | OH2 | WAT | S | 692 | 18.178 | −7.756 | 40.325 | 1.00 | 19.70 | S |
| ATOM | 7235 | OH2 | WAT | S | 696 | 7.112 | −5.132 | 42.047 | 1.00 | 21.00 | S |
| ATOM | 7237 | OH2 | WAT | S | 698 | 8.595 | −7.307 | 41.589 | 1.00 | 30.04 | S |
| ATOM | 7238 | OH2 | WAT | S | 699 | 13.321 | −7.321 | 42.140 | 1.00 | 27.80 | S |
| ATOM | 7240 | OH2 | WAT | S | 702 | −6.903 | −2.845 | 28.812 | 1.00 | 20.55 | S |
| ATOM | 7245 | OH2 | WAT | S | 707 | 10.773 | 3.112 | 22.561 | 1.00 | 18.01 | S |
| ATOM | 7249 | OH2 | WAT | S | 713 | 14.133 | −12.827 | 37.720 | 1.00 | 37.72 | S |
| ATOM | 7257 | OH2 | WAT | S | 729 | 9.660 | −4.357 | 34.020 | 1.00 | 40.28 | S |
| ATOM | 7260 | OH2 | WAT | S | 735 | 10.625 | −2.519 | 35.392 | 1.00 | 46.30 | S |
| ATOM | 7291 | OH2 | WAT | S | 783 | 8.130 | −9.654 | 27.367 | 1.00 | 21.27 | S |
| ATOM | 7318 | OH2 | WAT | S | 831 | 5.332 | −11.112 | 19.145 | 1.00 | 24.71 | S |
| ATOM | 7333 | OH2 | WAT | S | 860 | 15.591 | −0.692 | 20.940 | 1.00 | 38.98 | S |
| ATOM | 7334 | OH2 | WAT | S | 861 | 15.057 | −5.068 | 23.204 | 1.00 | 45.10 | S |
| ATOM | 7336 | OH2 | WAT | S | 864 | 17.064 | −8.176 | 25.940 | 1.00 | 41.30 | S |
| ATOM | 7368 | OH2 | WAT | S | 916 | 4.717 | −6.156 | 42.468 | 1.00 | 32.94 | S |
| ATOM | 7371 | OH2 | WAT | S | 920 | 19.610 | −12.642 | 30.175 | 1.00 | 31.99 | S |
| ATOM | 7386 | OH2 | WAT | S | 948 | 12.372 | 1.268 | 20.616 | 1.00 | 22.94 | S |
| ATOM | 7399 | OH2 | WAT | S | 968 | 7.575 | −13.636 | 26.467 | 1.00 | 40.77 | S |
| ATOM | 7400 | OH2 | WAT | S | 969 | 13.034 | −12.270 | 21.957 | 1.00 | 29.54 | S |
| ATOM | 7415 | OH2 | WAT | T | 1 | 13.128 | −8.340 | 38.325 | 1.00 | 43.19 | T |
| ATOM | 7416 | OH2 | WAT | T | 2 | 9.607 | −8.619 | 44.219 | 1.00 | 27.56 | T |
| ATOM | 7503 | OH2 | WAT | T | 98 | 3.711 | −6.417 | 45.304 | 1.00 | 30.04 | T |
| ATOM | 7507 | OH2 | WAT | T | 102 | −3.417 | −7.320 | 40.850 | 1.00 | 33.06 | T |
| ATOM | 7602 | OH2 | WAT | T | 203 | 14.604 | −1.609 | 23.500 | 1.00 | 40.59 | T |
| ATOM | 7612 | OH2 | WAT | T | 215 | 4.850 | −13.737 | 39.498 | 1.00 | 42.03 | T |
| ATOM | 7613 | OH2 | WAT | T | 216 | 5.093 | −14.055 | 32.065 | 1.00 | 39.20 | T |
| ATOM | 7616 | OH2 | WAT | T | 219 | 11.030 | −2.293 | 26.081 | 1.00 | 37.10 | T |
| ATOM | 7619 | OH2 | WAT | T | 225 | 7.449 | −9.230 | 35.544 | 1.00 | 45.80 | T |
| ATOM | 7620 | OH2 | WAT | T | 226 | 10.479 | −7.325 | 36.925 | 1.00 | 40.53 | T |
| ATOM | 7632 | OH2 | WAT | T | 263 | 16.989 | −4.269 | 24.857 | 1.00 | 37.79 | T |
| ATOM | 7633 | OH2 | WAT | T | 264 | 16.818 | −0.589 | 23.119 | 1.00 | 33.03 | T |
| ATOM | 7634 | OH2 | WAT | T | 265 | 12.877 | −2.966 | 24.468 | 1.00 | 44.25 | T |
| ATOM | 7637 | OH2 | WAT | T | 268 | 15.829 | −10.496 | 25.604 | 1.00 | 39.46 | T |
| ATOM | 7638 | OH2 | WAT | T | 269 | 12.401 | −18.158 | 31.715 | 1.00 | 28.89 | T |
| ATOM | 7669 | OH2 | WAT | T | 341 | 6.084 | −13.571 | 24.399 | 1.00 | 44.58 | T |
| ATOM | 7670 | OH2 | WAT | T | 342 | 12.132 | −14.509 | 26.051 | 1.00 | 36.17 | T |
| ATOM | 7723 | OH2 | WAT | T | 439 | 10.138 | −4.873 | 30.054 | 1.00 | 32.06 | T |

TABLE 2

Three-dimensional coordinate of the complex of human hematopoietic PGDS (SEQ ID NO: 1) with magnesium and glutathione

| ATOM | 4966 | N | TYR | A | 8 | 24.798 | 32.294 | 34.444 | 1.00 | 27.67 | A |
|------|------|------|-----|---|----|--------|--------|--------|------|-------|---|
| ATOM | 4967 | CA | TYR | A | 8 | 23.375 | 32.556 | 34.622 | 1.00 | 27.57 | A |
| ATOM | 4968 | CB | TYR | A | 8 | 22.609 | 31.228 | 34.679 | 1.00 | 26.91 | A |
| ATOM | 4969 | CG | TYR | A | 8 | 21.105 | 31.363 | 34.647 | 1.00 | 26.02 | A |
| ATOM | 4970 | CD1 | TYR | A | 8 | 20.462 | 31.990 | 33.580 | 1.00 | 25.80 | A |
| ATOM | 4971 | CE1 | TYR | A | 8 | 19.075 | 32.097 | 33.536 | 1.00 | 25.34 | A |
| ATOM | 4972 | CD2 | TYR | A | 8 | 20.319 | 30.843 | 35.674 | 1.00 | 25.72 | A |
| ATOM | 4973 | CE2 | TYR | A | 8 | 18.935 | 30.943 | 35.642 | 1.00 | 25.34 | A |
| ATOM | 4974 | CZ | TYR | A | 8 | 18.315 | 31.571 | 34.570 | 1.00 | 25.28 | A |
| ATOM | 4975 | OH | TYR | A | 8 | 16.945 | 31.672 | 34.539 | 1.00 | 24.76 | A |
| ATOM | 4976 | C | TYR | A | 8 | 23.147 | 33.349 | 35.907 | 1.00 | 28.01 | A |
| ATOM | 4977 | O | TYR | A | 8 | 24.086 | 33.591 | 36.667 | 1.00 | 28.14 | A |
| ATOM | 4978 | N | PHE | A | 9 | 21.906 | 33.767 | 36.140 | 1.00 | 28.37 | A |
| ATOM | 4979 | CA | PHE | A | 9 | 21.572 | 34.518 | 37.349 | 1.00 | 28.74 | A |
| ATOM | 4980 | CB | PHE | A | 9 | 20.161 | 35.097 | 37.247 | 1.00 | 28.79 | A |
| ATOM | 4981 | CG | PHE | A | 9 | 20.034 | 36.202 | 36.236 | 1.00 | 29.08 | A |
| ATOM | 4982 | CD1 | PHE | A | 9 | 19.031 | 36.169 | 35.273 | 1.00 | 29.16 | A |
| ATOM | 4983 | CD2 | PHE | A | 9 | 20.917 | 37.276 | 36.250 | 1.00 | 29.06 | A |
| ATOM | 4984 | CE1 | PHE | A | 9 | 18.905 | 37.192 | 34.335 | 1.00 | 29.23 | A |
| ATOM | 4985 | CE2 | PHE | A | 9 | 20.800 | 38.303 | 35.319 | 1.00 | 29.41 | A |
| ATOM | 4986 | CZ | PHE | A | 9 | 19.792 | 38.260 | 34.357 | 1.00 | 29.36 | A |
| ATOM | 4987 | C | PHE | A | 9 | 21.656 | 33.583 | 38.547 | 1.00 | 28.97 | A |
| ATOM | 4988 | O | PHE | A | 9 | 21.790 | 32.369 | 38.385 | 1.00 | 29.03 | A |
| ATOM | 4989 | N | ASN | A | 10 | 21.590 | 34.145 | 39.749 | 1.00 | 29.09 | A |
| ATOM | 4990 | CA | ASN | A | 10 | 21.650 | 33.326 | 40.952 | 1.00 | 29.24 | A |
| ATOM | 4991 | CB | ASN | A | 10 | 22.167 | 34.143 | 42.140 | 1.00 | 29.62 | A |
| ATOM | 4992 | CG | ASN | A | 10 | 22.162 | 33.350 | 43.434 | 1.00 | 30.03 | A |
| ATOM | 4993 | OD1 | ASN | A | 10 | 22.370 | 32.134 | 43.432 | 1.00 | 30.13 | A |
| ATOM | 4994 | ND2 | ASN | A | 10 | 21.936 | 34.037 | 44.548 | 1.00 | 30.35 | A |
| ATOM | 4995 | C | ASN | A | 10 | 20.276 | 32.753 | 41.266 | 1.00 | 29.04 | A |
| ATOM | 4996 | O | ASN | A | 10 | 19.516 | 33.318 | 42.049 | 1.00 | 29.10 | A |
| ATOM | 4997 | N | MET | A | 11 | 19.962 | 31.627 | 40.631 | 1.00 | 28.94 | A |
| ATOM | 4998 | CA | MET | A | 11 | 18.685 | 30.942 | 40.824 | 1.00 | 28.66 | A |
| ATOM | 4999 | CB | MET | A | 11 | 17.514 | 31.854 | 40.429 | 1.00 | 29.86 | A |
| ATOM | 5000 | CG | MET | A | 11 | 17.483 | 32.272 | 38.969 | 1.00 | 31.35 | A |
| ATOM | 5001 | SD | MET | A | 11 | 16.034 | 33.301 | 38.540 | 1.00 | 33.72 | A |
| ATOM | 5002 | CE | MET | A | 11 | 16.695 | 34.947 | 38.769 | 1.00 | 33.16 | A |
| ATOM | 5003 | C | MET | A | 11 | 18.663 | 29.681 | 39.972 | 1.00 | 27.66 | A |
| ATOM | 5004 | O | MET | A | 11 | 19.541 | 29.479 | 39.139 | 1.00 | 27.28 | A |
| ATOM | 5005 | N | ARG | A | 12 | 17.674 | 28.822 | 40.193 | 1.00 | 26.89 | A |
| ATOM | 5006 | CA | ARG | A | 12 | 17.568 | 27.598 | 39.410 | 1.00 | 25.99 | A |
| ATOM | 5007 | CB | ARG | A | 12 | 16.467 | 26.700 | 39.978 | 1.00 | 26.19 | A |
| ATOM | 5008 | CG | ARG | A | 12 | 16.714 | 26.250 | 41.418 | 1.00 | 26.84 | A |
| ATOM | 5009 | CD | ARG | A | 12 | 15.638 | 25.265 | 41.874 | 1.00 | 26.77 | A |
| ATOM | 5010 | NE | ARG | A | 12 | 14.298 | 25.835 | 41.763 | 1.00 | 27.30 | A |
| ATOM | 5011 | CZ | ARG | A | 12 | 13.794 | 26.737 | 42.598 | 1.00 | 27.44 | A |
| ATOM | 5012 | NH1 | ARG | A | 12 | 14.518 | 27.177 | 43.621 | 1.00 | 27.56 | A |
| ATOM | 5013 | NH2 | ARG | A | 12 | 12.570 | 27.209 | 42.404 | 1.00 | 27.81 | A |
| ATOM | 5014 | C | ARG | A | 12 | 17.236 | 28.011 | 37.977 | 1.00 | 25.35 | A |
| ATOM | 5015 | O | ARG | A | 12 | 18.030 | 27.800 | 37.065 | 1.00 | 25.01 | A |
| ATOM | 5016 | N | GLY | A | 13 | 16.062 | 28.607 | 37.797 | 1.00 | 24.64 | A |
| ATOM | 5017 | CA | GLY | A | 13 | 15.645 | 29.067 | 36.485 | 1.00 | 23.90 | A |
| ATOM | 5018 | C | GLY | A | 13 | 15.900 | 28.126 | 35.326 | 1.00 | 23.52 | A |
| ATOM | 5019 | O | GLY | A | 13 | 15.728 | 26.911 | 35.437 | 1.00 | 23.18 | A |
| ATOM | 5020 | N | ARG | A | 14 | 16.333 | 28.696 | 34.205 | 1.00 | 22.72 | A |
| ATOM | 5021 | CA | ARG | A | 14 | 16.592 | 27.920 | 32.998 | 1.00 | 22.38 | A |
| ATOM | 5022 | CB | ARG | A | 14 | 16.417 | 28.824 | 31.781 | 1.00 | 22.47 | A |
| ATOM | 5023 | CG | ARG | A | 14 | 15.004 | 29.342 | 31.659 | 1.00 | 22.96 | A |
| ATOM | 5024 | CD | ARG | A | 14 | 14.807 | 30.214 | 30.443 | 1.00 | 23.81 | A |
| ATOM | 5025 | NE | ARG | A | 14 | 13.386 | 30.325 | 30.135 | 1.00 | 24.80 | A |
| ATOM | 5026 | CZ | ARG | A | 14 | 12.680 | 29.375 | 29.529 | 1.00 | 25.43 | A |
| ATOM | 5027 | NH1 | ARG | A | 14 | 13.267 | 28.245 | 29.154 | 1.00 | 25.67 | A |
| ATOM | 5028 | NH2 | ARG | A | 14 | 11.381 | 29.547 | 29.319 | 1.00 | 26.33 | A |
| ATOM | 5029 | C | ARG | A | 14 | 17.946 | 27.221 | 32.940 | 1.00 | 21.87 | A |
| ATOM | 5030 | O | ARG | A | 14 | 18.206 | 26.450 | 32.021 | 1.00 | 21.54 | A |
| ATOM | 5031 | N | ALA | A | 15 | 18.811 | 27.474 | 33.914 | 1.00 | 21.26 | A |
| ATOM | 5032 | CA | ALA | A | 15 | 20.109 | 26.826 | 33.910 | 1.00 | 20.98 | A |
| ATOM | 5033 | CB | ALA | A | 15 | 21.180 | 27.785 | 34.416 | 1.00 | 21.37 | A |
| ATOM | 5034 | C | ALA | A | 15 | 20.106 | 25.567 | 34.761 | 1.00 | 20.63 | A |
| ATOM | 5035 | O | ALA | A | 15 | 21.055 | 24.785 | 34.724 | 1.00 | 20.56 | A |
| ATOM | 5036 | N | GLU | A | 16 | 19.040 | 25.361 | 35.524 | 1.00 | 20.39 | A |
| ATOM | 5037 | CA | GLU | A | 16 | 18.985 | 24.198 | 36.401 | 1.00 | 20.26 | A |
| ATOM | 5038 | CB | GLU | A | 16 | 17.739 | 24.260 | 37.284 | 1.00 | 20.92 | A |
| ATOM | 5039 | CG | GLU | A | 16 | 17.825 | 23.399 | 38.537 | 1.00 | 21.66 | A |
| ATOM | 5040 | CD | GLU | A | 16 | 19.007 | 23.757 | 39.425 | 1.00 | 22.12 | A |
| ATOM | 5041 | OE1 | GLU | A | 16 | 19.405 | 24.943 | 39.461 | 1.00 | 22.58 | A |

TABLE 2-continued

Three-dimensional coordinate of the complex of human
hematopoietic PGDS (SEQ ID NO: 1) with magnesium and glutathione

| ATOM | 5042 | OE2 | GLU | A | 16 | 19.537 | 22.850 | 40.097 | 1.00 | 22.29 | A |
|------|------|-----|-----|---|----|--------|--------|--------|------|-------|---|
| ATOM | 5043 | C   | GLU | A | 16 | 19.030 | 22.871 | 35.656 | 1.00 | 19.57 | A |
| ATOM | 5044 | O   | GLU | A | 16 | 19.665 | 21.924 | 36.121 | 1.00 | 19.37 | A |
| ATOM | 5045 | N   | ILE | A | 17 | 18.371 | 22.791 | 34.502 | 1.00 | 19.00 | A |
| ATOM | 5046 | CA  | ILE | A | 17 | 18.374 | 21.539 | 33.749 | 1.00 | 18.27 | A |
| ATOM | 5047 | CB  | ILE | A | 17 | 17.459 | 21.621 | 32.483 | 1.00 | 18.13 | A |
| ATOM | 5048 | CG2 | ILE | A | 17 | 17.933 | 22.726 | 31.549 | 1.00 | 17.76 | A |
| ATOM | 5049 | CG1 | ILE | A | 17 | 17.431 | 20.262 | 31.771 | 1.00 | 17.74 | A |
| ATOM | 5050 | CD1 | ILE | A | 17 | 16.815 | 19.144 | 32.603 | 1.00 | 17.40 | A |
| ATOM | 5051 | C   | ILE | A | 17 | 19.795 | 21.141 | 33.354 | 1.00 | 18.40 | A |
| ATOM | 5052 | O   | ILE | A | 17 | 20.135 | 19.956 | 33.327 | 1.00 | 18.19 | A |
| ATOM | 5242 | N   | TRP | A | 39 | 24.784 | 42.507 | 34.947 | 1.00 | 44.42 | A |
| ATOM | 5243 | CA  | TRP | A | 39 | 24.103 | 41.994 | 33.763 | 1.00 | 44.13 | A |
| ATOM | 5244 | CB  | TRP | A | 39 | 22.630 | 41.726 | 34.082 | 1.00 | 44.08 | A |
| ATOM | 5245 | CG  | TRP | A | 39 | 21.834 | 41.243 | 32.905 | 1.00 | 44.04 | A |
| ATOM | 5246 | CD2 | TRP | A | 39 | 22.234 | 40.267 | 31.932 | 1.00 | 43.94 | A |
| ATOM | 5247 | CE2 | TRP | A | 39 | 21.162 | 40.122 | 31.023 | 1.00 | 43.97 | A |
| ATOM | 5248 | CE3 | TRP | A | 39 | 23.391 | 39.500 | 31.741 | 1.00 | 43.89 | A |
| ATOM | 5249 | CD1 | TRP | A | 39 | 20.576 | 41.637 | 32.555 | 1.00 | 44.04 | A |
| ATOM | 5250 | NE1 | TRP | A | 39 | 20.166 | 40.970 | 31.427 | 1.00 | 44.07 | A |
| ATOM | 5251 | CZ2 | TRP | A | 39 | 21.212 | 39.242 | 29.936 | 1.00 | 43.96 | A |
| ATOM | 5252 | CZ3 | TRP | A | 39 | 23.442 | 38.623 | 30.657 | 1.00 | 43.92 | A |
| ATOM | 5253 | CH2 | TRP | A | 39 | 22.356 | 38.503 | 29.770 | 1.00 | 43.91 | A |
| ATOM | 5254 | C   | TRP | A | 39 | 24.202 | 42.927 | 32.553 | 1.00 | 44.00 | A |
| ATOM | 5255 | O   | TRP | A | 39 | 24.614 | 42.507 | 31.472 | 1.00 | 43.93 | A |
| ATOM | 5256 | N   | PRO | A | 40 | 23.828 | 44.207 | 32.720 | 1.00 | 43.84 | A |
| ATOM | 5257 | CD  | PRO | A | 40 | 23.435 | 44.869 | 33.978 | 1.00 | 43.81 | A |
| ATOM | 5258 | CA  | PRO | A | 40 | 23.881 | 45.178 | 31.622 | 1.00 | 43.62 | A |
| ATOM | 5259 | CB  | PRO | A | 40 | 23.764 | 46.516 | 32.347 | 1.00 | 43.72 | A |
| ATOM | 5260 | CG  | PRO | A | 40 | 22.860 | 46.182 | 33.488 | 1.00 | 43.84 | A |
| ATOM | 5261 | C   | PRO | A | 40 | 25.141 | 45.091 | 30.760 | 1.00 | 43.33 | A |
| ATOM | 5262 | O   | PRO | A | 40 | 25.059 | 45.100 | 29.533 | 1.00 | 43.30 | A |
| ATOM | 5263 | N   | GLU | A | 41 | 26.301 | 45.003 | 31.402 | 1.00 | 42.98 | A |
| ATOM | 5264 | CA  | GLU | A | 41 | 27.569 | 44.921 | 30.681 | 1.00 | 42.61 | A |
| ATOM | 5265 | CB  | GLU | A | 41 | 28.741 | 45.127 | 31.647 | 1.00 | 43.08 | A |
| ATOM | 5266 | CG  | GLU | A | 41 | 30.113 | 44.941 | 31.007 | 1.00 | 43.66 | A |
| ATOM | 5267 | CD  | GLU | A | 41 | 30.405 | 45.969 | 29.924 | 1.00 | 44.03 | A |
| ATOM | 5268 | OE1 | GLU | A | 41 | 31.411 | 45.800 | 29.198 | 1.00 | 44.15 | A |
| ATOM | 5269 | OE2 | GLU | A | 41 | 29.633 | 46.946 | 29.804 | 1.00 | 44.31 | A |
| ATOM | 5270 | C   | GLU | A | 41 | 27.742 | 43.593 | 29.953 | 1.00 | 42.03 | A |
| ATOM | 5271 | O   | GLU | A | 41 | 28.054 | 43.560 | 28.761 | 1.00 | 42.06 | A |
| ATOM | 5272 | N   | ILE | A | 42 | 27.541 | 42.501 | 30.681 | 1.00 | 41.22 | A |
| ATOM | 5273 | CA  | ILE | A | 42 | 27.682 | 41.162 | 30.124 | 1.00 | 40.49 | A |
| ATOM | 5274 | CB  | ILE | A | 42 | 27.419 | 40.098 | 31.209 | 1.00 | 40.55 | A |
| ATOM | 5275 | CG2 | ILE | A | 42 | 27.600 | 38.703 | 30.631 | 1.00 | 40.56 | A |
| ATOM | 5276 | CG1 | ILE | A | 42 | 28.376 | 40.319 | 32.382 | 1.00 | 40.56 | A |
| ATOM | 5277 | CD1 | ILE | A | 42 | 28.048 | 39.497 | 33.608 | 1.00 | 40.65 | A |
| ATOM | 5278 | C   | ILE | A | 42 | 26.722 | 40.933 | 28.959 | 1.00 | 39.90 | A |
| ATOM | 5279 | O   | ILE | A | 42 | 27.076 | 40.294 | 27.971 | 1.00 | 39.65 | A |
| ATOM | 5280 | N   | LYS | A | 43 | 25.511 | 41.468 | 29.083 | 1.00 | 39.26 | A |
| ATOM | 5281 | CA  | LYS | A | 43 | 24.485 | 41.321 | 28.055 | 1.00 | 38.70 | A |
| ATOM | 5282 | CB  | LYS | A | 43 | 23.218 | 42.066 | 28.482 | 1.00 | 38.64 | A |
| ATOM | 5283 | CG  | LYS | A | 43 | 22.040 | 41.922 | 27.529 | 1.00 | 38.63 | A |
| ATOM | 5284 | CD  | LYS | A | 43 | 20.862 | 42.769 | 27.995 | 1.00 | 38.51 | A |
| ATOM | 5285 | CE  | LYS | A | 43 | 19.702 | 42.725 | 27.010 | 1.00 | 38.59 | A |
| ATOM | 5286 | NZ  | LYS | A | 43 | 19.088 | 41.374 | 26.908 | 1.00 | 38.47 | A |
| ATOM | 5287 | C   | LYS | A | 43 | 24.941 | 41.821 | 26.682 | 1.00 | 38.32 | A |
| ATOM | 5288 | O   | LYS | A | 43 | 24.657 | 41.195 | 25.656 | 1.00 | 38.07 | A |
| ATOM | 5328 | N   | GLY | A | 49 | 22.169 | 38.393 | 23.696 | 1.00 | 27.72 | A |
| ATOM | 5329 | CA  | GLY | A | 49 | 21.892 | 39.053 | 24.959 | 1.00 | 26.80 | A |
| ATOM | 5330 | C   | GLY | A | 49 | 20.981 | 38.310 | 25.914 | 1.00 | 26.17 | A |
| ATOM | 5331 | O   | GLY | A | 49 | 20.163 | 38.922 | 26.607 | 1.00 | 25.97 | A |
| ATOM | 5332 | N   | LYS | A | 50 | 21.123 | 36.991 | 25.961 | 1.00 | 25.32 | A |
| ATOM | 5333 | CA  | LYS | A | 50 | 20.301 | 36.179 | 26.845 | 1.00 | 24.71 | A |
| ATOM | 5334 | CB  | LYS | A | 50 | 19.164 | 35.522 | 26.052 | 1.00 | 25.17 | A |
| ATOM | 5335 | CG  | LYS | A | 50 | 18.256 | 36.493 | 25.314 | 1.00 | 26.18 | A |
| ATOM | 5336 | CD  | LYS | A | 50 | 17.362 | 37.263 | 26.267 | 1.00 | 26.58 | A |
| ATOM | 5337 | CE  | LYS | A | 50 | 16.619 | 38.387 | 25.552 | 1.00 | 27.00 | A |
| ATOM | 5338 | NZ  | LYS | A | 50 | 15.862 | 37.901 | 24.367 | 1.00 | 27.09 | A |
| ATOM | 5339 | C   | LYS | A | 50 | 21.114 | 35.095 | 27.527 | 1.00 | 24.20 | A |
| ATOM | 5340 | O   | LYS | A | 50 | 22.118 | 34.625 | 26.994 | 1.00 | 23.51 | A |
| ATOM | 5341 | N   | ILE | A | 51 | 20.672 | 34.705 | 28.716 | 1.00 | 23.62 | A |
| ATOM | 5342 | CA  | ILE | A | 51 | 21.329 | 33.642 | 29.462 | 1.00 | 23.69 | A |
| ATOM | 5343 | CB  | ILE | A | 51 | 22.023 | 34.170 | 30.743 | 1.00 | 23.40 | A |
| ATOM | 5344 | CG2 | ILE | A | 51 | 23.331 | 34.852 | 30.373 | 1.00 | 23.31 | A |
| ATOM | 5345 | CG1 | ILE | A | 51 | 21.086 | 35.106 | 31.510 | 1.00 | 23.39 | A |

TABLE 2-continued

Three-dimensional coordinate of the complex of human hematopoietic PGDS (SEQ ID NO: 1) with magnesium and glutathione

| ATOM | 5346 | CD1 | ILE | A | 51 | 21.696 | 35.661 | 32.779 | 1.00 | 23.78 | A |
|---|---|---|---|---|---|---|---|---|---|---|---|
| ATOM | 5347 | C | ILE | A | 51 | 20.270 | 32.609 | 29.822 | 1.00 | 23.77 | A |
| ATOM | 5348 | O | ILE | A | 51 | 19.074 | 32.888 | 29.754 | 1.00 | 23.72 | A |
| ATOM | 5349 | N | PRO | A | 52 | 20.697 | 31.411 | 30.239 | 1.00 | 24.02 | A |
| ATOM | 5350 | CD | PRO | A | 52 | 19.778 | 30.321 | 30.607 | 1.00 | 24.22 | A |
| ATOM | 5351 | CA | PRO | A | 52 | 22.089 | 30.979 | 30.378 | 1.00 | 24.24 | A |
| ATOM | 5352 | CB | PRO | A | 52 | 21.958 | 29.708 | 31.211 | 1.00 | 24.34 | A |
| ATOM | 5353 | CG | PRO | A | 52 | 20.692 | 29.124 | 30.659 | 1.00 | 24.40 | A |
| ATOM | 5354 | C | PRO | A | 52 | 22.843 | 30.711 | 29.082 | 1.00 | 24.32 | A |
| ATOM | 5355 | O | PRO | A | 52 | 22.258 | 30.608 | 27.999 | 1.00 | 24.21 | A |
| ATOM | 5356 | N | ILE | A | 53 | 24.160 | 30.614 | 29.214 | 1.00 | 24.37 | A |
| ATOM | 5357 | CA | ILE | A | 53 | 25.030 | 30.287 | 28.099 | 1.00 | 24.60 | A |
| ATOM | 5358 | CB | ILE | A | 53 | 25.771 | 31.517 | 27.524 | 1.00 | 24.79 | A |
| ATOM | 5359 | CG2 | ILE | A | 53 | 24.772 | 32.471 | 26.876 | 1.00 | 24.74 | A |
| ATOM | 5360 | CG1 | ILE | A | 53 | 26.583 | 32.210 | 28.623 | 1.00 | 24.92 | A |
| ATOM | 5361 | CD1 | ILE | A | 53 | 27.597 | 33.207 | 28.088 | 1.00 | 25.21 | A |
| ATOM | 5362 | C | ILE | A | 53 | 26.051 | 29.318 | 28.659 | 1.00 | 24.74 | A |
| ATOM | 5363 | O | ILE | A | 53 | 26.312 | 29.312 | 29.864 | 1.00 | 24.56 | A |
| ATOM | 5423 | N | HIS | A | 62 | 24.282 | 28.843 | 23.471 | 1.00 | 20.06 | A |
| ATOM | 5424 | CA | HIS | A | 62 | 23.143 | 29.461 | 24.151 | 1.00 | 19.14 | A |
| ATOM | 5425 | CB | HIS | A | 62 | 22.885 | 30.885 | 23.631 | 1.00 | 19.13 | A |
| ATOM | 5426 | CG | HIS | A | 62 | 22.437 | 30.944 | 22.205 | 1.00 | 19.63 | A |
| ATOM | 5427 | CD2 | HIS | A | 62 | 21.300 | 31.421 | 21.646 | 1.00 | 19.62 | A |
| ATOM | 5428 | ND1 | HIS | A | 62 | 23.222 | 30.509 | 21.159 | 1.00 | 20.17 | A |
| ATOM | 5429 | CE1 | HIS | A | 62 | 22.592 | 30.721 | 20.018 | 1.00 | 19.92 | A |
| ATOM | 5430 | NE2 | HIS | A | 62 | 21.423 | 31.275 | 20.285 | 1.00 | 20.10 | A |
| ATOM | 5431 | C | HIS | A | 62 | 21.887 | 28.607 | 24.010 | 1.00 | 18.09 | A |
| ATOM | 5432 | O | HIS | A | 62 | 21.914 | 27.591 | 23.321 | 1.00 | 17.56 | A |
| ATOM | 5433 | N | GLN | A | 63 | 20.804 | 29.046 | 24.659 | 1.00 | 17.49 | A |
| ATOM | 5434 | CA | GLN | A | 63 | 19.512 | 28.342 | 24.693 | 1.00 | 16.80 | A |
| ATOM | 5435 | CB | GLN | A | 63 | 19.042 | 27.971 | 23.285 | 1.00 | 17.09 | A |
| ATOM | 5436 | CG | GLN | A | 63 | 18.397 | 29.137 | 22.515 | 1.00 | 17.33 | A |
| ATOM | 5437 | CD | GLN | A | 63 | 17.113 | 29.658 | 23.165 | 1.00 | 17.51 | A |
| ATOM | 5438 | OE1 | GLN | A | 63 | 16.514 | 28.993 | 24.013 | 1.00 | 17.71 | A |
| ATOM | 5439 | NE2 | GLN | A | 63 | 16.676 | 30.846 | 22.750 | 1.00 | 18.20 | A |
| ATOM | 5440 | C | GLN | A | 63 | 19.621 | 27.095 | 25.575 | 1.00 | 16.48 | A |
| ATOM | 5441 | O | GLN | A | 63 | 20.248 | 26.098 | 25.202 | 1.00 | 15.97 | A |
| ATOM | 5442 | N | SER | A | 64 | 18.983 | 27.166 | 26.740 | 1.00 | 16.15 | A |
| ATOM | 5443 | CA | SER | A | 64 | 19.038 | 26.099 | 27.733 | 1.00 | 16.55 | A |
| ATOM | 5444 | CB | SER | A | 64 | 18.163 | 26.463 | 28.948 | 1.00 | 16.41 | A |
| ATOM | 5445 | OG | SER | A | 64 | 16.780 | 26.507 | 28.637 | 1.00 | 17.25 | A |
| ATOM | 5446 | C | SER | A | 64 | 18.705 | 24.688 | 27.258 | 1.00 | 16.42 | A |
| ATOM | 5447 | O | SER | A | 64 | 19.395 | 23.736 | 27.625 | 1.00 | 16.29 | A |
| ATOM | 5448 | N | LEU | A | 65 | 17.661 | 24.545 | 26.449 | 1.00 | 16.61 | A |
| ATOM | 5449 | CA | LEU | A | 65 | 17.266 | 23.221 | 25.979 | 1.00 | 16.62 | A |
| ATOM | 5450 | CB | LEU | A | 65 | 15.803 | 23.242 | 25.518 | 1.00 | 17.28 | A |
| ATOM | 5451 | CG | LEU | A | 65 | 14.804 | 23.694 | 26.599 | 1.00 | 17.94 | A |
| ATOM | 5452 | CD1 | LEU | A | 65 | 13.381 | 23.514 | 26.100 | 1.00 | 18.29 | A |
| ATOM | 5453 | CD2 | LEU | A | 65 | 15.023 | 22.904 | 27.884 | 1.00 | 18.01 | A |
| ATOM | 5454 | C | LEU | A | 65 | 18.183 | 22.699 | 24.874 | 1.00 | 16.53 | A |
| ATOM | 5455 | O | LEU | A | 65 | 18.384 | 21.484 | 24.739 | 1.00 | 16.69 | A |
| ATOM | 5662 | N | ASP | A | 93 | 9.437 | 20.470 | 25.569 | 1.00 | 14.02 | A |
| ATOM | 5663 | CA | ASP | A | 93 | 8.852 | 21.675 | 24.974 | 1.00 | 15.28 | A |
| ATOM | 5664 | CB | ASP | A | 93 | 8.823 | 21.563 | 23.440 | 1.00 | 16.56 | A |
| ATOM | 5665 | CG | ASP | A | 93 | 10.139 | 22.002 | 22.800 | 1.00 | 18.16 | A |
| ATOM | 5666 | OD1 | ASP | A | 93 | 10.212 | 22.113 | 21.549 | 1.00 | 19.71 | A |
| ATOM | 5667 | OD2 | ASP | A | 93 | 11.116 | 22.243 | 23.549 | 1.00 | 19.34 | A |
| ATOM | 5668 | C | ASP | A | 93 | 7.457 | 22.002 | 25.521 | 1.00 | 15.10 | A |
| ATOM | 5669 | O | ASP | A | 93 | 7.103 | 23.178 | 25.671 | 1.00 | 15.47 | A |
| ATOM | 5670 | N | THR | A | 94 | 6.662 | 20.973 | 25.813 | 1.00 | 14.79 | A |
| ATOM | 5671 | CA | THR | A | 94 | 5.327 | 21.184 | 26.365 | 1.00 | 14.62 | A |
| ATOM | 5672 | CB | THR | A | 94 | 4.568 | 19.838 | 26.465 | 1.00 | 14.82 | A |
| ATOM | 5673 | OG1 | THR | A | 94 | 4.196 | 19.423 | 25.140 | 1.00 | 14.81 | A |
| ATOM | 5674 | CG2 | THR | A | 94 | 3.298 | 19.969 | 27.309 | 1.00 | 15.03 | A |
| ATOM | 5675 | C | THR | A | 94 | 5.475 | 21.860 | 27.736 | 1.00 | 15.22 | A |
| ATOM | 5676 | O | THR | A | 94 | 4.758 | 22.805 | 28.051 | 1.00 | 14.83 | A |
| ATOM | 5677 | N | LEU | A | 95 | 6.424 | 21.390 | 28.533 | 1.00 | 15.45 | A |
| ATOM | 5678 | CA | LEU | A | 95 | 6.664 | 21.978 | 29.846 | 1.00 | 16.14 | A |
| ATOM | 5679 | CB | LEU | A | 95 | 7.663 | 21.130 | 30.630 | 1.00 | 16.28 | A |
| ATOM | 5680 | CG | LEU | A | 95 | 7.107 | 19.798 | 31.120 | 1.00 | 16.61 | A |
| ATOM | 5681 | CD1 | LEU | A | 95 | 8.245 | 18.898 | 31.594 | 1.00 | 16.85 | A |
| ATOM | 5682 | CD2 | LEU | A | 95 | 6.103 | 20.052 | 32.240 | 1.00 | 17.08 | A |
| ATOM | 5683 | C | LEU | A | 95 | 7.215 | 23.388 | 29.693 | 1.00 | 16.49 | A |
| ATOM | 5684 | O | LEU | A | 95 | 6.745 | 24.327 | 30.344 | 1.00 | 16.45 | A |
| ATOM | 5685 | N | ASP | A | 96 | 8.208 | 23.540 | 28.823 | 1.00 | 16.67 | A |
| ATOM | 5686 | CA | ASP | A | 96 | 8.824 | 24.850 | 28.621 | 1.00 | 17.83 | A |

TABLE 2-continued

Three-dimensional coordinate of the complex of human
hematopoietic PGDS (SEQ ID NO: 1) with magnesium and glutathione

| ATOM | 5687 | CB  | ASP | A | 96  | 10.001 | 24.736 | 27.646 | 1.00 | 18.40 | A |
|------|------|-----|-----|---|-----|--------|--------|--------|------|-------|---|
| ATOM | 5688 | CG  | ASP | A | 96  | 11.004 | 25.860 | 27.815 | 1.00 | 19.35 | A |
| ATOM | 5689 | OD1 | ASP | A | 96  | 11.519 | 26.027 | 28.946 | 1.00 | 20.31 | A |
| ATOM | 5690 | OD2 | ASP | A | 96  | 11.278 | 26.572 | 26.827 | 1.00 | 19.91 | A |
| ATOM | 5691 | C   | ASP | A | 96  | 7.817  | 25.883 | 28.119 | 1.00 | 18.10 | A |
| ATOM | 5692 | O   | ASP | A | 96  | 7.850  | 27.046 | 28.536 | 1.00 | 17.78 | A |
| ATOM | 5693 | N   | ASP | A | 97  | 6.918  | 25.464 | 27.230 | 1.00 | 18.27 | A |
| ATOM | 5694 | CA  | ASP | A | 97  | 5.902  | 26.376 | 26.700 | 1.00 | 18.83 | A |
| ATOM | 5695 | CB  | ASP | A | 97  | 4.957  | 25.644 | 25.741 | 1.00 | 19.25 | A |
| ATOM | 5696 | CG  | ASP | A | 97  | 5.582  | 25.365 | 24.386 | 1.00 | 20.04 | A |
| ATOM | 5697 | OD1 | ASP | A | 97  | 4.980  | 24.595 | 23.611 | 1.00 | 20.50 | A |
| ATOM | 5698 | OD2 | ASP | A | 97  | 6.660  | 25.914 | 24.085 | 1.00 | 20.61 | A |
| ATOM | 5699 | C   | ASP | A | 97  | 5.070  | 26.968 | 27.835 | 1.00 | 18.89 | A |
| ATOM | 5700 | O   | ASP | A | 97  | 4.828  | 28.175 | 27.878 | 1.00 | 18.39 | A |
| ATOM | 5701 | N   | PHE | A | 98  | 4.630  | 26.107 | 28.750 | 1.00 | 19.13 | A |
| ATOM | 5702 | CA  | PHE | A | 98  | 3.814  | 26.547 | 29.875 | 1.00 | 19.65 | A |
| ATOM | 5703 | CB  | PHE | A | 98  | 3.311  | 25.342 | 30.686 | 1.00 | 20.03 | A |
| ATOM | 5704 | CG  | PHE | A | 98  | 2.426  | 25.718 | 31.854 | 1.00 | 20.47 | A |
| ATOM | 5705 | CD1 | PHE | A | 98  | 1.249  | 26.436 | 31.650 | 1.00 | 20.90 | A |
| ATOM | 5706 | CD2 | PHE | A | 98  | 2.794  | 25.390 | 33.159 | 1.00 | 20.78 | A |
| ATOM | 5707 | CE1 | PHE | A | 98  | 0.451  | 26.827 | 32.732 | 1.00 | 21.07 | A |
| ATOM | 5708 | CE2 | PHE | A | 98  | 2.007  | 25.773 | 34.246 | 1.00 | 21.32 | A |
| ATOM | 5709 | CZ  | PHE | A | 98  | 0.837  | 26.495 | 34.035 | 1.00 | 21.00 | A |
| ATOM | 5710 | C   | PHE | A | 98  | 4.598  | 27.495 | 30.776 | 1.00 | 20.02 | A |
| ATOM | 5711 | O   | PHE | A | 98  | 4.125  | 28.583 | 31.089 | 1.00 | 20.09 | A |
| ATOM | 5712 | N   | MET | A | 99  | 5.793  | 27.090 | 31.195 | 1.00 | 20.31 | A |
| ATOM | 5713 | CA  | MET | A | 99  | 6.607  | 27.937 | 32.064 | 1.00 | 21.46 | A |
| ATOM | 5714 | CB  | MET | A | 99  | 7.934  | 27.249 | 32.397 | 1.00 | 21.92 | A |
| ATOM | 5715 | CG  | MET | A | 99  | 7.805  | 25.906 | 33.110 | 1.00 | 22.64 | A |
| ATOM | 5716 | SD  | MET | A | 99  | 6.818  | 25.981 | 34.620 | 1.00 | 23.36 | A |
| ATOM | 5717 | CE  | MET | A | 99  | 7.919  | 26.938 | 35.719 | 1.00 | 23.75 | A |
| ATOM | 5718 | C   | MET | A | 99  | 6.885  | 29.294 | 31.416 | 1.00 | 21.88 | A |
| ATOM | 5719 | O   | MET | A | 99  | 6.921  | 30.321 | 32.101 | 1.00 | 21.92 | A |
| ATOM | 5720 | N   | SER | A | 100 | 7.068  | 29.297 | 30.097 | 1.00 | 22.34 | A |
| ATOM | 5721 | CA  | SER | A | 100 | 7.356  | 30.530 | 29.359 | 1.00 | 23.09 | A |
| ATOM | 5722 | CB  | SER | A | 100 | 7.848  | 30.196 | 27.946 | 1.00 | 22.97 | A |
| ATOM | 5723 | OG  | SER | A | 100 | 9.105  | 29.535 | 27.992 | 1.00 | 22.88 | A |
| ATOM | 5724 | C   | SER | A | 100 | 6.169  | 31.486 | 29.280 | 1.00 | 23.87 | A |
| ATOM | 5725 | O   | SER | A | 100 | 6.337  | 32.665 | 28.953 | 1.00 | 23.83 | A |
| ATOM | 5726 | N   | CYS | A | 101 | 4.973  | 30.980 | 29.569 | 1.00 | 24.59 | A |
| ATOM | 5727 | CA  | CYS | A | 101 | 3.769  | 31.812 | 29.551 | 1.00 | 25.73 | A |
| ATOM | 5728 | CB  | CYS | A | 101 | 2.504  | 30.950 | 29.642 | 1.00 | 26.18 | A |
| ATOM | 5729 | SG  | CYS | A | 101 | 2.072  | 30.045 | 28.134 | 1.00 | 27.14 | A |
| ATOM | 5730 | C   | CYS | A | 101 | 3.764  | 32.802 | 30.711 | 1.00 | 26.07 | A |
| ATOM | 5731 | O   | CYS | A | 101 | 3.164  | 33.869 | 30.611 | 1.00 | 26.17 | A |
| ATOM | 5732 | N   | PHE | A | 102 | 4.424  | 32.452 | 31.814 | 1.00 | 26.61 | A |
| ATOM | 5733 | CA  | PHE | A | 102 | 4.448  | 33.344 | 32.969 | 1.00 | 27.42 | A |
| ATOM | 5734 | CB  | PHE | A | 102 | 4.968  | 32.621 | 34.218 | 1.00 | 27.19 | A |
| ATOM | 5735 | CG  | PHE | A | 102 | 4.090  | 31.491 | 34.683 | 1.00 | 26.99 | A |
| ATOM | 5736 | CD1 | PHE | A | 102 | 4.118  | 30.261 | 34.035 | 1.00 | 26.96 | A |
| ATOM | 5737 | CD2 | PHE | A | 102 | 3.232  | 31.657 | 35.769 | 1.00 | 27.14 | A |
| ATOM | 5738 | CE1 | PHE | A | 102 | 3.308  | 29.205 | 34.459 | 1.00 | 27.01 | A |
| ATOM | 5739 | CE2 | PHE | A | 102 | 2.418  | 30.609 | 36.202 | 1.00 | 26.99 | A |
| ATOM | 5740 | CZ  | PHE | A | 102 | 2.456  | 29.378 | 35.542 | 1.00 | 27.14 | A |
| ATOM | 5741 | C   | PHE | A | 102 | 5.298  | 34.587 | 32.719 | 1.00 | 27.95 | A |
| ATOM | 5742 | O   | PHE | A | 102 | 6.423  | 34.495 | 32.237 | 1.00 | 27.67 | A |
| ATOM | 5743 | N   | PRO | A | 103 | 4.761  | 35.774 | 33.045 | 1.00 | 28.91 | A |
| ATOM | 5744 | CD  | PRO | A | 103 | 3.381  | 36.039 | 33.496 | 1.00 | 29.00 | A |
| ATOM | 5745 | CA  | PRO | A | 103 | 5.496  | 37.027 | 32.845 | 1.00 | 29.76 | A |
| ATOM | 5746 | CB  | PRO | A | 103 | 4.381  | 38.061 | 32.792 | 1.00 | 29.51 | A |
| ATOM | 5747 | CG  | PRO | A | 103 | 3.410  | 37.534 | 33.798 | 1.00 | 29.21 | A |
| ATOM | 5748 | C   | PRO | A | 103 | 6.470  | 37.276 | 33.995 | 1.00 | 30.76 | A |
| ATOM | 5749 | O   | PRO | A | 103 | 6.244  | 38.155 | 34.828 | 1.00 | 30.85 | A |
| ATOM | 5750 | N   | TRP | A | 104 | 7.555  | 36.508 | 34.027 | 1.00 | 31.83 | A |
| ATOM | 5751 | CA  | TRP | A | 104 | 8.551  | 36.628 | 35.089 | 1.00 | 33.11 | A |
| ATOM | 5752 | CB  | TRP | A | 104 | 9.647  | 35.572 | 34.917 | 1.00 | 32.91 | A |
| ATOM | 5753 | CG  | TRP | A | 104 | 9.124  | 34.178 | 34.737 | 1.00 | 32.96 | A |
| ATOM | 5754 | CD2 | TRP | A | 104 | 8.713  | 33.275 | 35.772 | 1.00 | 32.96 | A |
| ATOM | 5755 | CE2 | TRP | A | 104 | 8.269  | 32.092 | 35.141 | 1.00 | 33.00 | A |
| ATOM | 5756 | CE3 | TRP | A | 104 | 8.677  | 33.351 | 37.174 | 1.00 | 33.00 | A |
| ATOM | 5757 | CD1 | TRP | A | 104 | 8.918  | 33.525 | 33.555 | 1.00 | 32.88 | A |
| ATOM | 5758 | NE1 | TRP | A | 104 | 8.405  | 32.271 | 33.789 | 1.00 | 32.93 | A |
| ATOM | 5759 | CZ2 | TRP | A | 104 | 7.792  | 30.992 | 35.862 | 1.00 | 33.01 | A |
| ATOM | 5760 | CZ3 | TRP | A | 104 | 8.201  | 32.255 | 37.890 | 1.00 | 33.07 | A |
| ATOM | 5761 | CH2 | TRP | A | 104 | 7.766  | 31.093 | 37.231 | 1.00 | 32.98 | A |
| ATOM | 5762 | C   | TRP | A | 104 | 9.205  | 38.003 | 35.194 | 1.00 | 34.03 | A |

TABLE 2-continued

Three-dimensional coordinate of the complex of human hematopoietic PGDS (SEQ ID NO: 1) with magnesium and glutathione

| ATOM | 5763 | O | TRP | A | 104 | 9.515 | 38.460 | 36.291 | 1.00 | 34.18 | A |
|---|---|---|---|---|---|---|---|---|---|---|---|
| ATOM | 5764 | N | ALA | A | 105 | 9.414 | 38.657 | 34.055 | 1.00 | 35.15 | A |
| ATOM | 5765 | CA | ALA | A | 105 | 10.052 | 39.972 | 34.038 | 1.00 | 36.46 | A |
| ATOM | 5766 | CB | ALA | A | 105 | 10.943 | 40.095 | 32.804 | 1.00 | 36.36 | A |
| ATOM | 5767 | C | ALA | A | 105 | 9.054 | 41.128 | 34.075 | 1.00 | 37.41 | A |
| ATOM | 5768 | O | ALA | A | 105 | 9.450 | 42.294 | 34.080 | 1.00 | 37.56 | A |
| ATOM | 5769 | N | GLU | A | 106 | 7.765 | 40.806 | 34.101 | 1.00 | 38.52 | A |
| ATOM | 5770 | CA | GLU | A | 106 | 6.723 | 41.828 | 34.133 | 1.00 | 39.67 | A |
| ATOM | 5771 | CB | GLU | A | 106 | 5.344 | 41.166 | 34.069 | 1.00 | 39.95 | A |
| ATOM | 5772 | CG | GLU | A | 106 | 4.165 | 42.130 | 34.045 | 1.00 | 40.21 | A |
| ATOM | 5773 | CD | GLU | A | 106 | 4.304 | 43.209 | 32.989 | 1.00 | 40.48 | A |
| ATOM | 5774 | OE1 | GLU | A | 106 | 4.932 | 44.251 | 33.276 | 1.00 | 40.68 | A |
| ATOM | 5775 | OE2 | GLU | A | 106 | 3.796 | 43.014 | 31.864 | 1.00 | 40.58 | A |
| ATOM | 5776 | C | GLU | A | 106 | 6.819 | 42.701 | 35.381 | 1.00 | 40.42 | A |
| ATOM | 5777 | O | GLU | A | 106 | 6.609 | 42.231 | 36.500 | 1.00 | 40.56 | A |
| ATOM | 5778 | N | LYS | A | 107 | 7.136 | 43.978 | 35.189 | 1.00 | 41.30 | A |
| ATOM | 5779 | CA | LYS | A | 107 | 7.250 | 44.895 | 36.315 | 1.00 | 42.22 | A |
| ATOM | 5780 | CB | LYS | A | 107 | 8.092 | 46.110 | 35.927 | 1.00 | 42.33 | A |
| ATOM | 5781 | CG | LYS | A | 107 | 9.587 | 45.866 | 36.016 | 1.00 | 42.56 | A |
| ATOM | 5782 | CD | LYS | A | 107 | 10.000 | 45.596 | 37.457 | 1.00 | 42.79 | A |
| ATOM | 5783 | CE | LYS | A | 107 | 11.501 | 45.396 | 37.583 | 1.00 | 42.86 | A |
| ATOM | 5784 | NZ | LYS | A | 107 | 12.264 | 46.598 | 37.132 | 1.00 | 43.08 | A |
| ATOM | 5785 | C | LYS | A | 107 | 5.890 | 45.343 | 36.831 | 1.00 | 42.73 | A |
| ATOM | 5786 | O | LYS | A | 107 | 5.719 | 45.571 | 38.030 | 1.00 | 42.99 | A |
| ATOM | 5787 | N | LYS | A | 108 | 4.925 | 45.465 | 35.927 | 1.00 | 43.26 | A |
| ATOM | 5788 | CA | LYS | A | 108 | 3.575 | 45.875 | 36.299 | 1.00 | 43.78 | A |
| ATOM | 5789 | CB | LYS | A | 108 | 2.734 | 46.106 | 35.041 | 1.00 | 43.97 | A |
| ATOM | 5790 | CG | LYS | A | 108 | 3.322 | 47.146 | 34.099 | 1.00 | 44.32 | A |
| ATOM | 5791 | CD | LYS | A | 108 | 2.459 | 47.357 | 32.862 | 1.00 | 44.57 | A |
| ATOM | 5792 | CE | LYS | A | 108 | 2.469 | 46.142 | 31.950 | 1.00 | 44.80 | A |
| ATOM | 5793 | NZ | LYS | A | 108 | 1.672 | 46.386 | 30.716 | 1.00 | 45.09 | A |
| ATOM | 5794 | C | LYS | A | 108 | 2.937 | 44.793 | 37.169 | 1.00 | 44.07 | A |
| ATOM | 5795 | O | LYS | A | 108 | 2.342 | 43.841 | 36.662 | 1.00 | 44.03 | A |
| ATOM | 5796 | N | GLN | A | 109 | 3.069 | 44.954 | 38.483 | 1.00 | 44.42 | A |
| ATOM | 5797 | CA | GLN | A | 109 | 2.535 | 44.001 | 39.453 | 1.00 | 44.80 | A |
| ATOM | 5798 | CB | GLN | A | 109 | 2.686 | 44.569 | 40.870 | 1.00 | 45.10 | A |
| ATOM | 5799 | CG | GLN | A | 109 | 2.511 | 43.547 | 41.989 | 1.00 | 45.66 | A |
| ATOM | 5800 | CD | GLN | A | 109 | 3.703 | 42.612 | 42.129 | 1.00 | 45.85 | A |
| ATOM | 5801 | OE1 | GLN | A | 109 | 3.740 | 41.763 | 43.022 | 1.00 | 46.01 | A |
| ATOM | 5802 | NE2 | GLN | A | 109 | 4.688 | 42.767 | 41.247 | 1.00 | 46.00 | A |
| ATOM | 5803 | C | GLN | A | 109 | 1.070 | 43.648 | 39.197 | 1.00 | 44.83 | A |
| ATOM | 5804 | O | GLN | A | 109 | 0.675 | 42.484 | 39.288 | 1.00 | 44.88 | A |
| ATOM | 5805 | N | ASP | A | 110 | 0.267 | 44.656 | 38.876 | 1.00 | 44.78 | A |
| ATOM | 5806 | CA | ASP | A | 110 | −1.153 | 44.451 | 38.616 | 1.00 | 44.83 | A |
| ATOM | 5807 | CB | ASP | A | 110 | −1.816 | 45.784 | 38.257 | 1.00 | 45.28 | A |
| ATOM | 5808 | CG | ASP | A | 110 | −1.243 | 46.399 | 36.992 | 1.00 | 45.63 | A |
| ATOM | 5809 | OD1 | ASP | A | 110 | −0.023 | 46.675 | 36.958 | 1.00 | 45.86 | A |
| ATOM | 5810 | OD2 | ASP | A | 110 | −2.016 | 46.605 | 36.030 | 1.00 | 46.00 | A |
| ATOM | 5811 | C | ASP | A | 110 | −1.399 | 43.437 | 37.496 | 1.00 | 44.67 | A |
| ATOM | 5812 | O | ASP | A | 110 | −2.296 | 42.600 | 37.590 | 1.00 | 44.60 | A |
| ATOM | 5813 | N | VAL | A | 111 | −0.597 | 43.519 | 36.439 | 1.00 | 44.34 | A |
| ATOM | 5814 | CA | VAL | A | 111 | −0.730 | 42.621 | 35.298 | 1.00 | 44.07 | A |
| ATOM | 5815 | CB | VAL | A | 111 | −0.112 | 43.254 | 34.031 | 1.00 | 44.24 | A |
| ATOM | 5816 | CG1 | VAL | A | 111 | −0.338 | 42.352 | 32.828 | 1.00 | 44.21 | A |
| ATOM | 5817 | CG2 | VAL | A | 111 | −0.718 | 44.628 | 33.794 | 1.00 | 44.30 | A |
| ATOM | 5818 | C | VAL | A | 111 | −0.058 | 41.273 | 35.556 | 1.00 | 43.75 | A |
| ATOM | 5819 | O | VAL | A | 111 | −0.571 | 40.229 | 35.157 | 1.00 | 43.61 | A |
| ATOM | 5820 | N | LYS | A | 112 | 1.088 | 41.305 | 36.227 | 1.00 | 43.49 | A |
| ATOM | 5821 | CA | LYS | A | 112 | 1.834 | 40.093 | 36.534 | 1.00 | 43.29 | A |
| ATOM | 5822 | CB | LYS | A | 112 | 3.161 | 40.452 | 37.207 | 1.00 | 43.21 | A |
| ATOM | 5823 | CG | LYS | A | 112 | 4.040 | 39.255 | 37.531 | 1.00 | 43.24 | A |
| ATOM | 5824 | CD | LYS | A | 112 | 5.354 | 39.686 | 38.160 | 1.00 | 43.22 | A |
| ATOM | 5825 | CE | LYS | A | 112 | 6.284 | 38.499 | 38.369 | 1.00 | 43.30 | A |
| ATOM | 5826 | NZ | LYS | A | 112 | 7.585 | 38.911 | 38.962 | 1.00 | 43.09 | A |
| ATOM | 5827 | C | LYS | A | 112 | 1.036 | 39.159 | 37.440 | 1.00 | 43.21 | A |
| ATOM | 5828 | O | LYS | A | 112 | 0.865 | 37.976 | 37.136 | 1.00 | 43.01 | A |
| ATOM | 5829 | N | GLU | A | 113 | 0.547 | 39.703 | 38.551 | 1.00 | 43.11 | A |
| ATOM | 5830 | CA | GLU | A | 113 | −0.230 | 38.935 | 39.521 | 1.00 | 42.91 | A |
| ATOM | 5831 | CB | GLU | A | 113 | −0.676 | 39.849 | 40.670 | 1.00 | 43.22 | A |
| ATOM | 5832 | CG | GLU | A | 113 | −1.401 | 39.138 | 41.808 | 1.00 | 43.46 | A |
| ATOM | 5833 | CD | GLU | A | 113 | −0.473 | 38.290 | 42.660 | 1.00 | 43.66 | A |
| ATOM | 5834 | OE1 | GLU | A | 113 | −0.951 | 37.683 | 43.644 | 1.00 | 43.73 | A |
| ATOM | 5835 | OE2 | GLU | A | 113 | 0.738 | 38.232 | 42.348 | 1.00 | 43.75 | A |
| ATOM | 5836 | C | GLU | A | 113 | −1.460 | 38.288 | 38.884 | 1.00 | 42.68 | A |
| ATOM | 5837 | O | GLU | A | 113 | −1.799 | 37.142 | 39.187 | 1.00 | 42.56 | A |
| ATOM | 5838 | N | GLN | A | 114 | −2.121 | 39.031 | 38.002 | 1.00 | 42.28 | A |

TABLE 2-continued

Three-dimensional coordinate of the complex of human
hematopoietic PGDS (SEQ ID NO: 1) with magnesium and glutathione

| ATOM | 5839 | CA   | GLN | A | 114 | −3.323  | 38.552 | 37.326 | 1.00 | 41.94 | A |
|------|------|------|-----|---|-----|---------|--------|--------|------|-------|---|
| ATOM | 5840 | CB   | GLN | A | 114 | −3.979  | 39.712 | 36.568 | 1.00 | 42.26 | A |
| ATOM | 5841 | CG   | GLN | A | 114 | −5.404  | 39.462 | 36.083 | 1.00 | 42.72 | A |
| ATOM | 5842 | CD   | GLN | A | 114 | −5.470  | 38.624 | 34.821 | 1.00 | 42.97 | A |
| ATOM | 5843 | OE1  | GLN | A | 114 | −4.796  | 38.918 | 33.830 | 1.00 | 43.14 | A |
| ATOM | 5844 | NE2  | GLN | A | 114 | −6.302  | 37.584 | 34.841 | 1.00 | 43.11 | A |
| ATOM | 5845 | C    | GLN | A | 114 | −3.030  | 37.396 | 36.372 | 1.00 | 41.52 | A |
| ATOM | 5846 | O    | GLN | A | 114 | −3.796  | 36.435 | 36.294 | 1.00 | 41.60 | A |
| ATOM | 5847 | N    | MET | A | 115 | −1.919  | 37.488 | 35.648 | 1.00 | 40.93 | A |
| ATOM | 5848 | CA   | MET | A | 115 | −1.549  | 36.439 | 34.706 | 1.00 | 40.35 | A |
| ATOM | 5849 | CB   | MET | A | 115 | −0.437  | 36.930 | 33.774 | 1.00 | 40.74 | A |
| ATOM | 5850 | CG   | MET | A | 115 | −0.045  | 35.930 | 32.692 | 1.00 | 41.32 | A |
| ATOM | 5851 | SD   | MET | A | 115 | −1.436  | 35.356 | 31.684 | 1.00 | 42.13 | A |
| ATOM | 5852 | CE   | MET | A | 115 | −1.186  | 36.293 | 30.162 | 1.00 | 42.02 | A |
| ATOM | 5853 | C    | MET | A | 115 | −1.105  | 35.168 | 35.436 | 1.00 | 39.61 | A |
| ATOM | 5854 | O    | MET | A | 115 | −1.398  | 34.059 | 34.990 | 1.00 | 39.35 | A |
| ATOM | 5855 | N    | PHE | A | 116 | −0.405  | 35.332 | 36.556 | 1.00 | 38.88 | A |
| ATOM | 5856 | CA   | PHE | A | 116 | 0.056   | 34.188 | 37.335 | 1.00 | 38.26 | A |
| ATOM | 5857 | CB   | PHE | A | 116 | 0.942   | 34.638 | 38.501 | 1.00 | 38.13 | A |
| ATOM | 5858 | CG   | PHE | A | 116 | 2.406   | 34.690 | 38.170 | 1.00 | 37.93 | A |
| ATOM | 5859 | CD1  | PHE | A | 116 | 2.893   | 35.593 | 37.232 | 1.00 | 37.95 | A |
| ATOM | 5860 | CD2  | PHE | A | 116 | 3.304   | 33.838 | 38.808 | 1.00 | 37.87 | A |
| ATOM | 5861 | CE1  | PHE | A | 116 | 4.254   | 35.646 | 36.930 | 1.00 | 37.97 | A |
| ATOM | 5862 | CE2  | PHE | A | 116 | 4.665   | 33.882 | 38.514 | 1.00 | 37.79 | A |
| ATOM | 5863 | CZ   | PHE | A | 116 | 5.141   | 34.789 | 37.575 | 1.00 | 37.96 | A |
| ATOM | 5864 | C    | PHE | A | 116 | −1.114  | 33.385 | 37.886 | 1.00 | 38.04 | A |
| ATOM | 5865 | O    | PHE | A | 116 | −1.147  | 32.161 | 37.769 | 1.00 | 37.81 | A |
| ATOM | 6152 | N    | TYR | A | 152 | 13.539  | 17.574 | 33.797 | 1.00 | 16.38 | A |
| ATOM | 6153 | CA   | TYR | A | 152 | 12.825  | 18.812 | 33.538 | 1.00 | 16.80 | A |
| ATOM | 6154 | CB   | TYR | A | 152 | 12.658  | 19.044 | 32.028 | 1.00 | 17.06 | A |
| ATOM | 6155 | CG   | TYR | A | 152 | 12.623  | 20.514 | 31.669 | 1.00 | 17.96 | A |
| ATOM | 6156 | CD1  | TYR | A | 152 | 13.677  | 21.359 | 32.026 | 1.00 | 18.34 | A |
| ATOM | 6157 | CE1  | TYR | A | 152 | 13.642  | 22.720 | 31.737 | 1.00 | 19.38 | A |
| ATOM | 6158 | CD2  | TYR | A | 152 | 11.530  | 21.074 | 31.003 | 1.00 | 17.98 | A |
| ATOM | 6159 | CE2  | TYR | A | 152 | 11.491  | 22.442 | 30.706 | 1.00 | 19.01 | A |
| ATOM | 6160 | CZ   | TYR | A | 152 | 12.548  | 23.256 | 31.077 | 1.00 | 19.24 | A |
| ATOM | 6161 | OH   | TYR | A | 152 | 12.517  | 24.604 | 30.789 | 1.00 | 20.15 | A |
| ATOM | 6162 | C    | TYR | A | 152 | 11.470  | 18.861 | 34.239 | 1.00 | 16.67 | A |
| ATOM | 6163 | O    | TYR | A | 152 | 11.031  | 19.932 | 34.652 | 1.00 | 16.60 | A |
| ATOM | 6164 | N    | TRP | A | 153 | 10.804  | 17.713 | 34.379 | 1.00 | 16.52 | A |
| ATOM | 6165 | CA   | TRP | A | 153 | 9.518   | 17.691 | 35.071 | 1.00 | 16.67 | A |
| ATOM | 6166 | CB   | TRP | A | 153 | 8.870   | 16.299 | 35.002 | 1.00 | 16.89 | A |
| ATOM | 6167 | CG   | TRP | A | 153 | 7.851   | 16.082 | 36.080 | 1.00 | 17.11 | A |
| ATOM | 6168 | CD2  | TRP | A | 153 | 6.691   | 16.883 | 36.345 | 1.00 | 17.34 | A |
| ATOM | 6169 | CE2  | TRP | A | 153 | 6.067   | 16.349 | 37.496 | 1.00 | 17.61 | A |
| ATOM | 6170 | CE3  | TRP | A | 153 | 6.122   | 18.001 | 35.726 | 1.00 | 17.51 | A |
| ATOM | 6171 | CD1  | TRP | A | 153 | 7.879   | 15.120 | 37.053 | 1.00 | 17.56 | A |
| ATOM | 6172 | NE1  | TRP | A | 153 | 6.815   | 15.278 | 37.906 | 1.00 | 17.47 | A |
| ATOM | 6173 | CZ2  | TRP | A | 153 | 4.893   | 16.893 | 38.038 | 1.00 | 17.62 | A |
| ATOM | 6174 | CZ3  | TRP | A | 153 | 4.954   | 18.548 | 36.264 | 1.00 | 17.52 | A |
| ATOM | 6175 | CH2  | TRP | A | 153 | 4.352   | 17.990 | 37.410 | 1.00 | 17.93 | A |
| ATOM | 6176 | C    | TRP | A | 153 | 9.719   | 18.073 | 36.540 | 1.00 | 16.90 | A |
| ATOM | 6177 | O    | TRP | A | 153 | 8.963   | 18.874 | 37.101 | 1.00 | 16.93 | A |
| ATOM | 6178 | N    | GLU | A | 154 | 10.746  | 17.502 | 37.156 | 1.00 | 16.92 | A |
| ATOM | 6179 | CA   | GLU | A | 154 | 11.035  | 17.762 | 38.561 | 1.00 | 17.77 | A |
| ATOM | 6180 | CB   | GLU | A | 154 | 12.168  | 16.846 | 39.037 | 1.00 | 18.50 | A |
| ATOM | 6181 | CG   | GLU | A | 154 | 12.341  | 16.793 | 40.555 | 1.00 | 20.34 | A |
| ATOM | 6182 | CD   | GLU | A | 154 | 13.143  | 17.942 | 41.115 | 1.00 | 21.37 | A |
| ATOM | 6183 | OE1  | GLU | A | 154 | 13.106  | 18.142 | 42.352 | 1.00 | 22.31 | A |
| ATOM | 6184 | OE2  | GLU | A | 154 | 13.825  | 18.645 | 40.336 | 1.00 | 22.41 | A |
| ATOM | 6185 | C    | GLU | A | 154 | 11.409  | 19.223 | 38.779 | 1.00 | 17.80 | A |
| ATOM | 6186 | O    | GLU | A | 154 | 10.992  | 19.841 | 39.765 | 1.00 | 17.40 | A |
| ATOM | 6187 | N    | ILE | A | 155 | 12.189  | 19.766 | 37.848 | 1.00 | 17.91 | A |
| ATOM | 6188 | CA   | ILE | A | 155 | 12.632  | 21.158 | 37.916 | 1.00 | 18.46 | A |
| ATOM | 6189 | CB   | ILE | A | 155 | 13.704  | 21.442 | 36.837 | 1.00 | 18.42 | A |
| ATOM | 6190 | CG2  | ILE | A | 155 | 13.999  | 22.953 | 36.754 | 1.00 | 18.94 | A |
| ATOM | 6191 | CG1  | ILE | A | 155 | 14.972  | 20.643 | 37.160 | 1.00 | 18.56 | A |
| ATOM | 6192 | CD1  | ILE | A | 155 | 16.070  | 20.752 | 36.113 | 1.00 | 17.73 | A |
| ATOM | 6193 | C    | ILE | A | 155 | 11.468  | 22.133 | 37.748 | 1.00 | 18.60 | A |
| ATOM | 6194 | O    | ILE | A | 155 | 11.320  | 23.084 | 38.527 | 1.00 | 18.55 | A |
| ATOM | 6195 | N    | CYS | A | 156 | 10.640  | 21.901 | 36.734 | 1.00 | 18.62 | A |
| ATOM | 6196 | CA   | CYS | A | 156 | 9.495   | 22.768 | 36.498 | 1.00 | 19.08 | A |
| ATOM | 6197 | CB   | CYS | A | 156 | 8.808   | 22.418 | 35.170 | 1.00 | 19.21 | A |
| ATOM | 6198 | SG   | CYS | A | 156 | 9.783   | 22.809 | 33.694 | 1.00 | 20.15 | A |
| ATOM | 6199 | C    | CYS | A | 156 | 8.479   | 22.675 | 37.633 | 1.00 | 18.95 | A |
| ATOM | 6200 | O    | CYS | A | 156 | 7.950   | 23.689 | 38.082 | 1.00 | 19.21 | A |

TABLE 2-continued

Three-dimensional coordinate of the complex of human
hematopoietic PGDS (SEQ ID NO: 1) with magnesium and glutathione

| ATOM | 6201 | N | SER | A | 157 | 8.210 | 21.461 | 38.108 | 1.00 | 18.70 | A |
|------|------|------|-----|---|-----|--------|--------|--------|------|-------|---|
| ATOM | 6202 | CA | SER | A | 157 | 7.229 | 21.301 | 39.175 | 1.00 | 18.57 | A |
| ATOM | 6203 | CB | SER | A | 157 | 6.890 | 19.820 | 39.388 | 1.00 | 18.17 | A |
| ATOM | 6204 | OG | SER | A | 157 | 8.042 | 19.055 | 39.674 | 1.00 | 18.09 | A |
| ATOM | 6205 | C | SER | A | 157 | 7.715 | 21.933 | 40.476 | 1.00 | 18.73 | A |
| ATOM | 6206 | O | SER | A | 157 | 6.911 | 22.420 | 41.269 | 1.00 | 18.90 | A |
| ATOM | 6207 | N | THR | A | 158 | 9.025 | 21.928 | 40.694 | 1.00 | 18.86 | A |
| ATOM | 6208 | CA | THR | A | 158 | 9.586 | 22.536 | 41.898 | 1.00 | 19.39 | A |
| ATOM | 6209 | CB | THR | A | 158 | 11.124 | 22.436 | 41.915 | 1.00 | 19.38 | A |
| ATOM | 6210 | OG1 | THR | A | 158 | 11.513 | 21.058 | 41.992 | 1.00 | 19.86 | A |
| ATOM | 6211 | CG2 | THR | A | 158 | 11.697 | 23.181 | 43.111 | 1.00 | 19.72 | A |
| ATOM | 6212 | C | THR | A | 158 | 9.180 | 24.011 | 41.953 | 1.00 | 19.58 | A |
| ATOM | 6213 | O | THR | A | 158 | 8.727 | 24.502 | 42.989 | 1.00 | 19.55 | A |
| ATOM | 6214 | N | THR | A | 159 | 9.336 | 24.714 | 40.836 | 1.00 | 19.71 | A |
| ATOM | 6215 | CA | THR | A | 159 | 8.977 | 26.129 | 40.791 | 1.00 | 20.16 | A |
| ATOM | 6216 | CB | THR | A | 159 | 9.553 | 26.810 | 39.531 | 1.00 | 20.13 | A |
| ATOM | 6217 | OG1 | THR | A | 159 | 10.981 | 26.811 | 39.617 | 1.00 | 20.61 | A |
| ATOM | 6218 | CG2 | THR | A | 159 | 9.067 | 28.255 | 39.425 | 1.00 | 20.46 | A |
| ATOM | 6219 | C | THR | A | 159 | 7.468 | 26.347 | 40.855 | 1.00 | 20.37 | A |
| ATOM | 6220 | O | THR | A | 159 | 6.996 | 27.261 | 41.529 | 1.00 | 20.42 | A |
| ATOM | 6221 | N | LEU | A | 160 | 6.701 | 25.509 | 40.163 | 1.00 | 20.18 | A |
| ATOM | 6222 | CA | LEU | A | 160 | 5.258 | 25.651 | 40.195 | 1.00 | 20.20 | A |
| ATOM | 6223 | CB | LEU | A | 160 | 4.607 | 24.665 | 39.229 | 1.00 | 20.20 | A |
| ATOM | 6224 | CG | LEU | A | 160 | 4.790 | 24.985 | 37.742 | 1.00 | 20.36 | A |
| ATOM | 6225 | CD1 | LEU | A | 160 | 4.148 | 23.883 | 36.919 | 1.00 | 20.38 | A |
| ATOM | 6226 | CD2 | LEU | A | 160 | 4.171 | 26.340 | 37.411 | 1.00 | 20.08 | A |
| ATOM | 6227 | C | LEU | A | 160 | 4.720 | 25.430 | 41.607 | 1.00 | 20.21 | A |
| ATOM | 6228 | O | LEU | A | 160 | 3.812 | 26.133 | 42.043 | 1.00 | 19.87 | A |
| ATOM | 6229 | N | LEU | A | 161 | 5.290 | 24.459 | 42.321 | 1.00 | 20.19 | A |
| ATOM | 6230 | CA | LEU | A | 161 | 4.853 | 24.148 | 43.686 | 1.00 | 20.28 | A |
| ATOM | 6231 | CB | LEU | A | 161 | 5.580 | 22.902 | 44.207 | 1.00 | 20.48 | A |
| ATOM | 6232 | CG | LEU | A | 161 | 5.015 | 21.562 | 43.713 | 1.00 | 20.77 | A |
| ATOM | 6233 | CD1 | LEU | A | 161 | 6.014 | 20.435 | 43.957 | 1.00 | 20.74 | A |
| ATOM | 6234 | CD2 | LEU | A | 161 | 3.700 | 21.283 | 44.419 | 1.00 | 20.80 | A |
| ATOM | 6235 | C | LEU | A | 161 | 5.048 | 25.312 | 44.655 | 1.00 | 20.60 | A |
| ATOM | 6236 | O | LEU | A | 161 | 4.329 | 25.426 | 45.651 | 1.00 | 20.50 | A |
| ATOM | 6237 | N | VAL | A | 162 | 6.021 | 26.170 | 44.364 | 1.00 | 20.44 | A |
| ATOM | 6238 | CA | VAL | A | 162 | 6.282 | 27.335 | 45.207 | 1.00 | 20.53 | A |
| ATOM | 6239 | CB | VAL | A | 162 | 7.546 | 28.101 | 44.744 | 1.00 | 20.23 | A |
| ATOM | 6240 | CG1 | VAL | A | 162 | 7.622 | 29.466 | 45.434 | 1.00 | 20.06 | A |
| ATOM | 6241 | CG2 | VAL | A | 162 | 8.792 | 27.291 | 45.050 | 1.00 | 19.98 | A |
| ATOM | 6242 | C | VAL | A | 162 | 5.097 | 28.290 | 45.150 | 1.00 | 21.05 | A |
| ATOM | 6243 | O | VAL | A | 162 | 4.711 | 28.879 | 46.160 | 1.00 | 21.34 | A |
| ATOM | 6244 | N | PHE | A | 163 | 4.524 | 28.452 | 43.963 | 1.00 | 21.34 | A |
| ATOM | 6245 | CA | PHE | A | 163 | 3.395 | 29.356 | 43.785 | 1.00 | 21.75 | A |
| ATOM | 6246 | CB | PHE | A | 163 | 3.517 | 30.080 | 42.448 | 1.00 | 21.81 | A |
| ATOM | 6247 | CG | PHE | A | 163 | 4.798 | 30.832 | 42.290 | 1.00 | 22.12 | A |
| ATOM | 6248 | CD1 | PHE | A | 163 | 5.912 | 30.223 | 41.723 | 1.00 | 22.14 | A |
| ATOM | 6249 | CD2 | PHE | A | 163 | 4.904 | 32.147 | 42.735 | 1.00 | 22.21 | A |
| ATOM | 6250 | CE1 | PHE | A | 163 | 7.114 | 30.915 | 41.598 | 1.00 | 22.33 | A |
| ATOM | 6251 | CE2 | PHE | A | 163 | 6.103 | 32.845 | 42.615 | 1.00 | 22.06 | A |
| ATOM | 6252 | CZ | PHE | A | 163 | 7.211 | 32.232 | 42.048 | 1.00 | 22.23 | A |
| ATOM | 6253 | C | PHE | A | 163 | 2.035 | 28.679 | 43.866 | 1.00 | 21.93 | A |
| ATOM | 6254 | O | PHE | A | 163 | 1.016 | 29.351 | 44.006 | 1.00 | 22.09 | A |
| ATOM | 6528 | N | THR | A | 197 | 16.938 | 29.580 | 46.456 | 1.00 | 42.04 | A |
| ATOM | 6529 | CA | THR | A | 197 | 16.335 | 30.780 | 45.882 | 1.00 | 42.10 | A |
| ATOM | 6530 | CB | THR | A | 197 | 17.042 | 31.183 | 44.574 | 1.00 | 41.93 | A |
| ATOM | 6531 | OG1 | THR | A | 197 | 17.071 | 30.063 | 43.680 | 1.00 | 41.66 | A |
| ATOM | 6532 | CG2 | THR | A | 197 | 18.466 | 31.642 | 44.858 | 1.00 | 41.90 | A |
| ATOM | 6533 | C | THR | A | 197 | 14.852 | 30.565 | 45.588 | 1.00 | 42.37 | A |
| ATOM | 6534 | O | THR | A | 197 | 14.363 | 29.436 | 45.631 | 1.00 | 42.08 | A |
| ATOM | 6535 | N | LYS | A | 198 | 14.140 | 31.649 | 45.288 | 1.00 | 42.36 | A |
| ATOM | 6536 | CA | LYS | A | 198 | 12.712 | 31.566 | 44.992 | 1.00 | 42.71 | A |
| ATOM | 6537 | CB | LYS | A | 198 | 12.052 | 32.947 | 45.102 | 1.00 | 42.62 | A |
| ATOM | 6538 | CG | LYS | A | 198 | 10.532 | 32.914 | 44.946 | 1.00 | 42.36 | A |
| ATOM | 6539 | CD | LYS | A | 198 | 9.902 | 34.305 | 44.974 | 1.00 | 42.26 | A |
| ATOM | 6540 | CE | LYS | A | 198 | 10.279 | 35.121 | 43.746 | 1.00 | 42.29 | A |
| ATOM | 6541 | NZ | LYS | A | 198 | 9.661 | 36.480 | 43.744 | 1.00 | 42.09 | A |
| ATOM | 6542 | C | LYS | A | 198 | 12.451 | 30.995 | 43.599 | 1.00 | 42.44 | A |
| ATOM | 6543 | O | LYS | A | 198 | 11.440 | 30.331 | 43.376 | 1.00 | 43.10 | A |
| ATOM | 6544 | N | LEU | A | 199 | 13.359 | 31.257 | 42.664 | 1.00 | 42.38 | A |
| ATOM | 6545 | CA | LEU | A | 199 | 13.208 | 30.762 | 41.302 | 1.00 | 41.31 | A |
| ATOM | 6546 | CB | LEU | A | 199 | 13.021 | 31.929 | 40.328 | 1.00 | 41.79 | A |
| ATOM | 6547 | CG | LEU | A | 199 | 11.826 | 32.851 | 40.580 | 1.00 | 41.74 | A |
| ATOM | 6548 | CD1 | LEU | A | 199 | 11.825 | 33.976 | 39.562 | 1.00 | 41.87 | A |
| ATOM | 6549 | CD2 | LEU | A | 199 | 10.537 | 32.054 | 40.500 | 1.00 | 41.99 | A |

TABLE 2-continued

Three-dimensional coordinate of the complex of human
hematopoietic PGDS (SEQ ID NO: 1) with magnesium and glutathione

| ATOM | 6550 | C | LEU | A | 199 | 14.415 | 29.940 | 40.880 | 1.00 | 41.18 | A |
|---|---|---|---|---|---|---|---|---|---|---|---|
| ATOM | 6551 | O | LEU | A | 199 | 15.357 | 29.815 | 41.690 | 1.00 | 40.87 | A |
| ATOM | 6552 | OXT | LEU | A | 199 | 14.404 | 29.431 | 39.740 | 1.00 | 40.62 | A |
| ATOM | 6613 | N1 | GSH | H | 200 | 14.652 | 30.753 | 26.106 | 1.00 | 31.06 | H |
| ATOM | 6614 | CA1 | GSH | H | 200 | 16.043 | 30.929 | 26.532 | 1.00 | 30.39 | H |
| ATOM | 6615 | C1 | GSH | H | 200 | 16.615 | 29.624 | 27.134 | 1.00 | 29.87 | H |
| ATOM | 6616 | O11 | GSH | H | 200 | 15.850 | 28.693 | 27.401 | 1.00 | 29.01 | H |
| ATOM | 6617 | O12 | GSH | H | 200 | 17.912 | 29.630 | 27.407 | 1.00 | 29.27 | H |
| ATOM | 6618 | CB1 | GSH | H | 200 | 16.079 | 32.017 | 27.617 | 1.00 | 30.85 | H |
| ATOM | 6619 | CG1 | GSH | H | 200 | 16.018 | 33.443 | 27.054 | 1.00 | 30.90 | H |
| ATOM | 6620 | CD1 | GSH | H | 200 | 15.735 | 34.381 | 28.252 | 1.00 | 30.62 | H |
| ATOM | 6621 | OE1 | GSH | H | 200 | 14.695 | 35.035 | 28.263 | 1.00 | 30.67 | H |
| ATOM | 6622 | N2 | GSH | H | 200 | 16.666 | 34.424 | 29.226 | 1.00 | 30.63 | H |
| ATOM | 6623 | CA2 | GSH | H | 200 | 16.479 | 35.316 | 30.387 | 1.00 | 30.99 | H |
| ATOM | 6624 | C2 | GSH | H | 200 | 17.327 | 36.467 | 30.245 | 1.00 | 31.16 | H |
| ATOM | 6625 | O2 | GSH | H | 200 | 18.505 | 36.372 | 29.874 | 1.00 | 30.98 | H |
| ATOM | 6626 | CB2 | GSH | H | 200 | 16.883 | 34.616 | 31.709 | 1.00 | 30.96 | H |
| ATOM | 6627 | SG2 | GSH | H | 200 | 15.567 | 33.583 | 32.426 | 1.00 | 31.20 | H |
| ATOM | 6628 | N3 | GSH | H | 200 | 16.793 | 37.649 | 30.634 | 1.00 | 31.83 | H |
| ATOM | 6629 | CA3 | GSH | H | 200 | 17.595 | 38.892 | 30.738 | 1.00 | 32.45 | H |
| ATOM | 6630 | C3 | GSH | H | 200 | 17.196 | 39.860 | 29.638 | 1.00 | 32.93 | H |
| ATOM | 6631 | O31 | GSH | H | 200 | 17.851 | 40.926 | 29.570 | 1.00 | 33.18 | H |
| ATOM | 6632 | O32 | GSH | H | 200 | 16.268 | 39.526 | 28.858 | 1.00 | 33.08 | H |
| ATOM | 6634 | MG + 2 | MG2 | M | 902 | 10.400 | 26.589 | 23.001 | 1.00 | 23.91 | M |
| ATOM | 6641 | OH2 | WAT | S | 7 | 11.530 | 25.061 | 23.828 | 1.00 | 37.06 | S |
| ATOM | 6642 | OH2 | WAT | S | 8 | 9.540 | 27.210 | 24.684 | 1.00 | 24.57 | S |
| ATOM | 6643 | OH2 | WAT | S | 9 | 9.510 | 28.276 | 22.036 | 1.00 | 26.85 | S |
| ATOM | 6644 | OH2 | WAT | S | 10 | 11.074 | 26.182 | 21.146 | 1.00 | 25.39 | S |
| ATOM | 6645 | OH2 | WAT | S | 11 | 8.769 | 25.220 | 22.701 | 1.00 | 23.15 | S |
| ATOM | 6646 | OH2 | WAT | S | 12 | 12.343 | 27.736 | 23.214 | 1.00 | 21.75 | S |
| ATOM | 6655 | OH2 | WAT | S | 21 | 16.153 | 24.647 | 33.762 | 1.00 | 15.93 | S |
| ATOM | 6660 | OH2 | WAT | S | 26 | 22.016 | 34.735 | 24.315 | 1.00 | 19.54 | S |
| ATOM | 6690 | OH2 | WAT | S | 56 | 19.895 | 31.455 | 26.292 | 1.00 | 20.15 | S |
| ATOM | 6722 | OH2 | WAT | S | 88 | 15.099 | 33.768 | 23.429 | 1.00 | 20.21 | S |
| ATOM | 6746 | OH2 | WAT | S | 112 | 13.586 | 26.219 | 37.252 | 1.00 | 28.05 | S |
| ATOM | 6749 | OH2 | WAT | S | 115 | 29.682 | 31.074 | 30.423 | 1.00 | 32.25 | S |
| ATOM | 6757 | OH2 | WAT | S | 123 | 20.931 | 25.748 | 41.633 | 1.00 | 32.02 | S |
| ATOM | 6758 | OH2 | WAT | S | 124 | 17.734 | 33.757 | 22.543 | 1.00 | 19.10 | S |
| ATOM | 6770 | OH2 | WAT | S | 136 | 13.426 | 24.600 | 39.459 | 1.00 | 28.07 | S |
| ATOM | 6774 | OH2 | WAT | S | 140 | 16.050 | 26.391 | 24.708 | 1.00 | 22.82 | S |
| ATOM | 6782 | OH2 | WAT | S | 148 | 14.395 | 37.589 | 28.342 | 1.00 | 35.97 | S |
| ATOM | 6811 | OH2 | WAT | S | 177 | 19.958 | 32.909 | 23.887 | 1.00 | 18.07 | S |
| ATOM | 6829 | OH2 | WAT | S | 195 | 14.106 | 35.347 | 25.480 | 1.00 | 25.75 | S |
| ATOM | 6840 | OH2 | WAT | S | 206 | 14.044 | 35.490 | 20.956 | 1.00 | 20.11 | S |
| ATOM | 6928 | OH2 | WAT | S | 294 | 25.213 | 29.402 | 36.456 | 1.00 | 21.97 | S |
| ATOM | 6929 | OH2 | WAT | S | 295 | 4.780 | 29.656 | 25.498 | 1.00 | 28.39 | S |
| ATOM | 6940 | OH2 | WAT | S | 306 | 11.910 | 36.992 | 22.272 | 1.00 | 27.44 | S |
| ATOM | 7008 | OH2 | WAT | S | 374 | 19.731 | 28.119 | 43.144 | 1.00 | 34.76 | S |
| ATOM | 7079 | OH2 | WAT | S | 445 | 9.001 | 41.153 | 37.697 | 1.00 | 40.98 | S |
| ATOM | 7085 | OH2 | WAT | S | 451 | 14.312 | 39.335 | 22.120 | 1.00 | 52.27 | S |
| ATOM | 7095 | OH2 | WAT | S | 461 | 11.445 | 36.299 | 24.804 | 1.00 | 39.65 | S |
| ATOM | 7123 | OH2 | WAT | S | 489 | 11.366 | 30.498 | 26.166 | 1.00 | 37.93 | S |
| ATOM | 7129 | OH2 | WAT | S | 495 | 16.228 | 23.406 | 21.692 | 1.00 | 34.70 | S |
| ATOM | 7138 | OH2 | WAT | S | 504 | 21.673 | 36.938 | 40.112 | 1.00 | 39.58 | S |
| ATOM | 7140 | OH2 | WAT | S | 506 | 8.186 | 35.879 | 39.587 | 1.00 | 35.09 | S |
| ATOM | 7155 | OH2 | WAT | S | 521 | 17.208 | 36.485 | 21.785 | 1.00 | 33.85 | S |
| ATOM | 7179 | OH2 | WAT | S | 545 | 7.692 | 39.218 | 31.544 | 1.00 | 38.01 | S |
| ATOM | 7184 | OH2 | WAT | S | 550 | 16.301 | 40.121 | 43.773 | 1.00 | 42.74 | S |
| ATOM | 7205 | OH2 | WAT | S | 571 | 16.471 | 40.729 | 21.826 | 1.00 | 44.98 | S |
| ATOM | 7219 | OH2 | WAT | S | 585 | 12.552 | 26.597 | 33.929 | 1.00 | 43.65 | S |
| ATOM | 7229 | OH2 | WAT | S | 595 | 17.756 | 38.966 | 20.182 | 1.00 | 39.29 | S |
| ATOM | 7231 | OH2 | WAT | S | 597 | 13.596 | 27.392 | 25.614 | 1.00 | 33.67 | S |
| ATOM | 7235 | OH2 | WAT | S | 601 | 8.227 | 29.798 | 24.106 | 1.00 | 42.88 | S |
| ATOM | 7250 | OH2 | WAT | S | 616 | 12.430 | 28.404 | 38.196 | 1.00 | 28.06 | S |
| ATOM | 7302 | OH2 | WAT | S | 668 | 8.268 | 32.489 | 24.271 | 1.00 | 34.58 | S |
| ATOM | 7306 | OH2 | WAT | S | 672 | 13.738 | 43.695 | 22.850 | 1.00 | 40.33 | S |
| ATOM | 7350 | OH2 | WAT | S | 716 | 16.122 | 38.680 | 37.510 | 1.00 | 37.39 | S |
| ATOM | 7351 | OH2 | WAT | S | 717 | 12.657 | 31.864 | 34.383 | 1.00 | 37.30 | S |
| ATOM | 7362 | OH2 | WAT | S | 728 | 24.227 | 34.662 | 22.649 | 1.00 | 33.80 | S |
| ATOM | 7363 | OH2 | WAT | S | 729 | 25.788 | 32.632 | 21.734 | 1.00 | 31.91 | S |
| ATOM | 7398 | OH2 | WAT | S | 764 | 15.402 | 25.563 | 30.917 | 1.00 | 22.67 | S |
| ATOM | 7399 | OH2 | WAT | S | 765 | 13.051 | 32.782 | 31.072 | 1.00 | 31.89 | S |
| ATOM | 7400 | OH2 | WAT | S | 766 | 10.600 | 32.486 | 30.037 | 1.00 | 38.06 | S |
| ATOM | 7453 | OH2 | WAT | S | 818 | 10.407 | 33.035 | 26.315 | 1.00 | 34.27 | S |
| ATOM | 7454 | OH2 | WAT | S | 819 | 4.103 | 39.433 | 24.839 | 1.00 | 35.58 | S |
| ATOM | 7455 | OH2 | WAT | S | 820 | 8.800 | 40.482 | 25.686 | 1.00 | 38.38 | S |

TABLE 2-continued

Three-dimensional coordinate of the complex of human
hematopoietic PGDS (SEQ ID NO: 1) with magnesium and glutathione

| ATOM | 7466 | OH2 | WAT | S | 831 | 22.905 | 42.140 | 23.725 | 1.00 | 34.87 | S |
|---|---|---|---|---|---|---|---|---|---|---|---|
| ATOM | 7523 | OH2 | WAT | S | 890 | 11.498 | 40.681 | 41.811 | 1.00 | 34.74 | S |
| ATOM | 7533 | OH2 | WAT | S | 901 | 21.231 | 36.504 | 45.050 | 1.00 | 40.93 | S |
| ATOM | 7540 | OH2 | WAT | S | 908 | 16.196 | 42.111 | 32.687 | 1.00 | 37.19 | S |
| ATOM | 7588 | OH2 | WAT | S | 1234 | 13.747 | 22.487 | 22.995 | 1.00 | 32.97 | S |

TABLE 3

Three-dimensional structural coordinate of the complex of
human hematopoietic PGDS (SEQ ID NO: 1) with calcium, glutathione and
9,11-dideoxy-9α,11α-methanoepoxyprostaglandine $F_{2\alpha}$(U46)

| ATOM | 4966 | N | TYR | A | 8 | −2.271 | −4.196 | 32.836 | 1.00 | 14.93 | A |
|---|---|---|---|---|---|---|---|---|---|---|---|
| ATOM | 4967 | CA | TYR | A | 8 | −0.858 | −4.474 | 33.097 | 1.00 | 15.12 | A |
| ATOM | 4968 | CB | TYR | A | 8 | −0.097 | −3.155 | 33.272 | 1.00 | 14.72 | A |
| ATOM | 4969 | CG | TYR | A | 8 | 1.411 | −3.302 | 33.334 | 1.00 | 14.32 | A |
| ATOM | 4970 | CD1 | TYR | A | 8 | 2.128 | −3.846 | 32.262 | 1.00 | 13.92 | A |
| ATOM | 4971 | CE1 | TYR | A | 8 | 3.518 | −3.985 | 32.321 | 1.00 | 13.52 | A |
| ATOM | 4972 | CD2 | TYR | A | 8 | 2.125 | −2.898 | 34.469 | 1.00 | 14.03 | A |
| ATOM | 4973 | CE2 | TYR | A | 8 | 3.508 | −3.032 | 34.539 | 1.00 | 13.52 | A |
| ATOM | 4974 | CZ | TYR | A | 8 | 4.199 | −3.577 | 33.461 | 1.00 | 13.52 | A |
| ATOM | 4975 | OH | TYR | A | 8 | 5.563 | −3.718 | 33.529 | 1.00 | 13.03 | A |
| ATOM | 4976 | C | TYR | A | 8 | −0.758 | −5.293 | 34.384 | 1.00 | 15.52 | A |
| ATOM | 4977 | O | TYR | A | 8 | −1.775 | −5.603 | 35.002 | 1.00 | 15.35 | A |
| ATOM | 4978 | N | PHE | A | 9 | 0.460 | −5.652 | 34.782 | 1.00 | 15.96 | A |
| ATOM | 4979 | CA | PHE | A | 9 | 0.654 | −6.400 | 36.021 | 1.00 | 16.41 | A |
| ATOM | 4980 | CB | PHE | A | 9 | 2.049 | −7.029 | 36.071 | 1.00 | 16.62 | A |
| ATOM | 4981 | CG | PHE | A | 9 | 2.240 | −8.149 | 35.092 | 1.00 | 17.03 | A |
| ATOM | 4982 | CD1 | PHE | A | 9 | 3.165 | −8.035 | 34.055 | 1.00 | 17.22 | A |
| ATOM | 4983 | CD2 | PHE | A | 9 | 1.497 | −9.322 | 35.209 | 1.00 | 17.29 | A |
| ATOM | 4984 | CE1 | PHE | A | 9 | 3.352 | −9.072 | 33.143 | 1.00 | 17.28 | A |
| ATOM | 4985 | CE2 | PHE | A | 9 | 1.671 | −10.371 | 34.304 | 1.00 | 17.39 | A |
| ATOM | 4986 | CZ | PHE | A | 9 | 2.603 | −10.245 | 33.267 | 1.00 | 17.64 | A |
| ATOM | 4987 | C | PHE | A | 9 | 0.495 | −5.427 | 37.187 | 1.00 | 16.51 | A |
| ATOM | 4988 | O | PHE | A | 9 | 0.380 | −4.220 | 36.975 | 1.00 | 16.43 | A |
| ATOM | 4989 | N | ASN | A | 10 | 0.485 | −5.951 | 38.410 | 1.00 | 16.68 | A |
| ATOM | 4990 | CA | ASN | A | 10 | 0.345 | −5.114 | 39.595 | 1.00 | 17.13 | A |
| ATOM | 4991 | CB | ASN | A | 10 | −0.235 | −5.911 | 40.765 | 1.00 | 17.62 | A |
| ATOM | 4992 | CG | ASN | A | 10 | −0.251 | −5.111 | 42.053 | 1.00 | 18.18 | A |
| ATOM | 4993 | OD1 | ASN | A | 10 | −0.602 | −3.927 | 42.060 | 1.00 | 18.91 | A |
| ATOM | 4994 | ND2 | ASN | A | 10 | 0.120 | −5.751 | 43.151 | 1.00 | 18.74 | A |
| ATOM | 4995 | C | ASN | A | 10 | 1.695 | −4.539 | 39.996 | 1.00 | 17.08 | A |
| ATOM | 4996 | O | ASN | A | 10 | 2.278 | −4.934 | 41.002 | 1.00 | 17.04 | A |
| ATOM | 4997 | N | MET | A | 11 | 2.189 | −3.607 | 39.189 | 1.00 | 16.98 | A |
| ATOM | 4998 | CA | MET | A | 11 | 3.467 | −2.962 | 39.448 | 1.00 | 16.70 | A |
| ATOM | 4999 | CB | MET | A | 11 | 4.626 | −3.927 | 39.141 | 1.00 | 17.68 | A |
| ATOM | 5000 | CG | MET | A | 11 | 4.630 | −4.530 | 37.748 | 1.00 | 18.92 | A |
| ATOM | 5001 | SD | MET | A | 11 | 6.178 | −5.456 | 37.353 | 1.00 | 20.84 | A |
| ATOM | 5002 | CE | MET | A | 11 | 5.595 | −7.137 | 37.373 | 1.00 | 19.96 | A |
| ATOM | 5003 | C | MET | A | 11 | 3.561 | −1.708 | 38.587 | 1.00 | 15.92 | A |
| ATOM | 5004 | O | MET | A | 11 | 2.740 | −1.512 | 37.702 | 1.00 | 15.49 | A |
| ATOM | 5005 | N | ARG | A | 12 | 4.531 | −0.842 | 38.872 | 1.00 | 15.17 | A |
| ATOM | 5006 | CA | ARG | A | 12 | 4.697 | 0.372 | 38.084 | 1.00 | 14.70 | A |
| ATOM | 5007 | CB | ARG | A | 12 | 5.759 | 1.285 | 38.704 | 1.00 | 14.69 | A |
| ATOM | 5008 | CG | ARG | A | 12 | 5.418 | 1.777 | 40.110 | 1.00 | 15.00 | A |
| ATOM | 5009 | CD | ARG | A | 12 | 6.413 | 2.825 | 40.594 | 1.00 | 14.97 | A |
| ATOM | 5010 | NE | ARG | A | 12 | 7.785 | 2.323 | 40.634 | 1.00 | 15.22 | A |
| ATOM | 5011 | CZ | ARG | A | 12 | 8.265 | 1.490 | 41.556 | 1.00 | 15.45 | A |
| ATOM | 5012 | NH1 | ARG | A | 12 | 7.485 | 1.052 | 42.536 | 1.00 | 15.40 | A |
| ATOM | 5013 | NH2 | ARG | A | 12 | 9.533 | 1.096 | 41.502 | 1.00 | 15.26 | A |
| ATOM | 5014 | C | ARG | A | 12 | 5.136 | −0.069 | 36.695 | 1.00 | 14.31 | A |
| ATOM | 5015 | O | ARG | A | 12 | 4.432 | 0.147 | 35.710 | 1.00 | 13.90 | A |
| ATOM | 5016 | N | GLY | A | 13 | 6.301 | −0.708 | 36.639 | 1.00 | 13.97 | A |
| ATOM | 5017 | CA | GLY | A | 13 | 6.837 | −1.202 | 35.388 | 1.00 | 13.65 | A |
| ATOM | 5018 | C | GLY | A | 13 | 6.705 | −0.260 | 34.207 | 1.00 | 13.50 | A |
| ATOM | 5019 | O | GLY | A | 13 | 6.938 | 0.941 | 34.321 | 1.00 | 13.35 | A |
| ATOM | 5020 | N | ARG | A | 14 | 6.309 | −0.816 | 33.070 | 1.00 | 13.31 | A |
| ATOM | 5021 | CA | ARG | A | 14 | 6.179 | −0.047 | 31.848 | 1.00 | 13.30 | A |
| ATOM | 5022 | CB | ARG | A | 14 | 6.431 | −0.959 | 30.650 | 1.00 | 14.32 | A |
| ATOM | 5023 | CG | ARG | A | 14 | 7.877 | −1.395 | 30.542 | 1.00 | 16.00 | A |
| ATOM | 5024 | CD | ARG | A | 14 | 8.117 | −2.259 | 29.325 | 1.00 | 17.28 | A |
| ATOM | 5025 | NE | ARG | A | 14 | 9.532 | −2.265 | 28.979 | 1.00 | 18.88 | A |
| ATOM | 5026 | CZ | ARG | A | 14 | 10.134 | −1.329 | 28.246 | 1.00 | 19.26 | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine $F_{2\alpha}$(U46)

| ATOM | 5027 | NH1 | ARG | A | 14 | 9.444 | −0.304 | 27.762 | 1.00 | 19.28 | A |
|------|------|-----|-----|---|----|-------|--------|--------|------|-------|---|
| ATOM | 5028 | NH2 | ARG | A | 14 | 11.442 | −1.408 | 28.014 | 1.00 | 20.21 | A |
| ATOM | 5029 | C | ARG | A | 14 | 4.859 | 0.689 | 31.669 | 1.00 | 12.77 | A |
| ATOM | 5030 | O | ARG | A | 14 | 4.696 | 1.435 | 30.710 | 1.00 | 12.75 | A |
| ATOM | 5031 | N | ALA | A | 15 | 3.920 | 0.496 | 32.590 | 1.00 | 12.21 | A |
| ATOM | 5032 | CA | ALA | A | 15 | 2.624 | 1.159 | 32.493 | 1.00 | 11.48 | A |
| ATOM | 5033 | CB | ALA | A | 15 | 1.531 | 0.245 | 33.019 | 1.00 | 11.52 | A |
| ATOM | 5034 | C | ALA | A | 15 | 2.596 | 2.464 | 33.261 | 1.00 | 10.95 | A |
| ATOM | 5035 | O | ALA | A | 15 | 1.780 | 3.352 | 32.977 | 1.00 | 10.86 | A |
| ATOM | 5036 | N | GLU | A | 16 | 3.490 | 2.580 | 34.238 | 1.00 | 10.32 | A |
| ATOM | 5037 | CA | GLU | A | 16 | 3.546 | 3.771 | 35.087 | 1.00 | 9.76 | A |
| ATOM | 5038 | CB | GLU | A | 16 | 4.748 | 3.677 | 36.036 | 1.00 | 9.29 | A |
| ATOM | 5039 | CG | GLU | A | 16 | 4.648 | 4.565 | 37.277 | 1.00 | 8.91 | A |
| ATOM | 5040 | CD | GLU | A | 16 | 3.485 | 4.192 | 38.189 | 1.00 | 8.41 | A |
| ATOM | 5041 | OE1 | GLU | A | 16 | 2.858 | 3.134 | 37.983 | 1.00 | 8.43 | A |
| ATOM | 5042 | OE2 | GLU | A | 16 | 3.199 | 4.960 | 39.125 | 1.00 | 8.51 | A |
| ATOM | 5043 | C | GLU | A | 16 | 3.590 | 5.084 | 34.303 | 1.00 | 9.64 | A |
| ATOM | 5044 | O | GLU | A | 16 | 2.999 | 6.071 | 34.730 | 1.00 | 9.63 | A |
| ATOM | 5045 | N | ILE | A | 17 | 4.287 | 5.096 | 33.166 | 1.00 | 9.45 | A |
| ATOM | 5046 | CA | ILE | A | 17 | 4.377 | 6.312 | 32.368 | 1.00 | 9.29 | A |
| ATOM | 5047 | CB | ILE | A | 17 | 5.333 | 6.139 | 31.150 | 1.00 | 9.25 | A |
| ATOM | 5048 | CG2 | ILE | A | 17 | 4.867 | 5.015 | 30.251 | 1.00 | 9.64 | A |
| ATOM | 5049 | CG1 | ILE | A | 17 | 5.413 | 7.442 | 30.358 | 1.00 | 9.55 | A |
| ATOM | 5050 | CD1 | ILE | A | 17 | 5.988 | 8.596 | 31.168 | 1.00 | 9.78 | A |
| ATOM | 5051 | C | ILE | A | 17 | 2.984 | 6.717 | 31.892 | 1.00 | 9.19 | A |
| ATOM | 5052 | O | ILE | A | 17 | 2.648 | 7.897 | 31.845 | 1.00 | 8.98 | A |
| ATOM | 5242 | N | TRP | A | 39 | −2.591 | −14.181 | 33.457 | 1.00 | 37.71 | A |
| ATOM | 5243 | CA | TRP | A | 39 | −1.830 | −13.655 | 32.329 | 1.00 | 37.46 | A |
| ATOM | 5244 | CB | TRP | A | 39 | −0.376 | −13.394 | 32.737 | 1.00 | 37.38 | A |
| ATOM | 5245 | CG | TRP | A | 39 | 0.495 | −12.956 | 31.594 | 1.00 | 37.31 | A |
| ATOM | 5246 | CD2 | TRP | A | 39 | 0.174 | −11.987 | 30.583 | 1.00 | 37.22 | A |
| ATOM | 5247 | CE2 | TRP | A | 39 | 1.277 | −11.918 | 29.704 | 1.00 | 37.19 | A |
| ATOM | 5248 | CE3 | TRP | A | 39 | −0.940 | −11.171 | 30.336 | 1.00 | 37.22 | A |
| ATOM | 5249 | CD1 | TRP | A | 39 | 1.745 | −13.416 | 31.295 | 1.00 | 37.27 | A |
| ATOM | 5250 | NE1 | TRP | A | 39 | 2.220 | −12.801 | 30.160 | 1.00 | 37.23 | A |
| ATOM | 5251 | CZ2 | TRP | A | 39 | 1.300 | −11.068 | 28.594 | 1.00 | 37.19 | A |
| ATOM | 5252 | CZ3 | TRP | A | 39 | −0.916 | −10.323 | 29.230 | 1.00 | 37.17 | A |
| ATOM | 5253 | CH2 | TRP | A | 39 | 0.198 | −10.281 | 28.374 | 1.00 | 37.16 | A |
| ATOM | 5254 | C | TRP | A | 39 | −1.866 | −14.602 | 31.124 | 1.00 | 37.40 | A |
| ATOM | 5255 | O | TRP | A | 39 | −2.138 | −14.177 | 30.003 | 1.00 | 37.29 | A |
| ATOM | 5256 | N | PRO | A | 40 | −1.597 | −15.901 | 31.342 | 1.00 | 37.35 | A |
| ATOM | 5257 | CD | PRO | A | 40 | −1.235 | −16.548 | 32.616 | 1.00 | 37.43 | A |
| ATOM | 5258 | CA | PRO | A | 40 | −1.605 | −16.881 | 30.251 | 1.00 | 37.26 | A |
| ATOM | 5259 | CB | PRO | A | 40 | −1.489 | −18.212 | 30.987 | 1.00 | 37.31 | A |
| ATOM | 5260 | CG | PRO | A | 40 | −0.618 | −17.854 | 32.153 | 1.00 | 37.40 | A |
| ATOM | 5261 | C | PRO | A | 40 | −2.843 | −16.817 | 29.363 | 1.00 | 37.11 | A |
| ATOM | 5262 | O | PRO | A | 40 | −2.739 | −16.888 | 28.139 | 1.00 | 37.23 | A |
| ATOM | 5263 | N | GLU | A | 41 | −4.011 | −16.677 | 29.981 | 1.00 | 36.89 | A |
| ATOM | 5264 | CA | GLU | A | 41 | −5.265 | −16.614 | 29.236 | 1.00 | 36.63 | A |
| ATOM | 5265 | CB | GLU | A | 41 | −6.457 | −16.755 | 30.188 | 1.00 | 37.02 | A |
| ATOM | 5266 | CG | GLU | A | 41 | −7.757 | −17.156 | 29.501 | 1.00 | 37.64 | A |
| ATOM | 5267 | CD | GLU | A | 41 | −7.734 | −18.601 | 29.023 | 1.00 | 38.10 | A |
| ATOM | 5268 | OE1 | GLU | A | 41 | −8.709 | −19.033 | 28.364 | 1.00 | 38.32 | A |
| ATOM | 5269 | OE2 | GLU | A | 41 | −6.741 | −19.307 | 29.311 | 1.00 | 38.26 | A |
| ATOM | 5270 | C | GLU | A | 41 | −5.381 | −15.297 | 28.474 | 1.00 | 36.10 | A |
| ATOM | 5271 | O | GLU | A | 41 | −5.703 | −15.281 | 27.285 | 1.00 | 36.26 | A |
| ATOM | 5272 | N | ILE | A | 42 | −5.120 | −14.194 | 29.166 | 1.00 | 35.28 | A |
| ATOM | 5273 | CA | ILE | A | 42 | −5.204 | −12.874 | 28.553 | 1.00 | 34.47 | A |
| ATOM | 5274 | CB | ILE | A | 42 | −4.980 | −11.773 | 29.597 | 1.00 | 34.57 | A |
| ATOM | 5275 | CG2 | ILE | A | 42 | −5.152 | −10.406 | 28.953 | 1.00 | 34.48 | A |
| ATOM | 5276 | CG1 | ILE | A | 42 | −5.968 | −11.952 | 30.750 | 1.00 | 34.54 | A |
| ATOM | 5277 | CD1 | ILE | A | 42 | −5.687 | −11.076 | 31.944 | 1.00 | 34.74 | A |
| ATOM | 5278 | C | ILE | A | 42 | −4.173 | −12.715 | 27.441 | 1.00 | 33.83 | A |
| ATOM | 5279 | O | ILE | A | 42 | −4.466 | −12.161 | 26.384 | 1.00 | 33.69 | A |
| ATOM | 5280 | N | LYS | A | 43 | −2.968 | −13.213 | 27.691 | 1.00 | 33.07 | A |
| ATOM | 5281 | CA | LYS | A | 43 | −1.879 | −13.133 | 26.729 | 1.00 | 32.30 | A |
| ATOM | 5282 | CB | LYS | A | 43 | −0.664 | −13.899 | 27.258 | 1.00 | 32.18 | A |
| ATOM | 5283 | CG | LYS | A | 43 | 0.536 | −13.883 | 26.324 | 1.00 | 32.18 | A |
| ATOM | 5284 | CD | LYS | A | 43 | 1.622 | −14.833 | 26.798 | 1.00 | 32.02 | A |
| ATOM | 5285 | CE | LYS | A | 43 | 2.795 | −14.865 | 25.831 | 1.00 | 31.99 | A |
| ATOM | 5286 | NZ | LYS | A | 43 | 3.484 | −13.542 | 25.723 | 1.00 | 31.70 | A |
| ATOM | 5287 | C | LYS | A | 43 | −2.267 | −13.674 | 25.354 | 1.00 | 31.74 | A |
| ATOM | 5288 | O | LYS | A | 43 | −2.038 | −13.022 | 24.333 | 1.00 | 31.67 | A |
| ATOM | 5328 | N | GLY | A | 49 | 0.717 | −10.483 | 22.236 | 1.00 | 21.45 | A |
| ATOM | 5329 | CA | GLY | A | 49 | 0.900 | −11.142 | 23.516 | 1.00 | 20.85 | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine $F_{2\alpha}$(U46)

| ATOM | 5330 | C   | GLY | A | 49 | 1.735  | −10.433 | 24.567 | 1.00 | 20.53 | A |
|------|------|-----|-----|---|----|--------|---------|--------|------|-------|---|
| ATOM | 5331 | O   | GLY | A | 49 | 2.506  | −11.072 | 25.276 | 1.00 | 20.53 | A |
| ATOM | 5332 | N   | LYS | A | 50 | 1.590  | −9.120  | 24.688 | 1.00 | 20.06 | A |
| ATOM | 5333 | CA  | LYS | A | 50 | 2.354  | −8.390  | 25.686 | 1.00 | 19.66 | A |
| ATOM | 5334 | CB  | LYS | A | 50 | 3.683  | −7.916  | 25.085 | 1.00 | 19.97 | A |
| ATOM | 5335 | CG  | LYS | A | 50 | 4.636  | −9.061  | 24.812 | 1.00 | 20.63 | A |
| ATOM | 5336 | CD  | LYS | A | 50 | 5.846  | −8.644  | 24.024 | 1.00 | 21.03 | A |
| ATOM | 5337 | CE  | LYS | A | 50 | 6.699  | −9.864  | 23.706 | 1.00 | 21.10 | A |
| ATOM | 5338 | NZ  | LYS | A | 50 | 5.873  | −10.927 | 23.044 | 1.00 | 21.21 | A |
| ATOM | 5339 | C   | LYS | A | 50 | 1.601  | −7.206  | 26.271 | 1.00 | 19.21 | A |
| ATOM | 5340 | O   | LYS | A | 50 | 0.713  | −6.633  | 25.636 | 1.00 | 18.74 | A |
| ATOM | 5341 | N   | ILE | A | 51 | 1.963  | −6.852  | 27.497 | 1.00 | 18.42 | A |
| ATOM | 5342 | CA  | ILE | A | 51 | 1.354  | −5.720  | 28.162 | 1.00 | 18.05 | A |
| ATOM | 5343 | CB  | ILE | A | 51 | 0.574  | −6.149  | 29.414 | 1.00 | 18.14 | A |
| ATOM | 5344 | CG2 | ILE | A | 51 | −0.755 | −6.739  | 29.010 | 1.00 | 17.97 | A |
| ATOM | 5345 | CG1 | ILE | A | 51 | 1.404  | −7.128  | 30.246 | 1.00 | 18.34 | A |
| ATOM | 5346 | CD1 | ILE | A | 51 | 0.681  | −7.613  | 31.494 | 1.00 | 18.26 | A |
| ATOM | 5347 | C   | ILE | A | 51 | 2.424  | −4.699  | 28.538 | 1.00 | 17.67 | A |
| ATOM | 5348 | O   | ILE | A | 51 | 3.618  | −5.012  | 28.572 | 1.00 | 17.72 | A |
| ATOM | 5349 | N   | PRO | A | 52 | 2.002  | −3.473  | 28.874 | 1.00 | 17.15 | A |
| ATOM | 5350 | CD  | PRO | A | 52 | 2.906  | −2.369  | 29.239 | 1.00 | 17.33 | A |
| ATOM | 5351 | CA  | PRO | A | 52 | 0.610  | −3.021  | 28.909 | 1.00 | 16.82 | A |
| ATOM | 5352 | CB  | PRO | A | 52 | 0.703  | −1.736  | 29.713 | 1.00 | 16.81 | A |
| ATOM | 5353 | CG  | PRO | A | 52 | 1.968  | −1.159  | 29.205 | 1.00 | 16.96 | A |
| ATOM | 5354 | C   | PRO | A | 52 | −0.093 | −2.777  | 27.584 | 1.00 | 16.60 | A |
| ATOM | 5355 | O   | PRO | A | 52 | 0.526  | −2.674  | 26.526 | 1.00 | 16.29 | A |
| ATOM | 5356 | N   | ILE | A | 53 | −1.411 | −2.678  | 27.672 | 1.00 | 16.36 | A |
| ATOM | 5357 | CA  | ILE | A | 53 | −2.233 | −2.361  | 26.522 | 1.00 | 16.17 | A |
| ATOM | 5358 | CB  | ILE | A | 53 | −2.992 | −3.587  | 25.980 | 1.00 | 16.14 | A |
| ATOM | 5359 | CG2 | ILE | A | 53 | −2.000 | −4.620  | 25.440 | 1.00 | 16.39 | A |
| ATOM | 5360 | CG1 | ILE | A | 53 | −3.875 | −4.184  | 27.071 | 1.00 | 16.34 | A |
| ATOM | 5361 | CD1 | ILE | A | 53 | −4.859 | −5.218  | 26.544 | 1.00 | 16.22 | A |
| ATOM | 5362 | C   | ILE | A | 53 | −3.235 | −1.325  | 27.015 | 1.00 | 15.98 | A |
| ATOM | 5363 | O   | ILE | A | 53 | −3.563 | −1.277  | 28.202 | 1.00 | 15.70 | A |
| ATOM | 5423 | N   | HIS | A | 62 | −1.249 | −1.093  | 22.011 | 1.00 | 11.78 | A |
| ATOM | 5424 | CA  | HIS | A | 62 | −0.158 | −1.730  | 22.757 | 1.00 | 11.13 | A |
| ATOM | 5425 | CB  | HIS | A | 62 | 0.120  | −3.150  | 22.240 | 1.00 | 11.01 | A |
| ATOM | 5426 | CG  | HIS | A | 62 | 0.673  | −3.202  | 20.848 | 1.00 | 10.84 | A |
| ATOM | 5427 | CD2 | HIS | A | 62 | 1.903  | −3.533  | 20.392 | 1.00 | 10.56 | A |
| ATOM | 5428 | ND1 | HIS | A | 62 | −0.087 | −2.926  | 19.732 | 1.00 | 10.84 | A |
| ATOM | 5429 | CE1 | HIS | A | 62 | 0.650  | −3.090  | 18.648 | 1.00 | 10.55 | A |
| ATOM | 5430 | NE2 | HIS | A | 62 | 1.861  | −3.458  | 19.021 | 1.00 | 10.75 | A |
| ATOM | 5431 | C   | HIS | A | 62 | 1.112  | −0.882  | 22.665 | 1.00 | 10.62 | A |
| ATOM | 5432 | O   | HIS | A | 62 | 1.118  | 0.155   | 21.996 | 1.00 | 10.80 | A |
| ATOM | 5433 | N   | GLN | A | 63 | 2.176  | −1.337  | 23.332 | 1.00 | 10.07 | A |
| ATOM | 5434 | CA  | GLN | A | 63 | 3.465  | −0.641  | 23.377 | 1.00 | 9.39  | A |
| ATOM | 5435 | CB  | GLN | A | 63 | 3.957  | −0.289  | 21.969 | 1.00 | 9.20  | A |
| ATOM | 5436 | CG  | GLN | A | 63 | 4.702  | −1.417  | 21.248 | 1.00 | 8.99  | A |
| ATOM | 5437 | CD  | GLN | A | 63 | 5.911  | −1.932  | 22.027 | 1.00 | 8.95  | A |
| ATOM | 5438 | OE1 | GLN | A | 63 | 6.481  | −1.220  | 22.858 | 1.00 | 8.52  | A |
| ATOM | 5439 | NE2 | GLN | A | 63 | 6.315  | −3.165  | 21.745 | 1.00 | 8.76  | A |
| ATOM | 5440 | C   | GLN | A | 63 | 3.324  | 0.618   | 24.223 | 1.00 | 8.90  | A |
| ATOM | 5441 | O   | GLN | A | 63 | 2.781  | 1.629   | 23.769 | 1.00 | 9.08  | A |
| ATOM | 5442 | N   | SER | A | 64 | 3.830  | 0.554   | 25.452 | 1.00 | 8.48  | A |
| ATOM | 5443 | CA  | SER | A | 64 | 3.708  | 1.668   | 26.396 | 1.00 | 8.06  | A |
| ATOM | 5444 | CB  | SER | A | 64 | 4.440  | 1.342   | 27.706 | 1.00 | 7.67  | A |
| ATOM | 5445 | OG  | SER | A | 64 | 5.839  | 1.246   | 27.528 | 1.00 | 8.18  | A |
| ATOM | 5446 | C   | SER | A | 64 | 4.143  | 3.045   | 25.902 | 1.00 | 7.75  | A |
| ATOM | 5447 | O   | SER | A | 64 | 3.447  | 4.032   | 26.141 | 1.00 | 7.74  | A |
| ATOM | 5448 | N   | LEU | A | 65 | 5.284  | 3.126   | 25.225 | 1.00 | 7.75  | A |
| ATOM | 5449 | CA  | LEU | A | 65 | 5.754  | 4.424   | 24.752 | 1.00 | 7.47  | A |
| ATOM | 5450 | CB  | LEU | A | 65 | 7.224  | 4.346   | 24.359 | 1.00 | 7.66  | A |
| ATOM | 5451 | CG  | LEU | A | 65 | 8.162  | 3.849   | 25.461 | 1.00 | 7.74  | A |
| ATOM | 5452 | CD1 | LEU | A | 65 | 9.591  | 4.192   | 25.062 | 1.00 | 7.25  | A |
| ATOM | 5453 | CD2 | LEU | A | 65 | 7.820  | 4.516   | 26.812 | 1.00 | 7.33  | A |
| ATOM | 5454 | C   | LEU | A | 65 | 4.928  | 4.945   | 23.586 | 1.00 | 7.33  | A |
| ATOM | 5455 | O   | LEU | A | 65 | 4.768  | 6.151   | 23.426 | 1.00 | 7.33  | A |
| ATOM | 5662 | N   | ASP | A | 93 | 13.523 | 7.274   | 24.597 | 1.00 | 7.43  | A |
| ATOM | 5663 | CA  | ASP | A | 93 | 14.133 | 6.074   | 24.039 | 1.00 | 7.59  | A |
| ATOM | 5664 | CB  | ASP | A | 93 | 14.267 | 6.190   | 22.520 | 1.00 | 7.58  | A |
| ATOM | 5665 | CG  | ASP | A | 93 | 12.964 | 5.867   | 21.793 | 1.00 | 7.82  | A |
| ATOM | 5666 | OD1 | ASP | A | 93 | 12.977 | 5.837   | 20.550 | 1.00 | 8.49  | A |
| ATOM | 5667 | OD2 | ASP | A | 93 | 11.937 | 5.640   | 22.466 | 1.00 | 7.73  | A |
| ATOM | 5668 | C   | ASP | A | 93 | 15.494 | 5.763   | 24.674 | 1.00 | 7.65  | A |
| ATOM | 5669 | O   | ASP | A | 93 | 15.839 | 4.597   | 24.858 | 1.00 | 8.00  | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine F$_{2α}$(U46)

| ATOM | 5670 | N | THR | A | 94 | 16.259 | 6.800 | 25.009 | 1.00 | 7.91 | A |
|---|---|---|---|---|---|---|---|---|---|---|---|
| ATOM | 5671 | CA | THR | A | 94 | 17.561 | 6.608 | 25.646 | 1.00 | 8.08 | A |
| ATOM | 5672 | CB | THR | A | 94 | 18.281 | 7.963 | 25.879 | 1.00 | 8.13 | A |
| ATOM | 5673 | OG1 | THR | A | 94 | 18.619 | 8.547 | 24.617 | 1.00 | 8.31 | A |
| ATOM | 5674 | CG2 | THR | A | 94 | 19.557 | 7.772 | 26.701 | 1.00 | 8.08 | A |
| ATOM | 5675 | C | THR | A | 94 | 17.361 | 5.905 | 26.993 | 1.00 | 8.54 | A |
| ATOM | 5676 | O | THR | A | 94 | 18.046 | 4.925 | 27.308 | 1.00 | 8.42 | A |
| ATOM | 5677 | N | LEU | A | 95 | 16.424 | 6.410 | 27.788 | 1.00 | 8.76 | A |
| ATOM | 5678 | CA | LEU | A | 95 | 16.137 | 5.804 | 29.079 | 1.00 | 9.53 | A |
| ATOM | 5679 | CB | LEU | A | 95 | 15.107 | 6.642 | 29.851 | 1.00 | 9.33 | A |
| ATOM | 5680 | CG | LEU | A | 95 | 15.647 | 7.972 | 30.383 | 1.00 | 9.50 | A |
| ATOM | 5681 | CD1 | LEU | A | 95 | 14.517 | 8.827 | 30.949 | 1.00 | 9.22 | A |
| ATOM | 5682 | CD2 | LEU | A | 95 | 16.694 | 7.684 | 31.453 | 1.00 | 9.41 | A |
| ATOM | 5683 | C | LEU | A | 95 | 15.618 | 4.377 | 28.879 | 1.00 | 9.79 | A |
| ATOM | 5684 | O | LEU | A | 95 | 16.055 | 3.460 | 29.566 | 1.00 | 9.96 | A |
| ATOM | 5685 | N | ASP | A | 96 | 14.709 | 4.200 | 27.920 | 1.00 | 10.44 | A |
| ATOM | 5686 | CA | ASP | A | 96 | 14.123 | 2.896 | 27.626 | 1.00 | 11.05 | A |
| ATOM | 5687 | CB | ASP | A | 96 | 13.062 | 3.027 | 26.529 | 1.00 | 11.36 | A |
| ATOM | 5688 | CG | ASP | A | 96 | 12.107 | 1.841 | 26.499 | 1.00 | 11.78 | A |
| ATOM | 5689 | OD1 | ASP | A | 96 | 11.640 | 1.431 | 27.579 | 1.00 | 12.41 | A |
| ATOM | 5690 | OD2 | ASP | A | 96 | 11.806 | 1.334 | 25.409 | 1.00 | 12.03 | A |
| ATOM | 5691 | C | ASP | A | 96 | 15.182 | 1.876 | 27.201 | 1.00 | 11.34 | A |
| ATOM | 5692 | O | ASP | A | 96 | 15.169 | 0.734 | 27.650 | 1.00 | 11.33 | A |
| ATOM | 5693 | N | ASP | A | 97 | 16.092 | 2.294 | 26.329 | 1.00 | 11.73 | A |
| ATOM | 5694 | CA | ASP | A | 97 | 17.154 | 1.412 | 25.875 | 1.00 | 12.14 | A |
| ATOM | 5695 | CB | ASP | A | 97 | 18.136 | 2.154 | 24.963 | 1.00 | 11.82 | A |
| ATOM | 5696 | CG | ASP | A | 97 | 17.599 | 2.373 | 23.544 | 1.00 | 11.92 | A |
| ATOM | 5697 | OD1 | ASP | A | 97 | 18.280 | 3.083 | 22.784 | 1.00 | 11.78 | A |
| ATOM | 5698 | OD2 | ASP | A | 97 | 16.524 | 1.840 | 23.187 | 1.00 | 11.79 | A |
| ATOM | 5699 | C | ASP | A | 97 | 17.924 | 0.865 | 27.084 | 1.00 | 12.59 | A |
| ATOM | 5700 | O | ASP | A | 97 | 18.228 | −0.326 | 27.150 | 1.00 | 12.62 | A |
| ATOM | 5701 | N | PHE | A | 98 | 18.242 | 1.731 | 28.041 | 1.00 | 13.02 | A |
| ATOM | 5702 | CA | PHE | A | 98 | 18.992 | 1.296 | 29.219 | 1.00 | 13.80 | A |
| ATOM | 5703 | CB | PHE | A | 98 | 19.449 | 2.500 | 30.047 | 1.00 | 13.80 | A |
| ATOM | 5704 | CG | PHE | A | 98 | 20.332 | 2.127 | 31.203 | 1.00 | 14.07 | A |
| ATOM | 5705 | CD1 | PHE | A | 98 | 21.550 | 1.488 | 30.990 | 1.00 | 14.20 | A |
| ATOM | 5706 | CD2 | PHE | A | 98 | 19.937 | 2.391 | 32.507 | 1.00 | 14.15 | A |
| ATOM | 5707 | CE1 | PRE | A | 98 | 22.358 | 1.115 | 32.064 | 1.00 | 14.32 | A |
| ATOM | 5708 | CE2 | PHE | A | 98 | 20.736 | 2.022 | 33.583 | 1.00 | 14.28 | A |
| ATOM | 5709 | CZ | PHE | A | 98 | 21.948 | 1.384 | 33.361 | 1.00 | 14.12 | A |
| ATOM | 5710 | C | PHE | A | 98 | 18.209 | 0.335 | 30.112 | 1.00 | 14.33 | A |
| ATOM | 5711 | O | PHE | A | 98 | 18.705 | −0.739 | 30.467 | 1.00 | 14.62 | A |
| ATOM | 5712 | N | MET | A | 99 | 16.992 | 0.722 | 30.482 | 1.00 | 14.73 | A |
| ATOM | 5713 | CA | MET | A | 99 | 16.158 | −0.120 | 31.329 | 1.00 | 15.34 | A |
| ATOM | 5714 | CB | MET | A | 99 | 14.798 | 0.546 | 31.574 | 1.00 | 15.08 | A |
| ATOM | 5715 | CG | MET | A | 99 | 14.878 | 1.932 | 32.202 | 1.00 | 14.94 | A |
| ATOM | 5716 | SD | MET | A | 99 | 15.699 | 1.910 | 33.803 | 1.00 | 14.67 | A |
| ATOM | 5717 | CE | MET | A | 99 | 14.395 | 1.275 | 34.807 | 1.00 | 14.69 | A |
| ATOM | 5718 | C | MET | A | 99 | 15.938 | −1.489 | 30.691 | 1.00 | 16.11 | A |
| ATOM | 5719 | O | MET | A | 99 | 15.882 | −2.504 | 31.387 | 1.00 | 15.98 | A |
| ATOM | 5720 | N | SER | A | 100 | 15.811 | −1.516 | 29.366 | 1.00 | 16.74 | A |
| ATOM | 5721 | CA | SER | A | 100 | 15.576 | −2.767 | 28.656 | 1.00 | 17.44 | A |
| ATOM | 5722 | CB | SER | A | 100 | 15.116 | −2.479 | 27.225 | 1.00 | 17.47 | A |
| ATOM | 5723 | OG | SER | A | 100 | 13.823 | −1.884 | 27.234 | 1.00 | 17.51 | A |
| ATOM | 5724 | C | SER | A | 100 | 16.797 | −3.681 | 28.656 | 1.00 | 18.04 | A |
| ATOM | 5725 | O | SER | A | 100 | 16.674 | −4.888 | 28.436 | 1.00 | 18.07 | A |
| ATOM | 5726 | N | CYS | A | 101 | 17.972 | −3.111 | 28.912 | 1.00 | 18.65 | A |
| ATOM | 5727 | CA | CYS | A | 101 | 19.196 | −3.905 | 28.964 | 1.00 | 19.36 | A |
| ATOM | 5728 | CB | CYS | A | 101 | 20.428 | −3.006 | 29.108 | 1.00 | 19.22 | A |
| ATOM | 5729 | SG | CYS | A | 101 | 20.898 | −2.082 | 27.630 | 1.00 | 20.13 | A |
| ATOM | 5730 | C | CYS | A | 101 | 19.167 | −4.889 | 30.134 | 1.00 | 19.75 | A |
| ATOM | 5731 | O | CYS | A | 101 | 19.772 | −5.950 | 30.059 | 1.00 | 19.91 | A |
| ATOM | 5732 | N | PHE | A | 102 | 18.482 | −4.533 | 31.218 | 1.00 | 20.31 | A |
| ATOM | 5733 | CA | PHE | A | 102 | 18.410 | −5.420 | 32.376 | 1.00 | 21.09 | A |
| ATOM | 5734 | CB | PHE | A | 102 | 17.826 | −4.693 | 33.594 | 1.00 | 20.83 | A |
| ATOM | 5735 | CG | PHE | A | 102 | 18.672 | −3.551 | 34.087 | 1.00 | 20.72 | A |
| ATOM | 5736 | CD1 | PHE | A | 102 | 18.775 | −2.376 | 33.344 | 1.00 | 20.56 | A |
| ATOM | 5737 | CD2 | PHE | A | 102 | 19.374 | −3.652 | 35.290 | 1.00 | 20.64 | A |
| ATOM | 5738 | CE1 | PHE | A | 102 | 19.565 | −1.313 | 33.788 | 1.00 | 20.64 | A |
| ATOM | 5739 | CE2 | PHE | A | 102 | 20.170 | −2.597 | 35.750 | 1.00 | 20.52 | A |
| ATOM | 5740 | CZ | PHE | A | 102 | 20.267 | −1.423 | 34.996 | 1.00 | 20.66 | A |
| ATOM | 5741 | C | PHE | A | 102 | 17.554 | −6.645 | 32.060 | 1.00 | 21.79 | A |
| ATOM | 5742 | O | PHE | A | 102 | 16.490 | −6.525 | 31.456 | 1.00 | 21.62 | A |
| ATOM | 5743 | N | PRO | A | 103 | 18.024 | −7.844 | 32.450 | 1.00 | 22.58 | A |
| ATOM | 5744 | CD | PRO | A | 103 | 19.392 | −8.117 | 32.928 | 1.00 | 22.84 | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine F$_{2α}$(U46)

| ATOM | 5745 | CA | PRO | A | 103 | 17.297 | −9.098 | 32.211 | 1.00 | 23.41 | A |
|---|---|---|---|---|---|---|---|---|---|---|---|
| ATOM | 5746 | CB | PRO | A | 103 | 18.415 | −10.133 | 32.185 | 1.00 | 23.19 | A |
| ATOM | 5747 | CG | PRO | A | 103 | 19.353 | −9.611 | 33.222 | 1.00 | 23.10 | A |
| ATOM | 5748 | C | PRO | A | 103 | 16.272 | −9.366 | 33.321 | 1.00 | 24.25 | A |
| ATOM | 5749 | O | PRO | A | 103 | 16.459 | −10.248 | 34.160 | 1.00 | 24.19 | A |
| ATOM | 5750 | N | TRP | A | 104 | 15.191 | −8.594 | 33.313 | 1.00 | 25.16 | A |
| ATOM | 5751 | CA | TRP | A | 104 | 14.142 | −8.722 | 34.313 | 1.00 | 26.25 | A |
| ATOM | 5752 | CB | TRP | A | 104 | 13.049 | −7.673 | 34.072 | 1.00 | 25.95 | A |
| ATOM | 5753 | CG | TRP | A | 104 | 13.551 | −6.261 | 33.946 | 1.00 | 25.64 | A |
| ATOM | 5754 | CD2 | TRP | A | 104 | 13.907 | −5.375 | 35.016 | 1.00 | 25.47 | A |
| ATOM | 5755 | CE2 | TRP | A | 104 | 14.332 | −4.162 | 34.429 | 1.00 | 25.40 | A |
| ATOM | 5756 | CE3 | TRP | A | 104 | 13.909 | −5.488 | 36.412 | 1.00 | 25.27 | A |
| ATOM | 5757 | CD1 | TRP | A | 104 | 13.770 | −5.568 | 32.788 | 1.00 | 25.58 | A |
| ATOM | 5758 | NE1 | TRP | A | 104 | 14.237 | −4.307 | 33.070 | 1.00 | 25.45 | A |
| ATOM | 5759 | CZ2 | TRP | A | 104 | 14.757 | −3.067 | 35.193 | 1.00 | 25.38 | A |
| ATOM | 5760 | CZ3 | TRP | A | 104 | 14.331 | −4.398 | 37.173 | 1.00 | 25.16 | A |
| ATOM | 5761 | CR2 | TRP | A | 104 | 14.749 | −3.205 | 36.560 | 1.00 | 25.21 | A |
| ATOM | 5762 | C | TRP | A | 104 | 13.511 | −10.115 | 34.334 | 1.00 | 27.21 | A |
| ATOM | 5763 | O | TRP | A | 104 | 13.078 | −10.597 | 35.383 | 1.00 | 27.22 | A |
| ATOM | 5764 | N | ALA | A | 105 | 13.472 | −10.763 | 33.175 | 1.00 | 28.32 | A |
| ATOM | 5765 | CA | ALA | A | 105 | 12.872 | −12.087 | 33.058 | 1.00 | 29.49 | A |
| ATOM | 5766 | CB | ALA | A | 105 | 12.207 | −12.226 | 31.697 | 1.00 | 29.48 | A |
| ATOM | 5767 | C | ALA | A | 105 | 13.853 | −13.233 | 33.270 | 1.00 | 30.44 | A |
| ATOM | 5768 | O | ALA | A | 105 | 13.445 | −14.391 | 33.354 | 1.00 | 30.58 | A |
| ATOM | 5769 | N | GLU | A | 106 | 15.140 | −12.917 | 33.369 | 1.00 | 31.43 | A |
| ATOM | 5770 | CA | GLU | A | 106 | 16.147 | −13.954 | 33.552 | 1.00 | 32.55 | A |
| ATOM | 5771 | CB | GLU | A | 106 | 17.545 | −13.338 | 33.620 | 1.00 | 32.51 | A |
| ATOM | 5772 | CG | GLU | A | 106 | 18.634 | −14.386 | 33.634 | 1.00 | 32.51 | A |
| ATOM | 5773 | CD | GLU | A | 106 | 18.498 | −15.352 | 32.472 | 1.00 | 32.54 | A |
| ATOM | 5774 | OE1 | GLU | A | 106 | 18.761 | −16.555 | 32.662 | 1.00 | 32.34 | A |
| ATOM | 5775 | OE2 | GLU | A | 106 | 18.129 | −14.905 | 31.365 | 1.00 | 32.59 | A |
| ATOM | 5776 | C | GLU | A | 106 | 15.913 | −14.809 | 34.791 | 1.00 | 33.37 | A |
| ATOM | 5777 | O | GLU | A | 106 | 15.830 | −14.294 | 35.908 | 1.00 | 33.46 | A |
| ATOM | 5778 | N | LYS | A | 107 | 15.813 | −16.121 | 34.588 | 1.00 | 34.40 | A |
| ATOM | 5779 | CA | LYS | A | 107 | 15.592 | −17.048 | 35.695 | 1.00 | 35.40 | A |
| ATOM | 5780 | CB | LYS | A | 107 | 14.830 | −18.287 | 35.212 | 1.00 | 35.45 | A |
| ATOM | 5781 | CG | LYS | A | 107 | 13.486 | −17.992 | 34.553 | 1.00 | 35.72 | A |
| ATOM | 5782 | CD | LYS | A | 107 | 12.523 | −17.293 | 35.497 | 1.00 | 35.84 | A |
| ATOM | 5783 | CE | LYS | A | 107 | 12.103 | −18.197 | 36.639 | 1.00 | 36.12 | A |
| ATOM | 5784 | NZ | LYS | A | 107 | 11.273 | −17.459 | 37.636 | 1.00 | 36.20 | A |
| ATOM | 5785 | C | LYS | A | 107 | 16.915 | −17.471 | 36.336 | 1.00 | 36.00 | A |
| ATOM | 5786 | O | LYS | A | 107 | 16.947 | −17.902 | 37.490 | 1.00 | 36.10 | A |
| ATOM | 5787 | N | LYS | A | 108 | 18.003 | −17.346 | 35.584 | 1.00 | 36.66 | A |
| ATOM | 5788 | CA | LYS | A | 108 | 19.325 | −17.698 | 36.088 | 1.00 | 37.40 | A |
| ATOM | 5789 | CB | LYS | A | 108 | 20.295 | −17.894 | 34.923 | 1.00 | 37.54 | A |
| ATOM | 5790 | CG | LYS | A | 108 | 19.855 | −18.959 | 33.941 | 1.00 | 37.73 | A |
| ATOM | 5791 | CD | LYS | A | 108 | 20.783 | −19.026 | 32.748 | 1.00 | 37.95 | A |
| ATOM | 5792 | CE | LYS | A | 108 | 20.335 | −20.101 | 31.781 | 1.00 | 38.07 | A |
| ATOM | 5793 | NZ | LYS | A | 108 | 21.226 | −20.180 | 30.593 | 1.00 | 38.35 | A |
| ATOM | 5794 | C | LYS | A | 108 | 19.824 | −16.576 | 36.992 | 1.00 | 37.85 | A |
| ATOM | 5795 | O | LYS | A | 108 | 20.361 | −15.575 | 36.514 | 1.00 | 37.87 | A |
| ATOM | 5796 | N | GLN | A | 109 | 19.650 | −16.751 | 38.298 | 1.00 | 38.38 | A |
| ATOM | 5797 | CA | GLN | A | 109 | 20.057 | −15.742 | 39.274 | 1.00 | 38.89 | A |
| ATOM | 5798 | CB | GLN | A | 109 | 19.893 | −16.287 | 40.696 | 1.00 | 39.27 | A |
| ATOM | 5799 | CG | GLN | A | 109 | 19.103 | −15.372 | 41.621 | 1.00 | 39.77 | A |
| ATOM | 5800 | CD | GLN | A | 109 | 17.631 | −15.280 | 41.236 | 1.00 | 40.04 | A |
| ATOM | 5801 | OE1 | GLN | A | 109 | 16.878 | −14.472 | 41.791 | 1.00 | 40.13 | A |
| ATOM | 5802 | NE2 | GLN | A | 109 | 17.214 | −16.116 | 40.287 | 1.00 | 40.11 | A |
| ATOM | 5803 | C | GLN | A | 109 | 21.491 | −15.264 | 39.081 | 1.00 | 38.96 | A |
| ATOM | 5804 | O | GLN | A | 109 | 21.755 | −14.061 | 39.052 | 1.00 | 39.02 | A |
| ATOM | 5805 | N | ASP | A | 110 | 22.413 | −16.211 | 38.951 | 1.00 | 39.02 | A |
| ATOM | 5806 | CA | ASP | A | 110 | 23.826 | −15.890 | 38.773 | 1.00 | 39.02 | A |
| ATOM | 5807 | CB | ASP | A | 110 | 24.631 | −17.178 | 38.608 | 1.00 | 39.32 | A |
| ATOM | 5808 | CG | ASP | A | 110 | 24.226 | −17.956 | 37.375 | 1.00 | 39.50 | A |
| ATOM | 5809 | OD1 | ASP | A | 110 | 23.005 | −18.097 | 37.141 | 1.00 | 39.58 | A |
| ATOM | 5810 | OD2 | ASP | A | 110 | 25.124 | −18.429 | 36.648 | 1.00 | 39.67 | A |
| ATOM | 5811 | C | ASP | A | 110 | 24.061 | −14.977 | 37.571 | 1.00 | 38.89 | A |
| ATOM | 5812 | O | ASP | A | 110 | 24.802 | −13.999 | 37.663 | 1.00 | 38.88 | A |
| ATOM | 5813 | N | VAL | A | 111 | 23.433 | −15.302 | 36.445 | 1.00 | 38.64 | A |
| ATOM | 5814 | CA | VAL | A | 111 | 23.581 | −14.507 | 35.231 | 1.00 | 38.36 | A |
| ATOM | 5815 | CB | VAL | A | 111 | 23.054 | −15.270 | 34.001 | 1.00 | 38.38 | A |
| ATOM | 5816 | CG1 | VAL | A | 111 | 23.198 | −14.412 | 32.753 | 1.00 | 38.34 | A |
| ATOM | 5817 | CG2 | VAL | A | 111 | 23.812 | −16.573 | 33.842 | 1.00 | 38.44 | A |
| ATOM | 5818 | C | VAL | A | 111 | 22.829 | −13.183 | 35.349 | 1.00 | 38.10 | A |
| ATOM | 5819 | O | VAL | A | 111 | 23.297 | −12.145 | 34.880 | 1.00 | 37.99 | A |

TABLE 3-continued

Three-dimensional structural coordinate of the complex of human hematopoietic PGDS (SEQ ID NO: 1) with calcium, glutathione and 9,11-dideoxy-9α,11α-methanoepoxyprostaglandine $F_{2\alpha}$(U46)

| ATOM | 5820 | N | LYS | A | 112 | 21.663 | -13.229 | 35.980 | 1.00 | 37.84 | A |
|---|---|---|---|---|---|---|---|---|---|---|---|
| ATOM | 5821 | CA | LYS | A | 112 | 20.851 | -12.036 | 36.163 | 1.00 | 37.63 | A |
| ATOM | 5822 | CB | LYS | A | 112 | 19.477 | -12.414 | 36.719 | 1.00 | 37.62 | A |
| ATOM | 5823 | CG | LYS | A | 112 | 18.545 | -11.233 | 36.904 | 1.00 | 37.60 | A |
| ATOM | 5824 | CD | LYS | A | 112 | 17.185 | -11.663 | 37.410 | 1.00 | 37.64 | A |
| ATOM | 5825 | CE | LYS | A | 112 | 16.284 | -10.457 | 37.615 | 1.00 | 37.70 | A |
| ATOM | 5826 | NZ | LYS | A | 112 | 14.951 | -10.845 | 38.142 | 1.00 | 37.88 | A |
| ATOM | 5827 | C | LYS | A | 112 | 21.538 | -11.050 | 37.105 | 1.00 | 37.48 | A |
| ATOM | 5828 | O | LYS | A | 112 | 21.554 | -9.846 | 36.850 | 1.00 | 37.36 | A |
| ATOM | 5829 | N | GLU | A | 113 | 22.112 | -11.565 | 38.189 | 1.00 | 37.26 | A |
| ATOM | 5830 | CA | GLU | A | 113 | 22.796 | -10.723 | 39.166 | 1.00 | 37.10 | A |
| ATOM | 5831 | CB | GLU | A | 113 | 23.143 | -11.537 | 40.420 | 1.00 | 37.36 | A |
| ATOM | 5832 | CG | GLU | A | 113 | 23.579 | -10.692 | 41.622 | 1.00 | 37.69 | A |
| ATOM | 5833 | CD | GLU | A | 113 | 22.449 | -9.851 | 42.207 | 1.00 | 37.86 | A |
| ATOM | 5834 | OE1 | GLU | A | 113 | 22.711 | -9.076 | 43.157 | 1.00 | 37.95 | A |
| ATOM | 5835 | OE2 | GLU | A | 113 | 21.301 | -9.970 | 41.723 | 1.00 | 37.89 | A |
| ATOM | 5836 | C | GLU | A | 113 | 24.070 | -10.117 | 38.573 | 1.00 | 36.80 | A |
| ATOM | 5837 | O | GLU | A | 113 | 24.378 | -8.949 | 38.808 | 1.00 | 36.69 | A |
| ATOM | 5838 | N | GLN | A | 114 | 24.804 | -10.914 | 37.803 | 1.00 | 36.47 | A |
| ATOM | 5839 | CA | GLN | A | 114 | 26.037 | -10.448 | 37.181 | 1.00 | 36.17 | A |
| ATOM | 5840 | CB | GLN | A | 114 | 26.775 | -11.622 | 36.527 | 1.00 | 36.48 | A |
| ATOM | 5841 | CG | GLN | A | 114 | 27.387 | -12.597 | 37.525 | 1.00 | 37.03 | A |
| ATOM | 5842 | CD | GLN | A | 114 | 27.971 | -13.841 | 36.869 | 1.00 | 37.38 | A |
| ATOM | 5843 | OE1 | GLN | A | 114 | 28.847 | -13.752 | 36.005 | 1.00 | 37.53 | A |
| ATOM | 5844 | NE2 | GLN | A | 114 | 27.487 | -15.012 | 37.282 | 1.00 | 37.45 | A |
| ATOM | 5845 | C | GLN | A | 114 | 25.768 | -9.359 | 36.148 | 1.00 | 35.76 | A |
| ATOM | 5846 | O | GLN | A | 114 | 26.582 | -8.452 | 35.963 | 1.00 | 35.71 | A |
| ATOM | 5847 | N | MET | A | 115 | 24.622 | -9.447 | 35.481 | 1.00 | 35.26 | A |
| ATOM | 5848 | CA | MET | A | 115 | 24.253 | -8.459 | 34.474 | 1.00 | 34.74 | A |
| ATOM | 5849 | CB | MET | A | 115 | 23.147 | -9.006 | 33.573 | 1.00 | 35.14 | A |
| ATOM | 5850 | CG | MET | A | 115 | 22.929 | -8.183 | 32.322 | 1.00 | 35.72 | A |
| ATOM | 5851 | SD | MET | A | 115 | 24.425 | -8.101 | 31.312 | 1.00 | 36.85 | A |
| ATOM | 5852 | CE | MET | A | 115 | 25.020 | -6.470 | 31.691 | 1.00 | 36.19 | A |
| ATOM | 5853 | C | MET | A | 115 | 23.792 | -7.164 | 35.137 | 1.00 | 34.07 | A |
| ATOM | 5854 | O | MET | A | 115 | 24.214 | -6.079 | 34.745 | 1.00 | 34.00 | A |
| ATOM | 5855 | N | PHE | A | 116 | 22.926 | -7.280 | 36.140 | 1.00 | 33.41 | A |
| ATOM | 5856 | CA | PHE | A | 116 | 22.437 | -6.104 | 36.856 | 1.00 | 32.72 | A |
| ATOM | 5857 | CB | PHE | A | 116 | 21.485 | -6.507 | 37.982 | 1.00 | 32.41 | A |
| ATOM | 5858 | CG | PHE | A | 116 | 20.039 | -6.520 | 37.583 | 1.00 | 32.03 | A |
| ATOM | 5859 | CD1 | PHE | A | 116 | 19.574 | -7.415 | 36.627 | 1.00 | 31.76 | A |
| ATOM | 5860 | CD2 | PHE | A | 116 | 19.140 | -5.630 | 38.164 | 1.00 | 31.87 | A |
| ATOM | 5861 | CE1 | PHE | A | 116 | 18.235 | -7.426 | 36.257 | 1.00 | 31.75 | A |
| ATOM | 5862 | CE2 | PHE | A | 116 | 17.798 | -5.632 | 37.801 | 1.00 | 31.79 | A |
| ATOM | 5863 | CZ | PHE | A | 116 | 17.343 | -6.532 | 36.845 | 1.00 | 31.63 | A |
| ATOM | 5864 | C | PHE | A | 116 | 23.618 | -5.353 | 37.452 | 1.00 | 32.46 | A |
| ATOM | 5865 | O | PHE | A | 116 | 23.775 | -4.147 | 37.253 | 1.00 | 32.41 | A |
| ATOM | 6152 | N | TYR | A | 152 | 9.234 | 10.144 | 32.617 | 1.00 | 9.71 | A |
| ATOM | 6153 | CA | TYR | A | 152 | 9.916 | 8.878 | 32.397 | 1.00 | 9.80 | A |
| ATOM | 6154 | CB | TYR | A | 152 | 10.132 | 8.650 | 30.901 | 1.00 | 9.99 | A |
| ATOM | 6155 | CG | TYR | A | 152 | 10.202 | 7.183 | 30.526 | 1.00 | 10.38 | A |
| ATOM | 6156 | CD1 | TYR | A | 152 | 9.213 | 6.281 | 30.944 | 1.00 | 10.55 | A |
| ATOM | 6157 | CE1 | TYR | A | 152 | 9.267 | 4.928 | 30.581 | 1.00 | 10.77 | A |
| ATOM | 6158 | CD2 | TYR | A | 152 | 11.243 | 6.698 | 29.742 | 1.00 | 10.42 | A |
| ATOM | 6159 | CE2 | TYR | A | 152 | 11.308 | 5.353 | 29.375 | 1.00 | 10.66 | A |
| ATOM | 6160 | CZ | TYR | A | 152 | 10.325 | 4.477 | 29.792 | 1.00 | 10.74 | A |
| ATOM | 6161 | OH | TYR | A | 152 | 10.393 | 3.156 | 29.410 | 1.00 | 10.82 | A |
| ATOM | 6162 | C | TYR | A | 152 | 11.245 | 8.820 | 33.157 | 1.00 | 9.88 | A |
| ATOM | 6163 | O | TYR | A | 152 | 11.655 | 7.755 | 33.621 | 1.00 | 9.73 | A |
| ATOM | 6164 | N | TRP | A | 153 | 11.907 | 9.965 | 33.296 | 1.00 | 9.89 | A |
| ATOM | 6165 | CA | TRP | A | 153 | 13.158 | 10.012 | 34.036 | 1.00 | 10.03 | A |
| ATOM | 6166 | CB | TRP | A | 153 | 13.808 | 11.398 | 33.925 | 1.00 | 10.21 | A |
| ATOM | 6167 | CG | TRP | A | 153 | 14.774 | 11.688 | 35.031 | 1.00 | 10.40 | A |
| ATOM | 6168 | CD2 | TRP | A | 153 | 15.930 | 10.920 | 35.389 | 1.00 | 10.68 | A |
| ATOM | 6169 | CE2 | TRP | A | 153 | 16.491 | 11.521 | 36.539 | 1.00 | 10.78 | A |
| ATOM | 6170 | CE3 | TRP | A | 153 | 16.544 | 9.783 | 34.853 | 1.00 | 10.67 | A |
| ATOM | 6171 | CD1 | TRP | A | 153 | 14.688 | 12.696 | 35.943 | 1.00 | 10.44 | A |
| ATOM | 6172 | NE1 | TRP | A | 153 | 15.714 | 12.603 | 36.854 | 1.00 | 10.64 | A |
| ATOM | 6173 | CZ2 | TRP | A | 153 | 17.637 | 11.018 | 37.167 | 1.00 | 10.84 | A |
| ATOM | 6174 | CZ3 | TRP | A | 153 | 17.689 | 9.282 | 35.478 | 1.00 | 10.82 | A |
| ATOM | 6175 | CH2 | TRP | A | 153 | 18.220 | 9.902 | 36.623 | 1.00 | 10.64 | A |
| ATOM | 6176 | C | TRP | A | 153 | 12.893 | 9.676 | 35.502 | 1.00 | 10.03 | A |
| ATOM | 6177 | O | TRP | A | 153 | 13.602 | 8.861 | 36.098 | 1.00 | 10.17 | A |
| ATOM | 6178 | N | GLU | A | 154 | 11.869 | 10.295 | 36.078 | 1.00 | 10.10 | A |
| ATOM | 6179 | CA | GLU | A | 154 | 11.524 | 10.048 | 37.474 | 1.00 | 10.17 | A |
| ATOM | 6180 | CB | GLU | A | 154 | 10.403 | 11.001 | 37.919 | 1.00 | 10.10 | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine $F_{2α}$(U46)

| ATOM | 6181 | CG  | GLU | A | 154 | 10.138 | 11.016 | 39.422 | 1.00 | 9.74  | A |
|------|------|-----|-----|---|-----|--------|--------|--------|------|-------|---|
| ATOM | 6182 | CD  | GLU | A | 154 | 9.268  | 9.858  | 39.879 | 1.00 | 9.86  | A |
| ATOM | 6183 | OE1 | GLU | A | 154 | 9.252  | 9.560  | 41.095 | 1.00 | 9.89  | A |
| ATOM | 6184 | OE2 | GLU | A | 154 | 8.588  | 9.247  | 39.027 | 1.00 | 9.57  | A |
| ATOM | 6185 | C   | GLU | A | 154 | 11.095 | 8.587  | 37.641 | 1.00 | 10.51 | A |
| ATOM | 6186 | O   | GLU | A | 154 | 11.481 | 7.927  | 38.608 | 1.00 | 10.53 | A |
| ATOM | 6187 | N   | ILE | A | 155 | 10.321 | 8.079  | 36.683 | 1.00 | 10.63 | A |
| ATOM | 6188 | CA  | ILE | A | 155 | 9.855  | 6.700  | 36.739 | 1.00 | 10.71 | A |
| ATOM | 6189 | CB  | ILE | A | 155 | 8.823  | 6.430  | 35.625 | 1.00 | 10.90 | A |
| ATOM | 6190 | CG2 | ILE | A | 155 | 8.485  | 4.944  | 35.555 | 1.00 | 10.77 | A |
| ATOM | 6191 | CG1 | ILE | A | 155 | 7.559  | 7.254  | 35.908 | 1.00 | 10.69 | A |
| ATOM | 6192 | CD1 | ILE | A | 155 | 6.531  | 7.198  | 34.810 | 1.00 | 10.76 | A |
| ATOM | 6193 | C   | ILE | A | 155 | 11.013 | 5.710  | 36.641 | 1.00 | 10.99 | A |
| ATOM | 6194 | O   | ILE | A | 155 | 11.147 | 4.802  | 37.475 | 1.00 | 10.97 | A |
| ATOM | 6195 | N   | CYS | A | 156 | 11.863 | 5.902  | 35.638 | 1.00 | 11.08 | A |
| ATOM | 6196 | CA  | CYS | A | 156 | 13.017 | 5.030  | 35.434 | 1.00 | 11.24 | A |
| ATOM | 6197 | CB  | CYS | A | 156 | 13.719 | 5.390  | 34.120 | 1.00 | 11.05 | A |
| ATOM | 6198 | SG  | CYS | A | 156 | 12.789 | 4.896  | 32.650 | 1.00 | 11.30 | A |
| ATOM | 6199 | C   | CYS | A | 156 | 14.018 | 5.108  | 36.583 | 1.00 | 11.50 | A |
| ATOM | 6200 | O   | CYS | A | 156 | 14.495 | 4.078  | 37.065 | 1.00 | 11.70 | A |
| ATOM | 6201 | N   | SER | A | 157 | 14.334 | 6.325  | 37.019 | 1.00 | 11.70 | A |
| ATOM | 6202 | CA  | SER | A | 157 | 15.289 | 6.512  | 38.105 | 1.00 | 12.05 | A |
| ATOM | 6203 | CB  | SER | A | 157 | 15.615 | 7.997  | 38.287 | 1.00 | 11.74 | A |
| ATOM | 6204 | OG  | SER | A | 157 | 14.494 | 8.732  | 38.739 | 1.00 | 11.48 | A |
| ATOM | 6205 | C   | SER | A | 157 | 14.789 | 5.924  | 39.424 | 1.00 | 12.41 | A |
| ATOM | 6206 | O   | SER | A | 157 | 15.585 | 5.500  | 40.266 | 1.00 | 12.70 | A |
| ATOM | 6207 | N   | THR | A | 158 | 13.475 | 5.905  | 39.612 | 1.00 | 12.70 | A |
| ATOM | 6208 | CA  | THR | A | 158 | 12.913 | 5.341  | 40.829 | 1.00 | 13.05 | A |
| ATOM | 6209 | CB  | THR | A | 158 | 11.379 | 5.466  | 40.853 | 1.00 | 13.03 | A |
| ATOM | 6210 | OG1 | THR | A | 158 | 11.014 | 6.842  | 41.007 | 1.00 | 12.82 | A |
| ATOM | 6211 | CG2 | THR | A | 158 | 10.791 | 4.659  | 42.011 | 1.00 | 12.99 | A |
| ATOM | 6212 | C   | THR | A | 158 | 13.284 | 3.863  | 40.939 | 1.00 | 13.54 | A |
| ATOM | 6213 | O   | THR | A | 158 | 13.754 | 3.407  | 41.981 | 1.00 | 13.26 | A |
| ATOM | 6214 | N   | THR | A | 159 | 13.068 | 3.113  | 39.863 | 1.00 | 14.14 | A |
| ATOM | 6215 | CA  | THR | A | 159 | 13.397 | 1.694  | 39.872 | 1.00 | 14.95 | A |
| ATOM | 6216 | CB  | THR | A | 159 | 12.878 | 0.995  | 38.597 | 1.00 | 15.00 | A |
| ATOM | 6217 | OG1 | THR | A | 159 | 11.445 | 1.015  | 38.607 | 1.00 | 15.26 | A |
| ATOM | 6218 | CG2 | THR | A | 159 | 13.356 | -0.459 | 38.537 | 1.00 | 15.00 | A |
| ATOM | 6219 | C   | THR | A | 159 | 14.901 | 1.459  | 40.021 | 1.00 | 15.25 | A |
| ATOM | 6220 | O   | THR | A | 159 | 15.324 | 0.580  | 40.775 | 1.00 | 15.54 | A |
| ATOM | 6221 | N   | LEU | A | 160 | 15.709 | 2.249  | 39.323 | 1.00 | 15.71 | A |
| ATOM | 6222 | CA  | LEU | A | 160 | 17.158 | 2.105  | 39.410 | 1.00 | 16.22 | A |
| ATOM | 6223 | CB  | LEU | A | 160 | 17.851 | 3.066  | 38.437 | 1.00 | 16.17 | A |
| ATOM | 6224 | CG  | LEU | A | 160 | 17.681 | 2.778  | 36.940 | 1.00 | 16.23 | A |
| ATOM | 6225 | CD1 | LEU | A | 160 | 18.193 | 3.966  | 36.137 | 1.00 | 16.43 | A |
| ATOM | 6226 | CD2 | LEU | A | 160 | 18.413 | 1.502  | 36.548 | 1.00 | 15.89 | A |
| ATOM | 6227 | C   | LEU | A | 160 | 17.653 | 2.366  | 40.831 | 1.00 | 16.63 | A |
| ATOM | 6228 | O   | LEU | A | 160 | 18.557 | 1.683  | 41.316 | 1.00 | 16.60 | A |
| ATOM | 6229 | N   | LEU | A | 161 | 17.059 | 3.356  | 41.493 | 1.00 | 16.97 | A |
| ATOM | 6230 | CA  | LEU | A | 161 | 17.445 | 3.695  | 42.858 | 1.00 | 17.42 | A |
| ATOM | 6231 | CB  | LEU | A | 161 | 16.733 | 4.972  | 43.316 | 1.00 | 16.98 | A |
| ATOM | 6232 | CG  | LEU | A | 161 | 17.249 | 6.288  | 42.728 | 1.00 | 16.98 | A |
| ATOM | 6233 | CD1 | LEU | A | 161 | 16.334 | 7.429  | 43.147 | 1.00 | 16.61 | A |
| ATOM | 6234 | CD2 | LEU | A | 161 | 18.682 | 6.546  | 43.201 | 1.00 | 16.65 | A |
| ATOM | 6235 | C   | LEU | A | 161 | 17.132 | 2.548  | 43.818 | 1.00 | 17.85 | A |
| ATOM | 6236 | O   | LEU | A | 161 | 17.722 | 2.449  | 44.895 | 1.00 | 18.15 | A |
| ATOM | 6237 | N   | VAL | A | 162 | 16.196 | 1.691  | 43.428 | 1.00 | 17.99 | A |
| ATOM | 6238 | CA  | VAL | A | 162 | 15.831 | 0.548  | 44.245 | 1.00 | 18.31 | A |
| ATOM | 6239 | CB  | VAL | A | 162 | 14.611 | -0.199 | 43.647 | 1.00 | 18.37 | A |
| ATOM | 6240 | CG1 | VAL | A | 162 | 14.406 | -1.530 | 44.354 | 1.00 | 18.47 | A |
| ATOM | 6241 | CG2 | VAL | A | 162 | 13.356 | 0.660  | 43.788 | 1.00 | 18.42 | A |
| ATOM | 6242 | C   | VAL | A | 162 | 17.015 | -0.418 | 44.340 | 1.00 | 18.61 | A |
| ATOM | 6243 | O   | VAL | A | 162 | 17.236 | -1.048 | 45.378 | 1.00 | 18.71 | A |
| ATOM | 6244 | N   | PHE | A | 163 | 17.781 | -0.520 | 43.257 | 1.00 | 18.71 | A |
| ATOM | 6245 | CA  | PHE | A | 163 | 18.938 | -1.409 | 43.209 | 1.00 | 18.91 | A |
| ATOM | 6246 | CB  | PHE | A | 163 | 18.999 | -2.128 | 41.852 | 1.00 | 18.88 | A |
| ATOM | 6247 | CG  | PHE | A | 163 | 17.789 | -2.965 | 41.558 | 1.00 | 18.73 | A |
| ATOM | 6248 | CD1 | PHE | A | 163 | 16.734 | -2.448 | 40.822 | 1.00 | 18.63 | A |
| ATOM | 6249 | CD2 | PHE | A | 163 | 17.678 | -4.254 | 42.067 | 1.00 | 18.63 | A |
| ATOM | 6250 | CE1 | PHE | A | 163 | 15.584 | -3.198 | 40.599 | 1.00 | 18.60 | A |
| ATOM | 6251 | CE2 | PHE | A | 163 | 16.529 | -5.011 | 41.847 | 1.00 | 18.56 | A |
| ATOM | 6252 | CZ  | PHE | A | 163 | 15.483 | -4.480 | 41.114 | 1.00 | 18.40 | A |
| ATOM | 6253 | C   | PHE | A | 163 | 20.262 | -0.692 | 43.468 | 1.00 | 19.04 | A |
| ATOM | 6254 | O   | PHE | A | 163 | 21.251 | -1.326 | 43.832 | 1.00 | 18.99 | A |
| ATOM | 6528 | N   | THR | A | 197 | 4.484  | -1.111 | 45.252 | 1.00 | 22.77 | A |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine $F_{2α}$(U46)

| ATOM | 6529 | CA | THR | A | 197 | 5.126 | −2.297 | 44.695 | 1.00 | 22.69 | A |
|---|---|---|---|---|---|---|---|---|---|---|---|
| ATOM | 6530 | CB | THR | A | 197 | 4.568 | −2.649 | 43.296 | 1.00 | 22.64 | A |
| ATOM | 6531 | OG1 | THR | A | 197 | 4.713 | −1.524 | 42.419 | 1.00 | 22.39 | A |
| ATOM | 6532 | CG2 | THR | A | 197 | 3.096 | −3.040 | 43.393 | 1.00 | 22.49 | A |
| ATOM | 6533 | C | THR | A | 197 | 6.627 | −2.062 | 44.583 | 1.00 | 22.75 | A |
| ATOM | 6534 | O | THR | A | 197 | 7.087 | −0.922 | 44.636 | 1.00 | 22.48 | A |
| ATOM | 6535 | N | LYS | A | 198 | 7.390 | −3.139 | 44.428 | 1.00 | 22.84 | A |
| ATOM | 6536 | CA | LYS | A | 198 | 8.835 | −3.014 | 44.305 | 1.00 | 23.15 | A |
| ATOM | 6537 | CB | LYS | A | 198 | 9.503 | −4.385 | 44.446 | 1.00 | 23.45 | A |
| ATOM | 6538 | CG | LYS | A | 198 | 11.027 | −4.339 | 44.481 | 1.00 | 23.89 | A |
| ATOM | 6539 | CD | LYS | A | 198 | 11.617 | −5.719 | 44.748 | 1.00 | 24.34 | A |
| ATOM | 6540 | CE | LYS | A | 198 | 13.135 | −5.669 | 44.905 | 1.00 | 24.64 | A |
| ATOM | 6541 | NZ | LYS | A | 198 | 13.715 | −7.011 | 45.224 | 1.00 | 24.86 | A |
| ATOM | 6542 | C | LYS | A | 198 | 9.201 | −2.391 | 42.960 | 1.00 | 23.13 | A |
| ATOM | 6543 | O | LYS | A | 198 | 9.917 | −1.393 | 42.909 | 1.00 | 23.17 | A |
| ATOM | 6544 | N | LEU | A | 199 | 8.706 | −2.980 | 41.876 | 1.00 | 23.24 | A |
| ATOM | 6545 | CA | LEU | A | 199 | 8.989 | −2.475 | 40.537 | 1.00 | 23.52 | A |
| ATOM | 6546 | CB | LEU | A | 199 | 9.571 | −3.588 | 39.652 | 1.00 | 23.79 | A |
| ATOM | 6547 | CG | LEU | A | 199 | 10.941 | −4.180 | 40.010 | 1.00 | 24.11 | A |
| ATOM | 6548 | CD1 | LEU | A | 199 | 11.934 | −3.056 | 40.302 | 1.00 | 24.28 | A |
| ATOM | 6549 | CD2 | LEU | A | 199 | 10.810 | −5.078 | 41.220 | 1.00 | 24.55 | A |
| ATOM | 6550 | C | LEU | A | 199 | 7.739 | −1.894 | 39.871 | 1.00 | 23.53 | A |
| ATOM | 6551 | O | LEU | A | 199 | 6.704 | −1.767 | 40.557 | 1.00 | 23.60 | A |
| ATOM | 6552 | OXT | LEU | A | 199 | 7.807 | −1.566 | 38.669 | 1.00 | 23.55 | A |
| ATOM | 6688 | N1 | GSH | H | 200 | 8.305 | −2.844 | 24.998 | 1.00 | 20.97 | H |
| ATOM | 6689 | CA1 | GSH | H | 200 | 6.911 | −3.081 | 25.371 | 1.00 | 20.94 | H |
| ATOM | 6690 | C1 | GSH | H | 200 | 6.240 | −1.805 | 25.930 | 1.00 | 20.69 | H |
| ATOM | 6691 | O11 | GSH | H | 200 | 6.937 | −0.824 | 26.213 | 1.00 | 20.48 | H |
| ATOM | 6692 | O12 | GSH | H | 200 | 4.943 | −1.894 | 26.178 | 1.00 | 20.60 | H |
| ATOM | 6693 | CB1 | GSH | H | 200 | 6.878 | −4.158 | 26.465 | 1.00 | 21.02 | H |
| ATOM | 6694 | CG1 | GSH | H | 200 | 7.003 | −5.588 | 25.927 | 1.00 | 21.34 | H |
| ATOM | 6695 | CD1 | GSH | H | 200 | 7.105 | −6.535 | 27.153 | 1.00 | 21.26 | H |
| ATOM | 6696 | OE1 | GSH | H | 200 | 7.995 | −7.376 | 27.180 | 1.00 | 21.54 | H |
| ATOM | 6697 | N2 | GSH | H | 200 | 6.151 | −6.418 | 28.106 | 1.00 | 21.27 | H |
| ATOM | 6698 | CA2 | GSH | H | 200 | 6.171 | −7.317 | 29.280 | 1.00 | 21.32 | H |
| ATOM | 6699 | C2 | GSH | H | 200 | 5.234 | −8.508 | 29.053 | 1.00 | 21.45 | H |
| ATOM | 6700 | O2 | GSH | H | 200 | 4.092 | −8.371 | 28.603 | 1.00 | 21.33 | H |
| ATOM | 6701 | CB2 | GSH | H | 200 | 5.676 | −6.608 | 30.562 | 1.00 | 21.16 | H |
| ATOM | 6702 | SG2 | GSH | H | 200 | 6.895 | −5.457 | 31.266 | 1.00 | 20.43 | H |
| ATOM | 6703 | N3 | GSH | H | 200 | 5.687 | −9.697 | 29.521 | 1.00 | 21.62 | H |
| ATOM | 6704 | CA3 | GSH | H | 200 | 4.848 | −10.902 | 29.598 | 1.00 | 21.77 | H |
| ATOM | 6705 | C3 | GSH | H | 200 | 5.235 | −11.857 | 28.486 | 1.00 | 22.03 | H |
| ATOM | 6706 | O31 | GSH | H | 200 | 4.505 | −12.857 | 28.339 | 1.00 | 22.01 | H |
| ATOM | 6707 | O32 | GSH | H | 200 | 6.217 | −11.556 | 27.749 | 1.00 | 22.31 | H |
| ATOM | 6708 | C1 | U46 | X | 201 | 10.418 | −9.029 | 32.023 | 1.00 | 34.62 | X |
| ATOM | 6709 | C2 | U46 | X | 201 | 9.663 | −10.080 | 32.823 | 1.00 | 34.77 | X |
| ATOM | 6710 | C3 | U46 | X | 201 | 9.043 | −9.215 | 33.968 | 1.00 | 34.58 | X |
| ATOM | 6711 | C4 | U46 | X | 201 | 8.603 | −7.944 | 33.186 | 1.00 | 34.52 | X |
| ATOM | 6712 | C5 | U46 | X | 201 | 9.105 | −8.297 | 31.751 | 1.00 | 34.55 | X |
| ATOM | 6713 | O6 | U46 | X | 201 | 8.305 | −9.318 | 31.150 | 1.00 | 34.69 | X |
| ATOM | 6714 | C7 | U46 | X | 201 | 8.626 | −10.560 | 31.780 | 1.00 | 34.71 | X |
| ATOM | 6715 | C14 | U46 | X | 201 | 9.215 | −6.627 | 33.663 | 1.00 | 33.95 | X |
| ATOM | 6716 | C16 | U46 | X | 201 | 8.636 | −5.646 | 34.388 | 1.00 | 33.42 | X |
| ATOM | 6717 | C18 | U46 | X | 201 | 9.270 | −4.351 | 34.859 | 1.00 | 33.17 | X |
| ATOM | 6718 | C20 | U46 | X | 201 | 9.952 | −3.549 | 33.738 | 1.00 | 33.13 | X |
| ATOM | 6719 | C21 | U46 | X | 201 | 10.163 | −2.068 | 34.122 | 1.00 | 33.29 | X |
| ATOM | 6720 | C24 | U46 | X | 201 | 10.959 | −1.283 | 33.062 | 1.00 | 33.44 | X |
| ATOM | 6721 | C27 | U46 | X | 201 | 10.626 | −0.219 | 33.069 | 1.00 | 33.39 | X |
| ATOM | 6722 | C30 | U46 | X | 201 | 10.896 | −0.871 | 31.709 | 1.00 | 33.48 | X |
| ATOM | 6723 | O36 | U46 | X | 201 | 10.227 | −4.658 | 35.841 | 1.00 | 33.24 | X |
| ATOM | 6724 | C39 | U46 | X | 201 | 7.877 | −9.902 | 34.751 | 1.00 | 34.95 | X |
| ATOM | 6725 | C41 | U46 | X | 201 | 8.032 | −9.785 | 36.257 | 1.00 | 35.34 | X |
| ATOM | 6726 | C44 | U46 | X | 201 | 8.610 | −10.654 | 37.130 | 1.00 | 35.62 | X |
| ATOM | 6727 | C46 | U46 | X | 201 | 9.261 | −11.994 | 36.823 | 1.00 | 35.69 | X |
| ATOM | 6728 | C48 | U46 | X | 201 | 10.726 | −12.086 | 37.288 | 1.00 | 35.70 | X |
| ATOM | 6729 | C51 | U46 | X | 201 | 11.026 | −13.433 | 37.990 | 1.00 | 35.67 | X |
| ATOM | 6730 | C54 | U46 | X | 201 | 12.522 | −13.820 | 37.936 | 1.00 | 35.71 | X |
| ATOM | 6731 | O57 | U46 | X | 201 | 12.742 | −14.998 | 38.563 | 1.00 | 35.58 | X |
| ATOM | 6732 | O58 | U46 | X | 201 | 13.394 | −13.172 | 37.412 | 1.00 | 35.68 | X |
| ATOM | 6734 | CA + 2 | CA2 | M | 902 | 12.234 | 1.221 | 22.856 | 1.00 | 26.18 | M |
| ATOM | 6797 | OH2 | WAT | S | 66 | 8.810 | −7.551 | 20.104 | 1.00 | 14.22 | S |
| ATOM | 6798 | OH2 | WAT | S | 67 | 10.805 | −8.913 | 21.442 | 1.00 | 18.79 | S |
| ATOM | 6799 | OH2 | WAT | S | 68 | 7.756 | −6.308 | 22.319 | 1.00 | 11.88 | S |
| ATOM | 6800 | OH2 | WAT | S | 69 | 5.816 | −8.813 | 20.585 | 1.00 | 16.62 | S |
| ATOM | 6801 | OH2 | WAT | S | 70 | 5.092 | −6.137 | 21.429 | 1.00 | 8.34 | S |

TABLE 3-continued

Three-dimensional structural coordinate of the complex of
human hematopoietic PGDS (SEQ ID NO: 1) with calcium, glutathione and
9,11-dideoxy-9α,11α-methanoepoxyprostaglandine $F_{2\alpha}$(U46)

| ATOM | 6802 | OH2 | WAT | S | 71 | 5.256 | −11.109 | 19.213 | 1.00 | 14.67 | S |
|---|---|---|---|---|---|---|---|---|---|---|---|
| ATOM | 6803 | OH2 | WAT | S | 72 | 3.023 | −5.015 | 22.562 | 1.00 | 5.39 | S |
| ATOM | 6804 | OH2 | WAT | S | 73 | 0.826 | −6.659 | 23.058 | 1.00 | 10.24 | S |
| ATOM | 6805 | OH2 | WAT | S | 74 | 2.776 | −3.513 | 24.834 | 1.00 | 13.89 | S |
| ATOM | 6806 | OH2 | WAT | S | 75 | 11.519 | −4.838 | 25.573 | 1.00 | 37.60 | S |
| ATOM | 6807 | OH2 | WAT | S | 76 | 8.072 | −9.994 | 27.106 | 1.00 | 23.21 | S |
| ATOM | 6808 | OH2 | WAT | S | 77 | 17.600 | −2.336 | 25.194 | 1.00 | 29.44 | S |
| ATOM | 6955 | OH2 | WAT | S | 228 | −2.665 | −1.375 | 34.872 | 1.00 | 12.13 | S |
| ATOM | 6956 | OH2 | WAT | S | 229 | 0.635 | −8.538 | 38.751 | 1.00 | 19.36 | S |
| ATOM | 6957 | OH2 | WAT | S | 230 | 9.165 | −7.382 | 41.775 | 1.00 | 33.05 | S |
| ATOM | 6958 | OH2 | WAT | S | 231 | 1.469 | 2.057 | 40.259 | 1.00 | 10.55 | S |
| ATOM | 6959 | OH2 | WAT | S | 232 | 2.424 | −0.150 | 41.673 | 1.00 | 7.92 | S |
| ATOM | 6960 | OH2 | WAT | S | 233 | 4.681 | 1.576 | 43.702 | 1.00 | 20.75 | S |
| ATOM | 6961 | OH2 | WAT | S | 234 | 9.069 | 3.394 | 38.480 | 1.00 | 10.13 | S |
| ATOM | 6962 | OH2 | WAT | S | 235 | 8.873 | 1.530 | 36.291 | 1.00 | 19.33 | S |
| ATOM | 6963 | OH2 | WAT | S | 236 | 9.962 | −0.719 | 37.350 | 1.00 | 9.21 | S |
| ATOM | 6964 | OH2 | WAT | S | 237 | 6.538 | 3.283 | 32.602 | 1.00 | 4.33 | S |
| ATOM | 6966 | OH2 | WAT | S | 239 | 6.866 | −5.224 | 41.878 | 1.00 | 15.47 | S |
| ATOM | 7098 | OH2 | WAT | S | 376 | −2.658 | −5.119 | 20.477 | 1.00 | 32.13 | S |
| ATOM | 7100 | OH2 | WAT | S | 378 | 9.041 | 5.776 | 21.830 | 1.00 | 29.33 | S |
| ATOM | 7101 | OH2 | WAT | S | 379 | 16.468 | −6.279 | 25.400 | 1.00 | 37.77 | S |
| ATOM | 7102 | OH2 | WAT | S | 380 | 11.532 | −7.763 | 23.742 | 1.00 | 26.56 | S |
| ATOM | 7103 | OH2 | WAT | S | 381 | 20.121 | −7.464 | 24.596 | 1.00 | 31.37 | S |
| ATOM | 7206 | OH2 | WAT | S | 487 | −6.959 | −2.973 | 28.857 | 1.00 | 26.99 | S |
| ATOM | 7220 | OH2 | WAT | S | 502 | 19.741 | −12.637 | 30.102 | 1.00 | 30.06 | S |
| ATOM | 7228 | OH2 | WAT | S | 511 | 10.932 | 3.058 | 22.095 | 1.00 | 23.73 | S |
| ATOM | 7252 | OH2 | WAT | S | 537 | 14.068 | 2.624 | 22.159 | 1.00 | 17.19 | S |
| ATOM | 7253 | OH2 | WAT | S | 538 | 10.354 | −0.297 | 22.259 | 1.00 | 23.05 | S |
| ATOM | 7254 | OH2 | WAT | S | 539 | 14.359 | 0.199 | 23.830 | 1.00 | 17.88 | S |
| ATOM | 7255 | OH2 | WAT | S | 540 | 13.565 | −1.416 | 21.690 | 1.00 | 21.98 | S |
| ATOM | 7256 | OH2 | WAT | S | 541 | 14.359 | −2.488 | 23.994 | 1.00 | 24.68 | S |
| ATOM | 7257 | OH2 | WAT | S | 542 | 6.700 | 1.457 | 23.387 | 1.00 | 7.45 | S |
| ATOM | 7260 | OH2 | WAT | S | 545 | 6.810 | 4.437 | 20.115 | 1.00 | 9.33 | S |
| ATOM | 7262 | OH2 | WAT | S | 548 | 7.372 | 2.188 | 29.676 | 1.00 | 13.81 | S |
| ATOM | 7263 | OH2 | WAT | S | 551 | 12.593 | 1.210 | 20.664 | 1.00 | 23.28 | S |
| ATOM | 7279 | OH2 | WAT | S | 568 | 9.152 | −7.664 | 24.541 | 1.00 | 28.73 | S |
| ATOM | 7330 | OH2 | WAT | S | 621 | −0.052 | −8.417 | 43.049 | 1.00 | 41.72 | S |
| ATOM | 7331 | OH2 | WAT | S | 622 | 4.610 | −6.488 | 42.101 | 1.00 | 39.75 | S |
| ATOM | 7334 | OH2 | WAT | S | 625 | −5.505 | −11.363 | 37.210 | 1.00 | 32.13 | S |
| ATOM | 7365 | OH2 | WAT | S | 659 | 12.799 | −12.693 | 21.817 | 1.00 | 29.74 | S |
| ATOM | 7419 | OH2 | WAT | S | 719 | 3.738 | −8.441 | 39.590 | 1.00 | 44.76 | S |
| ATOM | 7420 | OH2 | WAT | S | 720 | −3.644 | −7.487 | 40.846 | 1.00 | 28.21 | S |
| ATOM | 7421 | OH2 | WAT | S | 721 | 9.250 | 0.354 | 24.552 | 1.00 | 31.35 | S |
| ATOM | 7469 | OH2 | WAT | S | 779 | 13.344 | −12.993 | 24.338 | 1.00 | 33.74 | S |
| ATOM | 7478 | OH2 | WAT | S | 797 | 9.999 | −4.902 | 29.944 | 1.00 | 42.20 | S |

TABLE 4

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 4966 | N | TYR | A | 8 | 52.373 | 40.696 | 69.223 | 1.00 | 5.08 | A |
|---|---|---|---|---|---|---|---|---|---|---|---|
| ATOM | 4967 | CA | TYR | A | 8 | 50.981 | 40.835 | 69.625 | 1.00 | 5.19 | A |
| ATOM | 4968 | CB | TYR | A | 8 | 50.387 | 42.136 | 69.066 | 1.00 | 5.85 | A |
| ATOM | 4969 | CG | TYR | A | 8 | 49.055 | 42.515 | 69.678 | 1.00 | 5.32 | A |
| ATOM | 4970 | CD1 | TYR | A | 8 | 48.943 | 42.758 | 71.047 | 1.00 | 5.34 | A |
| ATOM | 4971 | CE1 | TYR | A | 8 | 47.727 | 43.124 | 71.619 | 1.00 | 5.53 | A |
| ATOM | 4972 | CD2 | TYR | A | 8 | 47.908 | 42.646 | 68.889 | 1.00 | 5.77 | A |
| ATOM | 4973 | CE2 | TYR | A | 8 | 46.685 | 43.014 | 69.451 | 1.00 | 5.46 | A |
| ATOM | 4974 | CZ | TYR | A | 8 | 46.604 | 43.251 | 70.815 | 1.00 | 5.16 | A |
| ATOM | 4975 | OH | TYR | A | 8 | 45.399 | 43.630 | 71.365 | 1.00 | 5.90 | A |
| ATOM | 4976 | C | TYR | A | 8 | 50.221 | 39.643 | 69.062 | 1.00 | 5.81 | A |
| ATOM | 4977 | O | TYR | A | 8 | 50.803 | 38.783 | 68.405 | 1.00 | 6.16 | A |
| ATOM | 4978 | N | PHE | A | 9 | 48.928 | 39.581 | 69.347 | 1.00 | 6.65 | A |
| ATOM | 4979 | CA | PHE | A | 9 | 48.090 | 38.518 | 68.812 | 1.00 | 7.22 | A |
| ATOM | 4980 | CB | PHE | A | 9 | 46.752 | 38.461 | 69.556 | 1.00 | 10.27 | A |
| ATOM | 4981 | CG | PHE | A | 9 | 46.868 | 38.040 | 70.993 | 1.00 | 10.70 | A |
| ATOM | 4982 | CD1 | PHE | A | 9 | 46.584 | 38.935 | 72.021 | 1.00 | 13.85 | A |
| ATOM | 4983 | CD2 | PHE | A | 9 | 47.254 | 36.744 | 71.320 | 1.00 | 12.21 | A |
| ATOM | 4984 | CE1 | PHE | A | 9 | 46.683 | 38.540 | 73.355 | 1.00 | 15.04 | A |
| ATOM | 4985 | CE2 | PHE | A | 9 | 47.356 | 36.343 | 72.650 | 1.00 | 13.46 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 4986 | CZ | PHE | A | 9 | 47.070 | 37.242 | 73.668 | 1.00 | 14.40 | A |
|---|---|---|---|---|---|---|---|---|---|---|---|
| ATOM | 4987 | C | PHE | A | 9 | 47.811 | 38.860 | 67.350 | 1.00 | 6.45 | A |
| ATOM | 4988 | O | PHE | A | 9 | 48.173 | 39.943 | 66.873 | 1.00 | 6.51 | A |
| ATOM | 4989 | N | ASN | A | 10 | 47.178 | 37.938 | 66.632 | 1.00 | 7.20 | A |
| ATOM | 4990 | CA | ASN | A | 10 | 46.822 | 38.209 | 65.248 | 1.00 | 7.50 | A |
| ATOM | 4991 | CB | ASN | A | 10 | 46.676 | 36.915 | 64.445 | 1.00 | 8.81 | A |
| ATOM | 4992 | CG | ASN | A | 10 | 46.265 | 37.172 | 63.010 | 1.00 | 10.65 | A |
| ATOM | 4993 | OD1 | ASN | A | 10 | 46.628 | 38.191 | 62.423 | 1.00 | 9.77 | A |
| ATOM | 4994 | ND2 | ASN | A | 10 | 45.515 | 36.240 | 62.430 | 1.00 | 12.72 | A |
| ATOM | 4995 | C | ASN | A | 10 | 45.489 | 38.952 | 65.305 | 1.00 | 7.31 | A |
| ATOM | 4996 | O | ASN | A | 10 | 44.425 | 38.386 | 65.058 | 1.00 | 7.42 | A |
| ATOM | 4997 | N | MET | A | 11 | 45.573 | 40.228 | 65.668 | 1.00 | 6.93 | A |
| ATOM | 4998 | CA | MET | A | 11 | 44.424 | 41.120 | 65.791 | 1.00 | 6.61 | A |
| ATOM | 4999 | CB | MET | A | 11 | 43.816 | 41.082 | 67.202 | 1.00 | 9.76 | A |
| ATOM | 5000 | CG | MET | A | 11 | 43.251 | 39.768 | 67.703 | 1.00 | 12.58 | A |
| ATOM | 5001 | SD | MET | A | 11 | 42.429 | 40.034 | 69.312 | 1.00 | 16.46 | A |
| ATOM | 5002 | CE | MET | A | 11 | 43.822 | 40.416 | 70.355 | 1.00 | 18.60 | A |
| ATOM | 5003 | C | MET | A | 11 | 44.958 | 42.529 | 65.612 | 1.00 | 4.89 | A |
| ATOM | 5004 | O | MET | A | 11 | 46.165 | 42.765 | 65.730 | 1.00 | 5.10 | A |
| ATOM | 5005 | N | ARG | A | 12 | 44.065 | 43.471 | 65.333 | 1.00 | 4.88 | A |
| ATOM | 5006 | CA | ARG | A | 12 | 44.481 | 44.863 | 65.248 | 1.00 | 4.58 | A |
| ATOM | 5007 | CB | ARG | A | 12 | 43.377 | 45.722 | 64.630 | 1.00 | 4.90 | A |
| ATOM | 5008 | CG | ARG | A | 12 | 43.101 | 45.396 | 63.166 | 1.00 | 4.93 | A |
| ATOM | 5009 | CD | ARG | A | 12 | 42.125 | 46.404 | 62.550 | 1.00 | 5.92 | A |
| ATOM | 5010 | NE | ARG | A | 12 | 40.874 | 46.486 | 63.301 | 1.00 | 5.59 | A |
| ATOM | 5011 | CZ | ARG | A | 12 | 39.925 | 45.558 | 63.273 | 1.00 | 6.68 | A |
| ATOM | 5012 | NH1 | ARG | A | 12 | 40.073 | 44.477 | 62.519 | 1.00 | 6.84 | A |
| ATOM | 5013 | NH2 | ARG | A | 12 | 38.841 | 45.699 | 64.025 | 1.00 | 7.34 | A |
| ATOM | 5014 | C | ARG | A | 12 | 44.716 | 45.251 | 66.711 | 1.00 | 4.87 | A |
| ATOM | 5015 | O | ARG | A | 12 | 45.835 | 45.568 | 67.112 | 1.00 | 5.24 | A |
| ATOM | 5016 | N | GLY | A | 13 | 43.647 | 45.193 | 67.500 | 1.00 | 5.06 | A |
| ATOM | 5017 | CA | GLY | A | 13 | 43.722 | 45.495 | 68.916 | 1.00 | 4.83 | A |
| ATOM | 5018 | C | GLY | A | 13 | 44.620 | 46.641 | 69.327 | 1.00 | 4.65 | A |
| ATOM | 5019 | O | GLY | A | 13 | 44.611 | 47.717 | 68.718 | 1.00 | 5.04 | A |
| ATOM | 5020 | N | ARG | A | 14 | 45.404 | 46.397 | 70.373 | 1.00 | 4.18 | A |
| ATOM | 5021 | CA | ARG | A | 14 | 46.305 | 47.398 | 70.929 | 1.00 | 5.36 | A |
| ATOM | 5022 | CB | ARG | A | 14 | 46.573 | 47.085 | 72.401 | 1.00 | 5.09 | A |
| ATOM | 5023 | CG | ARG | A | 14 | 45.315 | 47.228 | 73.252 | 1.00 | 5.96 | A |
| ATOM | 5024 | CD | ARG | A | 14 | 45.594 | 46.965 | 74.727 | 1.00 | 8.03 | A |
| ATOM | 5025 | NE | ARG | A | 14 | 44.524 | 47.502 | 75.570 | 1.00 | 10.77 | A |
| ATOM | 5026 | CZ | ARG | A | 14 | 43.670 | 46.772 | 76.281 | 1.00 | 12.04 | A |
| ATOM | 5027 | NH1 | ARG | A | 14 | 43.742 | 45.449 | 76.268 | 1.00 | 13.88 | A |
| ATOM | 5028 | NH2 | ARG | A | 14 | 42.740 | 47.372 | 77.011 | 1.00 | 15.99 | A |
| ATOM | 5029 | C | ARG | A | 14 | 47.618 | 47.571 | 70.188 | 1.00 | 4.92 | A |
| ATOM | 5030 | O | ARG | A | 14 | 48.394 | 48.465 | 70.509 | 1.00 | 6.47 | A |
| ATOM | 5031 | N | ALA | A | 15 | 47.878 | 46.728 | 69.199 | 1.00 | 4.71 | A |
| ATOM | 5032 | CA | ALA | A | 15 | 49.111 | 46.864 | 68.439 | 1.00 | 4.73 | A |
| ATOM | 5033 | CB | ALA | A | 15 | 49.617 | 45.491 | 68.020 | 1.00 | 7.01 | A |
| ATOM | 5034 | C | ALA | A | 15 | 48.907 | 47.729 | 67.203 | 1.00 | 4.72 | A |
| ATOM | 5035 | O | ALA | A | 15 | 49.867 | 48.277 | 66.661 | 1.00 | 4.50 | A |
| ATOM | 5036 | N | GLU | A | 16 | 47.656 | 47.882 | 66.775 | 1.00 | 4.21 | A |
| ATOM | 5037 | CA | GLU | A | 16 | 47.386 | 48.606 | 65.542 | 1.00 | 4.17 | A |
| ATOM | 5038 | CB | GLU | A | 16 | 45.888 | 48.555 | 65.220 | 1.00 | 4.19 | A |
| ATOM | 5039 | CG | GLU | A | 16 | 45.564 | 48.801 | 63.741 | 1.00 | 5.10 | A |
| ATOM | 5040 | CD | GLU | A | 16 | 46.069 | 47.700 | 62.804 | 1.00 | 5.24 | A |
| ATOM | 5041 | OE1 | GLU | A | 16 | 46.619 | 46.682 | 63.283 | 1.00 | 5.72 | A |
| ATOM | 5042 | OE2 | GLU | A | 16 | 45.907 | 47.864 | 61.575 | 1.00 | 5.89 | A |
| ATOM | 5043 | C | GLU | A | 16 | 47.904 | 50.034 | 65.463 | 1.00 | 4.67 | A |
| ATOM | 5044 | O | GLU | A | 16 | 48.364 | 50.459 | 64.404 | 1.00 | 4.75 | A |
| ATOM | 5045 | N | ILE | A | 17 | 47.859 | 50.776 | 66.566 | 1.00 | 4.26 | A |
| ATOM | 5046 | CA | ILE | A | 17 | 48.351 | 52.146 | 66.529 | 1.00 | 4.04 | A |
| ATOM | 5047 | CB | ILE | A | 17 | 48.092 | 52.876 | 67.889 | 1.00 | 5.08 | A |
| ATOM | 5048 | CG2 | ILE | A | 17 | 48.797 | 52.165 | 69.029 | 1.00 | 5.12 | A |
| ATOM | 5049 | CG1 | ILE | A | 17 | 48.539 | 54.337 | 67.794 | 1.00 | 4.72 | A |
| ATOM | 5050 | CD1 | ILE | A | 17 | 47.815 | 55.138 | 66.720 | 1.00 | 6.77 | A |
| ATOM | 5051 | C | ILE | A | 17 | 49.841 | 52.150 | 66.158 | 1.00 | 4.37 | A |
| ATOM | 5052 | O | ILE | A | 17 | 50.301 | 53.003 | 65.394 | 1.00 | 5.08 | A |
| ATOM | 5242 | N | TRP | A | 39 | 50.877 | 31.481 | 73.859 | 1.00 | 14.53 | A |
| ATOM | 5243 | CA | TRP | A | 39 | 50.756 | 32.520 | 74.879 | 1.00 | 13.46 | A |
| ATOM | 5244 | CB | TRP | A | 39 | 49.282 | 32.747 | 75.231 | 1.00 | 13.58 | A |
| ATOM | 5245 | CG | TRP | A | 39 | 49.060 | 33.765 | 76.321 | 1.00 | 12.94 | A |
| ATOM | 5246 | CD2 | TRP | A | 39 | 49.582 | 35.102 | 76.384 | 1.00 | 12.06 | A |
| ATOM | 5247 | CE2 | TRP | A | 39 | 49.128 | 35.671 | 77.593 | 1.00 | 12.15 | A |
| ATOM | 5248 | CE3 | TRP | A | 39 | 50.392 | 35.874 | 75.537 | 1.00 | 10.40 | A |
| ATOM | 5249 | CD1 | TRP | A | 39 | 48.328 | 33.591 | 77.460 | 1.00 | 13.75 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine F$_{2α}$(U46)

| ATOM | 5250 | NE1 | TRP | A | 39 | 48.365 | 34.728 | 78.230 | 1.00 | 13.97 | A |
|------|------|-----|-----|---|----|--------|--------|--------|------|-------|---|
| ATOM | 5251 | CZ2 | TRP | A | 39 | 49.454 | 36.974 | 77.981 | 1.00 | 11.46 | A |
| ATOM | 5252 | CZ3 | TRP | A | 39 | 50.717 | 37.176 | 75.926 | 1.00 | 10.56 | A |
| ATOM | 5253 | CH2 | TRP | A | 39 | 50.247 | 37.709 | 77.137 | 1.00 | 10.60 | A |
| ATOM | 5254 | C | TRP | A | 39 | 51.564 | 32.262 | 76.156 | 1.00 | 14.42 | A |
| ATOM | 5255 | O | TRP | A | 39 | 52.316 | 33.127 | 76.592 | 1.00 | 13.42 | A |
| ATOM | 5256 | N | PRO | A | 40 | 51.424 | 31.076 | 76.774 | 1.00 | 13.83 | A |
| ATOM | 5257 | CD | PRO | A | 40 | 50.509 | 29.950 | 76.512 | 1.00 | 15.37 | A |
| ATOM | 5258 | CA | PRO | A | 40 | 52.202 | 30.843 | 77.995 | 1.00 | 13.84 | A |
| ATOM | 5259 | CB | PRO | A | 40 | 51.885 | 29.388 | 78.329 | 1.00 | 14.82 | A |
| ATOM | 5260 | CG | PRO | A | 40 | 50.467 | 29.254 | 77.861 | 1.00 | 15.27 | A |
| ATOM | 5261 | C | PRO | A | 40 | 53.697 | 31.089 | 77.809 | 1.00 | 14.02 | A |
| ATOM | 5262 | O | PRO | A | 40 | 54.342 | 31.712 | 78.656 | 1.00 | 14.68 | A |
| ATOM | 5263 | N | GLU | A | 41 | 54.245 | 30.606 | 76.700 | 1.00 | 14.37 | A |
| ATOM | 5264 | CA | GLU | A | 41 | 55.664 | 30.784 | 76.422 | 1.00 | 15.32 | A |
| ATOM | 5265 | CB | GLU | A | 41 | 56.079 | 29.953 | 75.205 | 1.00 | 18.64 | A |
| ATOM | 5266 | CG | GLU | A | 41 | 54.940 | 29.199 | 74.548 | 1.00 | 25.28 | A |
| ATOM | 5267 | CD | GLU | A | 41 | 55.423 | 28.170 | 73.548 | 1.00 | 27.49 | A |
| ATOM | 5268 | OE1 | GLU | A | 41 | 56.616 | 28.201 | 73.183 | 1.00 | 29.60 | A |
| ATOM | 5269 | OE2 | GLU | A | 41 | 54.608 | 27.334 | 73.116 | 1.00 | 30.19 | A |
| ATOM | 5270 | C | GLU | A | 41 | 56.005 | 32.253 | 76.188 | 1.00 | 13.50 | A |
| ATOM | 5271 | O | GLU | A | 41 | 56.988 | 32.761 | 76.723 | 1.00 | 15.87 | A |
| ATOM | 5272 | N | ILE | A | 42 | 55.190 | 32.931 | 75.388 | 1.00 | 12.31 | A |
| ATOM | 5273 | CA | ILE | A | 42 | 55.413 | 34.342 | 75.095 | 1.00 | 12.42 | A |
| ATOM | 5274 | CB | ILE | A | 42 | 54.407 | 34.852 | 74.031 | 1.00 | 12.64 | A |
| ATOM | 5275 | CG2 | ILE | A | 42 | 54.485 | 36.374 | 73.916 | 1.00 | 12.49 | A |
| ATOM | 5276 | CG1 | ILE | A | 42 | 54.697 | 34.197 | 72.677 | 1.00 | 14.88 | A |
| ATOM | 5277 | CD1 | ILE | A | 42 | 56.018 | 34.607 | 72.054 | 1.00 | 16.40 | A |
| ATOM | 5278 | C | ILE | A | 42 | 55.276 | 35.196 | 76.358 | 1.00 | 10.62 | A |
| ATOM | 5279 | O | ILE | A | 42 | 56.111 | 36.063 | 76.625 | 1.00 | 11.25 | A |
| ATOM | 5280 | N | LYS | A | 43 | 54.228 | 34.941 | 77.131 | 1.00 | 11.00 | A |
| ATOM | 5281 | CA | LYS | A | 43 | 53.969 | 35.697 | 78.351 | 1.00 | 10.64 | A |
| ATOM | 5282 | CB | LYS | A | 43 | 52.722 | 35.144 | 79.052 | 1.00 | 9.83 | A |
| ATOM | 5283 | CG | LYS | A | 43 | 52.292 | 35.936 | 80.279 | 1.00 | 10.83 | A |
| ATOM | 5284 | CD | LYS | A | 43 | 51.053 | 35.326 | 80.910 | 1.00 | 12.63 | A |
| ATOM | 5285 | CE | LYS | A | 43 | 50.652 | 36.051 | 82.183 | 1.00 | 14.51 | A |
| ATOM | 5286 | NZ | LYS | A | 43 | 49.477 | 35.397 | 82.820 | 1.00 | 14.93 | A |
| ATOM | 5287 | C | LYS | A | 43 | 55.143 | 35.703 | 79.323 | 1.00 | 12.13 | A |
| ATOM | 5288 | O | LYS | A | 43 | 55.384 | 36.699 | 80.005 | 1.00 | 12.18 | A |
| ATOM | 5328 | N | GLY | A | 49 | 53.610 | 40.833 | 81.753 | 1.00 | 7.16 | A |
| ATOM | 5329 | CA | GLY | A | 49 | 52.668 | 39.832 | 81.287 | 1.00 | 8.61 | A |
| ATOM | 5330 | C | GLY | A | 49 | 51.654 | 40.290 | 80.260 | 1.00 | 6.93 | A |
| ATOM | 5331 | O | GLY | A | 49 | 50.653 | 39.608 | 80.038 | 1.00 | 7.98 | A |
| ATOM | 5332 | N | LYS | A | 50 | 51.907 | 41.429 | 79.619 | 1.00 | 6.55 | A |
| ATOM | 5333 | CA | LYS | A | 50 | 50.976 | 41.949 | 78.625 | 1.00 | 6.43 | A |
| ATOM | 5334 | CB | LYS | A | 50 | 50.305 | 43.240 | 79.120 | 1.00 | 7.04 | A |
| ATOM | 5335 | CG | LYS | A | 50 | 49.749 | 43.196 | 80.530 | 1.00 | 9.59 | A |
| ATOM | 5336 | CD | LYS | A | 50 | 48.616 | 42.198 | 80.672 | 1.00 | 11.11 | A |
| ATOM | 5337 | CE | LYS | A | 50 | 48.089 | 42.190 | 82.097 | 1.00 | 15.13 | A |
| ATOM | 5338 | NZ | LYS | A | 50 | 49.205 | 42.086 | 83.079 | 1.00 | 17.69 | A |
| ATOM | 5339 | C | LYS | A | 50 | 51.641 | 42.272 | 77.300 | 1.00 | 5.28 | A |
| ATOM | 5340 | O | LYS | A | 50 | 52.846 | 42.538 | 77.232 | 1.00 | 5.40 | A |
| ATOM | 5341 | N | ILE | A | 51 | 50.837 | 42.241 | 76.247 | 1.00 | 4.98 | A |
| ATOM | 5342 | CA | ILE | A | 51 | 51.300 | 42.612 | 74.923 | 1.00 | 5.31 | A |
| ATOM | 5343 | CB | ILE | A | 51 | 51.297 | 41.414 | 73.929 | 1.00 | 6.08 | A |
| ATOM | 5344 | CG2 | ILE | A | 51 | 52.577 | 40.606 | 74.121 | 1.00 | 7.61 | A |
| ATOM | 5345 | CG1 | ILE | A | 51 | 50.044 | 40.552 | 74.104 | 1.00 | 7.83 | A |
| ATOM | 5346 | CD1 | ILE | A | 51 | 49.971 | 39.380 | 73.132 | 1.00 | 11.35 | A |
| ATOM | 5347 | C | ILE | A | 51 | 50.350 | 43.716 | 74.449 | 1.00 | 4.83 | A |
| ATOM | 5348 | O | ILE | A | 51 | 49.228 | 43.847 | 74.929 | 1.00 | 5.85 | A |
| ATOM | 5349 | N | PRO | A | 52 | 50.778 | 44.515 | 73.461 | 1.00 | 4.61 | A |
| ATOM | 5350 | CD | PRO | A | 52 | 50.013 | 45.710 | 73.057 | 1.00 | 4.91 | A |
| ATOM | 5351 | CA | PRO | A | 52 | 52.047 | 44.434 | 72.746 | 1.00 | 4.74 | A |
| ATOM | 5352 | CB | PRO | A | 52 | 51.803 | 45.352 | 71.556 | 1.00 | 5.22 | A |
| ATOM | 5353 | CG | PRO | A | 52 | 51.008 | 46.472 | 72.190 | 1.00 | 6.07 | A |
| ATOM | 5354 | C | PRO | A | 52 | 53.327 | 44.841 | 73.456 | 1.00 | 5.16 | A |
| ATOM | 5355 | O | PRO | A | 52 | 53.326 | 45.548 | 74.469 | 1.00 | 4.84 | A |
| ATOM | 5356 | N | ILE | A | 53 | 54.423 | 44.329 | 72.909 | 1.00 | 4.77 | A |
| ATOM | 5357 | CA | ILE | A | 53 | 55.747 | 44.742 | 73.323 | 1.00 | 4.63 | A |
| ATOM | 5358 | CB | ILE | A | 53 | 56.576 | 43.680 | 74.116 | 1.00 | 5.58 | A |
| ATOM | 5359 | CG2 | ILE | A | 53 | 55.986 | 43.498 | 75.498 | 1.00 | 6.57 | A |
| ATOM | 5360 | CG1 | ILE | A | 53 | 56.711 | 42.376 | 73.332 | 1.00 | 6.10 | A |
| ATOM | 5361 | CD1 | ILE | A | 53 | 57.853 | 41.501 | 73.831 | 1.00 | 8.86 | A |
| ATOM | 5362 | C | ILE | A | 53 | 56.439 | 45.024 | 71.998 | 1.00 | 4.92 | A |
| ATOM | 5363 | O | ILE | A | 53 | 56.056 | 44.484 | 70.951 | 1.00 | 4.78 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 5423 | N   | HIS | A | 62 | 57.230 | 48.257 | 76.387 | 1.00 | 5.48 | A |
|------|------|-----|-----|---|----|--------|--------|--------|------|------|---|
| ATOM | 5424 | CA  | HIS | A | 62 | 55.869 | 47.762 | 76.529 | 1.00 | 5.13 | A |
| ATOM | 5425 | CB  | HIS | A | 62 | 55.742 | 46.832 | 77.744 | 1.00 | 5.58 | A |
| ATOM | 5426 | CG  | HIS | A | 62 | 55.930 | 47.514 | 79.060 | 1.00 | 4.58 | A |
| ATOM | 5427 | CD2 | HIS | A | 62 | 57.037 | 48.000 | 79.664 | 1.00 | 5.33 | A |
| ATOM | 5428 | ND1 | HIS | A | 62 | 54.877 | 47.778 | 79.911 | 1.00 | 5.59 | A |
| ATOM | 5429 | CE1 | HIS | A | 62 | 55.333 | 48.400 | 80.982 | 1.00 | 5.03 | A |
| ATOM | 5430 | NE2 | HIS | A | 62 | 56.639 | 48.549 | 80.860 | 1.00 | 6.03 | A |
| ATOM | 5431 | C   | HIS | A | 62 | 54.925 | 48.962 | 76.626 | 1.00 | 4.66 | A |
| ATOM | 5432 | O   | HIS | A | 62 | 55.386 | 50.105 | 76.654 | 1.00 | 5.51 | A |
| ATOM | 5433 | N   | GLN | A | 63 | 53.619 | 48.684 | 76.647 | 1.00 | 4.29 | A |
| ATOM | 5434 | CA  | GLN | A | 63 | 52.542 | 49.684 | 76.704 | 1.00 | 4.47 | A |
| ATOM | 5435 | CB  | GLN | A | 63 | 52.799 | 50.722 | 77.803 | 1.00 | 5.14 | A |
| ATOM | 5436 | CG  | GLN | A | 63 | 52.408 | 50.230 | 79.196 | 1.00 | 5.62 | A |
| ATOM | 5437 | CD  | GLN | A | 63 | 50.906 | 50.052 | 79.366 | 1.00 | 5.35 | A |
| ATOM | 5438 | OE1 | GLN | A | 63 | 50.112 | 50.483 | 78.523 | 1.00 | 4.91 | A |
| ATOM | 5439 | NE2 | GLN | A | 63 | 50.508 | 49.434 | 80.474 | 1.00 | 5.54 | A |
| ATOM | 5440 | C   | GLN | A | 63 | 52.378 | 50.337 | 75.335 | 1.00 | 4.53 | A |
| ATOM | 5441 | O   | GLN | A | 63 | 53.197 | 51.150 | 74.908 | 1.00 | 4.75 | A |
| ATOM | 5442 | N   | SER | A | 64 | 51.298 | 49.970 | 74.652 | 1.00 | 4.47 | A |
| ATOM | 5443 | CA  | SER | A | 64 | 51.049 | 50.446 | 73.299 | 1.00 | 5.16 | A |
| ATOM | 5444 | CB  | SER | A | 64 | 49.693 | 49.935 | 72.796 | 1.00 | 4.88 | A |
| ATOM | 5445 | OG  | SER | A | 64 | 48.605 | 50.551 | 73.460 | 1.00 | 5.68 | A |
| ATOM | 5446 | C   | SER | A | 64 | 51.149 | 51.942 | 73.054 | 1.00 | 4.97 | A |
| ATOM | 5447 | O   | SER | A | 64 | 51.742 | 52.366 | 72.062 | 1.00 | 5.10 | A |
| ATOM | 5448 | N   | LEU | A | 65 | 50.583 | 52.749 | 73.943 | 1.00 | 4.29 | A |
| ATOM | 5449 | CA  | LEU | A | 65 | 50.616 | 54.189 | 73.744 | 1.00 | 4.24 | A |
| ATOM | 5450 | CB  | LEU | A | 65 | 49.468 | 54.843 | 74.514 | 1.00 | 5.94 | A |
| ATOM | 5451 | CG  | LEU | A | 65 | 48.110 | 54.218 | 74.171 | 1.00 | 6.96 | A |
| ATOM | 5452 | CD1 | LEU | A | 65 | 47.017 | 54.953 | 74.937 | 1.00 | 9.08 | A |
| ATOM | 5453 | CD2 | LEU | A | 65 | 47.857 | 54.274 | 72.666 | 1.00 | 8.54 | A |
| ATOM | 5454 | C   | LEU | A | 65 | 51.962 | 54.802 | 74.114 | 1.00 | 4.91 | A |
| ATOM | 5455 | O   | LEU | A | 65 | 52.360 | 55.817 | 73.544 | 1.00 | 5.28 | A |
| ATOM | 5662 | N   | ASP | A | 93 | 44.344 | 59.210 | 75.556 | 1.00 | 4.56 | A |
| ATOM | 5663 | CA  | ASP | A | 93 | 43.975 | 58.590 | 76.829 | 1.00 | 4.81 | A |
| ATOM | 5664 | CB  | ASP | A | 93 | 44.674 | 59.281 | 78.008 | 1.00 | 5.82 | A |
| ATOM | 5665 | CG  | ASP | A | 93 | 46.052 | 58.688 | 78.299 | 1.00 | 6.27 | A |
| ATOM | 5666 | OD1 | ASP | A | 93 | 46.654 | 59.050 | 79.336 | 1.00 | 8.17 | A |
| ATOM | 5667 | OD2 | ASP | A | 93 | 46.534 | 57.858 | 77.497 | 1.00 | 6.94 | A |
| ATOM | 5668 | C   | ASP | A | 93 | 42.455 | 58.581 | 77.031 | 1.00 | 4.64 | A |
| ATOM | 5669 | O   | ASP | A | 93 | 41.914 | 57.667 | 77.647 | 1.00 | 5.45 | A |
| ATOM | 5670 | N   | THR | A | 94 | 41.760 | 59.589 | 76.513 | 1.00 | 4.84 | A |
| ATOM | 5671 | CA  | THR | A | 94 | 40.307 | 59.616 | 76.642 | 1.00 | 5.76 | A |
| ATOM | 5672 | CB  | THR | A | 94 | 39.745 | 60.972 | 76.166 | 1.00 | 6.34 | A |
| ATOM | 5673 | OG1 | THR | A | 94 | 40.156 | 61.992 | 77.086 | 1.00 | 7.42 | A |
| ATOM | 5674 | CG2 | THR | A | 94 | 38.223 | 60.943 | 76.110 | 1.00 | 8.19 | A |
| ATOM | 5675 | C   | THR | A | 94 | 39.718 | 58.460 | 75.825 | 1.00 | 6.13 | A |
| ATOM | 5676 | O   | THR | A | 94 | 38.803 | 57.764 | 76.276 | 1.00 | 6.09 | A |
| ATOM | 5677 | N   | LEU | A | 95 | 40.253 | 58.247 | 74.628 | 1.00 | 4.62 | A |
| ATOM | 5678 | CA  | LEU | A | 95 | 39.788 | 57.153 | 73.785 | 1.00 | 5.06 | A |
| ATOM | 5679 | CB  | LEU | A | 95 | 40.426 | 57.233 | 72.400 | 1.00 | 5.92 | A |
| ATOM | 5680 | CG  | LEU | A | 95 | 39.966 | 58.395 | 71.519 | 1.00 | 6.51 | A |
| ATOM | 5681 | CD1 | LEU | A | 95 | 40.809 | 58.448 | 70.253 | 1.00 | 7.81 | A |
| ATOM | 5682 | CD2 | LEU | A | 95 | 38.495 | 58.215 | 71.174 | 1.00 | 8.77 | A |
| ATOM | 5683 | C   | LEU | A | 95 | 40.143 | 55.819 | 74.423 | 1.00 | 4.85 | A |
| ATOM | 5684 | O   | LEU | A | 95 | 39.321 | 54.907 | 74.480 | 1.00 | 5.32 | A |
| ATOM | 5685 | N   | ASP | A | 96 | 41.373 | 55.711 | 74.912 | 1.00 | 5.08 | A |
| ATOM | 5686 | CA  | ASP | A | 96 | 41.830 | 54.472 | 75.524 | 1.00 | 4.86 | A |
| ATOM | 5687 | CB  | ASP | A | 96 | 43.328 | 54.556 | 75.817 | 1.00 | 5.00 | A |
| ATOM | 5688 | CG  | ASP | A | 96 | 43.975 | 53.191 | 75.916 | 1.00 | 6.28 | A |
| ATOM | 5689 | OD1 | ASP | A | 96 | 43.865 | 52.415 | 74.945 | 1.00 | 7.24 | A |
| ATOM | 5690 | OD2 | ASP | A | 96 | 44.593 | 52.896 | 76.958 | 1.00 | 8.87 | A |
| ATOM | 5691 | C   | ASP | A | 96 | 41.056 | 54.146 | 76.797 | 1.00 | 5.03 | A |
| ATOM | 5692 | O   | ASP | A | 96 | 40.784 | 52.978 | 77.082 | 1.00 | 5.59 | A |
| ATOM | 5693 | N   | ASP | A | 97 | 40.702 | 55.173 | 77.564 | 1.00 | 5.23 | A |
| ATOM | 5694 | CA  | ASP | A | 97 | 39.926 | 54.974 | 78.784 | 1.00 | 5.46 | A |
| ATOM | 5695 | CB  | ASP | A | 97 | 39.585 | 56.317 | 79.436 | 1.00 | 6.58 | A |
| ATOM | 5696 | CG  | ASP | A | 97 | 40.721 | 56.890 | 80.261 | 1.00 | 6.62 | A |
| ATOM | 5697 | OD1 | ASP | A | 97 | 40.597 | 58.061 | 80.677 | 1.00 | 7.17 | A |
| ATOM | 5698 | OD2 | ASP | A | 97 | 41.721 | 56.185 | 80.504 | 1.00 | 7.79 | A |
| ATOM | 5699 | C   | ASP | A | 97 | 38.621 | 54.269 | 78.426 | 1.00 | 6.00 | A |
| ATOM | 5700 | O   | ASP | A | 97 | 38.207 | 53.322 | 79.100 | 1.00 | 6.84 | A |
| ATOM | 5701 | N   | PHE | A | 98 | 37.969 | 54.732 | 77.364 | 1.00 | 5.70 | A |
| ATOM | 5702 | CA  | PHE | A | 98 | 36.712 | 54.122 | 76.964 | 1.00 | 5.97 | A |
| ATOM | 5703 | CB  | PHE | A | 98 | 36.013 | 54.962 | 75.898 | 1.00 | 6.49 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 5704 | CG  | PHE | A | 98  | 34.603 | 54.532 | 75.635 | 1.00 | 7.36  | A |
|------|------|-----|-----|---|-----|--------|--------|--------|------|-------|---|
| ATOM | 5705 | CD1 | PHE | A | 98  | 33.662 | 54.547 | 76.659 | 1.00 | 9.72  | A |
| ATOM | 5706 | CD2 | PHE | A | 98  | 34.217 | 54.088 | 74.379 | 1.00 | 7.45  | A |
| ATOM | 5707 | CE1 | PHE | A | 98  | 32.354 | 54.123 | 76.434 | 1.00 | 10.12 | A |
| ATOM | 5708 | CE2 | PHE | A | 98  | 32.911 | 53.662 | 74.140 | 1.00 | 9.08  | A |
| ATOM | 5709 | CZ  | PHE | A | 98  | 31.979 | 53.680 | 75.172 | 1.00 | 9.33  | A |
| ATOM | 5710 | C   | PHE | A | 98  | 36.906 | 52.698 | 76.452 | 1.00 | 6.08  | A |
| ATOM | 5711 | O   | PHE | A | 98  | 36.168 | 51.789 | 76.839 | 1.00 | 6.41  | A |
| ATOM | 5712 | N   | MET | A | 99  | 37.896 | 52.490 | 75.589 | 1.00 | 6.17  | A |
| ATOM | 5713 | CA  | MET | A | 99  | 38.146 | 51.152 | 75.062 | 1.00 | 5.91  | A |
| ATOM | 5714 | CB  | MET | A | 99  | 39.330 | 51.155 | 74.091 | 1.00 | 7.58  | A |
| ATOM | 5715 | CG  | MET | A | 99  | 39.159 | 52.043 | 72.860 | 1.00 | 7.35  | A |
| ATOM | 5716 | SD  | MET | A | 99  | 37.673 | 51.709 | 71.886 | 1.00 | 7.56  | A |
| ATOM | 5717 | CE  | MET | A | 99  | 38.136 | 50.177 | 71.036 | 1.00 | 9.56  | A |
| ATOM | 5718 | C   | MET | A | 99  | 38.439 | 50.178 | 76.198 | 1.00 | 6.10  | A |
| ATOM | 5719 | O   | MET | A | 99  | 38.060 | 49.005 | 76.139 | 1.00 | 7.35  | A |
| ATOM | 5720 | N   | SER | A | 100 | 39.108 | 50.671 | 77.236 | 1.00 | 6.09  | A |
| ATOM | 5721 | CA  | SER | A | 100 | 39.465 | 49.839 | 78.382 | 1.00 | 8.79  | A |
| ATOM | 5722 | CB  | SER | A | 100 | 40.533 | 50.546 | 79.220 | 1.00 | 9.54  | A |
| ATOM | 5723 | OG  | SER | A | 100 | 41.722 | 50.717 | 78.466 | 1.00 | 15.41 | A |
| ATOM | 5724 | C   | SER | A | 100 | 38.279 | 49.449 | 79.266 | 1.00 | 9.77  | A |
| ATOM | 5725 | O   | SER | A | 100 | 38.415 | 48.591 | 80.142 | 1.00 | 12.78 | A |
| ATOM | 5726 | N   | CYS | A | 101 | 37.123 | 50.067 | 79.033 | 1.00 | 9.75  | A |
| ATOM | 5727 | CA  | CYS | A | 101 | 35.920 | 49.764 | 79.808 | 1.00 | 11.59 | A |
| ATOM | 5728 | CB  | CYS | A | 101 | 34.892 | 50.892 | 79.680 | 1.00 | 12.49 | A |
| ATOM | 5729 | SG  | CYS | A | 101 | 35.263 | 52.370 | 80.617 | 1.00 | 15.69 | A |
| ATOM | 5730 | C   | CYS | A | 101 | 35.260 | 48.469 | 79.351 | 1.00 | 10.47 | A |
| ATOM | 5731 | O   | CYS | A | 101 | 34.497 | 47.857 | 80.100 | 1.00 | 12.82 | A |
| ATOM | 5732 | N   | PHE | A | 102 | 35.542 | 48.063 | 78.119 | 1.00 | 10.24 | A |
| ATOM | 5733 | CA  | PHE | A | 102 | 34.941 | 46.855 | 77.571 | 1.00 | 10.36 | A |
| ATOM | 5734 | CB  | PHE | A | 102 | 35.009 | 46.877 | 76.045 | 1.00 | 10.28 | A |
| ATOM | 5735 | CG  | PHE | A | 102 | 34.151 | 47.936 | 75.420 | 1.00 | 8.84  | A |
| ATOM | 5736 | CD1 | PHE | A | 102 | 34.567 | 49.263 | 75.386 | 1.00 | 9.33  | A |
| ATOM | 5737 | CD2 | PHE | A | 102 | 32.910 | 47.609 | 74.884 | 1.00 | 9.36  | A |
| ATOM | 5738 | CE1 | PHE | A | 102 | 33.756 | 50.251 | 74.829 | 1.00 | 8.74  | A |
| ATOM | 5739 | CE2 | PHE | A | 102 | 32.092 | 48.586 | 74.325 | 1.00 | 9.38  | A |
| ATOM | 5740 | CZ  | PHE | A | 102 | 32.516 | 49.911 | 74.297 | 1.00 | 7.96  | A |
| ATOM | 5741 | C   | PHE | A | 102 | 35.581 | 45.577 | 78.097 | 1.00 | 11.75 | A |
| ATOM | 5742 | O   | PHE | A | 102 | 36.801 | 45.487 | 78.213 | 1.00 | 12.38 | A |
| ATOM | 5743 | N   | PRO | A | 103 | 34.755 | 44.566 | 78.420 | 1.00 | 12.10 | A |
| ATOM | 5744 | CD  | PRO | A | 103 | 33.282 | 44.633 | 78.463 | 1.00 | 12.55 | A |
| ATOM | 5745 | CA  | PRO | A | 103 | 35.232 | 43.278 | 78.937 | 1.00 | 13.72 | A |
| ATOM | 5746 | CB  | PRO | A | 103 | 34.005 | 42.730 | 79.650 | 1.00 | 14.58 | A |
| ATOM | 5747 | CG  | PRO | A | 103 | 32.898 | 43.194 | 78.758 | 1.00 | 13.49 | A |
| ATOM | 5748 | C   | PRO | A | 103 | 35.709 | 42.361 | 77.815 | 1.00 | 14.61 | A |
| ATOM | 5749 | O   | PRO | A | 103 | 35.101 | 41.325 | 77.544 | 1.00 | 15.36 | A |
| ATOM | 5750 | N   | TRP | A | 104 | 36.804 | 42.744 | 77.171 | 1.00 | 14.45 | A |
| ATOM | 5751 | CA  | TRP | A | 104 | 37.352 | 41.968 | 76.068 | 1.00 | 15.73 | A |
| ATOM | 5752 | CB  | TRP | A | 104 | 38.617 | 42.634 | 75.529 | 1.00 | 15.71 | A |
| ATOM | 5753 | CG  | TRP | A | 104 | 38.438 | 44.071 | 75.158 | 1.00 | 13.26 | A |
| ATOM | 5754 | CD2 | TRP | A | 104 | 37.817 | 44.572 | 73.972 | 1.00 | 13.03 | A |
| ATOM | 5755 | CE2 | TRP | A | 104 | 37.825 | 45.981 | 74.063 | 1.00 | 11.27 | A |
| ATOM | 5756 | CE3 | TRP | A | 104 | 37.242 | 43.965 | 72.848 | 1.00 | 12.96 | A |
| ATOM | 5757 | CD1 | TRP | A | 104 | 38.797 | 45.163 | 75.895 | 1.00 | 12.87 | A |
| ATOM | 5758 | NE1 | TRP | A | 104 | 38.433 | 46.315 | 75.242 | 1.00 | 11.57 | A |
| ATOM | 5759 | CZ2 | TRP | A | 104 | 37.288 | 46.796 | 73.060 | 1.00 | 13.14 | A |
| ATOM | 5760 | CZ3 | TRP | A | 104 | 36.707 | 44.776 | 71.853 | 1.00 | 13.80 | A |
| ATOM | 5761 | CH2 | TRP | A | 104 | 36.731 | 46.176 | 71.970 | 1.00 | 14.33 | A |
| ATOM | 5762 | C   | TRP | A | 104 | 37.670 | 40.516 | 76.424 | 1.00 | 17.38 | A |
| ATOM | 5763 | O   | TRP | A | 104 | 37.534 | 39.628 | 75.591 | 1.00 | 18.27 | A |
| ATOM | 5764 | N   | ALA | A | 105 | 38.088 | 40.265 | 77.658 | 1.00 | 18.99 | A |
| ATOM | 5765 | CA  | ALA | A | 105 | 38.443 | 38.907 | 78.053 | 1.00 | 21.60 | A |
| ATOM | 5766 | CB  | ALA | A | 105 | 39.670 | 38.942 | 78.956 | 1.00 | 21.34 | A |
| ATOM | 5767 | C   | ALA | A | 105 | 37.330 | 38.111 | 78.726 | 1.00 | 23.19 | A |
| ATOM | 5768 | O   | ALA | A | 105 | 37.545 | 36.968 | 79.130 | 1.00 | 23.27 | A |
| ATOM | 5769 | N   | GLU | A | 106 | 36.144 | 38.700 | 78.843 | 1.00 | 24.01 | A |
| ATOM | 5770 | CA  | GLU | A | 106 | 35.028 | 38.009 | 79.480 | 1.00 | 25.35 | A |
| ATOM | 5771 | CB  | GLU | A | 106 | 33.773 | 38.884 | 79.457 | 1.00 | 25.81 | A |
| ATOM | 5772 | CG  | GLU | A | 106 | 32.545 | 38.207 | 80.053 | 1.00 | 26.97 | A |
| ATOM | 5773 | CD  | GLU | A | 106 | 32.799 | 37.651 | 81.443 | 1.00 | 27.81 | A |
| ATOM | 5774 | OE1 | GLU | A | 106 | 33.119 | 38.441 | 82.356 | 1.00 | 28.08 | A |
| ATOM | 5775 | OE2 | GLU | A | 106 | 32.681 | 36.419 | 81.620 | 1.00 | 28.82 | A |
| ATOM | 5776 | C   | GLU | A | 106 | 34.735 | 36.666 | 78.819 | 1.00 | 25.88 | A |
| ATOM | 5777 | O   | GLU | A | 106 | 34.530 | 36.582 | 77.609 | 1.00 | 25.18 | A |
| ATOM | 5778 | N   | LYS | A | 107 | 34.713 | 35.618 | 79.637 | 1.00 | 27.20 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine F$_{2α}$(U46)

| ATOM | 5779 | CA  | LYS | A | 107 | 34.462 | 34.255 | 79.179 | 1.00 | 28.80 | A |
|------|------|-----|-----|---|-----|--------|--------|--------|------|-------|---|
| ATOM | 5780 | CB  | LYS | A | 107 | 34.794 | 33.252 | 80.292 | 1.00 | 29.93 | A |
| ATOM | 5781 | CG  | LYS | A | 107 | 36.017 | 33.600 | 81.132 | 1.00 | 31.92 | A |
| ATOM | 5782 | CD  | LYS | A | 107 | 35.769 | 34.840 | 81.986 | 1.00 | 33.29 | A |
| ATOM | 5783 | CE  | LYS | A | 107 | 36.998 | 35.235 | 82.776 | 1.00 | 35.16 | A |
| ATOM | 5784 | NZ  | LYS | A | 107 | 36.888 | 36.631 | 83.286 | 1.00 | 36.27 | A |
| ATOM | 5785 | C   | LYS | A | 107 | 33.000 | 34.085 | 78.779 | 1.00 | 28.48 | A |
| ATOM | 5786 | O   | LYS | A | 107 | 32.693 | 33.623 | 77.681 | 1.00 | 29.44 | A |
| ATOM | 5787 | N   | LYS | A | 108 | 32.107 | 34.456 | 79.690 | 1.00 | 28.29 | A |
| ATOM | 5788 | CA  | LYS | A | 108 | 30.671 | 34.350 | 79.462 | 1.00 | 28.16 | A |
| ATOM | 5789 | CB  | LYS | A | 108 | 29.920 | 34.648 | 80.761 | 1.00 | 29.14 | A |
| ATOM | 5790 | CG  | LYS | A | 108 | 30.297 | 33.723 | 81.911 | 1.00 | 30.38 | A |
| ATOM | 5791 | CD  | LYS | A | 108 | 29.548 | 34.069 | 83.188 | 1.00 | 32.02 | A |
| ATOM | 5792 | CE  | LYS | A | 108 | 29.946 | 35.439 | 83.720 | 1.00 | 33.28 | A |
| ATOM | 5793 | NZ  | LYS | A | 108 | 31.394 | 35.501 | 84.063 | 1.00 | 34.77 | A |
| ATOM | 5794 | C   | LYS | A | 108 | 30.227 | 35.311 | 78.364 | 1.00 | 27.82 | A |
| ATOM | 5795 | O   | LYS | A | 108 | 30.147 | 36.521 | 78.576 | 1.00 | 26.75 | A |
| ATOM | 5796 | N   | GLN | A | 109 | 29.932 | 34.759 | 77.191 | 1.00 | 27.48 | A |
| ATOM | 5797 | CA  | GLN | A | 109 | 29.510 | 35.559 | 76.046 | 1.00 | 27.67 | A |
| ATOM | 5798 | CB  | GLN | A | 109 | 29.326 | 34.662 | 74.820 | 1.00 | 29.61 | A |
| ATOM | 5799 | CG  | GLN | A | 109 | 30.615 | 34.010 | 74.345 | 1.00 | 32.22 | A |
| ATOM | 5800 | CD  | GLN | A | 109 | 31.706 | 35.024 | 74.043 | 1.00 | 33.48 | A |
| ATOM | 5801 | OE1 | GLN | A | 109 | 31.559 | 35.869 | 73.161 | 1.00 | 35.21 | A |
| ATOM | 5802 | NE2 | GLN | A | 109 | 32.808 | 34.943 | 74.779 | 1.00 | 33.63 | A |
| ATOM | 5803 | C   | GLN | A | 109 | 28.238 | 36.362 | 76.290 | 1.00 | 26.71 | A |
| ATOM | 5804 | O   | GLN | A | 109 | 28.121 | 37.497 | 75.833 | 1.00 | 25.25 | A |
| ATOM | 5805 | N   | ASP | A | 110 | 27.284 | 35.774 | 77.004 | 1.00 | 26.14 | A |
| ATOM | 5806 | CA  | ASP | A | 110 | 26.030 | 36.459 | 77.293 | 1.00 | 25.81 | A |
| ATOM | 5807 | CB  | ASP | A | 110 | 25.071 | 35.516 | 78.031 | 1.00 | 28.34 | A |
| ATOM | 5808 | CG  | ASP | A | 110 | 25.701 | 34.879 | 79.254 | 1.00 | 30.43 | A |
| ATOM | 5809 | OD1 | ASP | A | 110 | 25.955 | 35.597 | 80.242 | 1.00 | 31.82 | A |
| ATOM | 5810 | OD2 | ASP | A | 110 | 25.945 | 33.654 | 79.226 | 1.00 | 33.72 | A |
| ATOM | 5811 | C   | ASP | A | 110 | 26.275 | 37.722 | 78.115 | 1.00 | 24.06 | A |
| ATOM | 5812 | O   | ASP | A | 110 | 25.718 | 38.781 | 77.823 | 1.00 | 23.68 | A |
| ATOM | 5813 | N   | VAL | A | 111 | 27.117 | 37.610 | 79.138 | 1.00 | 22.43 | A |
| ATOM | 5814 | CA  | VAL | A | 111 | 27.433 | 38.748 | 79.994 | 1.00 | 20.34 | A |
| ATOM | 5815 | CB  | VAL | A | 111 | 28.257 | 38.311 | 81.226 | 1.00 | 21.27 | A |
| ATOM | 5816 | CG1 | VAL | A | 111 | 28.620 | 39.523 | 82.070 | 1.00 | 22.02 | A |
| ATOM | 5817 | CG2 | VAL | A | 111 | 27.464 | 37.313 | 82.053 | 1.00 | 22.25 | A |
| ATOM | 5818 | C   | VAL | A | 111 | 28.240 | 39.778 | 79.215 | 1.00 | 18.84 | A |
| ATOM | 5819 | O   | VAL | A | 111 | 28.005 | 40.980 | 79.309 | 1.00 | 17.77 | A |
| ATOM | 5820 | N   | LYS | A | 112 | 29.195 | 39.292 | 78.442 | 1.00 | 17.36 | A |
| ATOM | 5821 | CA  | LYS | A | 112 | 30.048 | 40.154 | 77.650 | 1.00 | 16.73 | A |
| ATOM | 5822 | CB  | LYS | A | 112 | 31.037 | 39.287 | 76.919 | 1.00 | 17.64 | A |
| ATOM | 5823 | CG  | LYS | A | 112 | 32.075 | 40.014 | 76.182 | 1.00 | 18.95 | A |
| ATOM | 5824 | CD  | LYS | A | 112 | 32.954 | 38.942 | 75.717 | 1.00 | 21.64 | A |
| ATOM | 5825 | CE  | LYS | A | 112 | 34.038 | 39.471 | 74.948 | 1.00 | 22.51 | A |
| ATOM | 5826 | NZ  | LYS | A | 112 | 34.561 | 38.318 | 74.176 | 1.00 | 25.51 | A |
| ATOM | 5827 | C   | LYS | A | 112 | 29.242 | 40.977 | 76.656 | 1.00 | 15.52 | A |
| ATOM | 5828 | O   | LYS | A | 112 | 29.410 | 42.192 | 76.550 | 1.00 | 13.43 | A |
| ATOM | 5829 | N   | GLU | A | 113 | 28.366 | 40.298 | 75.925 | 1.00 | 14.92 | A |
| ATOM | 5830 | CA  | GLU | A | 113 | 27.520 | 40.947 | 74.938 | 1.00 | 15.67 | A |
| ATOM | 5831 | CB  | GLU | A | 113 | 26.626 | 39.904 | 74.271 | 1.00 | 18.01 | A |
| ATOM | 5832 | CG  | GLU | A | 113 | 25.680 | 40.492 | 73.263 | 1.00 | 23.31 | A |
| ATOM | 5833 | CD  | GLU | A | 113 | 24.799 | 39.452 | 72.598 | 1.00 | 25.74 | A |
| ATOM | 5834 | OE1 | GLU | A | 113 | 25.338 | 38.456 | 72.073 | 1.00 | 27.13 | A |
| ATOM | 5835 | OE2 | GLU | A | 113 | 23.565 | 39.642 | 72.587 | 1.00 | 28.97 | A |
| ATOM | 5836 | C   | GLU | A | 113 | 26.659 | 42.036 | 75.575 | 1.00 | 14.49 | A |
| ATOM | 5837 | O   | GLU | A | 113 | 26.556 | 43.148 | 75.053 | 1.00 | 13.30 | A |
| ATOM | 5838 | N   | GLN | A | 114 | 26.046 | 41.709 | 76.708 | 1.00 | 14.04 | A |
| ATOM | 5839 | CA  | GLN | A | 114 | 25.196 | 42.657 | 77.418 | 1.00 | 14.13 | A |
| ATOM | 5840 | CB  | GLN | A | 114 | 24.622 | 42.011 | 78.685 | 1.00 | 15.69 | A |
| ATOM | 5841 | CG  | GLN | A | 114 | 23.799 | 42.961 | 79.545 | 1.00 | 18.28 | A |
| ATOM | 5842 | CD  | GLN | A | 114 | 22.512 | 43.407 | 78.874 | 1.00 | 19.74 | A |
| ATOM | 5843 | OE1 | GLN | A | 114 | 21.856 | 44.344 | 79.330 | 1.00 | 23.56 | A |
| ATOM | 5844 | NE2 | GLN | A | 114 | 22.140 | 42.733 | 77.792 | 1.00 | 21.05 | A |
| ATOM | 5845 | C   | GLN | A | 114 | 25.966 | 43.920 | 77.793 | 1.00 | 13.10 | A |
| ATOM | 5846 | O   | GLN | A | 114 | 25.486 | 45.033 | 77.583 | 1.00 | 12.07 | A |
| ATOM | 5847 | N   | MET | A | 115 | 27.161 | 43.744 | 78.347 | 1.00 | 12.86 | A |
| ATOM | 5848 | CA  | MET | A | 115 | 27.986 | 44.876 | 78.750 | 1.00 | 11.47 | A |
| ATOM | 5849 | CB  | MET | A | 115 | 29.219 | 44.375 | 79.516 | 1.00 | 14.17 | A |
| ATOM | 5850 | CG  | MET | A | 115 | 30.295 | 45.433 | 79.785 | 1.00 | 19.50 | A |
| ATOM | 5851 | SD  | MET | A | 115 | 31.315 | 45.040 | 81.253 | 1.00 | 26.29 | A |
| ATOM | 5852 | CE  | MET | A | 115 | 31.200 | 46.546 | 82.323 | 1.00 | 25.88 | A |
| ATOM | 5853 | C   | MET | A | 115 | 28.398 | 45.721 | 77.546 | 1.00 | 10.85 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 5854 | O | MET | A | 115 | 28.364 | 46.951 | 77.602 | 1.00 | 10.44 | A |
| ATOM | 5855 | N | PHE | A | 116 | 28.786 | 45.063 | 76.458 | 1.00 | 10.25 | A |
| ATOM | 5856 | CA | PHE | A | 116 | 29.172 | 45.783 | 75.249 | 1.00 | 9.42 | A |
| ATOM | 5857 | CB | PHE | A | 116 | 29.552 | 44.810 | 74.126 | 1.00 | 9.27 | A |
| ATOM | 5858 | CG | PHE | A | 116 | 31.026 | 44.519 | 74.038 | 1.00 | 11.09 | A |
| ATOM | 5859 | CD1 | PHE | A | 116 | 31.687 | 43.865 | 75.070 | 1.00 | 10.32 | A |
| ATOM | 5860 | CD2 | PHE | A | 116 | 31.749 | 44.897 | 72.912 | 1.00 | 12.11 | A |
| ATOM | 5861 | CE1 | PHE | A | 116 | 33.053 | 43.589 | 74.985 | 1.00 | 12.71 | A |
| ATOM | 5862 | CE2 | PHE | A | 116 | 33.113 | 44.629 | 72.814 | 1.00 | 11.83 | A |
| ATOM | 5863 | CZ | PHE | A | 116 | 33.766 | 43.972 | 73.853 | 1.00 | 11.75 | A |
| ATOM | 5864 | C | PHE | A | 116 | 28.013 | 46.652 | 74.772 | 1.00 | 7.94 | A |
| ATOM | 5865 | O | PHE | A | 116 | 28.193 | 47.826 | 74.460 | 1.00 | 8.19 | A |
| ATOM | 6152 | N | TYR | A | 152 | 44.548 | 57.094 | 66.166 | 1.00 | 5.28 | A |
| ATOM | 6153 | CA | TYR | A | 152 | 43.884 | 56.348 | 67.225 | 1.00 | 4.93 | A |
| ATOM | 6154 | CB | TYR | A | 152 | 44.409 | 56.744 | 68.612 | 1.00 | 5.14 | A |
| ATOM | 6155 | CG | TYR | A | 152 | 44.300 | 55.605 | 69.611 | 1.00 | 5.38 | A |
| ATOM | 6156 | CD1 | TYR | A | 152 | 44.726 | 54.319 | 69.273 | 1.00 | 6.68 | A |
| ATOM | 6157 | CE1 | TYR | A | 152 | 44.646 | 53.268 | 70.177 | 1.00 | 6.58 | A |
| ATOM | 6158 | CD2 | TYR | A | 152 | 43.784 | 55.806 | 70.888 | 1.00 | 4.95 | A |
| ATOM | 6159 | CE2 | TYR | A | 152 | 43.702 | 54.755 | 71.804 | 1.00 | 4.84 | A |
| ATOM | 6160 | CZ | TYR | A | 152 | 44.136 | 53.492 | 71.439 | 1.00 | 5.18 | A |
| ATOM | 6161 | OH | TYR | A | 152 | 44.081 | 52.443 | 72.330 | 1.00 | 6.87 | A |
| ATOM | 6162 | C | TYR | A | 152 | 42.372 | 56.492 | 67.156 | 1.00 | 5.08 | A |
| ATOM | 6163 | O | TYR | A | 152 | 41.647 | 55.557 | 67.485 | 1.00 | 5.51 | A |
| ATOM | 6164 | N | TRP | A | 153 | 41.884 | 57.656 | 66.736 | 1.00 | 5.39 | A |
| ATOM | 6165 | CA | TRP | A | 153 | 40.442 | 57.818 | 66.600 | 1.00 | 5.76 | A |
| ATOM | 6166 | CB | TRP | A | 153 | 40.073 | 59.242 | 66.171 | 1.00 | 5.97 | A |
| ATOM | 6167 | CG | TRP | A | 153 | 38.665 | 59.325 | 65.648 | 1.00 | 5.87 | A |
| ATOM | 6168 | CD2 | TRP | A | 153 | 37.471 | 58.920 | 66.332 | 1.00 | 5.91 | A |
| ATOM | 6169 | CE2 | TRP | A | 153 | 36.396 | 59.086 | 65.429 | 1.00 | 5.96 | A |
| ATOM | 6170 | CE3 | TRP | A | 153 | 37.207 | 58.420 | 67.615 | 1.00 | 6.22 | A |
| ATOM | 6171 | CD1 | TRP | A | 153 | 38.274 | 59.723 | 64.399 | 1.00 | 7.17 | A |
| ATOM | 6172 | NE1 | TRP | A | 153 | 36.912 | 59.582 | 64.261 | 1.00 | 7.77 | A |
| ATOM | 6173 | CZ2 | TRP | A | 153 | 35.072 | 58.781 | 65.772 | 1.00 | 6.91 | A |
| ATOM | 6174 | CZ3 | TRP | A | 153 | 35.886 | 58.116 | 67.956 | 1.00 | 7.15 | A |
| ATOM | 6175 | CH2 | TRP | A | 153 | 34.839 | 58.294 | 67.032 | 1.00 | 7.76 | A |
| ATOM | 6176 | C | TRP | A | 153 | 39.930 | 56.835 | 65.546 | 1.00 | 5.37 | A |
| ATOM | 6177 | O | TRP | A | 153 | 38.934 | 56.144 | 65.756 | 1.00 | 5.17 | A |
| ATOM | 6178 | N | GLU | A | 154 | 40.611 | 56.772 | 64.406 | 1.00 | 5.96 | A |
| ATOM | 6179 | CA | GLU | A | 154 | 40.176 | 55.877 | 63.343 | 1.00 | 5.72 | A |
| ATOM | 6180 | CB | GLU | A | 154 | 41.009 | 56.110 | 62.079 | 1.00 | 6.13 | A |
| ATOM | 6181 | CG | GLU | A | 154 | 40.449 | 55.429 | 60.833 | 1.00 | 6.44 | A |
| ATOM | 6182 | CD | GLU | A | 154 | 40.878 | 53.979 | 60.703 | 1.00 | 6.70 | A |
| ATOM | 6183 | OE1 | GLU | A | 154 | 40.229 | 53.235 | 59.938 | 1.00 | 8.97 | A |
| ATOM | 6184 | OE2 | GLU | A | 154 | 41.876 | 53.586 | 61.345 | 1.00 | 8.06 | A |
| ATOM | 6185 | C | GLU | A | 154 | 40.247 | 54.414 | 63.774 | 1.00 | 5.12 | A |
| ATOM | 6186 | O | GLU | A | 154 | 39.355 | 53.625 | 63.467 | 1.00 | 6.20 | A |
| ATOM | 6187 | N | ILE | A | 155 | 41.305 | 54.059 | 64.497 | 1.00 | 5.18 | A |
| ATOM | 6188 | CA | ILE | A | 155 | 41.489 | 52.696 | 64.975 | 1.00 | 4.86 | A |
| ATOM | 6189 | CB | ILE | A | 155 | 42.901 | 52.549 | 65.580 | 1.00 | 5.47 | A |
| ATOM | 6190 | CG2 | ILE | A | 155 | 42.987 | 51.319 | 66.475 | 1.00 | 6.67 | A |
| ATOM | 6191 | CG1 | ILE | A | 155 | 43.925 | 52.501 | 64.440 | 1.00 | 5.20 | A |
| ATOM | 6192 | CD1 | ILE | A | 155 | 45.357 | 52.705 | 64.879 | 1.00 | 6.49 | A |
| ATOM | 6193 | C | ILE | A | 155 | 40.413 | 52.296 | 65.987 | 1.00 | 5.58 | A |
| ATOM | 6194 | O | ILE | A | 155 | 39.780 | 51.247 | 65.851 | 1.00 | 5.20 | A |
| ATOM | 6195 | N | CYS | A | 156 | 40.196 | 53.136 | 66.992 | 1.00 | 4.65 | A |
| ATOM | 6196 | CA | CYS | A | 156 | 39.190 | 52.838 | 68.007 | 1.00 | 5.13 | A |
| ATOM | 6197 | CB | CYS | A | 156 | 39.216 | 53.888 | 69.121 | 1.00 | 5.71 | A |
| ATOM | 6198 | SG | CYS | A | 156 | 40.667 | 53.829 | 70.192 | 1.00 | 6.49 | A |
| ATOM | 6199 | C | CYS | A | 156 | 37.789 | 52.779 | 67.420 | 1.00 | 5.66 | A |
| ATOM | 6200 | O | CYS | A | 156 | 37.026 | 51.855 | 67.710 | 1.00 | 6.21 | A |
| ATOM | 6201 | N | SER | A | 157 | 37.448 | 53.766 | 66.594 | 1.00 | 6.00 | A |
| ATOM | 6202 | CA | SER | A | 157 | 36.114 | 53.797 | 66.009 | 1.00 | 5.99 | A |
| ATOM | 6203 | CB | SER | A | 157 | 35.843 | 55.146 | 65.317 | 1.00 | 6.89 | A |
| ATOM | 6204 | OG | SER | A | 157 | 36.766 | 55.420 | 64.282 | 1.00 | 6.66 | A |
| ATOM | 6205 | C | SER | A | 157 | 35.868 | 52.633 | 65.053 | 1.00 | 6.25 | A |
| ATOM | 6206 | O | SER | A | 157 | 34.746 | 52.146 | 64.952 | 1.00 | 6.68 | A |
| ATOM | 6207 | N | THR | A | 158 | 36.902 | 52.170 | 64.358 | 1.00 | 6.04 | A |
| ATOM | 6208 | CA | THR | A | 158 | 36.717 | 51.043 | 63.452 | 1.00 | 6.77 | A |
| ATOM | 6209 | CB | THR | A | 158 | 38.027 | 50.693 | 62.720 | 1.00 | 7.66 | A |
| ATOM | 6210 | OG1 | THR | A | 158 | 38.194 | 51.589 | 61.617 | 1.00 | 8.90 | A |
| ATOM | 6211 | CG2 | THR | A | 158 | 38.004 | 49.253 | 62.214 | 1.00 | 8.99 | A |
| ATOM | 6212 | C | THR | A | 158 | 36.219 | 49.827 | 64.225 | 1.00 | 7.46 | A |
| ATOM | 6213 | O | THR | A | 158 | 35.299 | 49.137 | 63.792 | 1.00 | 7.44 | A |
| ATOM | 6214 | N | THR | A | 159 | 36.813 | 49.572 | 65.380 | 1.00 | 6.82 | A |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 6215 | CA | THR | A | 159 | 36.400 | 48.428 | 66.174 | 1.00 | 8.47 | A |
|---|---|---|---|---|---|---|---|---|---|---|---|
| ATOM | 6216 | CB | THR | A | 159 | 37.480 | 48.070 | 67.201 | 1.00 | 8.32 | A |
| ATOM | 6217 | OG1 | THR | A | 159 | 38.641 | 47.615 | 66.494 | 1.00 | 9.56 | A |
| ATOM | 6218 | CG2 | THR | A | 159 | 37.005 | 46.971 | 68.140 | 1.00 | 8.90 | A |
| ATOM | 6219 | C | THR | A | 159 | 35.049 | 48.651 | 66.849 | 1.00 | 7.49 | A |
| ATOM | 6220 | O | THR | A | 159 | 34.222 | 47.740 | 66.900 | 1.00 | 8.33 | A |
| ATOM | 6221 | N | LEU | A | 160 | 34.804 | 49.857 | 67.354 | 1.00 | 6.78 | A |
| ATOM | 6222 | CA | LEU | A | 160 | 33.519 | 50.125 | 67.988 | 1.00 | 6.38 | A |
| ATOM | 6223 | CB | LEU | A | 160 | 33.498 | 51.531 | 68.588 | 1.00 | 6.84 | A |
| ATOM | 6224 | CG | LEU | A | 160 | 34.480 | 51.773 | 69.736 | 1.00 | 8.63 | A |
| ATOM | 6225 | CD1 | LEU | A | 160 | 34.360 | 53.209 | 70.217 | 1.00 | 11.20 | A |
| ATOM | 6226 | CD2 | LEU | A | 160 | 34.194 | 50.799 | 70.871 | 1.00 | 11.27 | A |
| ATOM | 6227 | C | LEU | A | 160 | 32.384 | 49.979 | 66.974 | 1.00 | 7.24 | A |
| ATOM | 6228 | O | LEU | A | 160 | 31.300 | 49.503 | 67.311 | 1.00 | 7.48 | A |
| ATOM | 6229 | N | LEU | A | 161 | 32.642 | 50.383 | 65.733 | 1.00 | 6.66 | A |
| ATOM | 6230 | CA | LEU | A | 161 | 31.641 | 50.297 | 64.673 | 1.00 | 8.42 | A |
| ATOM | 6231 | CB | LEU | A | 161 | 32.156 | 50.972 | 63.403 | 1.00 | 9.08 | A |
| ATOM | 6232 | CG | LEU | A | 161 | 32.054 | 52.499 | 63.404 | 1.00 | 8.17 | A |
| ATOM | 6233 | CD1 | LEU | A | 161 | 32.903 | 53.074 | 62.283 | 1.00 | 9.90 | A |
| ATOM | 6234 | CD2 | LEU | A | 161 | 30.594 | 52.915 | 63.251 | 1.00 | 9.54 | A |
| ATOM | 6235 | C | LEU | A | 161 | 31.232 | 48.862 | 64.366 | 1.00 | 8.60 | A |
| ATOM | 6236 | O | LEU | A | 161 | 30.132 | 48.619 | 63.874 | 1.00 | 9.07 | A |
| ATOM | 6237 | N | VAL | A | 162 | 32.116 | 47.914 | 64.652 | 1.00 | 8.54 | A |
| ATOM | 6238 | CA | VAL | A | 162 | 31.806 | 46.511 | 64.421 | 1.00 | 10.19 | A |
| ATOM | 6239 | CB | VAL | A | 162 | 33.025 | 45.605 | 64.724 | 1.00 | 9.33 | A |
| ATOM | 6240 | CG1 | VAL | A | 162 | 32.617 | 44.139 | 64.661 | 1.00 | 12.54 | A |
| ATOM | 6241 | CG2 | VAL | A | 162 | 34.147 | 45.883 | 63.735 | 1.00 | 10.70 | A |
| ATOM | 6242 | C | VAL | A | 162 | 30.656 | 46.102 | 65.337 | 1.00 | 10.61 | A |
| ATOM | 6243 | O | VAL | A | 162 | 29.756 | 45.367 | 64.933 | 1.00 | 12.29 | A |
| ATOM | 6244 | N | PHE | A | 163 | 30.685 | 46.593 | 66.574 | 1.00 | 9.62 | A |
| ATOM | 6245 | CA | PHE | A | 163 | 29.657 | 46.250 | 67.550 | 1.00 | 9.97 | A |
| ATOM | 6246 | CB | PHE | A | 163 | 30.284 | 46.124 | 68.940 | 1.00 | 10.40 | A |
| ATOM | 6247 | CG | PHE | A | 163 | 31.388 | 45.111 | 69.010 | 1.00 | 13.43 | A |
| ATOM | 6248 | CD1 | PHE | A | 163 | 32.699 | 45.461 | 68.698 | 1.00 | 14.97 | A |
| ATOM | 6249 | CD2 | PHE | A | 163 | 31.112 | 43.796 | 69.360 | 1.00 | 16.10 | A |
| ATOM | 6250 | CE1 | PHE | A | 163 | 33.718 | 44.511 | 68.735 | 1.00 | 16.79 | A |
| ATOM | 6251 | CE2 | PHE | A | 163 | 32.118 | 42.846 | 69.398 | 1.00 | 17.88 | A |
| ATOM | 6252 | CZ | PHE | A | 163 | 33.428 | 43.199 | 69.086 | 1.00 | 18.31 | A |
| ATOM | 6253 | C | PHE | A | 163 | 28.476 | 47.214 | 67.605 | 1.00 | 9.96 | A |
| ATOM | 6254 | O | PHE | A | 163 | 27.414 | 46.865 | 68.116 | 1.00 | 10.98 | A |
| ATOM | 6528 | N | THR | A | 197 | 41.100 | 40.642 | 60.451 | 1.00 | 6.55 | A |
| ATOM | 6529 | CA | THR | A | 197 | 40.708 | 40.042 | 61.711 | 1.00 | 6.54 | A |
| ATOM | 6530 | CB | THR | A | 197 | 41.867 | 40.118 | 62.727 | 1.00 | 7.01 | A |
| ATOM | 6531 | OG1 | THR | A | 197 | 42.283 | 41.481 | 62.890 | 1.00 | 6.91 | A |
| ATOM | 6532 | CG2 | THR | A | 197 | 43.048 | 39.300 | 62.229 | 1.00 | 7.77 | A |
| ATOM | 6533 | C | THR | A | 197 | 39.489 | 40.776 | 62.251 | 1.00 | 6.16 | A |
| ATOM | 6534 | O | THR | A | 197 | 39.252 | 41.929 | 61.910 | 1.00 | 7.50 | A |
| ATOM | 6535 | N | LYS | A | 198 | 38.708 | 40.110 | 63.091 | 1.00 | 7.12 | A |
| ATOM | 6536 | CA | LYS | A | 198 | 37.522 | 40.742 | 63.647 | 1.00 | 7.25 | A |
| ATOM | 6537 | CB | LYS | A | 198 | 36.729 | 39.729 | 64.481 | 1.00 | 9.37 | A |
| ATOM | 6538 | CG | LYS | A | 198 | 35.536 | 40.316 | 65.222 | 1.00 | 12.51 | A |
| ATOM | 6539 | CD | LYS | A | 198 | 34.529 | 40.978 | 64.294 | 1.00 | 16.24 | A |
| ATOM | 6540 | CE | LYS | A | 198 | 33.878 | 39.974 | 63.358 | 1.00 | 16.57 | A |
| ATOM | 6541 | NZ | LYS | A | 198 | 32.726 | 40.573 | 62.615 | 1.00 | 16.81 | A |
| ATOM | 6542 | C | LYS | A | 198 | 37.910 | 41.945 | 64.507 | 1.00 | 7.23 | A |
| ATOM | 6543 | O | LYS | A | 198 | 37.377 | 43.043 | 64.331 | 1.00 | 8.34 | A |
| ATOM | 6544 | N | LEU | A | 199 | 38.853 | 41.729 | 65.419 | 1.00 | 7.65 | A |
| ATOM | 6545 | CA | LEU | A | 199 | 39.316 | 42.775 | 66.325 | 1.00 | 7.68 | A |
| ATOM | 6546 | CB | LEU | A | 199 | 39.247 | 42.283 | 67.772 | 1.00 | 10.39 | A |
| ATOM | 6547 | CG | LEU | A | 199 | 37.902 | 41.731 | 68.242 | 1.00 | 12.70 | A |
| ATOM | 6548 | CD1 | LEU | A | 199 | 38.057 | 41.197 | 69.652 | 1.00 | 15.45 | A |
| ATOM | 6549 | CD2 | LEU | A | 199 | 36.837 | 42.817 | 68.182 | 1.00 | 14.13 | A |
| ATOM | 6550 | C | LEU | A | 199 | 40.735 | 43.235 | 66.028 | 1.00 | 7.07 | A |
| ATOM | 6551 | OT1 | LEU | A | 199 | 41.384 | 42.659 | 65.131 | 1.00 | 7.11 | A |
| ATOM | 6552 | OT2 | LEU | A | 199 | 41.186 | 44.168 | 66.721 | 1.00 | 8.05 | A |
| ATOM | 6613 | N1 | GSH | H | 200 | 47.240 | 49.426 | 78.365 | 1.00 | 5.76 | H |
| ATOM | 6614 | CA1 | GSH | H | 200 | 48.071 | 48.329 | 77.882 | 1.00 | 6.49 | H |
| ATOM | 6615 | C1 | GSH | H | 200 | 48.552 | 48.593 | 76.433 | 1.00 | 5.96 | H |
| ATOM | 6616 | O11 | GSH | H | 200 | 47.961 | 49.446 | 75.764 | 1.00 | 6.16 | H |
| ATOM | 6617 | O12 | GSH | H | 200 | 49.623 | 47.939 | 76.023 | 1.00 | 5.89 | H |
| ATOM | 6618 | CB1 | GSH | H | 200 | 47.193 | 47.058 | 77.940 | 1.00 | 7.07 | H |
| ATOM | 6619 | CG1 | GSH | H | 200 | 47.971 | 45.743 | 77.668 | 1.00 | 7.43 | H |
| ATOM | 6620 | CD1 | GSH | H | 200 | 46.947 | 44.584 | 77.671 | 1.00 | 7.37 | H |
| ATOM | 6621 | OE1 | GSH | H | 200 | 46.223 | 44.381 | 78.652 | 1.00 | 7.91 | H |
| ATOM | 6622 | N2 | GSH | H | 200 | 47.074 | 43.729 | 76.649 | 1.00 | 6.87 | H |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine $F_{2\alpha}$(U46)

| ATOM | 6623 | CA2 | GSH | H | 200 | 46.310 | 42.477 | 76.623 | 1.00 | 6.95 | H |
|---|---|---|---|---|---|---|---|---|---|---|---|
| ATOM | 6624 | C2 | GSH | H | 200 | 47.130 | 41.349 | 77.273 | 1.00 | 8.08 | H |
| ATOM | 6625 | O2 | GSH | H | 200 | 48.345 | 41.290 | 77.178 | 1.00 | 8.04 | H |
| ATOM | 6626 | CB2 | GSH | H | 200 | 46.025 | 42.056 | 75.164 | 1.00 | 7.00 | H |
| ATOM | 6627 | SG2 | GSH | H | 200 | 44.867 | 43.164 | 74.287 | 1.00 | 8.63 | H |
| ATOM | 6628 | N3 | GSH | H | 200 | 46.473 | 40.585 | 78.154 | 1.00 | 10.11 | H |
| ATOM | 6629 | CA3 | GSH | H | 200 | 47.063 | 39.404 | 78.824 | 1.00 | 12.26 | H |
| ATOM | 6630 | C3 | GSH | H | 200 | 46.455 | 39.280 | 80.221 | 1.00 | 14.36 | H |
| ATOM | 6631 | O31 | GSH | H | 200 | 46.823 | 38.312 | 80.902 | 1.00 | 17.27 | H |
| ATOM | 6632 | O32 | GSH | H | 200 | 45.621 | 40.144 | 80.600 | 1.00 | 17.25 | H |
| ATOM | 6677 | OH2 | WAT | S | 1 | 45.932 | 55.216 | 78.140 | 1.00 | 11.00 | S |
| ATOM | 6678 | OH2 | WAT | S | 2 | 44.001 | 53.704 | 79.474 | 1.00 | 8.61 | S |
| ATOM | 6679 | OH2 | WAT | S | 3 | 45.044 | 54.147 | 82.027 | 1.00 | 9.47 | S |
| ATOM | 6680 | OH2 | WAT | S | 4 | 47.066 | 56.184 | 80.641 | 1.00 | 11.51 | S |
| ATOM | 6681 | OH2 | WAT | S | 5 | 44.400 | 56.542 | 80.238 | 1.00 | 6.66 | S |
| ATOM | 6682 | OH2 | WAT | S | 6 | 46.942 | 53.261 | 80.035 | 1.00 | 7.38 | S |
| ATOM | 6689 | OH2 | WAT | S | 13 | 44.802 | 42.314 | 61.828 | 1.00 | 6.00 | S |
| ATOM | 6692 | OH2 | WAT | S | 16 | 46.602 | 44.435 | 61.593 | 1.00 | 6.08 | S |
| ATOM | 6693 | OH2 | WAT | S | 17 | 51.844 | 46.380 | 76.801 | 1.00 | 5.53 | S |
| ATOM | 6694 | OH2 | WAT | S | 18 | 46.016 | 50.205 | 68.769 | 1.00 | 4.93 | S |
| ATOM | 6697 | OH2 | WAT | S | 21 | 46.289 | 50.659 | 71.607 | 1.00 | 6.24 | S |
| ATOM | 6699 | OH2 | WAT | S | 23 | 51.226 | 46.303 | 81.832 | 1.00 | 7.26 | S |
| ATOM | 6701 | OH2 | WAT | S | 25 | 49.891 | 52.595 | 76.855 | 1.00 | 6.35 | S |
| ATOM | 6702 | OH2 | WAT | S | 26 | 52.165 | 42.023 | 65.879 | 1.00 | 6.86 | S |
| ATOM | 6703 | OH2 | WAT | S | 27 | 54.167 | 43.535 | 79.506 | 1.00 | 6.85 | S |
| ATOM | 6714 | OH2 | WAT | S | 38 | 47.233 | 52.192 | 77.524 | 1.00 | 8.27 | S |
| ATOM | 6718 | OH2 | WAT | S | 42 | 48.563 | 46.768 | 84.725 | 1.00 | 8.57 | S |
| ATOM | 6719 | OH2 | WAT | S | 43 | 58.660 | 41.683 | 70.327 | 1.00 | 7.93 | S |
| ATOM | 6733 | OH2 | WAT | S | 57 | 48.526 | 46.955 | 81.917 | 1.00 | 7.89 | S |
| ATOM | 6748 | OH2 | WAT | S | 72 | 39.916 | 39.195 | 66.189 | 1.00 | 12.20 | S |
| ATOM | 6762 | OH2 | WAT | S | 88 | 52.225 | 56.098 | 78.210 | 1.00 | 11.05 | S |
| ATOM | 6783 | OH2 | WAT | S | 109 | 41.879 | 49.920 | 62.315 | 1.00 | 9.83 | S |
| ATOM | 6784 | OH2 | WAT | S | 110 | 41.843 | 43.595 | 60.246 | 1.00 | 7.19 | S |
| ATOM | 6788 | OH2 | WAT | S | 114 | 50.291 | 44.524 | 83.978 | 1.00 | 11.55 | S |
| ATOM | 6791 | OH2 | WAT | S | 117 | 45.204 | 49.983 | 75.259 | 1.00 | 11.59 | S |
| ATOM | 6794 | OH2 | WAT | S | 121 | 36.093 | 43.586 | 61.844 | 1.00 | 10.06 | S |
| ATOM | 6812 | OH2 | WAT | S | 140 | 46.502 | 35.525 | 67.908 | 1.00 | 16.03 | S |
| ATOM | 6818 | OH2 | WAT | S | 146 | 46.548 | 45.276 | 81.207 | 1.00 | 11.87 | S |
| ATOM | 6848 | OH2 | WAT | S | 177 | 47.305 | 35.643 | 80.850 | 1.00 | 15.13 | S |
| ATOM | 6851 | OH2 | WAT | S | 180 | 42.393 | 49.873 | 82.928 | 1.00 | 14.77 | S |
| ATOM | 6888 | OH2 | WAT | S | 219 | 49.260 | 57.057 | 77.605 | 1.00 | 11.44 | S |
| ATOM | 6894 | OH2 | WAT | S | 225 | 39.600 | 37.346 | 63.532 | 1.00 | 14.35 | S |
| ATOM | 6908 | OH2 | WAT | S | 239 | 44.676 | 42.614 | 80.064 | 1.00 | 17.81 | S |
| ATOM | 6923 | OH2 | WAT | S | 256 | 51.755 | 42.823 | 85.972 | 1.00 | 15.23 | S |
| ATOM | 6936 | OH2 | WAT | S | 269 | 43.744 | 50.995 | 80.612 | 1.00 | 22.66 | S |
| ATOM | 6977 | OH2 | WAT | S | 310 | 41.854 | 37.441 | 65.183 | 1.00 | 14.71 | S |
| ATOM | 6988 | OH2 | WAT | S | 321 | 52.715 | 31.754 | 68.251 | 1.00 | 25.02 | S |
| ATOM | 7004 | OH2 | WAT | S | 338 | 47.955 | 36.940 | 60.191 | 1.00 | 23.06 | S |
| ATOM | 7020 | OH2 | WAT | S | 356 | 52.697 | 38.727 | 84.915 | 1.00 | 25.89 | S |
| ATOM | 7035 | OH2 | WAT | S | 371 | 52.695 | 46.000 | 79.504 | 1.00 | 6.20 | S |
| ATOM | 7044 | OH2 | WAT | S | 380 | 45.939 | 45.946 | 85.168 | 1.00 | 15.59 | S |
| ATOM | 7069 | OH2 | WAT | S | 409 | 58.139 | 37.692 | 70.855 | 1.00 | 19.42 | S |
| ATOM | 7121 | OH2 | WAT | S | 463 | 44.454 | 49.864 | 78.620 | 1.00 | 17.85 | S |
| ATOM | 7141 | OH2 | WAT | S | 486 | 38.783 | 46.154 | 59.815 | 1.00 | 18.01 | S |
| ATOM | 7185 | OH2 | WAT | S | 533 | 55.398 | 32.865 | 68.634 | 1.00 | 26.34 | S |
| ATOM | 7218 | OH2 | WAT | S | 568 | 39.362 | 52.746 | 81.658 | 1.00 | 20.82 | S |
| ATOM | 7276 | OH2 | WAT | S | 630 | 54.033 | 36.951 | 83.283 | 1.00 | 30.87 | S |
| ATOM | 7291 | OH2 | WAT | S | 647 | 59.120 | 37.414 | 73.286 | 1.00 | 30.13 | S |
| ATOM | 7297 | OH2 | WAT | S | 653 | 43.339 | 48.112 | 81.026 | 1.00 | 26.20 | S |
| ATOM | 7315 | OH2 | WAT | S | 677 | 41.879 | 54.425 | 82.374 | 1.00 | 22.86 | S |
| ATOM | 7345 | OH2 | WAT | S | 707 | 49.594 | 41.237 | 85.951 | 1.00 | 26.42 | S |
| ATOM | 7396 | OH2 | WAT | S | 760 | 33.326 | 48.774 | 82.446 | 1.00 | 41.01 | S |
| ATOM | 7397 | OH2 | WAT | S | 761 | 44.428 | 46.156 | 82.727 | 1.00 | 21.46 | S |
| ATOM | 7432 | OH2 | WAT | S | 798 | 37.760 | 35.933 | 64.870 | 1.00 | 24.86 | S |
| ATOM | 7447 | OH2 | WAT | S | 815 | 44.586 | 33.922 | 63.810 | 1.00 | 27.17 | S |
| ATOM | 7451 | OH2 | WAT | S | 819 | 42.590 | 49.990 | 76.103 | 1.00 | 37.29 | S |
| ATOM | 7491 | OH2 | WAT | S | 865 | 49.313 | 34.257 | 64.053 | 1.00 | 23.25 | S |
| ATOM | 7551 | OH2 | WAT | S | 936 | 38.403 | 45.727 | 86.224 | 1.00 | 34.77 | S |
| ATOM | 7559 | OH2 | WAT | S | 947 | 39.267 | 36.269 | 81.440 | 1.00 | 35.93 | S |
| ATOM | 7562 | OH2 | WAT | S | 950 | 46.311 | 34.424 | 83.694 | 1.00 | 37.47 | S |
| ATOM | 7566 | OH2 | WAT | S | 954 | 49.354 | 35.076 | 61.559 | 1.00 | 34.30 | S |
| ATOM | 7573 | OH2 | WAT | S | 962 | 41.074 | 48.947 | 64.727 | 1.00 | 6.62 | S |
| ATOM | 7576 | OH2 | WAT | S | 965 | 42.360 | 48.144 | 66.991 | 1.00 | 8.16 | S |
| ATOM | 7580 | OH2 | WAT | S | 969 | 40.070 | 46.736 | 70.359 | 1.00 | 15.63 | S |
| ATOM | 7581 | OH2 | WAT | S | 970 | 40.472 | 46.466 | 67.816 | 1.00 | 11.14 | S |

TABLE 4-continued

Three-dimensional structural coordinate of the complex of
human hematopoietic PGDS (SEQ ID NO: 1) with magnesium, glutathione and
9,11-dideoxy-9α,11α-methanoepoxyprostaglandine F$_{2α}$(U46)

| ATOM | 7584 | OH2 | WAT | S | 974 | 46.488 | 28.447 | 69.078 | 1.00 | 22.47 | S |
|---|---|---|---|---|---|---|---|---|---|---|---|
| ATOM | 7664 | OH2 | WAT | S | 1104 | 49.140 | 39.068 | 82.273 | 1.00 | 19.35 | S |
| ATOM | 7673 | OH2 | WAT | S | 1117 | 49.385 | 36.341 | 85.538 | 1.00 | 28.59 | S |
| ATOM | 7675 | OH2 | WAT | S | 1119 | 41.071 | 46.806 | 79.458 | 1.00 | 26.70 | S |
| ATOM | 7676 | OH2 | WAT | S | 1120 | 38.224 | 37.620 | 67.988 | 1.00 | 32.98 | S |
| ATOM | 7678 | OH2 | WAT | S | 1123 | 41.996 | 35.058 | 66.930 | 1.00 | 32.93 | S |
| ATOM | 7683 | OH2 | WAT | S | 1129 | 47.152 | 42.956 | 85.367 | 1.00 | 37.94 | S |
| ATOM | 7722 | OH2 | WAT | S | 1180 | 36.068 | 36.649 | 75.341 | 1.00 | 43.94 | S |
| ATOM | 7732 | OH2 | WAT | S | 1191 | 42.482 | 52.407 | 81.689 | 1.00 | 21.38 | S |
| ATOM | 7733 | OH2 | WAT | S | 1192 | 39.535 | 50.355 | 82.874 | 1.00 | 32.24 | S |
| ATOM | 7737 | OH2 | WAT | S | 1196 | 50.213 | 38.953 | 84.774 | 1.00 | 27.44 | S |
| ATOM | 7843 | OH2 | WAT | S | 1339 | 35.818 | 45.711 | 82.635 | 1.00 | 44.01 | S |
| ATOM | 7853 | OH2 | WAT | S | 1354 | 46.962 | 39.117 | 87.092 | 1.00 | 36.93 | S |
| ATOM | 7874 | OH2 | WAT | S | 1383 | 32.545 | 41.137 | 82.654 | 1.00 | 33.68 | S |
| ATOM | 7884 | OH2 | WAT | S | 1401 | 45.736 | 37.693 | 83.360 | 1.00 | 44.69 | S |
| ATOM | 7926 | OH2 | WAT | S | 1447 | 45.667 | 30.953 | 67.849 | 1.00 | 35.68 | S |
| ATOM | 7927 | OH2 | WAT | S | 1448 | 55.702 | 38.128 | 82.442 | 1.00 | 36.01 | S |
| ATOM | 7948 | OH2 | WAT | S | 1474 | 44.404 | 43.677 | 86.488 | 1.00 | 42.40 | S |
| ATOM | 7952 | OH2 | WAT | S | 1480 | 40.448 | 40.603 | 87.707 | 1.00 | 38.53 | S |
| ATOM | 7954 | OH2 | WAT | S | 1482 | 48.226 | 42.042 | 87.524 | 1.00 | 41.24 | S |
| ATOM | 7996 | OH2 | WAT | S | 1530 | 41.155 | 35.723 | 62.708 | 1.00 | 35.51 | S |
| ATOM | 8019 | OH2 | WAT | S | 1558 | 44.128 | 34.781 | 68.900 | 1.00 | 42.94 | S |
| ATOM | 8020 | OH2 | WAT | S | 1559 | 43.571 | 35.946 | 71.823 | 1.00 | 42.74 | S |
| ATOM | 8127 | C1 | U46 | X | 201 | 41.871 | 38.419 | 75.254 | 1.00 | 41.44 | X |
| ATOM | 8128 | C2 | U46 | X | 201 | 40.838 | 38.243 | 74.213 | 1.00 | 41.53 | X |
| ATOM | 8129 | C3 | U46 | X | 201 | 40.546 | 39.776 | 73.818 | 1.00 | 41.45 | X |
| ATOM | 8130 | C4 | U46 | X | 201 | 42.010 | 40.338 | 73.856 | 1.00 | 41.07 | X |
| ATOM | 8131 | C5 | U46 | X | 201 | 42.792 | 39.065 | 74.274 | 1.00 | 41.56 | X |
| ATOM | 8132 | O6 | U46 | X | 201 | 42.922 | 38.036 | 73.307 | 1.00 | 41.32 | X |
| ATOM | 8133 | C7 | U46 | X | 201 | 41.676 | 37.405 | 73.215 | 1.00 | 41.76 | X |
| ATOM | 8134 | C14 | U46 | X | 201 | 42.399 | 41.346 | 74.949 | 1.00 | 40.61 | X |
| ATOM | 8135 | C16 | U46 | X | 201 | 41.701 | 42.023 | 75.922 | 1.00 | 40.28 | X |
| ATOM | 8136 | C18 | U46 | X | 201 | 42.762 | 42.478 | 76.971 | 1.00 | 40.54 | X |
| ATOM | 8137 | C20 | U46 | X | 201 | 42.973 | 41.118 | 77.340 | 1.00 | 40.10 | X |
| ATOM | 8138 | C21 | U46 | X | 201 | 43.792 | 40.318 | 78.232 | 1.00 | 39.99 | X |
| ATOM | 8139 | C24 | U46 | X | 201 | 43.404 | 38.935 | 77.644 | 1.00 | 40.60 | X |
| ATOM | 8140 | C27 | U46 | X | 201 | 43.941 | 37.551 | 78.094 | 1.00 | 41.02 | X |
| ATOM | 8141 | C30 | U46 | X | 201 | 43.168 | 36.476 | 77.301 | 1.00 | 41.85 | X |
| ATOM | 8142 | O36 | U46 | X | 201 | 42.312 | 43.249 | 77.943 | 1.00 | 40.95 | X |
| ATOM | 8143 | C39 | U46 | X | 201 | 39.913 | 39.986 | 72.481 | 1.00 | 41.80 | X |
| ATOM | 8144 | C41 | U46 | X | 201 | 38.932 | 38.921 | 72.298 | 1.00 | 42.50 | X |
| ATOM | 8145 | C44 | U46 | X | 201 | 37.645 | 38.825 | 72.466 | 1.00 | 43.42 | X |
| ATOM | 8146 | C46 | U46 | X | 201 | 36.596 | 39.762 | 72.916 | 1.00 | 43.47 | X |
| ATOM | 8147 | C48 | U46 | X | 201 | 35.496 | 39.760 | 71.872 | 1.00 | 44.38 | X |
| ATOM | 8148 | C51 | U46 | X | 201 | 34.385 | 40.531 | 72.463 | 1.00 | 45.27 | X |
| ATOM | 8149 | C54 | U46 | X | 201 | 33.109 | 40.654 | 71.681 | 1.00 | 45.90 | X |
| ATOM | 8150 | O57 | U46 | X | 201 | 32.181 | 41.256 | 72.479 | 1.00 | 46.00 | X |
| ATOM | 8151 | O58 | U46 | X | 201 | 32.887 | 40.235 | 70.603 | 1.00 | 46.55 | X |

TABLE 5

Three-dimensional structural coordinate of the complex of
human hematopoietic PGDS (SEQ ID NO: 1) with calcium, glutathione and
9,11-dideoxy-9α,11α-epoxymethanoprostaglandine F$_{2α}$(U44)

| ATOM | 4966 | N | TYR | A | 8 | 24.336 | 32.545 | 34.593 | 1.00 | 23.71 | A |
|---|---|---|---|---|---|---|---|---|---|---|---|
| ATOM | 4967 | CA | TYR | A | 8 | 22.908 | 32.784 | 34.729 | 1.00 | 23.39 | A |
| ATOM | 4968 | CB | TYR | A | 8 | 22.170 | 31.441 | 34.781 | 1.00 | 22.82 | A |
| ATOM | 4969 | CG | TYR | A | 8 | 20.663 | 31.544 | 34.721 | 1.00 | 22.10 | A |
| ATOM | 4970 | CD1 | TYR | A | 8 | 20.024 | 32.094 | 33.606 | 1.00 | 21.74 | A |
| ATOM | 4971 | CE1 | TYR | A | 8 | 18.634 | 32.184 | 33.541 | 1.00 | 21.38 | A |
| ATOM | 4972 | CD2 | TYR | A | 8 | 19.872 | 31.084 | 35.777 | 1.00 | 21.64 | A |
| ATOM | 4973 | CE2 | TYR | A | 8 | 18.481 | 31.170 | 35.723 | 1.00 | 21.52 | A |
| ATOM | 4974 | CZ | TYR | A | 8 | 17.872 | 31.721 | 34.602 | 1.00 | 21.33 | A |
| ATOM | 4975 | OH | TYR | A | 8 | 16.504 | 31.801 | 34.542 | 1.00 | 21.12 | A |
| ATOM | 4976 | C | TYR | A | 8 | 22.659 | 33.572 | 36.016 | 1.00 | 23.34 | A |
| ATOM | 4977 | O | TYR | A | 8 | 23.597 | 33.866 | 36.755 | 1.00 | 23.65 | A |
| ATOM | 4978 | N | PHE | A | 9 | 21.402 | 33.921 | 36.273 | 1.00 | 23.18 | A |
| ATOM | 4979 | CA | PHE | A | 9 | 21.042 | 34.657 | 37.478 | 1.00 | 23.08 | A |
| ATOM | 4980 | CB | PHE | A | 9 | 19.635 | 35.237 | 37.348 | 1.00 | 23.27 | A |
| ATOM | 4981 | CG | PHE | A | 9 | 19.527 | 36.344 | 36.342 | 1.00 | 23.76 | A |
| ATOM | 4982 | CD1 | PHE | A | 9 | 18.642 | 36.248 | 35.273 | 1.00 | 23.77 | A |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine F$_{2α}$(U44)

| ATOM | 4983 | CD2 | PHE | A | 9 | 20.298 | 37.494 | 36.471 | 1.00 | 24.01 | A |
|---|---|---|---|---|---|---|---|---|---|---|---|
| ATOM | 4984 | CE1 | PHE | A | 9 | 18.524 | 37.286 | 34.346 | 1.00 | 24.05 | A |
| ATOM | 4985 | CE2 | PHE | A | 9 | 20.190 | 38.535 | 35.552 | 1.00 | 24.19 | A |
| ATOM | 4986 | CZ | PHE | A | 9 | 19.300 | 38.431 | 34.488 | 1.00 | 24.13 | A |
| ATOM | 4987 | C | PHE | A | 9 | 21.085 | 33.712 | 38.666 | 1.00 | 22.94 | A |
| ATOM | 4988 | O | PHE | A | 9 | 21.182 | 32.497 | 38.491 | 1.00 | 22.79 | A |
| ATOM | 4989 | N | ASN | A | 10 | 21.014 | 34.263 | 39.873 | 1.00 | 22.88 | A |
| ATOM | 4990 | CA | ASN | A | 10 | 21.039 | 33.427 | 41.064 | 1.00 | 22.79 | A |
| ATOM | 4991 | CB | ASN | A | 10 | 21.504 | 34.217 | 42.288 | 1.00 | 22.91 | A |
| ATOM | 4992 | CG | ASN | A | 10 | 21.505 | 33.369 | 43.546 | 1.00 | 22.98 | A |
| ATOM | 4993 | OD1 | ASN | A | 10 | 21.877 | 32.191 | 43.508 | 1.00 | 22.82 | A |
| ATOM | 4994 | ND2 | ASN | A | 10 | 21.091 | 33.957 | 44.666 | 1.00 | 23.07 | A |
| ATOM | 4995 | C | ASN | A | 10 | 19.674 | 32.817 | 41.345 | 1.00 | 22.64 | A |
| ATOM | 4996 | O | ASN | A | 10 | 18.942 | 33.272 | 42.225 | 1.00 | 22.44 | A |
| ATOM | 4997 | N | MET | A | 11 | 19.340 | 31.785 | 40.576 | 1.00 | 22.50 | A |
| ATOM | 4998 | CA | NET | A | 11 | 18.080 | 31.070 | 40.723 | 1.00 | 22.24 | A |
| ATOM | 4999 | CB | MET | A | 11 | 16.895 | 31.982 | 40.360 | 1.00 | 23.52 | A |
| ATOM | 5000 | CG | MET | A | 11 | 17.007 | 32.727 | 39.047 | 1.00 | 24.37 | A |
| ATOM | 5001 | SD | MET | A | 11 | 15.802 | 34.129 | 38.850 | 1.00 | 26.46 | A |
| ATOM | 5002 | CE | MET | A | 11 | 16.836 | 35.517 | 39.396 | 1.00 | 25.81 | A |
| ATOM | 5003 | C | MET | A | 11 | 18.090 | 29.814 | 39.857 | 1.00 | 21.50 | A |
| ATOM | 5004 | O | MET | A | 11 | 18.967 | 29.645 | 39.006 | 1.00 | 21.28 | A |
| ATOM | 5005 | N | ARG | A | 12 | 17.141 | 28.916 | 40.107 | 1.00 | 20.53 | A |
| ATOM | 5006 | CA | ARG | A | 12 | 17.043 | 27.684 | 39.339 | 1.00 | 19.59 | A |
| ATOM | 5007 | CB | ARG | A | 12 | 15.934 | 26.791 | 39.911 | 1.00 | 19.37 | A |
| ATOM | 5008 | CG | ARG | A | 12 | 16.161 | 26.371 | 41.367 | 1.00 | 19.34 | A |
| ATOM | 5009 | CD | ARG | A | 12 | 15.131 | 25.327 | 41.823 | 1.00 | 18.54 | A |
| ATOM | 5010 | NE | ARG | A | 12 | 13.767 | 25.844 | 41.732 | 1.00 | 18.63 | A |
| ATOM | 5011 | CZ | ARG | A | 12 | 13.276 | 26.789 | 42.524 | 1.00 | 18.61 | A |
| ATOM | 5012 | NH1 | ARG | A | 12 | 14.038 | 27.316 | 43.477 | 1.00 | 18.60 | A |
| ATOM | 5013 | NH2 | ARG | A | 12 | 12.033 | 27.219 | 42.354 | 1.00 | 18.16 | A |
| ATOM | 5014 | C | ARG | A | 12 | 16.720 | 28.094 | 37.909 | 1.00 | 19.15 | A |
| ATOM | 5015 | O | ARG | A | 12 | 17.536 | 27.922 | 37.003 | 1.00 | 18.76 | A |
| ATOM | 5016 | N | GLY | A | 13 | 15.531 | 28.659 | 37.729 | 1.00 | 18.65 | A |
| ATOM | 5017 | CA | GLY | A | 13 | 15.102 | 29.119 | 36.421 | 1.00 | 18.28 | A |
| ATOM | 5018 | C | GLY | A | 13 | 15.414 | 28.194 | 35.262 | 1.00 | 18.14 | A |
| ATOM | 5019 | O | GLY | A | 13 | 15.277 | 26.972 | 35.366 | 1.00 | 17.63 | A |
| ATOM | 5020 | N | ARG | A | 14 | 15.863 | 28.793 | 34.162 | 1.00 | 17.96 | A |
| ATOM | 5021 | CA | ARG | A | 14 | 16.177 | 28.069 | 32.933 | 1.00 | 18.29 | A |
| ATOM | 5022 | CB | ARG | A | 14 | 16.047 | 29.022 | 31.738 | 1.00 | 18.89 | A |
| ATOM | 5023 | CG | ARG | A | 14 | 14.666 | 29.644 | 31.606 | 1.00 | 19.92 | A |
| ATOM | 5024 | CD | ARG | A | 14 | 14.549 | 30.514 | 30.365 | 1.00 | 21.37 | A |
| ATOM | 5025 | NE | ARG | A | 14 | 13.164 | 30.648 | 29.917 | 1.00 | 22.61 | A |
| ATOM | 5026 | CZ | ARG | A | 14 | 12.361 | 31.673 | 30.191 | 1.00 | 23.60 | A |
| ATOM | 5027 | NH1 | ARG | A | 14 | 11.110 | 31.677 | 29.727 | 1.00 | 24.26 | A |
| ATOM | 5028 | NH2 | ARG | A | 14 | 12.799 | 32.701 | 30.906 | 1.00 | 23.64 | A |
| ATOM | 5029 | C | ARG | A | 14 | 17.552 | 27.412 | 32.912 | 1.00 | 18.18 | A |
| ATOM | 5030 | O | ARG | A | 14 | 17.885 | 26.703 | 31.970 | 1.00 | 18.06 | A |
| ATOM | 5031 | N | ALA | A | 15 | 18.355 | 27.634 | 33.943 | 1.00 | 18.06 | A |
| ATOM | 5032 | CA | ALA | A | 15 | 19.680 | 27.027 | 33.964 | 1.00 | 18.18 | A |
| ATOM | 5033 | CB | ALA | A | 15 | 20.689 | 27.991 | 34.579 | 1.00 | 18.24 | A |
| ATOM | 5034 | C | ALA | A | 15 | 19.694 | 25.710 | 34.735 | 1.00 | 18.01 | A |
| ATOM | 5035 | O | ALA | A | 15 | 20.576 | 24.875 | 34.541 | 1.00 | 17.87 | A |
| ATOM | 5036 | N | GLU | A | 16 | 18.712 | 25.520 | 35.607 | 1.00 | 18.14 | A |
| ATOM | 5037 | CA | GLU | A | 16 | 18.671 | 24.313 | 36.426 | 1.00 | 17.94 | A |
| ATOM | 5038 | CB | GLU | A | 16 | 17.412 | 24.314 | 37.295 | 1.00 | 18.23 | A |
| ATOM | 5039 | CG | GLU | A | 16 | 17.518 | 23.451 | 38.545 | 1.00 | 18.77 | A |
| ATOM | 5040 | CD | GLU | A | 16 | 18.639 | 23.897 | 39.478 | 1.00 | 19.23 | A |
| ATOM | 5041 | OE1 | GLU | A | 16 | 19.109 | 25.046 | 39.354 | 1.00 | 19.68 | A |
| ATOM | 5042 | OE2 | GLU | A | 16 | 19.043 | 23.099 | 40.349 | 1.00 | 19.82 | A |
| ATOM | 5043 | C | GLU | A | 16 | 18.774 | 22.991 | 35.653 | 1.00 | 17.71 | A |
| ATOM | 5044 | O | GLU | A | 16 | 19.443 | 22.063 | 36.102 | 1.00 | 17.63 | A |
| ATOM | 5045 | N | ILE | A | 17 | 18.124 | 22.900 | 34.497 | 1.00 | 17.52 | A |
| ATOM | 5046 | CA | ILE | A | 17 | 18.176 | 21.667 | 33.715 | 1.00 | 17.48 | A |
| ATOM | 5047 | CB | ILE | A | 17 | 17.312 | 21.776 | 32.436 | 1.00 | 17.22 | A |
| ATOM | 5048 | CG2 | ILE | A | 17 | 17.790 | 22.941 | 31.585 | 1.00 | 17.01 | A |
| ATOM | 5049 | CG1 | ILE | A | 17 | 17.366 | 20.462 | 31.652 | 1.00 | 17.08 | A |
| ATOM | 5050 | CD1 | ILE | A | 17 | 16.797 | 19.262 | 32.406 | 1.00 | 17.66 | A |
| ATOM | 5051 | C | ILE | A | 17 | 19.611 | 21.316 | 33.330 | 1.00 | 17.59 | A |
| ATOM | 5052 | O | ILE | A | 17 | 19.977 | 20.143 | 33.255 | 1.00 | 17.72 | A |
| ATOM | 5242 | N | TRP | A | 39 | 24.145 | 42.736 | 35.174 | 1.00 | 42.17 | A |
| ATOM | 5243 | CA | TRP | A | 39 | 23.529 | 42.160 | 33.983 | 1.00 | 41.90 | A |
| ATOM | 5244 | CB | TRP | A | 39 | 22.062 | 41.812 | 34.261 | 1.00 | 41.67 | A |
| ATOM | 5245 | CG | TRP | A | 39 | 21.310 | 41.341 | 33.047 | 1.00 | 41.34 | A |
| ATOM | 5246 | CD2 | TRP | A | 39 | 21.735 | 40.353 | 32.097 | 1.00 | 41.24 | A |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine $F_{2\alpha}$(U44)

| | | | | | | | | | | |
|---|---|---|---|---|---|---|---|---|---|---|
| ATOM | 5247 | CE2 | TRP | A | 39 | 20.708 | 40.233 | 31.133 | 1.00 | 41.24 A |
| ATOM | 5248 | CE3 | TRP | A | 39 | 22.881 | 39.559 | 31.967 | 1.00 | 41.17 A |
| ATOM | 5249 | CD1 | TRP | A | 39 | 20.082 | 41.765 | 32.632 | 1.00 | 41.33 A |
| ATOM | 5250 | NE1 | TRP | A | 39 | 19.713 | 41.106 | 31.484 | 1.00 | 41.21 A |
| ATOM | 5251 | CZ2 | TRP | A | 39 | 20.794 | 39.348 | 30.051 | 1.00 | 41.18 A |
| ATOM | 5252 | CZ3 | TRP | A | 39 | 22.967 | 38.678 | 30.891 | 1.00 | 41.18 A |
| ATOM | 5253 | CH2 | TRP | A | 39 | 21.927 | 38.582 | 29.947 | 1.00 | 41.22 A |
| ATOM | 5254 | C | TRP | A | 39 | 23.610 | 43.095 | 32.774 | 1.00 | 41.82 A |
| ATOM | 5255 | O | TRP | A | 39 | 23.990 | 42.678 | 31.681 | 1.00 | 41.83 A |
| ATOM | 5256 | N | PRO | A | 40 | 23.253 | 44.376 | 32.956 | 1.00 | 41.74 A |
| ATOM | 5257 | CD | PRO | A | 40 | 22.790 | 45.032 | 34.194 | 1.00 | 41.72 A |
| ATOM | 5258 | CA | PRO | A | 40 | 23.299 | 45.335 | 31.850 | 1.00 | 41.61 A |
| ATOM | 5259 | CB | PRO | A | 40 | 23.085 | 46.672 | 32.553 | 1.00 | 41.71 A |
| ATOM | 5260 | CG | PRO | A | 40 | 22.158 | 46.304 | 33.670 | 1.00 | 41.78 A |
| ATOM | 5261 | C | PRO | A | 40 | 24.598 | 45.298 | 31.047 | 1.00 | 41.46 A |
| ATOM | 5262 | O | PRO | A | 40 | 24.571 | 45.278 | 29.818 | 1.00 | 41.46 A |
| ATOM | 5263 | N | GLU | A | 41 | 25.731 | 45.284 | 31.742 | 1.00 | 41.23 A |
| ATOM | 5264 | CA | GLU | A | 41 | 27.030 | 45.262 | 31.079 | 1.00 | 41.03 A |
| ATOM | 5265 | CB | GLU | A | 41 | 28.147 | 45.542 | 32.088 | 1.00 | 41.50 A |
| ATOM | 5266 | CG | GLU | A | 41 | 27.983 | 46.835 | 32.868 | 1.00 | 42.28 A |
| ATOM | 5267 | CD | GLU | A | 41 | 26.844 | 46.776 | 33.870 | 1.00 | 42.66 A |
| ATOM | 5268 | OE1 | GLU | A | 41 | 26.899 | 45.926 | 34.783 | 1.00 | 42.97 A |
| ATOM | 5269 | OE2 | GLU | A | 41 | 25.895 | 47.579 | 33.746 | 1.00 | 43.13 A |
| ATOM | 5270 | C | GLU | A | 41 | 27.301 | 43.929 | 30.391 | 1.00 | 40.57 A |
| ATOM | 5271 | O | GLU | A | 41 | 27.795 | 43.889 | 29.265 | 1.00 | 40.56 A |
| ATOM | 5272 | N | ILE | A | 42 | 26.977 | 42.839 | 31.078 | 1.00 | 39.94 A |
| ATOM | 5273 | CA | ILE | A | 42 | 27.193 | 41.499 | 30.547 | 1.00 | 39.34 A |
| ATOM | 5274 | CB | ILE | A | 42 | 26.899 | 40.434 | 31.624 | 1.00 | 39.29 A |
| ATOM | 5275 | CG2 | ILE | A | 42 | 27.163 | 39.043 | 31.071 | 1.00 | 39.27 A |
| ATOM | 5276 | CG1 | ILE | A | 42 | 27.776 | 40.691 | 32.851 | 1.00 | 39.26 A |
| ATOM | 5277 | CD1 | ILE | A | 42 | 27.446 | 39.819 | 34.036 | 1.00 | 39.48 A |
| ATOM | 5278 | C | ILE | A | 42 | 26.316 | 41.223 | 29.332 | 1.00 | 38.87 A |
| ATOM | 5279 | O | ILE | A | 42 | 26.780 | 40.678 | 28.331 | 1.00 | 38.77 A |
| ATOM | 5280 | N | LYS | A | 43 | 25.047 | 41.605 | 29.434 | 1.00 | 38.49 A |
| ATOM | 5281 | CA | LYS | A | 43 | 24.077 | 41.404 | 28.363 | 1.00 | 38.12 A |
| ATOM | 5282 | CB | LYS | A | 43 | 22.759 | 42.086 | 28.722 | 1.00 | 38.17 A |
| ATOM | 5283 | CG | LYS | A | 43 | 21.711 | 41.995 | 27.630 | 1.00 | 38.16 A |
| ATOM | 5284 | CD | LYS | A | 43 | 20.457 | 42.760 | 28.004 | 1.00 | 38.30 A |
| ATOM | 5285 | CE | LYS | A | 43 | 19.412 | 42.658 | 26.909 | 1.00 | 38.35 A |
| ATOM | 5286 | NZ | LYS | A | 43 | 18.211 | 43.462 | 27.231 | 1.00 | 38.78 A |
| ATOM | 5287 | C | LYS | A | 43 | 24.555 | 41.940 | 27.021 | 1.00 | 37.94 A |
| ATOM | 5288 | O | LYS | A | 43 | 24.300 | 41.345 | 25.973 | 1.00 | 37.89 A |
| ATOM | 5328 | N | GLY | A | 49 | 22.030 | 38.588 | 23.868 | 1.00 | 27.57 A |
| ATOM | 5329 | CA | GLY | A | 49 | 21.714 | 39.214 | 25.141 | 1.00 | 26.68 A |
| ATOM | 5330 | C | GLY | A | 49 | 20.783 | 38.447 | 26.055 | 1.00 | 26.11 A |
| ATOM | 5331 | O | GLY | A | 49 | 19.969 | 39.047 | 26.759 | 1.00 | 26.15 A |
| ATOM | 5332 | N | LYS | A | 50 | 20.902 | 37.124 | 26.055 | 1.00 | 25.32 A |
| ATOM | 5333 | CA | LYS | A | 50 | 20.058 | 36.286 | 26.899 | 1.00 | 24.83 A |
| ATOM | 5334 | CB | LYS | A | 50 | 18.987 | 35.584 | 26.055 | 1.00 | 25.06 A |
| ATOM | 5335 | CG | LYS | A | 50 | 18.013 | 36.530 | 25.374 | 1.00 | 25.51 A |
| ATOM | 5336 | CD | LYS | A | 50 | 17.150 | 37.251 | 26.398 | 1.00 | 25.84 A |
| ATOM | 5337 | CE | LYS | A | 50 | 16.263 | 38.306 | 25.752 | 1.00 | 26.47 A |
| ATOM | 5338 | NZ | LYS | A | 50 | 15.382 | 37.745 | 24.694 | 1.00 | 26.77 A |
| ATOM | 5339 | C | LYS | A | 50 | 20.879 | 35.240 | 27.634 | 1.00 | 24.41 A |
| ATOM | 5340 | O | LYS | A | 50 | 21.944 | 34.833 | 27.172 | 1.00 | 24.16 A |
| ATOM | 5341 | N | ILE | A | 51 | 20.383 | 34.825 | 28.794 | 1.00 | 23.98 A |
| ATOM | 5342 | CA | ILE | A | 51 | 21.045 | 33.800 | 29.586 | 1.00 | 23.81 A |
| ATOM | 5343 | CB | ILE | A | 51 | 21.654 | 34.373 | 30.889 | 1.00 | 23.59 A |
| ATOM | 5344 | CG2 | ILE | A | 51 | 22.946 | 35.101 | 30.569 | 1.00 | 23.66 A |
| ATOM | 5345 | CG1 | ILE | A | 51 | 20.647 | 35.286 | 31.588 | 1.00 | 23.56 A |
| ATOM | 5346 | CD1 | ILE | A | 51 | 21.166 | 35.889 | 32.865 | 1.00 | 24.20 A |
| ATOM | 5347 | C | ILE | A | 51 | 20.012 | 32.737 | 29.925 | 1.00 | 23.69 A |
| ATOM | 5348 | O | ILE | A | 51 | 18.812 | 32.984 | 29.833 | 1.00 | 23.80 A |
| ATOM | 5349 | N | PRO | A | 52 | 20.461 | 31.545 | 30.341 | 1.00 | 23.80 A |
| ATOM | 5350 | CD | PRO | A | 52 | 19.562 | 30.408 | 30.617 | 1.00 | 23.80 A |
| ATOM | 5351 | CA | PRO | A | 52 | 21.862 | 31.148 | 30.517 | 1.00 | 23.83 A |
| ATOM | 5352 | CB | PRO | A | 52 | 21.744 | 29.860 | 31.315 | 1.00 | 23.75 A |
| ATOM | 5353 | CG | PRO | A | 52 | 20.522 | 29.241 | 30.696 | 1.00 | 23.82 A |
| ATOM | 5354 | C | PRO | A | 52 | 22.657 | 30.935 | 29.234 | 1.00 | 24.05 A |
| ATOM | 5355 | O | PRO | A | 52 | 22.107 | 30.869 | 28.132 | 1.00 | 23.56 A |
| ATOM | 5356 | N | ILE | A | 53 | 23.969 | 30.831 | 29.405 | 1.00 | 24.37 A |
| ATOM | 5357 | CA | ILE | A | 53 | 24.883 | 30.580 | 28.305 | 1.00 | 24.89 A |
| ATOM | 5358 | CB | ILE | A | 53 | 25.598 | 31.865 | 27.845 | 1.00 | 25.02 A |
| ATOM | 5359 | CG2 | ILE | A | 53 | 24.582 | 32.851 | 27.265 | 1.00 | 25.04 A |
| ATOM | 5360 | CG1 | ILE | A | 53 | 26.353 | 32.488 | 29.018 | 1.00 | 25.09 A |

TABLE 5-continued

Three-dimensional structural coordinate of the complex of human hematopoietic PGDS (SEQ ID NO: 1) with calcium, glutathione and 9,11-dideoxy-9α,11α-epoxymethanoprostaglandine $F_{2\alpha}$(U44)

| ATOM | 5361 | CD1 | ILE | A | 53 | 27.139 | 33.725 | 28.651 | 1.00 | 25.71 | A |
|------|------|-----|-----|---|----|--------|--------|--------|------|-------|---|
| ATOM | 5362 | C | ILE | A | 53 | 25.920 | 29.600 | 28.830 | 1.00 | 25.23 | A |
| ATOM | 5363 | O | ILE | A | 53 | 26.251 | 29.620 | 30.017 | 1.00 | 25.22 | A |
| ATOM | 5423 | N | HIS | A | 62 | 24.143 | 29.233 | 23.623 | 1.00 | 22.53 | A |
| ATOM | 5424 | CA | HIS | A | 62 | 22.973 | 29.778 | 24.304 | 1.00 | 21.30 | A |
| ATOM | 5425 | CB | HIS | A | 62 | 22.641 | 31.181 | 23.777 | 1.00 | 21.36 | A |
| ATOM | 5426 | CG | HIS | A | 62 | 22.241 | 31.212 | 22.334 | 1.00 | 21.08 | A |
| ATOM | 5427 | CD2 | HIS | A | 62 | 21.074 | 31.557 | 21.739 | 1.00 | 20.76 | A |
| ATOM | 5428 | ND1 | HIS | A | 62 | 23.112 | 30.897 | 21.314 | 1.00 | 21.06 | A |
| ATOM | 5429 | CE1 | HIS | A | 62 | 22.502 | 31.050 | 20.152 | 1.00 | 20.77 | A |
| ATOM | 5430 | NE2 | HIS | A | 62 | 21.264 | 31.449 | 20.382 | 1.00 | 21.11 | A |
| ATOM | 5431 | C | HIS | A | 62 | 21.754 | 28.875 | 24.145 | 1.00 | 20.50 | A |
| ATOM | 5432 | O | HIS | A | 62 | 21.812 | 27.856 | 23.457 | 1.00 | 20.45 | A |
| ATOM | 5433 | N | GLN | A | 63 | 20.653 | 29.279 | 24.776 | 1.00 | 19.38 | A |
| ATOM | 5434 | CA | GLN | A | 63 | 19.395 | 28.531 | 24.759 | 1.00 | 18.32 | A |
| ATOM | 5435 | CB | GLN | A | 63 | 19.006 | 28.135 | 23.327 | 1.00 | 18.21 | A |
| ATOM | 5436 | CG | GLN | A | 63 | 18.351 | 29.257 | 22.523 | 1.00 | 17.55 | A |
| ATOM | 5437 | CD | GLN | A | 63 | 17.052 | 29.748 | 23.159 | 1.00 | 17.51 | A |
| ATOM | 5438 | OE1 | GLN | A | 63 | 16.447 | 29.061 | 23.990 | 1.00 | 16.96 | A |
| ATOM | 5439 | NE2 | GLN | A | 63 | 16.614 | 30.932 | 22.760 | 1.00 | 16.64 | A |
| ATOM | 5440 | C | GLN | A | 63 | 19.548 | 27.295 | 25.640 | 1.00 | 17.51 | A |
| ATOM | 5441 | O | GLN | A | 63 | 20.204 | 26.326 | 25.262 | 1.00 | 17.52 | A |
| ATOM | 5442 | N | SER | A | 64 | 18.922 | 27.343 | 26.810 | 1.00 | 16.62 | A |
| ATOM | 5443 | CA | SER | A | 64 | 19.005 | 26.266 | 27.787 | 1.00 | 16.23 | A |
| ATOM | 5444 | CB | SER | A | 64 | 18.109 | 26.580 | 28.994 | 1.00 | 15.75 | A |
| ATOM | 5445 | OG | SER | A | 64 | 16.739 | 26.636 | 28.636 | 1.00 | 16.02 | A |
| ATOM | 5446 | C | SER | A | 64 | 18.690 | 24.871 | 27.264 | 1.00 | 16.04 | A |
| ATOM | 5447 | O | SER | A | 64 | 19.416 | 23.927 | 27.561 | 1.00 | 15.93 | A |
| ATOM | 5448 | N | LEU | A | 65 | 17.623 | 24.736 | 26.484 | 1.00 | 15.93 | A |
| ATOM | 5449 | CA | LEU | A | 65 | 17.243 | 23.426 | 25.969 | 1.00 | 16.08 | A |
| ATOM | 5450 | CB | LEU | A | 65 | 15.781 | 23.445 | 25.509 | 1.00 | 16.21 | A |
| ATOM | 5451 | CG | LEU | A | 65 | 14.757 | 23.960 | 26.532 | 1.00 | 16.82 | A |
| ATOM | 5452 | CD1 | LEU | A | 65 | 13.348 | 23.839 | 25.954 | 1.00 | 17.04 | A |
| ATOM | 5453 | CD2 | LEU | A | 65 | 14.862 | 23.156 | 27.831 | 1.00 | 16.97 | A |
| ATOM | 5454 | C | LEU | A | 65 | 18.168 | 22.953 | 24.846 | 1.00 | 16.25 | A |
| ATOM | 5455 | O | LEU | A | 65 | 18.403 | 21.753 | 24.693 | 1.00 | 16.15 | A |
| ATOM | 5662 | N | ASP | A | 93 | 9.463 | 20.540 | 25.416 | 1.00 | 15.24 | A |
| ATOM | 5663 | CA | ASP | A | 93 | 8.886 | 21.742 | 24.818 | 1.00 | 15.43 | A |
| ATOM | 5664 | CB | ASP | A | 93 | 8.800 | 21.598 | 23.289 | 1.00 | 16.54 | A |
| ATOM | 5665 | CG | ASP | A | 93 | 10.083 | 22.013 | 22.578 | 1.00 | 17.29 | A |
| ATOM | 5666 | OD1 | ASP | A | 93 | 10.162 | 21.833 | 21.338 | 1.00 | 18.80 | A |
| ATOM | 5667 | OD2 | ASP | A | 93 | 11.014 | 22.527 | 23.240 | 1.00 | 17.97 | A |
| ATOM | 5668 | C | ASP | A | 93 | 7.496 | 22.053 | 25.388 | 1.00 | 15.31 | A |
| ATOM | 5669 | O | ASP | A | 93 | 7.138 | 23.220 | 25.568 | 1.00 | 15.25 | A |
| ATOM | 5670 | N | THR | A | 94 | 6.707 | 21.016 | 25.658 | 1.00 | 15.02 | A |
| ATOM | 5671 | CA | THR | A | 94 | 5.371 | 21.207 | 26.224 | 1.00 | 15.27 | A |
| ATOM | 5672 | CB | THR | A | 94 | 4.640 | 19.861 | 26.399 | 1.00 | 15.32 | A |
| ATOM | 5673 | OG1 | THR | A | 94 | 4.193 | 19.397 | 25.118 | 1.00 | 16.10 | A |
| ATOM | 5674 | CG2 | THR | A | 94 | 3.432 | 20.011 | 27.323 | 1.00 | 15.76 | A |
| ATOM | 5675 | C | THR | A | 94 | 5.483 | 21.895 | 27.584 | 1.00 | 15.32 | A |
| ATOM | 5676 | O | THR | A | 94 | 4.756 | 22.843 | 27.878 | 1.00 | 14.89 | A |
| ATOM | 5677 | N | LEU | A | 95 | 6.406 | 21.408 | 28.407 | 1.00 | 15.54 | A |
| ATOM | 5678 | CA | LEU | A | 95 | 6.615 | 21.982 | 29.732 | 1.00 | 16.01 | A |
| ATOM | 5679 | CB | LEU | A | 95 | 7.593 | 21.115 | 30.535 | 1.00 | 16.19 | A |
| ATOM | 5680 | CG | LEU | A | 95 | 7.089 | 19.738 | 30.998 | 1.00 | 16.12 | A |
| ATOM | 5681 | CD1 | LEU | A | 95 | 8.230 | 18.966 | 31.648 | 1.00 | 16.47 | A |
| ATOM | 5682 | CD2 | LEU | A | 95 | 5.934 | 19.903 | 31.975 | 1.00 | 16.46 | A |
| ATOM | 5683 | C | LEU | A | 95 | 7.167 | 23.402 | 29.590 | 1.00 | 16.45 | A |
| ATOM | 5684 | O | LEU | A | 95 | 6.744 | 24.320 | 30.296 | 1.00 | 16.19 | A |
| ATOM | 5685 | N | ASP | A | 96 | 8.112 | 23.576 | 28.667 | 1.00 | 16.83 | A |
| ATOM | 5686 | CA | ASP | A | 96 | 8.718 | 24.886 | 28.435 | 1.00 | 17.42 | A |
| ATOM | 5687 | CB | ASP | A | 96 | 9.834 | 24.776 | 27.388 | 1.00 | 17.70 | A |
| ATOM | 5688 | CG | ASP | A | 96 | 10.761 | 25.977 | 27.397 | 1.00 | 18.24 | A |
| ATOM | 5689 | OD1 | ASP | A | 96 | 11.259 | 26.318 | 28.496 | 1.00 | 19.16 | A |
| ATOM | 5690 | OD2 | ASP | A | 96 | 11.004 | 26.566 | 26.314 | 1.00 | 17.96 | A |
| ATOM | 5691 | C | ASP | A | 96 | 7.670 | 25.906 | 27.982 | 1.00 | 17.76 | A |
| ATOM | 5692 | O | ASP | A | 96 | 7.707 | 27.074 | 28.383 | 1.00 | 17.65 | A |
| ATOM | 5693 | N | ASP | A | 97 | 6.741 | 25.463 | 27.140 | 1.00 | 18.16 | A |
| ATOM | 5694 | CA | ASP | A | 97 | 5.672 | 26.328 | 26.642 | 1.00 | 18.58 | A |
| ATOM | 5695 | CB | ASP | A | 97 | 4.759 | 25.559 | 25.681 | 1.00 | 18.77 | A |
| ATOM | 5696 | CG | ASP | A | 97 | 5.388 | 25.333 | 24.313 | 1.00 | 19.31 | A |
| ATOM | 5697 | OD1 | ASP | A | 97 | 4.838 | 24.515 | 23.539 | 1.00 | 19.60 | A |
| ATOM | 5698 | OD2 | ASP | A | 97 | 6.420 | 25.973 | 24.007 | 1.00 | 19.36 | A |
| ATOM | 5699 | C | ASP | A | 97 | 4.820 | 26.880 | 27.786 | 1.00 | 18.77 | A |
| ATOM | 5700 | O | ASP | A | 97 | 4.480 | 28.063 | 27.799 | 1.00 | 18.43 | A |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine $F_{2\alpha}$(U44)

| ATOM | 5701 | N | PHE | A | 98 | 4.473 | 26.017 | 28.738 | 1.00 | 18.98 | A |
|---|---|---|---|---|---|---|---|---|---|---|---|
| ATOM | 5702 | CA | PHE | A | 98 | 3.644 | 26.427 | 29.865 | 1.00 | 19.59 | A |
| ATOM | 5703 | CB | PHE | A | 98 | 3.170 | 25.208 | 30.662 | 1.00 | 19.85 | A |
| ATOM | 5704 | CG | PHE | A | 98 | 2.225 | 25.554 | 31.787 | 1.00 | 20.49 | A |
| ATOM | 5705 | CD1 | PHE | A | 98 | 1.002 | 26.164 | 31.520 | 1.00 | 20.75 | A |
| ATOM | 5706 | CD2 | PHE | A | 98 | 2.561 | 25.279 | 33.110 | 1.00 | 21.00 | A |
| ATOM | 5707 | CE1 | PHE | A | 98 | 0.126 | 26.496 | 32.557 | 1.00 | 21.20 | A |
| ATOM | 5708 | CE2 | PHE | A | 98 | 1.690 | 25.608 | 34.156 | 1.00 | 20.81 | A |
| ATOM | 5709 | CZ | PHE | A | 98 | 0.473 | 26.216 | 33.876 | 1.00 | 21.25 | A |
| ATOM | 5710 | C | PHE | A | 98 | 4.382 | 27.373 | 30.798 | 1.00 | 19.70 | A |
| ATOM | 5711 | O | PHE | A | 98 | 3.849 | 28.407 | 31.193 | 1.00 | 19.84 | A |
| ATOM | 5712 | N | MET | A | 99 | 5.610 | 27.010 | 31.148 | 1.00 | 19.93 | A |
| ATOM | 5713 | CA | NET | A | 99 | 6.422 | 27.834 | 32.038 | 1.00 | 20.62 | A |
| ATOM | 5714 | CB | MET | A | 99 | 7.759 | 27.150 | 32.323 | 1.00 | 20.56 | A |
| ATOM | 5715 | CG | MET | A | 99 | 7.642 | 25.794 | 32.999 | 1.00 | 20.77 | A |
| ATOM | 5716 | SD | MET | A | 99 | 6.765 | 25.897 | 34.599 | 1.00 | 20.94 | A |
| ATOM | 5717 | CE | MET | A | 99 | 7.971 | 26.856 | 35.571 | 1.00 | 21.40 | A |
| ATOM | 5718 | C | MET | A | 99 | 6.684 | 29.200 | 31.418 | 1.00 | 21.19 | A |
| ATOM | 5719 | O | MET | A | 99 | 6.770 | 30.205 | 32.123 | 1.00 | 20.97 | A |
| ATOM | 5720 | N | SER | A | 100 | 6.817 | 29.232 | 30.094 | 1.00 | 21.87 | A |
| ATOM | 5721 | CA | SER | A | 100 | 7.088 | 30.480 | 29.391 | 1.00 | 22.86 | A |
| ATOM | 5722 | CB | SER | A | 100 | 7.626 | 30.190 | 27.986 | 1.00 | 22.52 | A |
| ATOM | 5723 | OG | SER | A | 100 | 8.932 | 29.641 | 28.064 | 1.00 | 23.15 | A |
| ATOM | 5724 | C | SER | A | 100 | 5.874 | 31.400 | 29.310 | 1.00 | 23.42 | A |
| ATOM | 5725 | O | SER | A | 100 | 5.999 | 32.570 | 28.944 | 1.00 | 23.43 | A |
| ATOM | 5726 | N | CYS | A | 101 | 4.705 | 30.871 | 29.656 | 1.00 | 24.43 | A |
| ATOM | 5727 | CA | CYS | A | 101 | 3.470 | 31.649 | 29.642 | 1.00 | 25.43 | A |
| ATOM | 5728 | CB | CYS | A | 101 | 2.246 | 30.732 | 29.736 | 1.00 | 25.71 | A |
| ATOM | 5729 | SG | CYS | A | 101 | 1.749 | 29.932 | 28.189 | 1.00 | 27.17 | A |
| ATOM | 5730 | C | CYS | A | 101 | 3.427 | 32.631 | 30.806 | 1.00 | 25.95 | A |
| ATOM | 5731 | O | CYS | A | 101 | 2.818 | 33.695 | 30.704 | 1.00 | 25.87 | A |
| ATOM | 5732 | N | PHE | A | 102 | 4.060 | 32.272 | 31.919 | 1.00 | 26.64 | A |
| ATOM | 5733 | CA | PHE | A | 102 | 4.055 | 33.150 | 33.084 | 1.00 | 27.61 | A |
| ATOM | 5734 | CB | PHE | A | 102 | 4.567 | 32.416 | 34.328 | 1.00 | 27.12 | A |
| ATOM | 5735 | CG | PHE | A | 102 | 3.679 | 31.293 | 34.780 | 1.00 | 26.71 | A |
| ATOM | 5736 | CD1 | PHE | A | 102 | 3.627 | 30.100 | 34.067 | 1.00 | 26.53 | A |
| ATOM | 5737 | CD2 | PHE | A | 102 | 2.904 | 31.422 | 35.930 | 1.00 | 26.49 | A |
| ATOM | 5738 | CE1 | PHE | A | 102 | 2.814 | 29.047 | 34.495 | 1.00 | 26.51 | A |
| ATOM | 5739 | CE2 | PHE | A | 102 | 2.089 | 30.378 | 36.366 | 1.00 | 26.35 | A |
| ATOM | 5740 | CZ | PHE | A | 102 | 2.044 | 29.187 | 35.648 | 1.00 | 26.32 | A |
| ATOM | 5741 | C | PHE | A | 102 | 4.896 | 34.401 | 32.862 | 1.00 | 28.66 | A |
| ATOM | 5742 | O | PHE | A | 102 | 6.020 | 34.328 | 32.366 | 1.00 | 28.59 | A |
| ATOM | 5743 | N | PRO | A | 103 | 4.353 | 35.572 | 33.228 | 1.00 | 29.73 | A |
| ATOM | 5744 | CD | PRO | A | 103 | 2.973 | 35.797 | 33.697 | 1.00 | 29.81 | A |
| ATOM | 5745 | CA | PRO | A | 103 | 5.059 | 36.846 | 33.070 | 1.00 | 30.81 | A |
| ATOM | 5746 | CB | PRO | A | 103 | 3.927 | 37.865 | 33.132 | 1.00 | 30.54 | A |
| ATOM | 5747 | CG | PRO | A | 103 | 3.012 | 37.251 | 34.137 | 1.00 | 30.22 | A |
| ATOM | 5748 | C | PRO | A | 103 | 6.087 | 37.050 | 34.183 | 1.00 | 31.87 | A |
| ATOM | 5749 | O | PRO | A | 103 | 5.896 | 37.883 | 35.069 | 1.00 | 31.89 | A |
| ATOM | 5750 | N | TRP | A | 104 | 7.173 | 36.284 | 34.134 | 1.00 | 33.14 | A |
| ATOM | 5751 | CA | TRP | A | 104 | 8.218 | 36.373 | 35.147 | 1.00 | 34.59 | A |
| ATOM | 5752 | CB | TRP | A | 104 | 9.315 | 35.340 | 34.874 | 1.00 | 34.65 | A |
| ATOM | 5753 | CG | TRP | A | 104 | 8.796 | 33.949 | 34.643 | 1.00 | 34.60 | A |
| ATOM | 5754 | CD2 | TRP | A | 104 | 8.342 | 33.023 | 35.639 | 1.00 | 34.60 | A |
| ATOM | 5755 | CE2 | TRP | A | 104 | 7.930 | 31.852 | 34.965 | 1.00 | 34.60 | A |
| ATOM | 5756 | CE3 | TRP | A | 104 | 8.243 | 33.068 | 37.038 | 1.00 | 34.59 | A |
| ATOM | 5757 | CD1 | TRP | A | 104 | 8.644 | 33.320 | 33.440 | 1.00 | 34.55 | A |
| ATOM | 5758 | NE1 | TRP | A | 104 | 8.126 | 32.060 | 33.624 | 1.00 | 34.48 | A |
| ATOM | 5759 | CZ2 | TRP | A | 104 | 7.427 | 30.736 | 35.641 | 1.00 | 34.52 | A |
| ATOM | 5760 | CZ3 | TRP | A | 104 | 7.743 | 31.959 | 37.709 | 1.00 | 34.54 | A |
| ATOM | 5761 | CH2 | TRP | A | 104 | 7.341 | 30.809 | 37.009 | 1.00 | 34.78 | A |
| ATOM | 5762 | C | TRP | A | 104 | 8.837 | 37.765 | 35.207 | 1.00 | 35.65 | A |
| ATOM | 5763 | O | TRP | A | 104 | 9.139 | 38.270 | 36.286 | 1.00 | 35.74 | A |
| ATOM | 5764 | N | ALA | A | 105 | 9.024 | 38.379 | 34.044 | 1.00 | 37.02 | A |
| ATOM | 5765 | CA | ALA | A | 105 | 9.612 | 39.712 | 33.960 | 1.00 | 38.45 | A |
| ATOM | 5766 | CB | ALA | A | 105 | 10.630 | 39.762 | 32.826 | 1.00 | 38.40 | A |
| ATOM | 5767 | C | ALA | A | 105 | 8.541 | 40.776 | 33.743 | 1.00 | 39.42 | A |
| ATOM | 5768 | O | ALA | A | 105 | 8.562 | 41.497 | 32.744 | 1.00 | 39.67 | A |
| ATOM | 5769 | N | GLU | A | 106 | 7.604 | 40.871 | 34.677 | 1.00 | 40.55 | A |
| ATOM | 5770 | CA | GLU | A | 106 | 6.536 | 41.854 | 34.566 | 1.00 | 41.69 | A |
| ATOM | 5771 | CB | GLU | A | 106 | 5.178 | 41.152 | 34.484 | 1.00 | 41.79 | A |
| ATOM | 5772 | CG | GLU | A | 106 | 3.996 | 42.101 | 34.385 | 1.00 | 42.04 | A |
| ATOM | 5773 | CD | GLU | A | 106 | 4.119 | 43.062 | 33.219 | 1.00 | 42.17 | A |
| ATOM | 5774 | OE1 | GLU | A | 106 | 4.135 | 42.600 | 32.059 | 1.00 | 42.24 | A |
| ATOM | 5775 | OE2 | GLU | A | 106 | 4.207 | 44.282 | 33.461 | 1.00 | 42.30 | A |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine F$_{2α}$(U44)

| ATOM | 5776 | C | GLU | A | 106 | 6.549 | 42.817 | 35.745 | 1.00 | 42.38 | A |
|---|---|---|---|---|---|---|---|---|---|---|---|
| ATOM | 5777 | O | GLU | A | 106 | 6.252 | 42.433 | 36.877 | 1.00 | 42.50 | A |
| ATOM | 5778 | N | LYS | A | 107 | 6.902 | 44.071 | 35.471 | 1.00 | 43.32 | A |
| ATOM | 5779 | CA | LYS | A | 107 | 6.949 | 45.105 | 36.498 | 1.00 | 44.17 | A |
| ATOM | 5780 | CB | LYS | A | 107 | 7.501 | 46.408 | 35.916 | 1.00 | 44.38 | A |
| ATOM | 5781 | CG | LYS | A | 107 | 9.001 | 46.575 | 36.067 | 1.00 | 44.83 | A |
| ATOM | 5782 | CD | LYS | A | 107 | 9.773 | 45.472 | 35.376 | 1.00 | 45.12 | A |
| ATOM | 5783 | CE | LYS | A | 107 | 11.261 | 45.611 | 35.654 | 1.00 | 45.28 | A |
| ATOM | 5784 | NZ | LYS | A | 107 | 11.534 | 45.551 | 37.119 | 1.00 | 45.38 | A |
| ATOM | 5785 | C | LYS | A | 107 | 5.573 | 45.364 | 37.100 | 1.00 | 44.67 | A |
| ATOM | 5786 | O | LYS | A | 107 | 5.431 | 45.477 | 38.318 | 1.00 | 44.70 | A |
| ATOM | 5787 | N | LYS | A | 108 | 4.563 | 45.460 | 36.240 | 1.00 | 45.16 | A |
| ATOM | 5788 | CA | LYS | A | 108 | 3.197 | 45.701 | 36.688 | 1.00 | 45.71 | A |
| ATOM | 5789 | CB | LYS | A | 108 | 2.268 | 45.869 | 35.483 | 1.00 | 45.85 | A |
| ATOM | 5790 | CG | LYS | A | 108 | 2.686 | 46.978 | 34.531 | 1.00 | 46.17 | A |
| ATOM | 5791 | CD | LYS | A | 108 | 1.639 | 47.224 | 33.455 | 1.00 | 46.42 | A |
| ATOM | 5792 | CE | LYS | A | 108 | 1.458 | 46.017 | 32.549 | 1.00 | 46.68 | A |
| ATOM | 5793 | NZ | LYS | A | 108 | 0.371 | 46.242 | 31.554 | 1.00 | 46.81 | A |
| ATOM | 5794 | C | LYS | A | 108 | 2.731 | 44.533 | 37.551 | 1.00 | 46.00 | A |
| ATOM | 5795 | O | LYS | A | 108 | 2.296 | 43.501 | 37.038 | 1.00 | 45.89 | A |
| ATOM | 5796 | N | GLN | A | 109 | 2.825 | 44.704 | 38.865 | 1.00 | 46.38 | A |
| ATOM | 5797 | CA | GLN | A | 109 | 2.438 | 43.660 | 39.809 | 1.00 | 46.76 | A |
| ATOM | 5798 | CB | GLN | A | 109 | 2.710 | 44.125 | 41.242 | 1.00 | 47.02 | A |
| ATOM | 5799 | CG | GLN | A | 109 | 4.150 | 44.545 | 41.500 | 1.00 | 47.38 | A |
| ATOM | 5800 | CD | GLN | A | 109 | 5.148 | 43.428 | 41.243 | 1.00 | 47.66 | A |
| ATOM | 5801 | OE1 | GLN | A | 109 | 5.062 | 42.353 | 41.842 | 1.00 | 47.81 | A |
| ATOM | 5802 | NE2 | GLN | A | 109 | 6.105 | 43.679 | 40.350 | 1.00 | 47.68 | A |
| ATOM | 5803 | C | GLN | A | 109 | 0.977 | 43.252 | 39.674 | 1.00 | 46.90 | A |
| ATOM | 5804 | O | GLN | A | 109 | 0.627 | 42.091 | 39.890 | 1.00 | 46.97 | A |
| ATOM | 5805 | N | ASP | A | 110 | 0.127 | 44.209 | 39.315 | 1.00 | 47.00 | A |
| ATOM | 5806 | CA | ASP | A | 110 | −1.301 | 43.948 | 39.159 | 1.00 | 47.06 | A |
| ATOM | 5807 | CB | ASP | A | 110 | −2.046 | 45.251 | 38.853 | 1.00 | 47.31 | A |
| ATOM | 5808 | CG | ASP | A | 110 | −1.945 | 46.256 | 39.982 | 1.00 | 47.59 | A |
| ATOM | 5809 | OD1 | ASP | A | 110 | −2.246 | 45.881 | 41.136 | 1.00 | 47.70 | A |
| ATOM | 5810 | OD2 | ASP | A | 110 | −1.571 | 47.419 | 39.717 | 1.00 | 47.82 | A |
| ATOM | 5811 | C | ASP | A | 110 | −1.584 | 42.926 | 38.063 | 1.00 | 46.90 | A |
| ATOM | 5812 | O | ASP | A | 110 | −2.203 | 41.891 | 38.314 | 1.00 | 46.87 | A |
| ATOM | 5813 | N | VAL | A | 111 | −1.127 | 43.220 | 36.850 | 1.00 | 46.72 | A |
| ATOM | 5814 | CA | VAL | A | 111 | −1.338 | 42.326 | 35.719 | 1.00 | 46.57 | A |
| ATOM | 5815 | CB | VAL | A | 111 | −0.918 | 42.999 | 34.391 | 1.00 | 46.71 | A |
| ATOM | 5816 | CG1 | VAL | A | 111 | 0.588 | 43.192 | 34.357 | 1.00 | 46.96 | A |
| ATOM | 5817 | CG2 | VAL | A | 111 | −1.378 | 42.160 | 33.213 | 1.00 | 46.81 | A |
| ATOM | 5818 | C | VAL | A | 111 | −0.550 | 41.029 | 35.894 | 1.00 | 46.33 | A |
| ATOM | 5819 | O | VAL | A | 111 | −0.967 | 39.970 | 35.426 | 1.00 | 46.33 | A |
| ATOM | 5820 | N | LYS | A | 112 | 0.588 | 41.117 | 36.573 | 1.00 | 45.98 | A |
| ATOM | 5821 | CA | LYS | A | 112 | 1.427 | 39.949 | 36.810 | 1.00 | 45.58 | A |
| ATOM | 5822 | CB | LYS | A | 112 | 2.772 | 40.383 | 37.397 | 1.00 | 45.70 | A |
| ATOM | 5823 | CG | LYS | A | 112 | 3.753 | 39.245 | 37.630 | 1.00 | 45.79 | A |
| ATOM | 5824 | CD | LYS | A | 112 | 5.070 | 39.765 | 38.187 | 1.00 | 45.95 | A |
| ATOM | 5825 | CE | LYS | A | 112 | 6.087 | 38.646 | 38.340 | 1.00 | 45.99 | A |
| ATOM | 5826 | NZ | LYS | A | 112 | 5.582 | 37.571 | 39.237 | 1.00 | 46.23 | A |
| ATOM | 5827 | C | LYS | A | 112 | 0.732 | 38.985 | 37.768 | 1.00 | 45.31 | A |
| ATOM | 5828 | O | LYS | A | 112 | 0.597 | 37.793 | 37.481 | 1.00 | 45.18 | A |
| ATOM | 5829 | N | GLU | A | 113 | 0.290 | 39.515 | 38.904 | 1.00 | 44.80 | A |
| ATOM | 5830 | CA | GLU | A | 113 | −0.390 | 38.718 | 39.920 | 1.00 | 44.37 | A |
| ATOM | 5831 | CB | GLU | A | 113 | −0.817 | 39.615 | 41.089 | 1.00 | 44.56 | A |
| ATOM | 5832 | CG | GLU | A | 113 | −1.246 | 38.872 | 42.346 | 1.00 | 44.72 | A |
| ATOM | 5833 | CD | GLU | A | 113 | −0.069 | 38.326 | 43.135 | 1.00 | 44.84 | A |
| ATOM | 5834 | OE1 | GLU | A | 113 | 0.653 | 37.451 | 42.611 | 1.00 | 44.74 | A |
| ATOM | 5835 | OE2 | GLU | A | 113 | 0.138 | 38.780 | 44.281 | 1.00 | 44.95 | A |
| ATOM | 5836 | C | GLU | A | 113 | −1.620 | 38.044 | 39.316 | 1.00 | 43.91 | A |
| ATOM | 5837 | O | GLU | A | 113 | −1.907 | 36.878 | 39.594 | 1.00 | 43.88 | A |
| ATOM | 5838 | N | GLN | A | 114 | −2.343 | 38.789 | 38.486 | 1.00 | 43.23 | A |
| ATOM | 5839 | CA | GLN | A | 114 | −3.545 | 38.276 | 37.843 | 1.00 | 42.55 | A |
| ATOM | 5840 | CB | GLN | A | 114 | −4.243 | 39.392 | 37.063 | 1.00 | 43.01 | A |
| ATOM | 5841 | CG | GLN | A | 114 | −5.502 | 38.952 | 36.330 | 1.00 | 43.48 | A |
| ATOM | 5842 | CD | GLN | A | 114 | −6.660 | 38.643 | 37.266 | 1.00 | 43.87 | A |
| ATOM | 5843 | OE1 | GLN | A | 114 | −7.716 | 38.182 | 36.831 | 1.00 | 44.27 | A |
| ATOM | 5844 | NE2 | GLN | A | 114 | −6.469 | 38.902 | 38.556 | 1.00 | 44.00 | A |
| ATOM | 5845 | C | GLN | A | 114 | −3.241 | 37.115 | 36.902 | 1.00 | 41.82 | A |
| ATOM | 5846 | O | GLN | A | 114 | −3.862 | 36.058 | 36.993 | 1.00 | 41.68 | A |
| ATOM | 5847 | N | MET | A | 115 | −2.287 | 37.318 | 35.999 | 1.00 | 40.95 | A |
| ATOM | 5848 | CA | MET | A | 115 | −1.914 | 36.286 | 35.039 | 1.00 | 40.08 | A |
| ATOM | 5849 | CB | MET | A | 115 | −0.823 | 36.806 | 34.096 | 1.00 | 40.62 | A |
| ATOM | 5850 | CG | MET | A | 115 | −1.283 | 37.947 | 33.197 | 1.00 | 41.32 | A |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine $F_{2\alpha}$(U44)

| ATOM | 5851 | SD | MET | A | 115 | −0.084 | 38.396 | 31.912 | 1.00 | 42.25 | A |
|------|------|------|-----|---|-----|--------|--------|--------|------|-------|---|
| ATOM | 5852 | CE | MET | A | 115 | 0.892 | 39.641 | 32.771 | 1.00 | 42.06 | A |
| ATOM | 5853 | C | MET | A | 115 | −1.451 | 34.995 | 35.711 | 1.00 | 39.18 | A |
| ATOM | 5854 | O | MET | A | 115 | −1.750 | 33.899 | 35.233 | 1.00 | 38.94 | A |
| ATOM | 5855 | N | PHE | A | 116 | −0.723 | 35.120 | 36.817 | 1.00 | 38.04 | A |
| ATOM | 5856 | CA | PHE | A | 116 | −0.246 | 33.943 | 37.535 | 1.00 | 37.08 | A |
| ATOM | 5857 | CB | PHE | A | 116 | 0.632 | 34.347 | 38.725 | 1.00 | 36.65 | A |
| ATOM | 5858 | CG | PHE | A | 116 | 2.104 | 34.250 | 38.453 | 1.00 | 36.16 | A |
| ATOM | 5859 | CD1 | PHE | A | 116 | 2.707 | 35.072 | 37.509 | 1.00 | 36.15 | A |
| ATOM | 5860 | CD2 | PHE | A | 116 | 2.887 | 33.323 | 39.130 | 1.00 | 36.09 | A |
| ATOM | 5861 | CE1 | PHE | A | 116 | 4.070 | 34.970 | 37.241 | 1.00 | 36.00 | A |
| ATOM | 5862 | CE2 | PHE | A | 116 | 4.250 | 33.213 | 38.870 | 1.00 | 36.03 | A |
| ATOM | 5863 | CZ | PHE | A | 116 | 4.841 | 34.038 | 37.923 | 1.00 | 36.03 | A |
| ATOM | 5864 | C | PHE | A | 116 | −1.406 | 33.087 | 38.033 | 1.00 | 36.66 | A |
| ATOM | 5865 | O | PHE | A | 116 | −1.454 | 31.882 | 37.782 | 1.00 | 36.40 | A |
| ATOM | 6152 | N | TYR | A | 152 | 13.399 | 17.626 | 33.588 | 1.00 | 17.13 | A |
| ATOM | 6153 | CA | TYR | A | 152 | 12.704 | 18.883 | 33.352 | 1.00 | 16.94 | A |
| ATOM | 6154 | CB | TYR | A | 152 | 12.549 | 19.144 | 31.854 | 1.00 | 17.23 | A |
| ATOM | 6155 | CG | TYR | A | 152 | 12.463 | 20.619 | 31.522 | 1.00 | 17.59 | A |
| ATOM | 6156 | CD1 | TYR | A | 152 | 13.414 | 21.519 | 32.010 | 1.00 | 17.83 | A |
| ATOM | 6157 | CE1 | TYR | A | 152 | 13.368 | 22.871 | 31.673 | 1.00 | 18.02 | A |
| ATOM | 6158 | CD2 | TYR | A | 152 | 11.459 | 21.111 | 30.693 | 1.00 | 17.66 | A |
| ATOM | 6159 | CE2 | TYR | A | 152 | 11.407 | 22.460 | 30.349 | 1.00 | 17.94 | A |
| ATOM | 6160 | CZ | TYR | A | 152 | 12.363 | 23.331 | 30.837 | 1.00 | 18.06 | A |
| ATOM | 6161 | OH | TYR | A | 152 | 12.339 | 24.652 | 30.461 | 1.00 | 18.13 | A |
| ATOM | 6162 | C | TYR | A | 152 | 11.342 | 18.931 | 34.031 | 1.00 | 17.03 | A |
| ATOM | 6163 | O | TYR | A | 152 | 10.893 | 19.996 | 34.459 | 1.00 | 16.79 | A |
| ATOM | 6164 | N | TRP | A | 153 | 10.684 | 17.780 | 34.127 | 1.00 | 16.68 | A |
| ATOM | 6165 | CA | TRP | A | 153 | 9.391 | 17.714 | 34.782 | 1.00 | 16.70 | A |
| ATOM | 6166 | CB | TRP | A | 153 | 8.792 | 16.311 | 34.662 | 1.00 | 17.07 | A |
| ATOM | 6167 | CG | TRP | A | 153 | 7.822 | 16.001 | 35.761 | 1.00 | 18.05 | A |
| ATOM | 6168 | CD2 | TRP | A | 153 | 6.615 | 16.708 | 36.066 | 1.00 | 18.42 | A |
| ATOM | 6169 | CE2 | TRP | A | 153 | 6.049 | 16.095 | 37.206 | 1.00 | 18.78 | A |
| ATOM | 6170 | CE3 | TRP | A | 153 | 5.956 | 17.800 | 35.488 | 1.00 | 18.93 | A |
| ATOM | 6171 | CD1 | TRP | A | 153 | 7.936 | 15.014 | 36.699 | 1.00 | 18.52 | A |
| ATOM | 6172 | NE1 | TRP | A | 153 | 6.874 | 15.065 | 37.570 | 1.00 | 18.65 | A |
| ATOM | 6173 | CZ2 | TRP | A | 153 | 4.852 | 16.540 | 37.781 | 1.00 | 18.98 | A |
| ATOM | 6174 | CZ3 | TRP | A | 153 | 4.761 | 18.245 | 36.063 | 1.00 | 19.09 | A |
| ATOM | 6175 | CH2 | TRP | A | 153 | 4.225 | 17.613 | 37.198 | 1.00 | 18.95 | A |
| ATOM | 6176 | C | TRP | A | 153 | 9.578 | 18.055 | 36.253 | 1.00 | 16.19 | A |
| ATOM | 6177 | O | TRP | A | 153 | 8.844 | 18.868 | 36.804 | 1.00 | 16.11 | A |
| ATOM | 6178 | N | GLU | A | 154 | 10.571 | 17.429 | 36.879 | 1.00 | 15.99 | A |
| ATOM | 6179 | CA | GLU | A | 154 | 10.850 | 17.652 | 38.301 | 1.00 | 15.99 | A |
| ATOM | 6180 | CB | GLU | A | 154 | 11.985 | 16.725 | 38.759 | 1.00 | 16.41 | A |
| ATOM | 6181 | CG | GLU | A | 154 | 12.159 | 16.644 | 40.282 | 1.00 | 17.45 | A |
| ATOM | 6182 | CD | GLU | A | 154 | 12.954 | 17.795 | 40.864 | 1.00 | 17.87 | A |
| ATOM | 6183 | OE1 | GLU | A | 154 | 12.895 | 18.000 | 42.103 | 1.00 | 18.47 | A |
| ATOM | 6184 | OE2 | GLU | A | 154 | 13.648 | 18.489 | 40.093 | 1.00 | 18.04 | A |
| ATOM | 6185 | C | GLU | A | 154 | 11.208 | 19.112 | 38.564 | 1.00 | 15.58 | A |
| ATOM | 6186 | O | GLU | A | 154 | 10.793 | 19.697 | 39.568 | 1.00 | 15.32 | A |
| ATOM | 6187 | N | ILE | A | 155 | 11.973 | 19.694 | 37.647 | 1.00 | 14.97 | A |
| ATOM | 6188 | CA | ILE | A | 155 | 12.391 | 21.088 | 37.747 | 1.00 | 14.96 | A |
| ATOM | 6189 | CB | ILE | A | 155 | 13.460 | 21.401 | 36.665 | 1.00 | 14.64 | A |
| ATOM | 6190 | CG2 | ILE | A | 155 | 13.621 | 22.906 | 36.479 | 1.00 | 14.51 | A |
| ATOM | 6191 | CG1 | ILE | A | 155 | 14.779 | 20.722 | 37.054 | 1.00 | 14.76 | A |
| ATOM | 6192 | CD1 | ILE | A | 155 | 15.871 | 20.787 | 35.989 | 1.00 | 14.27 | A |
| ATOM | 6193 | C | ILE | A | 155 | 11.207 | 22.044 | 37.609 | 1.00 | 15.18 | A |
| ATOM | 6194 | O | ILE | A | 155 | 11.032 | 22.952 | 38.425 | 1.00 | 15.10 | A |
| ATOM | 6195 | N | CYS | A | 156 | 10.394 | 21.840 | 36.574 | 1.00 | 15.13 | A |
| ATOM | 6196 | CA | CYS | A | 156 | 9.225 | 22.688 | 36.351 | 1.00 | 15.67 | A |
| ATOM | 6197 | CB | CYS | A | 156 | 8.573 | 22.365 | 34.998 | 1.00 | 15.61 | A |
| ATOM | 6198 | SG | CYS | A | 156 | 9.519 | 22.879 | 33.537 | 1.00 | 16.74 | A |
| ATOM | 6199 | C | CYS | A | 156 | 8.175 | 22.557 | 37.462 | 1.00 | 15.81 | A |
| ATOM | 6200 | O | CYS | A | 156 | 7.612 | 23.558 | 37.904 | 1.00 | 15.91 | A |
| ATOM | 6201 | N | SER | A | 157 | 7.904 | 21.331 | 37.905 | 1.00 | 15.84 | A |
| ATOM | 6202 | CA | SER | A | 157 | 6.908 | 21.113 | 38.954 | 1.00 | 16.04 | A |
| ATOM | 6203 | CB | SER | A | 157 | 6.614 | 19.614 | 39.117 | 1.00 | 15.82 | A |
| ATOM | 6204 | OG | SER | A | 157 | 7.799 | 18.879 | 39.353 | 1.00 | 15.23 | A |
| ATOM | 6205 | C | SER | A | 157 | 7.375 | 21.713 | 40.279 | 1.00 | 16.34 | A |
| ATOM | 6206 | O | SER | A | 157 | 6.566 | 22.205 | 41.075 | 1.00 | 16.25 | A |
| ATOM | 6207 | N | THR | A | 158 | 8.681 | 21.678 | 40.519 | 1.00 | 16.57 | A |
| ATOM | 6208 | CA | THR | A | 158 | 9.218 | 22.252 | 41.750 | 1.00 | 17.18 | A |
| ATOM | 6209 | CB | THR | A | 158 | 10.756 | 22.149 | 41.796 | 1.00 | 17.24 | A |
| ATOM | 6210 | OG1 | THR | A | 158 | 11.129 | 20.790 | 42.058 | 1.00 | 17.94 | A |
| ATOM | 6211 | CG2 | THR | A | 158 | 11.324 | 23.039 | 42.895 | 1.00 | 17.40 | A |

TABLE 5-continued

Three-dimensional structural coordinate of the complex of human hematopoietic PGDS (SEQ ID NO: 1) with calcium, glutathione and 9,11-dideoxy-9α,11α-epoxymethanoprostaglandine $F_{2\alpha}$(U44)

| ATOM | 6212 | C | THR | A | 158 | 8.807 | 23.721 | 41.862 | 1.00 | 17.28 | A |
|---|---|---|---|---|---|---|---|---|---|---|---|
| ATOM | 6213 | O | THR | A | 158 | 8.266 | 24.154 | 42.884 | 1.00 | 17.37 | A |
| ATOM | 6214 | N | THR | A | 159 | 9.056 | 24.484 | 40.805 | 1.00 | 17.51 | A |
| ATOM | 6215 | CA | THR | A | 159 | 8.705 | 25.900 | 40.790 | 1.00 | 17.92 | A |
| ATOM | 6216 | CB | THR | A | 159 | 9.303 | 26.594 | 39.543 | 1.00 | 17.65 | A |
| ATOM | 6217 | OG1 | THR | A | 159 | 10.730 | 26.596 | 39.653 | 1.00 | 17.96 | A |
| ATOM | 6218 | CG2 | THR | A | 159 | 8.812 | 28.033 | 39.421 | 1.00 | 18.36 | A |
| ATOM | 6219 | C | THR | A | 159 | 7.193 | 26.107 | 40.836 | 1.00 | 17.91 | A |
| ATOM | 6220 | O | THR | A | 159 | 6.702 | 26.981 | 41.554 | 1.00 | 18.18 | A |
| ATOM | 6221 | N | LEU | A | 160 | 6.446 | 25.307 | 40.084 | 1.00 | 18.04 | A |
| ATOM | 6222 | CA | LEU | A | 160 | 4.995 | 25.448 | 40.098 | 1.00 | 18.10 | A |
| ATOM | 6223 | CB | LEU | A | 160 | 4.350 | 24.485 | 39.102 | 1.00 | 18.30 | A |
| ATOM | 6224 | CG | LEU | A | 160 | 4.599 | 24.829 | 37.627 | 1.00 | 18.44 | A |
| ATOM | 6225 | CD1 | LEU | A | 160 | 3.998 | 23.744 | 36.741 | 1.00 | 18.61 | A |
| ATOM | 6226 | CD2 | LEU | A | 160 | 3.995 | 26.185 | 37.298 | 1.00 | 18.31 | A |
| ATOM | 6227 | C | LEU | A | 160 | 4.445 | 25.190 | 41.500 | 1.00 | 18.29 | A |
| ATOM | 6228 | O | LEU | A | 160 | 3.524 | 25.874 | 41.939 | 1.00 | 18.04 | A |
| ATOM | 6229 | N | LEU | A | 161 | 5.014 | 24.209 | 42.199 | 1.00 | 18.58 | A |
| ATOM | 6230 | CA | LEU | A | 161 | 4.562 | 23.867 | 43.554 | 1.00 | 18.65 | A |
| ATOM | 6231 | CB | LEU | A | 161 | 5.288 | 22.617 | 44.061 | 1.00 | 18.76 | A |
| ATOM | 6232 | CG | LEU | A | 161 | 4.830 | 21.269 | 43.494 | 1.00 | 18.94 | A |
| ATOM | 6233 | CD1 | LEU | A | 161 | 5.881 | 20.206 | 43.761 | 1.00 | 18.87 | A |
| ATOM | 6234 | CD2 | LEU | A | 161 | 3.494 | 20.881 | 44.115 | 1.00 | 18.81 | A |
| ATOM | 6235 | C | LEU | A | 161 | 4.769 | 25.009 | 44.545 | 1.00 | 18.70 | A |
| ATOM | 6236 | O | LEU | A | 161 | 4.100 | 25.078 | 45.580 | 1.00 | 18.70 | A |
| ATOM | 6237 | N | VAL | A | 162 | 5.713 | 25.892 | 44.242 | 1.00 | 18.91 | A |
| ATOM | 6238 | CA | VAL | A | 162 | 5.982 | 27.038 | 45.111 | 1.00 | 19.05 | A |
| ATOM | 6239 | CB | VAL | A | 162 | 7.268 | 27.775 | 44.679 | 1.00 | 18.98 | A |
| ATOM | 6240 | CG1 | VAL | A | 162 | 7.376 | 29.108 | 45.403 | 1.00 | 19.21 | A |
| ATOM | 6241 | CG2 | VAL | A | 162 | 8.485 | 26.911 | 44.990 | 1.00 | 18.86 | A |
| ATOM | 6242 | C | VAL | A | 162 | 4.807 | 28.012 | 45.079 | 1.00 | 19.45 | A |
| ATOM | 6243 | O | VAL | A | 162 | 4.496 | 28.669 | 46.076 | 1.00 | 19.46 | A |
| ATOM | 6244 | N | PHE | A | 163 | 4.144 | 28.096 | 43.932 | 1.00 | 19.57 | A |
| ATOM | 6245 | CA | PHE | A | 163 | 3.013 | 28.998 | 43.797 | 1.00 | 20.03 | A |
| ATOM | 6246 | CB | PHE | A | 163 | 3.087 | 29.734 | 42.458 | 1.00 | 20.31 | A |
| ATOM | 6247 | CG | PHE | A | 163 | 4.337 | 30.550 | 42.291 | 1.00 | 20.50 | A |
| ATOM | 6248 | CD1 | PHE | A | 163 | 5.466 | 29.999 | 41.696 | 1.00 | 20.62 | A |
| ATOM | 6249 | CD2 | PHE | A | 163 | 4.403 | 31.856 | 42.771 | 1.00 | 20.68 | A |
| ATOM | 6250 | CE1 | PHE | A | 163 | 6.644 | 30.732 | 41.581 | 1.00 | 20.55 | A |
| ATOM | 6251 | CE2 | PHE | A | 163 | 5.578 | 32.598 | 42.661 | 1.00 | 20.66 | A |
| ATOM | 6252 | CZ | PHE | A | 163 | 6.701 | 32.032 | 42.064 | 1.00 | 20.63 | A |
| ATOM | 6253 | C | PHE | A | 163 | 1.669 | 28.302 | 43.933 | 1.00 | 20.28 | A |
| ATOM | 6254 | O | PHE | A | 163 | 0.664 | 28.948 | 44.218 | 1.00 | 20.48 | A |
| ATOM | 6528 | N | THR | A | 197 | 16.338 | 29.399 | 46.423 | 1.00 | 26.20 | A |
| ATOM | 6529 | CA | THR | A | 197 | 15.751 | 30.609 | 45.863 | 1.00 | 25.74 | A |
| ATOM | 6530 | CB | THR | A | 197 | 16.490 | 31.036 | 44.577 | 1.00 | 25.61 | A |
| ATOM | 6531 | OG1 | THR | A | 197 | 16.472 | 29.955 | 43.637 | 1.00 | 25.05 | A |
| ATOM | 6532 | CG2 | THR | A | 197 | 17.930 | 31.404 | 44.885 | 1.00 | 25.60 | A |
| ATOM | 6533 | C | THR | A | 197 | 14.275 | 30.422 | 45.534 | 1.00 | 25.48 | A |
| ATOM | 6534 | O | THR | A | 197 | 13.779 | 29.297 | 45.478 | 1.00 | 25.55 | A |
| ATOM | 6535 | N | LYS | A | 198 | 13.579 | 31.533 | 45.321 | 1.00 | 25.39 | A |
| ATOM | 6536 | CA | LYS | A | 198 | 12.158 | 31.503 | 44.987 | 1.00 | 25.33 | A |
| ATOM | 6537 | CB | LYS | A | 198 | 11.588 | 32.923 | 44.977 | 1.00 | 25.43 | A |
| ATOM | 6538 | CG | LYS | A | 198 | 10.103 | 32.992 | 44.646 | 1.00 | 25.92 | A |
| ATOM | 6539 | CD | LYS | A | 198 | 9.614 | 34.427 | 44.597 | 1.00 | 26.17 | A |
| ATOM | 6540 | CE | LYS | A | 198 | 8.186 | 34.502 | 44.089 | 1.00 | 26.49 | A |
| ATOM | 6541 | NZ | LYS | A | 198 | 7.712 | 35.915 | 43.956 | 1.00 | 26.69 | A |
| ATOM | 6542 | C | LYS | A | 198 | 11.943 | 30.855 | 43.621 | 1.00 | 25.18 | A |
| ATOM | 6543 | O | LYS | A | 198 | 11.110 | 29.962 | 43.473 | 1.00 | 24.95 | A |
| ATOM | 6544 | N | LEU | A | 199 | 12.699 | 31.313 | 42.628 | 1.00 | 25.13 | A |
| ATOM | 6545 | CA | LEU | A | 199 | 12.595 | 30.781 | 41.270 | 1.00 | 25.12 | A |
| ATOM | 6546 | CB | LEU | A | 199 | 12.408 | 31.930 | 40.275 | 1.00 | 25.36 | A |
| ATOM | 6547 | CG | LEU | A | 199 | 10.969 | 32.324 | 39.926 | 1.00 | 25.73 | A |
| ATOM | 6548 | CD1 | LEU | A | 199 | 10.105 | 32.362 | 41.171 | 1.00 | 25.91 | A |
| ATOM | 6549 | CD2 | LEU | A | 199 | 10.981 | 33.665 | 39.212 | 1.00 | 25.98 | A |
| ATOM | 6550 | C | LEU | A | 199 | 13.812 | 29.952 | 40.870 | 1.00 | 25.09 | A |
| ATOM | 6551 | O | LEU | A | 199 | 14.823 | 29.989 | 41.603 | 1.00 | 24.71 | A |
| ATOM | 6552 | OXT | LEU | A | 199 | 13.742 | 29.281 | 39.817 | 1.00 | 24.81 | A |
| ATOM | 6613 | N1 | GSH | H | 200 | 14.696 | 30.844 | 25.962 | 1.00 | 23.65 | H |
| ATOM | 6614 | CA1 | GSH | H | 200 | 16.039 | 31.001 | 26.524 | 1.00 | 23.55 | H |
| ATOM | 6615 | C1 | GSH | H | 200 | 16.542 | 29.694 | 27.171 | 1.00 | 23.17 | H |
| ATOM | 6616 | O11 | GSH | H | 200 | 15.739 | 28.768 | 27.396 | 1.00 | 22.46 | H |
| ATOM | 6617 | O12 | GSH | H | 200 | 17.802 | 29.693 | 27.562 | 1.00 | 22.86 | H |
| ATOM | 6618 | CB1 | GSH | H | 200 | 15.985 | 32.066 | 27.622 | 1.00 | 23.81 | H |
| ATOM | 6619 | CG1 | GSH | H | 200 | 15.892 | 33.498 | 27.090 | 1.00 | 24.34 | H |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine $F_{2\alpha}$(U44)

| ATOM | 6620 | CD1 | GSH | H | 200 | 15.490 | 34.394 | 28.280 | 1.00 | 23.98 | H |
|---|---|---|---|---|---|---|---|---|---|---|---|
| ATOM | 6621 | OE1 | GSH | H | 200 | 14.442 | 35.015 | 28.215 | 1.00 | 24.41 | H |
| ATOM | 6622 | N2 | GSH | H | 200 | 16.359 | 34.466 | 29.315 | 1.00 | 24.28 | H |
| ATOM | 6623 | CA2 | GSH | H | 200 | 16.110 | 35.405 | 30.441 | 1.00 | 24.46 | H |
| ATOM | 6624 | C2 | GSH | H | 200 | 16.959 | 36.558 | 30.276 | 1.00 | 24.90 | H |
| ATOM | 6625 | O2 | GSH | H | 200 | 18.145 | 36.447 | 29.952 | 1.00 | 24.83 | H |
| ATOM | 6626 | CB2 | GSH | H | 200 | 16.495 | 34.762 | 31.809 | 1.00 | 24.14 | H |
| ATOM | 6627 | SG2 | GSH | H | 200 | 15.212 | 33.684 | 32.529 | 1.00 | 23.62 | H |
| ATOM | 6628 | N3 | GSH | H | 200 | 16.418 | 37.764 | 30.605 | 1.00 | 25.69 | H |
| ATOM | 6629 | CA3 | GSH | H | 200 | 17.234 | 39.007 | 30.688 | 1.00 | 26.56 | H |
| ATOM | 6630 | C3 | GSH | H | 200 | 16.858 | 39.970 | 29.572 | 1.00 | 27.05 | H |
| ATOM | 6631 | O31 | GSH | H | 200 | 17.544 | 41.013 | 29.478 | 1.00 | 27.21 | H |
| ATOM | 6632 | O32 | GSH | H | 200 | 15.926 | 39.647 | 28.800 | 1.00 | 27.38 | H |
| ATOM | 6708 | C1 | U44 | X | 201 | 12.551 | 37.412 | 34.770 | 1.00 | 51.36 | X |
| ATOM | 6709 | C2 | U44 | X | 201 | 12.942 | 38.049 | 36.088 | 1.00 | 51.45 | X |
| ATOM | 6710 | C3 | U44 | X | 201 | 13.074 | 36.818 | 37.021 | 1.00 | 51.46 | X |
| ATOM | 6711 | C4 | U44 | X | 201 | 13.773 | 35.785 | 36.065 | 1.00 | 51.25 | X |
| ATOM | 6712 | C5 | U44 | X | 201 | 13.862 | 36.633 | 34.758 | 1.00 | 51.32 | X |
| ATOM | 6713 | C7 | U44 | X | 201 | 14.906 | 37.744 | 34.890 | 1.00 | 51.38 | X |
| ATOM | 6714 | O6 | U44 | X | 201 | 14.219 | 38.627 | 35.787 | 1.00 | 51.43 | X |
| ATOM | 6715 | C14 | U44 | X | 201 | 13.023 | 34.496 | 35.785 | 1.00 | 50.82 | X |
| ATOM | 6716 | C16 | U44 | X | 201 | 13.358 | 33.226 | 36.116 | 1.00 | 50.17 | X |
| ATOM | 6717 | C18 | U44 | X | 201 | 12.548 | 31.983 | 35.806 | 1.00 | 49.75 | X |
| ATOM | 6718 | C20 | U44 | X | 201 | 12.422 | 31.711 | 34.291 | 1.00 | 49.34 | X |
| ATOM | 6719 | C21 | U44 | X | 201 | 11.452 | 30.558 | 33.949 | 1.00 | 48.88 | X |
| ATOM | 6720 | C24 | U44 | X | 201 | 12.111 | 29.171 | 34.031 | 1.00 | 48.50 | X |
| ATOM | 6721 | C27 | U44 | X | 201 | 11.176 | 28.042 | 33.569 | 1.00 | 48.26 | X |
| ATOM | 6722 | C30 | U44 | X | 201 | 11.730 | 26.655 | 33.911 | 1.00 | 47.93 | X |
| ATOM | 6723 | O36 | U44 | X | 201 | 11.255 | 32.146 | 36.348 | 1.00 | 49.97 | X |
| ATOM | 6724 | C39 | U44 | X | 201 | 13.871 | 37.120 | 38.326 | 1.00 | 51.81 | X |
| ATOM | 6725 | C41 | U44 | X | 201 | 13.309 | 36.423 | 39.545 | 1.00 | 52.19 | X |
| ATOM | 6726 | C44 | U44 | X | 201 | 12.673 | 36.957 | 40.612 | 1.00 | 52.52 | X |
| ATOM | 6727 | C46 | U44 | X | 201 | 12.354 | 38.413 | 40.860 | 1.00 | 52.74 | X |
| ATOM | 6728 | C48 | U44 | X | 201 | 11.089 | 38.600 | 41.702 | 1.00 | 52.91 | X |
| ATOM | 6729 | C51 | U44 | X | 201 | 10.411 | 39.953 | 41.420 | 1.00 | 53.03 | X |
| ATOM | 6730 | C54 | U44 | X | 201 | 8.878 | 39.832 | 41.396 | 1.00 | 53.12 | X |
| ATOM | 6731 | O57 | U44 | X | 201 | 8.298 | 41.019 | 41.144 | 1.00 | 53.23 | X |
| ATOM | 6732 | O58 | U44 | X | 201 | 8.266 | 38.823 | 41.572 | 1.00 | 53.07 | X |
| ATOM | 6734 | CA + 2 | CA2 | M | 901 | 9.824 | 26.883 | 22.168 | 1.00 | 37.63 | M |
| ATOM | 6747 | OH2 | WAT | S | 53 | 10.720 | 26.574 | 23.734 | 1.00 | 13.42 | S |
| ATOM | 6748 | OH2 | WAT | S | 54 | 8.700 | 27.621 | 24.867 | 1.00 | 30.29 | S |
| ATOM | 6749 | OH2 | WAT | S | 55 | 11.193 | 25.711 | 20.926 | 1.00 | 38.39 | S |
| ATOM | 6750 | OH2 | WAT | S | 56 | 8.649 | 29.181 | 22.554 | 1.00 | 40.32 | S |
| ATOM | 6751 | OH2 | WAT | S | 57 | 8.686 | 24.965 | 22.598 | 1.00 | 24.31 | S |
| ATOM | 6753 | OH2 | WAT | S | 59 | 12.609 | 27.997 | 22.910 | 1.00 | 26.01 | S |
| ATOM | 6754 | OH2 | WAT | S | 60 | 16.147 | 26.525 | 24.446 | 1.00 | 13.92 | S |
| ATOM | 6805 | OH2 | WAT | S | 119 | 15.889 | 24.704 | 33.708 | 1.00 | 12.20 | S |
| ATOM | 6817 | OH2 | WAT | S | 131 | 21.842 | 34.840 | 24.519 | 1.00 | 17.76 | S |
| ATOM | 6831 | OH2 | WAT | S | 145 | 13.761 | 25.970 | 37.415 | 1.00 | 14.51 | S |
| ATOM | 6838 | OH2 | WAT | S | 152 | 19.797 | 31.378 | 26.404 | 1.00 | 15.01 | S |
| ATOM | 6840 | OH2 | WAT | S | 154 | 17.705 | 34.244 | 22.558 | 1.00 | 19.55 | S |
| ATOM | 6862 | OH2 | WAT | S | 176 | 15.045 | 34.087 | 23.449 | 1.00 | 22.78 | S |
| ATOM | 6865 | OH2 | WAT | S | 179 | 24.231 | 27.246 | 21.186 | 1.00 | 17.23 | S |
| ATOM | 6868 | OH2 | WAT | S | 182 | 15.019 | 25.681 | 30.985 | 1.00 | 20.42 | S |
| ATOM | 6880 | OH2 | WAT | S | 194 | 18.957 | 28.395 | 43.148 | 1.00 | 25.25 | S |
| ATOM | 6884 | OH2 | WAT | S | 198 | 29.524 | 31.402 | 30.656 | 1.00 | 21.38 | S |
| ATOM | 6891 | OH2 | WAT | S | 205 | 12.982 | 24.357 | 39.397 | 1.00 | 27.06 | S |
| ATOM | 6911 | OH2 | WAT | S | 225 | 20.243 | 26.057 | 41.600 | 1.00 | 17.45 | S |
| ATOM | 6915 | OH2 | WAT | S | 229 | 13.072 | 28.340 | 28.775 | 1.00 | 23.00 | S |
| ATOM | 6920 | OH2 | WAT | S | 234 | 14.180 | 35.687 | 21.027 | 1.00 | 19.10 | S |
| ATOM | 6925 | OH2 | WAT | S | 239 | 16.432 | 26.840 | 45.110 | 1.00 | 20.16 | S |
| ATOM | 6963 | OH2 | WAT | S | 277 | 9.688 | 38.330 | 46.556 | 1.00 | 22.33 | S |
| ATOM | 6971 | OH2 | WAT | S | 285 | 14.267 | 37.710 | 28.281 | 1.00 | 27.08 | S |
| ATOM | 6979 | OH2 | WAT | S | 293 | 14.265 | 21.922 | 40.759 | 1.00 | 26.98 | S |
| ATOM | 7003 | OH2 | WAT | S | 318 | 14.285 | 33.826 | 42.961 | 1.00 | 21.76 | S |
| ATOM | 7004 | OH2 | WAT | S | 319 | 18.057 | 40.943 | 23.782 | 1.00 | 35.39 | S |
| ATOM | 7031 | OH2 | WAT | S | 349 | 17.934 | 35.785 | 45.678 | 1.00 | 28.45 | S |
| ATOM | 7060 | OH2 | WAT | S | 383 | 19.852 | 33.145 | 23.977 | 1.00 | 20.17 | S |
| ATOM | 7071 | OH2 | WAT | S | 394 | 11.887 | 37.040 | 22.324 | 1.00 | 21.27 | S |
| ATOM | 7083 | OH2 | WAT | S | 407 | 13.826 | 35.564 | 25.333 | 1.00 | 32.89 | S |
| ATOM | 7091 | OH2 | WAT | S | 415 | 12.313 | 24.839 | 23.220 | 1.00 | 28.21 | S |
| ATOM | 7128 | OH2 | WAT | S | 454 | 4.663 | 29.761 | 25.692 | 1.00 | 33.93 | S |
| ATOM | 7130 | OH2 | WAT | S | 456 | 21.062 | 36.900 | 40.187 | 1.00 | 38.49 | S |
| ATOM | 7141 | OH2 | WAT | S | 467 | 16.347 | 39.603 | 43.840 | 1.00 | 38.49 | S |
| ATOM | 7172 | OH2 | WAT | S | 501 | 16.867 | 34.824 | 43.591 | 1.00 | 33.65 | S |

TABLE 5-continued

Three-dimensional structural coordinate of the complex of
human hematopoietic PGDS (SEQ ID NO: 1) with calcium, glutathione and
9,11-dideoxy-9α,11α-epoxymethanoprostaglandine $F_{2\alpha}$(U44)

| ATOM | 7178 | OH2 | WAT | S | 508 | 13.919 | 42.210 | 21.359 | 1.00 | 42.62 | S |
|---|---|---|---|---|---|---|---|---|---|---|---|
| ATOM | 7203 | OH2 | WAT | S | 535 | 24.768 | 29.671 | 36.812 | 1.00 | 21.16 | S |
| ATOM | 7278 | OH2 | WAT | S | 624 | 9.448 | 41.034 | 37.745 | 1.00 | 45.08 | S |
| ATOM | 7311 | OH2 | WAT | S | 661 | 10.417 | 43.064 | 40.521 | 1.00 | 48.24 | S |
| ATOM | 7338 | OH2 | WAT | S | 690 | 4.520 | 39.297 | 24.898 | 1.00 | 35.89 | S |
| ATOM | 7357 | OH2 | WAT | S | 710 | 11.398 | 29.430 | 37.336 | 1.00 | 55.44 | S |
| ATOM | 7372 | OH2 | WAT | S | 725 | 29.681 | 36.478 | 31.530 | 1.00 | 46.34 | S |
| ATOM | 7377 | OH2 | WAT | S | 730 | 22.836 | 45.124 | 25.173 | 1.00 | 37.85 | S |
| ATOM | 7421 | OH2 | WAT | S | 777 | 9.127 | 46.643 | 25.394 | 1.00 | 40.66 | S |
| ATOM | 7479 | OH2 | WAT | S | 842 | 17.602 | 38.997 | 20.277 | 1.00 | 32.58 | S |
| ATOM | 7534 | OH2 | WAT | S | 900 | 16.041 | 43.445 | 43.323 | 1.00 | 38.46 | S |
| ATOM | 7540 | OH2 | WAT | S | 906 | 21.141 | 36.590 | 45.196 | 1.00 | 37.28 | S |
| ATOM | 7541 | OH2 | WAT | S | 907 | 25.332 | 34.472 | 44.401 | 1.00 | 47.03 | S |
| ATOM | 7551 | OH2 | WAT | S | 917 | 16.854 | 44.879 | 23.884 | 1.00 | 42.35 | S |
| ATOM | 7554 | OH2 | WAT | S | 920 | 8.757 | 33.269 | 28.017 | 1.00 | 43.49 | S |
| ATOM | 7647 | OH2 | WAT | T | 22 | 14.573 | 42.133 | 41.410 | 1.00 | 38.47 | T |
| ATOM | 7652 | OH2 | WAT | T | 27 | 19.585 | 45.803 | 29.005 | 1.00 | 44.65 | T |
| ATOM | 7655 | OH2 | WAT | T | 30 | 17.572 | 36.979 | 22.241 | 1.00 | 37.46 | T |
| ATOM | 7658 | OH2 | WAT | T | 35 | 6.940 | 39.912 | 44.003 | 1.00 | 34.76 | T |

TABLE 6

Three-dimensional structural coordinate of the complex of
human hematopoietic PGDS (SEQ ID NO: 1) with magnesium, glutathione and
9,11-dideoxy-9α,11α-epoxymethanoprostaglandine $F_{2\alpha}$ (U44)

| ATOM | 4966 | N | TYR | A | 8 | −24.963 | 2.816 | 34.571 | 1.00 | 17.22 | A | N |
|---|---|---|---|---|---|---|---|---|---|---|---|---|
| ATOM | 4967 | CA | TYR | A | 8 | −23.542 | 2.548 | 34.744 | 1.00 | 17.23 | A | C |
| ATOM | 4968 | CB | TYR | A | 8 | −22.782 | 3.882 | 34.816 | 1.00 | 18.03 | A | C |
| ATOM | 4969 | CG | TYR | A | 8 | −21.275 | 3.759 | 34.770 | 1.00 | 16.45 | A | C |
| ATOM | 4970 | CD1 | TYR | A | 8 | −20.632 | 3.243 | 33.642 | 1.00 | 15.64 | A | C |
| ATOM | 4971 | CE1 | TYR | A | 8 | −19.248 | 3.117 | 33.595 | 1.00 | 15.32 | A | C |
| ATOM | 4972 | CD2 | TYR | A | 8 | −20.491 | 4.152 | 35.854 | 1.00 | 15.73 | A | C |
| ATOM | 4973 | CE2 | TYR | A | 8 | −19.101 | 4.032 | 35.821 | 1.00 | 16.61 | A | C |
| ATOM | 4974 | CZ | TYR | A | 8 | −18.486 | 3.511 | 34.688 | 1.00 | 15.90 | A | C |
| ATOM | 4975 | OH | TYR | A | 8 | −17.116 | 3.369 | 34.652 | 1.00 | 14.22 | A | O |
| ATOM | 4976 | C | TYR | A | 8 | −23.334 | 1.757 | 36.033 | 1.00 | 18.22 | A | C |
| ATOM | 4977 | O | TYR | A | 8 | −24.286 | 1.500 | 36.765 | 1.00 | 18.88 | A | O |
| ATOM | 4978 | N | PHE | A | 9 | −22.090 | 1.365 | 36.297 | 1.00 | 19.45 | A | N |
| ATOM | 4979 | CA | PHE | A | 9 | −21.755 | 0.631 | 37.511 | 1.00 | 18.46 | A | C |
| ATOM | 4980 | CB | PHE | A | 9 | −20.326 | 0.086 | 37.442 | 1.00 | 20.61 | A | C |
| ATOM | 4981 | CG | PHE | A | 9 | −20.127 | −0.989 | 36.416 | 1.00 | 21.63 | A | C |
| ATOM | 4982 | CD1 | PHE | A | 9 | −19.215 | −0.817 | 35.380 | 1.00 | 23.34 | A | C |
| ATOM | 4983 | CD2 | PHE | A | 9 | −20.830 | −2.184 | 36.497 | 1.00 | 23.29 | A | C |
| ATOM | 4984 | CE1 | PHE | A | 9 | −19.003 | −1.824 | 34.439 | 1.00 | 23.36 | A | C |
| ATOM | 4985 | CE2 | PHE | A | 9 | −20.627 | −3.197 | 35.564 | 1.00 | 23.79 | A | C |
| ATOM | 4986 | CZ | PHE | A | 9 | −19.710 | −3.016 | 34.531 | 1.00 | 24.43 | A | C |
| ATOM | 4987 | C | PHE | A | 9 | −21.844 | 1.610 | 38.669 | 1.00 | 19.26 | A | C |
| ATOM | 4988 | O | PHE | A | 9 | −22.025 | 2.812 | 38.457 | 1.00 | 18.28 | A | O |
| ATOM | 4989 | N | ASN | A | 10 | −21.720 | 1.102 | 39.892 | 1.00 | 19.26 | A | N |
| ATOM | 4990 | CA | ASN | A | 10 | −21.768 | 1.967 | 41.062 | 1.00 | 20.39 | A | C |
| ATOM | 4991 | CB | ASN | A | 10 | −22.307 | 1.229 | 42.289 | 1.00 | 19.56 | A | C |
| ATOM | 4992 | CG | ASN | A | 10 | −22.172 | 2.053 | 43.558 | 1.00 | 20.32 | A | C |
| ATOM | 4993 | OD1 | ASN | A | 10 | −22.514 | 3.239 | 43.580 | 1.00 | 20.34 | A | O |
| ATOM | 4994 | ND2 | ASN | A | 10 | −21.675 | 1.432 | 44.618 | 1.00 | 19.12 | A | N |
| ATOM | 4995 | C | ASN | A | 10 | −20.382 | 2.503 | 41.374 | 1.00 | 20.96 | A | C |
| ATOM | 4996 | O | ASN | A | 10 | −19.672 | 1.971 | 42.228 | 1.00 | 20.75 | A | O |
| ATOM | 4997 | N | MET | A | 11 | −19.998 | 3.547 | 40.651 | 1.00 | 21.28 | A | N |
| ATOM | 4998 | CA | MET | A | 11 | −18.712 | 4.202 | 40.837 | 1.00 | 21.14 | A | C |
| ATOM | 4999 | CB | MET | A | 11 | −17.558 | 3.255 | 40.479 | 1.00 | 24.46 | A | C |
| ATOM | 5000 | CG | MET | A | 11 | −17.593 | 2.644 | 39.097 | 1.00 | 28.37 | A | C |
| ATOM | 5001 | SD | MET | A | 11 | −16.405 | 1.269 | 38.962 | 1.00 | 31.57 | A | S |
| ATOM | 5002 | CE | MET | A | 11 | −17.463 | −0.102 | 39.381 | 1.00 | 33.95 | A | C |
| ATOM | 5003 | C | MET | A | 11 | −18.690 | 5.449 | 39.971 | 1.00 | 17.84 | A | C |
| ATOM | 5004 | O | MET | A | 11 | −19.542 | 5.614 | 39.102 | 1.00 | 17.49 | A | O |
| ATOM | 5005 | N | ARG | A | 12 | −17.747 | 6.346 | 40.230 | 1.00 | 15.79 | A | N |
| ATOM | 5006 | CA | ARG | A | 12 | −17.652 | 7.567 | 39.440 | 1.00 | 14.18 | A | C |
| ATOM | 5007 | CB | ARG | A | 12 | −16.607 | 8.512 | 40.040 | 1.00 | 13.02 | A | C |
| ATOM | 5008 | CG | ARG | A | 12 | −16.888 | 8.917 | 41.491 | 1.00 | 15.40 | A | C |
| ATOM | 5009 | CD | ARG | A | 12 | −15.857 | 9.928 | 41.986 | 1.00 | 14.27 | A | C |
| ATOM | 5010 | NE | ARG | A | 12 | −14.488 | 9.425 | 41.848 | 1.00 | 15.20 | A | N |
| ATOM | 5011 | CZ | ARG | A | 12 | −13.945 | 8.494 | 42.627 | 1.00 | 14.91 | A | C |

TABLE 6-continued

Three-dimensional structural coordinate of the complex of
human hematopoietic PGDS (SEQ ID NO: 1) with magnesium, glutathione and
9,11-dideoxy-9α,11α-epoxymethanoprostaglandine $F_{2\alpha}$ (U44)

| ATOM | 5012 | NH1 | ARG | A | 12 | −14.649 | 7.957 | 43.613 | 1.00 | 15.94 | A | N |
|------|------|-----|-----|---|----|---------|-------|--------|------|-------|---|---|
| ATOM | 5013 | NH2 | ARG | A | 2 | −12.700 | 8.094 | 42.416 | 1.00 | 14.17 | A | N |
| ATOM | 5014 | C | ARG | A | 12 | −17.258 | 7.170 | 38.020 | 1.00 | 14.06 | A | C |
| ATOM | 5015 | O | ARG | A | 12 | −18.014 | 7.373 | 37.076 | 1.00 | 12.72 | A | O |
| ATOM | 5016 | N | GLY | A | 13 | −16.067 | 6.598 | 37.889 | 1.00 | 13.50 | A | N |
| ATOM | 5017 | CA | GLY | A | 13 | −15.581 | 6.151 | 36.598 | 1.00 | 13.43 | A | C |
| ATOM | 5018 | C | GLY | A | 13 | −15.880 | 7.031 | 35.397 | 1.00 | 11.86 | A | C |
| ATOM | 5019 | O | GLY | A | 13 | −15.654 | 8.240 | 35.420 | 1.00 | 10.45 | A | O |
| ATOM | 5020 | N | ARG | A | 14 | −16.398 | 6.406 | 34.343 | 1.00 | 11.37 | A | N |
| ATOM | 5021 | CA | ARG | A | 14 | −16.708 | 7.100 | 33.096 | 1.00 | 12.46 | A | C |
| ATOM | 5022 | CB | ARG | A | 14 | −16.606 | 6.111 | 31.928 | 1.00 | 11.33 | A | C |
| ATOM | 5023 | CG | ARG | A | 14 | −15.177 | 5.691 | 31.628 | 1.00 | 13.46 | A | C |
| ATOM | 5024 | CD | ARG | A | 14 | −15.077 | 4.572 | 30.606 | 1.00 | 17.48 | A | C |
| ATOM | 5025 | NE | ARG | A | 14 | −13.738 | 4.519 | 30.019 | 1.00 | 20.64 | A | N |
| ATOM | 5026 | CZ | ARG | A | 14 | −12.890 | 3.499 | 30.132 | 1.00 | 22.84 | A | C |
| ATOM | 5027 | NH1 | ARG | A | 14 | −13.224 | 2.410 | 30.817 | 1.00 | 23.14 | A | N |
| ATOM | 5028 | NH2 | ARG | A | 14 | −11.696 | 3.575 | 29.559 | 1.00 | 23.88 | A | N |
| ATOM | 5029 | C | ARG | A | 14 | −18.058 | 7.809 | 33.049 | 1.00 | 11.90 | A | C |
| ATOM | 5030 | O | ARG | A | 14 | −18.353 | 8.511 | 32.087 | 1.00 | 12.49 | A | O |
| ATOM | 5031 | N | ALA | A | 15 | −18.871 | 7.637 | 34.084 | 1.00 | 12.15 | A | N |
| ATOM | 5032 | CA | ALA | A | 15 | −20.190 | 8.263 | 34.118 | 1.00 | 12.60 | A | C |
| ATOM | 5033 | CB | ALA | A | 15 | −21.206 | 7.305 | 34.762 | 1.00 | 13.45 | A | C |
| ATOM | 5034 | C | ALA | A | 15 | −20.199 | 9.592 | 34.866 | 1.00 | 11.68 | A | C |
| ATOM | 5035 | O | ALA | A | 15 | −21.085 | 10.423 | 34.658 | 1.00 | 11.89 | A | O |
| ATOM | 5036 | N | GLU | A | 16 | −19.209 | 9.795 | 35.727 | 1.00 | 13.81 | A | N |
| ATOM | 5037 | CA | GLU | A | 16 | −19.141 | 11.007 | 36.534 | 1.00 | 13.28 | A | C |
| ATOM | 5038 | CB | GLU | A | 16 | −17.877 | 10.986 | 37.399 | 1.00 | 12.67 | A | C |
| ATOM | 5039 | CG | GLU | A | 16 | −17.971 | 11.841 | 38.672 | 1.00 | 13.36 | A | C |
| ATOM | 5040 | CD | GLU | A | 16 | −19.146 | 11.457 | 39.575 | 1.00 | 13.41 | A | C |
| ATOM | 5041 | OE1 | GLU | A | 16 | −19.695 | 10.345 | 39.422 | 1.00 | 12.47 | A | O |
| ATOM | 5042 | OE2 | GLU | A | 16 | −19.512 | 12.266 | 40.452 | 1.00 | 14.67 | A | O |
| ATOM | 5043 | C | GLU | A | 16 | −19.216 | 12.314 | 35.748 | 1.00 | 13.25 | A | C |
| ATOM | 5044 | O | GLU | A | 16 | −19.903 | 13.245 | 36.167 | 1.00 | 11.55 | A | O |
| ATOM | 5045 | N | ILE | A | 17 | −18.521 | 12.393 | 34.614 | 1.00 | 12.65 | A | N |
| ATOM | 5046 | CA | ILE | A | 17 | −18.549 | 13.621 | 33.823 | 1.00 | 12.45 | A | C |
| ATOM | 5047 | CB | ILE | A | 17 | −17.659 | 13.507 | 32.548 | 1.00 | 11.09 | A | C |
| ATOM | 5048 | CG2 | ILE | A | 17 | −18.158 | 12.384 | 31.642 | 1.00 | 9.92 | A | C |
| ATOM | 5049 | CG1 | ILE | A | 17 | −17.663 | 14.836 | 31.790 | 1.00 | 11.02 | A | C |
| ATOM | 5050 | CD1 | ILE | A | 17 | −17.127 | 16.025 | 32.594 | 1.00 | 13.12 | A | C |
| ATOM | 5051 | C | ILE | A | 17 | −19.981 | 13.984 | 33.430 | 1.00 | 12.64 | A | C |
| ATOM | 5052 | O | ILE | A | 17 | −20.348 | 15.155 | 33.421 | 1.00 | 13.53 | A | O |
| ATOM | 5242 | N | TRP | A | 39 | −24.802 | −7.318 | 35.073 | 1.00 | 35.03 | A | N |
| ATOM | 5243 | CA | TRP | A | 39 | −24.074 | −6.905 | 33.874 | 1.00 | 33.95 | A | C |
| ATOM | 5244 | CB | TRP | A | 39 | −22.586 | −6.705 | 34.193 | 1.00 | 30.71 | A | C |
| ATOM | 5245 | G | TRP | A | 39 | −21.787 | −6.208 | 33.021 | 1.00 | 27.71 | A | C |
| ATOM | 5246 | CD2 | TRP | A | 39 | −22.182 | −5.206 | 32.072 | 1.00 | 26.24 | A | C |
| ATOM | 5247 | CE2 | TRP | A | 39 | −21.134 | −5.085 | 31.130 | 1.00 | 27.24 | A | C |
| ATOM | 5248 | CE3 | TRP | A | 39 | −23.319 | −4.401 | 31.925 | 1.00 | 25.00 | A | C |
| ATOM | 5249 | CD1 | TRP | A | 39 | −20.549 | −6.637 | 32.630 | 1.00 | 28.16 | A | C |
| ATOM | 5250 | NE1 | TRP | A | 39 | −20.152 | −5.969 | 31.493 | 1.00 | 28.63 | A | N |
| ATOM | 5251 | CZ2 | TRP | A | 39 | −21.191 | −4.191 | 30.054 | 1.00 | 26.14 | A | C |
| ATOM | 5252 | CZ3 | TRP | A | 39 | −23.377 | −3.511 | 30.850 | 1.00 | 24.88 | A | C |
| ATOM | 5253 | CH2 | TRP | A | 39 | −22.318 | −3.416 | 29.931 | 1.00 | 25.30 | A | C |
| ATOM | 5254 | C | TRP | A | 39 | −24.217 | −7.861 | 32.683 | 1.00 | 34.33 | A | C |
| ATOM | 5255 | O | TRP | A | 39 | −24.633 | −7.451 | 31.600 | 1.00 | 34.30 | A | O |
| ATOM | 5256 | N | PRO | A | 40 | −23.880 | −9.149 | 32.869 | 1.00 | 35.19 | A | N |
| ATOM | 5257 | CD | PRO | A | 40 | −23.513 | −9.824 | 34.128 | 1.00 | 35.28 | A | C |
| ATOM | 5258 | CA | PRO | A | 40 | −23.985 | −10.120 | 31.775 | 1.00 | 35.54 | A | C |
| ATOM | 5259 | CB | PRO | A | 40 | −23.906 | −11.460 | 32.499 | 1.00 | 36.12 | A | C |
| ATOM | 5260 | CG | PRO | A | 40 | −22.984 | −11.156 | 33.638 | 1.00 | 36.50 | A | C |
| ATOM | 5261 | C | PRO | A | 40 | −25.259 | −9.985 | 30.946 | 1.00 | 35.56 | A | C |
| ATOM | 5262 | O | PRO | A | 40 | −25.200 | −9.824 | 29.727 | 1.00 | 36.61 | A | O |
| ATOM | 5263 | N | GLU | A | 41 | −26.406 | −10.043 | 31.614 | 1.00 | 34.82 | A | N |
| ATOM | 5264 | CA | GLU | A | 41 | −27.693 | −9.942 | 30.935 | 1.00 | 35.20 | A | C |
| ATOM | 5265 | CB | GLU | A | 41 | −28.833 | −10.189 | 31.931 | 1.00 | 37.14 | A | C |
| ATOM | 5266 | CG | GLU | A | 41 | −30.221 | −10.044 | 31.328 | 1.00 | 41.54 | A | C |
| ATOM | 5267 | CD | GLU | A | 41 | −30.489 | −11.046 | 30.219 | 1.00 | 44.14 | A | C |
| ATOM | 5268 | OE1 | GLU | A | 41 | −31.529 | −10.915 | 29.536 | 1.00 | 46.32 | A | O |
| ATOM | 5269 | OE2 | GLU | A | 41 | −29.665 | −11.967 | 30.030 | 1.00 | 45.36 | A | O |
| ATOM | 5270 | C | GLU | A | 41 | −27.911 | −8.603 | 30.237 | 1.00 | 33.75 | A | C |
| ATOM | 5271 | O | GLU | A | 41 | −28.460 | −8.553 | 29.135 | 1.00 | 34.40 | A | O |
| ATOM | 5272 | N | ILE | A | 42 | −27.483 | −7.521 | 30.880 | 1.00 | 31.53 | A | N |
| ATOM | 5273 | CA | ILE | A | 42 | −27.648 | −6.181 | 30.322 | 1.00 | 28.99 | A | C |
| ATOM | 5274 | CB | ILE | A | 42 | −27.401 | −5.106 | 31.402 | 1.00 | 28.48 | A | C |
| ATOM | 5275 | CG2 | ILE | A | 42 | −27.689 | −3.721 | 30.833 | 1.00 | 27.91 | A | C |

TABLE 6-continued

Three-dimensional structural coordinate of the complex of
human hematopoietic PGDS (SEQ ID NO: 1) with magnesium, glutathione and
9,11-dideoxy-9α,11α-epoxymethanoprostaglandine $F_{2\alpha}$ (U44)

| ATOM | 5276 | CG1 | ILE | A | 42 | −28.304 | −5.369 | 32.608 | 1.00 | 27.61 | A | C |
|---|---|---|---|---|---|---|---|---|---|---|---|---|
| ATOM | 5277 | CD1 | ILE | A | 42 | −27.975 | −4.530 | 33.821 | 1.00 | 29.35 | A | C |
| ATOM | 5278 | C | ILE | A | 42 | −26.709 | −5.926 | 29.143 | 1.00 | 27.64 | A | C |
| ATOM | 5279 | O | ILE | A | 42 | −27.114 | −5.355 | 28.129 | 1.00 | 27.10 | A | O |
| ATOM | 5280 | N | LYS | A | 43 | −25.459 | −6.353 | 29.283 | 1.00 | 26.84 | A | N |
| ATOM | 5281 | CA | LYS | A | 43 | −24.457 | −6.173 | 28.237 | 1.00 | 27.71 | A | C |
| ATOM | 5282 | CB | LYS | A | 43 | −23.160 | −6.886 | 28.629 | 1.00 | 26.22 | A | C |
| ATOM | 5283 | CG | LYS | A | 43 | −22.062 | −6.814 | 27.579 | 1.00 | 23.72 | A | C |
| ATOM | 5284 | CD | LYS | A | 43 | −20.871 | −7.669 | 27.981 | 1.00 | 22.67 | A | C |
| ATOM | 5285 | CE | LYS | A | 43 | −19.747 | −7.576 | 26.965 | 1.00 | 23.33 | A | C |
| ATOM | 5286 | NZ | LYS | A | 43 | −19.134 | −6.217 | 26.936 | 1.00 | 21.56 | A | N |
| ATOM | 5287 | C | LYS | A | 43 | −24.940 | −6.708 | 26.893 | 1.00 | 28.75 | A | C |
| ATOM | 5288 | O | LYS | A | 43 | −24.719 | −6.090 | 25.852 | 1.00 | 28.75 | A | O |
| ATOM | 5328 | N | GLY | A | 49 | −22.268 | −3.248 | 23.763 | 1.00 | 15.23 | A | N |
| ATOM | 5329 | CA | GLY | A | 49 | −21.927 | −3.903 | 25.015 | 1.00 | 15.04 | A | C |
| ATOM | 5330 | C | GLY | A | 49 | −21.064 | −3.144 | 26.005 | 1.00 | 15.33 | A | C |
| ATOM | 5331 | O | GLY | A | 49 | −20.313 | −3.754 | 26.768 | 1.00 | 15.11 | A | O |
| ATOM | 5332 | N | LYS | A | 50 | −21.169 | −1.821 | 26.007 | 1.00 | 13.57 | A | N |
| ATOM | 5333 | CA | LYS | A | 50 | −20.380 | −1.008 | 26.926 | 1.00 | 14.57 | A | C |
| ATOM | 5334 | CB | LYS | A | 50 | −19.259 | −0.274 | 26.173 | 1.00 | 15.57 | A | C |
| ATOM | 5335 | CG | LYS | A | 50 | −18.310 | −1.166 | 25.391 | 1.00 | 18.60 | A | C |
| ATOM | 5336 | CD | LYS | A | 50 | −17.505 | −2.069 | 26.308 | 1.00 | 21.95 | A | C |
| ATOM | 5337 | CE | LYS | A | 50 | −16.603 | −2.992 | 25.504 | 1.00 | 24.43 | A | C |
| ATOM | 5338 | NZ | LYS | A | 50 | −15.681 | −2.218 | 24.631 | 1.00 | 25.99 | A | N |
| ATOM | 5339 | C | LYS | A | 50 | −21.246 | 0.030 | 27.625 | 1.00 | 14.42 | A | C |
| ATOM | 5340 | O | LYS | A | 50 | −22.253 | 0.488 | 27.081 | 1.00 | 14.19 | A | O |
| ATOM | 5341 | N | ILE | A | 51 | −20.848 | 0.394 | 28.840 | 1.00 | 14.37 | A | N |
| ATOM | 5342 | CA | ILE | A | 51 | −21.553 | 1.416 | 29.597 | 1.00 | 14.74 | A | C |
| ATOM | 5343 | CB | ILE | A | 51 | −22.203 | 0.840 | 30.876 | 1.00 | 15.30 | A | C |
| ATOM | 5344 | CG2 | ILE | A | 51 | −23.403 | −0.008 | 30.497 | 1.00 | 17.79 | A | C |
| ATOM | 5345 | CG1 | ILE | A | 51 | −21.187 | 0.020 | 31.675 | 1.00 | 15.08 | A | C |
| ATOM | 5346 | CD1 | ILE | A | 51 | −21.764 | −0.585 | 32.950 | 1.00 | 15.84 | A | C |
| ATOM | 5347 | C | ILE | A | 51 | −20.526 | 2.490 | 29.949 | 1.00 | 14.66 | A | C |
| ATOM | 5348 | O | ILE | A | 51 | −19.324 | 2.232 | 29.931 | 1.00 | 16.06 | A | O |
| ATOM | 5349 | N | PRO | A | 52 | −20.982 | 3.700 | 30.299 | 1.00 | 15.26 | A | N |
| ATOM | 5350 | CD | PRO | A | 52 | −20.083 | 4.841 | 30.562 | 1.00 | 16.04 | A | C |
| ATOM | 5351 | CA | PRO | A | 52 | −22.379 | 4.124 | 30.396 | 1.00 | 15.40 | A | C |
| ATOM | 5352 | CB | PRO | A | 52 | −22.276 | 5.409 | 31.197 | 1.00 | 15.83 | A | C |
| ATOM | 5353 | CG | PRO | A | 52 | −21.045 | 6.024 | 30.593 | 1.00 | 15.77 | A | C |
| ATOM | 5354 | C | PRO | A | 52 | −23.101 | 4.365 | 29.080 | 1.00 | 16.83 | A | C |
| ATOM | 5355 | O | PRO | A | 52 | −22.492 | 4.484 | 28.015 | 1.00 | 14.90 | A | O |
| ATOM | 5356 | N | ILE | A | 53 | −24.420 | 4.438 | 29.188 | 1.00 | 17.77 | A | N |
| ATOM | 5357 | CA | ILE | A | 53 | −25.288 | 4.730 | 28.067 | 1.00 | 18.90 | A | C |
| ATOM | 5358 | CB | ILE | A | 53 | −26.045 | 3.483 | 27.563 | 1.00 | 20.61 | A | C |
| ATOM | 5359 | CG2 | ILE | A | 53 | −25.054 | 2.435 | 27.075 | 1.00 | 20.84 | A | C |
| ATOM | 5360 | CG1 | ILE | A | 53 | −26.938 | 2.928 | 28.675 | 1.00 | 21.82 | A | C |
| ATOM | 5361 | CD1 | ILE | A | 53 | −27.891 | 1.842 | 28.211 | 1.00 | 24.03 | A | C |
| ATOM | 5362 | C | ILE | A | 53 | −26.286 | 5.708 | 28.662 | 1.00 | 18.88 | A | C |
| ATOM | 5363 | O | ILE | A | 53 | −26.494 | 5.722 | 29.878 | 1.00 | 18.43 | A | O |
| ATOM | 5423 | N | HIS | A | 62 | −24.373 | 6.192 | 23.498 | 1.00 | 15.70 | A | N |
| ATOM | 5424 | CA | HIS | A | 62 | −23.236 | 5.561 | 24.160 | 1.00 | 15.77 | A | C |
| ATOM | 5425 | CB | HIS | A | 62 | −22.957 | 4.167 | 23.568 | 1.00 | 15.57 | A | C |
| ATOM | 5426 | CG | HIS | A | 62 | −22.517 | 4.179 | 22.134 | 1.00 | 14.35 | A | C |
| ATOM | 5427 | CD2 | HIS | A | 62 | −21.358 | 3.778 | 21.556 | 1.00 | 15.17 | A | C |
| ATOM | 5428 | ND1 | HIS | A | 62 | −23.332 | 4.598 | 21.104 | 1.00 | 17.10 | A | N |
| ATOM | 5429 | CE1 | HIS | A | 62 | −22.697 | 4.451 | 19.953 | 1.00 | 14.96 | A | C |
| ATOM | 5430 | NE2 | HIS | A | 62 | −21.498 | 3.955 | 20.200 | 1.00 | 15.48 | A | N |
| ATOM | 5431 | C | HIS | A | 62 | −21.988 | 6.437 | 24.080 | 1.00 | 14.50 | A | C |
| ATOM | 5432 | O | HIS | A | 62 | −22.007 | 7.489 | 23.442 | 1.00 | 13.29 | A | O |
| ATOM | 5433 | N | GLN | A | 63 | −20.913 | 5.997 | 24.734 | 1.00 | 13.87 | A | N |
| ATOM | 5434 | CA | GLN | A | 63 | −19.654 | 6.740 | 24.764 | 1.00 | 12.90 | A | C |
| ATOM | 5435 | CB | GLN | A | 63 | −19.224 | 7.137 | 23.345 | 1.00 | 12.53 | A | C |
| ATOM | 5436 | CG | GLN | A | 63 | −18.581 | 6.001 | 22.545 | 1.00 | 11.52 | A | C |
| ATOM | 5437 | CD | GLN | A | 63 | −17.268 | 5.533 | 23.160 | 1.00 | 12.20 | A | C |
| ATOM | 5438 | OE1 | GLN | A | 63 | −16.730 | 6.176 | 24.062 | 1.00 | 10.43 | A | O |
| ATOM | 5439 | NE2 | GLN | A | 63 | −16.741 | 4.421 | 22.664 | 1.00 | 9.56 | A | N |
| ATOM | 5440 | C | GLN | A | 63 | −19.805 | 7.976 | 25.653 | 1.00 | 13.56 | A | C |
| ATOM | 5441 | O | GLN | A | 63 | −20.476 | 8.947 | 25.289 | 1.00 | 14.92 | A | O |
| ATOM | 5442 | N | SER | A | 64 | −19.167 | 7.924 | 26.817 | 1.00 | 10.97 | A | N |
| ATOM | 5443 | CA | SER | A | 64 | −19.236 | 8.993 | 27.807 | 1.00 | 10.05 | A | C |
| ATOM | 5444 | CB | SER | A | 64 | −18.322 | 8.658 | 28.995 | 1.00 | 9.89 | A | C |
| ATOM | 5445 | OG | SER | A | 64 | −16.955 | 8.727 | 28.627 | 1.00 | 8.82 | A | O |
| ATOM | 5446 | C | SER | A | 64 | −18.932 | 10.411 | 27.323 | 1.00 | 8.80 | A | C |
| ATOM | 5447 | O | SER | A | 64 | −19.674 | 11.339 | 27.636 | 1.00 | 9.79 | A | O |
| ATOM | 5448 | N | LEU | A | 65 | −17.853 | 10.586 | 26.565 | 1.00 | 8.85 | A | N |

TABLE 6-continued

Three-dimensional structural coordinate of the complex of human hematopoietic PGDS (SEQ ID NO: 1) with magnesium, glutathione and 9,11-dideoxy-9α,11α-epoxymethanoprostaglandine $F_{2\alpha}$ (U44)

| ATOM | 5449 | CA | LEU | A | 65 | −17.483 | 11.917 | 26.091 | 1.00 | 8.19 | A | C |
|---|---|---|---|---|---|---|---|---|---|---|---|---|
| ATOM | 5450 | CB | LEU | A | 65 | −16.009 | 11.933 | 25.671 | 1.00 | 7.83 | A | C |
| ATOM | 5451 | CG | LEU | A | 65 | −15.054 | 11.409 | 26.757 | 1.00 | 11.60 | A | C |
| ATOM | 5452 | CD1 | LEU | A | 65 | −13.618 | 11.479 | 26.253 | 1.00 | 11.43 | A | C |
| ATOM | 5453 | CD2 | LEU | A | 65 | −15.220 | 12.226 | 28.041 | 1.00 | 8.48 | A | C |
| ATOM | 5454 | C | LEU | A | 65 | −18.374 | 12.419 | 24.956 | 1.00 | 10.81 | A | C |
| ATOM | 5455 | O | LEU | A | 65 | −18.539 | 13.627 | 24.779 | 1.00 | 11.65 | A | O |
| ATOM | 5662 | N | ASP | A | 93 | −9.664 | 14.664 | 25.566 | 1.00 | 7.26 | A | N |
| ATOM | 5663 | CA | ASP | A | 93 | −9.071 | 13.449 | 25.009 | 1.00 | 6.80 | A | C |
| ATOM | 5664 | CB | ASP | A | 93 | −9.016 | 13.526 | 23.476 | 1.00 | 7.94 | A | C |
| ATOM | 5665 | CG | ASP | A | 93 | −10.318 | 13.092 | 22.823 | 1.00 | 9.46 | A | C |
| ATOM | 5666 | OD1 | ASP | A | 93 | −10.361 | 12.988 | 21.577 | 1.00 | 10.43 | A | O |
| ATOM | 5667 | OD2 | ASP | A | 93 | −11.302 | 12.855 | 23.556 | 1.00 | 6.66 | A | O |
| ATOM | 5668 | C | ASP | A | 93 | −7.678 | 13.144 | 25.562 | 1.00 | 8.24 | A | C |
| ATOM | 5669 | O | ASP | A | 93 | −7.325 | 11.979 | 25.751 | 1.00 | 8.03 | A | O |
| ATOM | 5670 | N | THR | A | 94 | −6.879 | 14.179 | 25.808 | 1.00 | 7.87 | A | N |
| ATOM | 5671 | CA | THR | A | 94 | −5.541 | 13.973 | 26.354 | 1.00 | 7.89 | A | C |
| ATOM | 5672 | CB | THR | A | 94 | −4.753 | 15.305 | 26.444 | 1.00 | 8.49 | A | C |
| ATOM | 5673 | OG1 | THR | A | 94 | −4.329 | 15.693 | 25.125 | 1.00 | 8.47 | A | O |
| ATOM | 5674 | CG2 | THR | A | 94 | −3.520 | 15.155 | 27.342 | 1.00 | 8.64 | A | C |
| ATOM | 5675 | C | THR | A | 94 | −5.679 | 13.342 | 27.740 | 1.00 | 8.60 | A | C |
| ATOM | 5676 | O | THR | A | 94 | −4.912 | 12.455 | 28.110 | 1.00 | 8.25 | A | O |
| ATOM | 5677 | N | LEU | A | 95 | −6.669 | 13.797 | 28.499 | 1.00 | 8.02 | A | N |
| ATOM | 5678 | CA | LEU | A | 95 | −6.905 | 13.248 | 29.826 | 1.00 | 7.48 | A | C |
| ATOM | 5679 | CB | LEU | A | 95 | −7.884 | 14.135 | 30.606 | 1.00 | 6.39 | A | C |
| ATOM | 5680 | CG | LEU | A | 95 | −7.345 | 15.483 | 31.102 | 1.00 | 6.45 | A | C |
| ATOM | 5681 | CD1 | LEU | A | 95 | −8.480 | 16.323 | 31.676 | 1.00 | 7.27 | A | C |
| ATOM | 5682 | CD2 | LEU | A | 95 | −6.270 | 15.244 | 32.156 | 1.00 | 8.71 | A | C |
| ATOM | 5683 | C | LEU | A | 95 | −7.464 | 11.829 | 29.700 | 1.00 | 8.84 | A | C |
| ATOM | 5684 | O | LEU | A | 95 | −7.013 | 10.921 | 30.394 | 1.00 | 6.72 | A | O |
| ATOM | 5685 | N | ASP | A | 96 | −8.426 | 11.639 | 28.794 | 1.00 | 9.13 | A | N |
| ATOM | 5686 | CA | ASP | A | 96 | −9.042 | 10.328 | 28.600 | 1.00 | 8.40 | A | C |
| ATOM | 5687 | CB | ASP | A | 96 | −10.213 | 10.421 | 27.614 | 1.00 | 9.89 | A | C |
| ATOM | 5688 | CG | ASP | A | 96 | −11.200 | 9.271 | 27.768 | 1.00 | 8.95 | A | C |
| ATOM | 5689 | OD1 | ASP | A | 96 | −11.674 | 9.046 | 28.903 | 1.00 | 11.48 | A | O |
| ATOM | 5690 | OD2 | ASP | A | 96 | −11.515 | 8.599 | 26.761 | 1.00 | 8.48 | A | O |
| ATOM | 5691 | C | ASP | A | 96 | −8.029 | 9.294 | 28.113 | 1.00 | 11.25 | A | C |
| ATOM | 5692 | O | ASP | A | 96 | −8.083 | 8.129 | 28.516 | 1.00 | 11.68 | A | O |
| ATOM | 5693 | N | ASP | A | 97 | −7.107 | 9.714 | 27.249 | 1.00 | 10.40 | A | N |
| ATOM | 5694 | CA | ASP | A | 97 | −6.074 | 8.815 | 26.748 | 1.00 | 10.66 | A | C |
| ATOM | 5695 | CB | ASP | A | 97 | −5.108 | 9.552 | 25.815 | 1.00 | 9.42 | A | C |
| ATOM | 5696 | CG | ASP | A | 97 | −5.684 | 9.804 | 24.429 | 1.00 | 10.69 | A | C |
| ATOM | 5697 | OD1 | ASP | A | 97 | −5.100 | 10.644 | 23.708 | 1.00 | 8.34 | A | O |
| ATOM | 5698 | OD2 | ASP | A | 97 | −6.693 | 9.166 | 24.050 | 1.00 | 9.39 | A | O |
| ATOM | 5699 | C | ASP | A | 97 | −5.266 | 8.241 | 27.914 | 1.00 | 10.28 | A | C |
| ATOM | 5700 | O | ASP | A | 97 | −5.013 | 7.039 | 27.972 | 1.00 | 9.67 | A | O |
| ATOM | 5701 | N | PHE | A | 98 | −4.856 | 9.106 | 28.839 | 1.00 | 11.06 | A | N |
| ATOM | 5702 | CA | PHE | A | 98 | −4.057 | 8.667 | 29.984 | 1.00 | 13.17 | A | C |
| ATOM | 5703 | CB | PHE | A | 98 | −3.508 | 9.871 | 30.767 | 1.00 | 12.79 | A | C |
| ATOM | 5704 | CG | PHE | A | 98 | −2.540 | 9.487 | 31.861 | 1.00 | 14.46 | A | C |
| ATOM | 5705 | CD1 | PHE | A | 98 | −1.365 | 8.800 | 31.558 | 1.00 | 14.40 | A | C |
| ATOM | 5706 | CD2 | PHE | A | 98 | −2.817 | 9.781 | 33.191 | 1.00 | 15.98 | A | C |
| ATOM | 5707 | CE1 | PHE | A | 98 | −0.480 | 8.409 | 32.568 | 1.00 | 17.26 | A | C |
| ATOM | 5708 | CE2 | PHE | A | 98 | −1.938 | 9.394 | 34.214 | 1.00 | 16.31 | A | C |
| ATOM | 5709 | CZ | PHE | A | 98 | −0.769 | 8.706 | 33.899 | 1.00 | 14.31 | A | C |
| ATOM | 5710 | C | PHE | A | 98 | −4.828 | 7.754 | 30.935 | 1.00 | 14.11 | A | C |
| ATOM | 5711 | O | PHE | A | 98 | −4.308 | 6.731 | 31.381 | 1.00 | 14.82 | A | O |
| ATOM | 5712 | N | MET | A | 99 | −6.063 | 8.125 | 31.252 | 1.00 | 14.73 | A | N |
| ATOM | 5713 | CA | MET | A | 99 | −6.886 | 7.318 | 32.149 | 1.00 | 14.22 | A | C |
| ATOM | 5714 | CB | MET | A | 99 | −8.225 | 8.013 | 32.420 | 1.00 | 15.31 | A | C |
| ATOM | 5715 | CG | MET | A | 99 | −8.121 | 9.374 | 33.109 | 1.00 | 15.68 | A | C |
| ATOM | 5716 | SD | MET | A | 99 | −7.267 | 9.310 | 34.694 | 1.00 | 15.84 | A | S |
| ATOM | 5717 | CE | MET | A | 99 | −8.515 | 8.541 | 35.722 | 1.00 | 16.08 | A | C |
| ATOM | 5718 | C | MET | A | 99 | −7.150 | 5.939 | 31.548 | 1.00 | 16.86 | A | C |
| ATOM | 5719 | O | MET | A | 99 | −7.220 | 4.939 | 32.267 | 1.00 | 14.67 | A | O |
| ATOM | 5720 | N | SER | A | 100 | −7.292 | 5.892 | 30.225 | 1.00 | 16.11 | A | N |
| ATOM | 5721 | CA | SER | A | 100 | −7.561 | 4.641 | 29.523 | 1.00 | 16.96 | A | C |
| ATOM | 5722 | CB | SER | A | 100 | −8.084 | 4.936 | 28.115 | 1.00 | 16.86 | A | C |
| ATOM | 5723 | OG | SER | A | 100 | −9.356 | 5.556 | 28.184 | 1.00 | 16.40 | A | O |
| ATOM | 5724 | C | SER | A | 100 | −6.350 | 3.717 | 29.442 | 1.00 | 19.01 | A | C |
| ATOM | 5725 | O | SER | A | 100 | −6.489 | 2.528 | 29.149 | 1.00 | 19.47 | A | O |
| ATOM | 5726 | N | CYS | A | 101 | −5.166 | 4.262 | 29.697 | 1.00 | 20.58 | A | N |
| ATOM | 5727 | CA | CYS | A | 101 | −3.944 | 3.464 | 29.665 | 1.00 | 23.67 | A | C |
| ATOM | 5728 | CB | CYS | A | 101 | −2.707 | 4.368 | 29.693 | 1.00 | 26.07 | A | C |
| ATOM | 5729 | SG | CYS | A | 101 | −2.263 | 5.097 | 28.099 | 1.00 | 30.40 | A | S |

TABLE 6-continued

Three-dimensional structural coordinate of the complex of human hematopoietic PGDS (SEQ ID NO: 1) with magnesium, glutathione and 9,11-dideoxy-9α,11α-epoxymethanoprostaglandine $F_{2α}$ (U44)

| ATOM | 5730 | C | CYS | A | 101 | −3.876 | 2.484 | 30.836 | 1.00 | 23.47 | A | C |
|---|---|---|---|---|---|---|---|---|---|---|---|---|
| ATOM | 5731 | O | CYS | A | 101 | −3.257 | 1.426 | 30.729 | 1.00 | 24.00 | A | O |
| ATOM | 5732 | N | PHE | A | 102 | −4.504 | 2.833 | 31.953 | 1.00 | 23.47 | A | N |
| ATOM | 5733 | CA | PHE | A | 102 | −4.485 | 1.955 | 33.117 | 1.00 | 24.57 | A | C |
| ATOM | 5734 | CB | PHE | A | 102 | −5.012 | 2.681 | 34.360 | 1.00 | 22.30 | A | C |
| ATOM | 5735 | CG | PHE | A | 102 | −4.128 | 3.798 | 34.832 | 1.00 | 21.46 | A | C |
| ATOM | 5736 | CD1 | PHE | A | 102 | −4.099 | 5.014 | 34.158 | 1.00 | 20.64 | A | C |
| ATOM | 5737 | CD2 | PHE | A | 102 | −3.313 | 3.631 | 35.949 | 1.00 | 20.02 | A | C |
| ATOM | 5738 | CE1 | PHE | A | 102 | −3.267 | 6.055 | 34.590 | 1.00 | 21.12 | A | C |
| ATOM | 5739 | CE2 | PHE | A | 102 | −2.480 | 4.662 | 36.387 | 1.00 | 20.36 | A | C |
| ATOM | 5740 | CZ | PHE | A | 102 | −2.458 | 5.875 | 35.705 | 1.00 | 18.32 | A | C |
| ATOM | 5741 | C | PHE | A | 102 | −5.313 | 0.698 | 32.881 | 1.00 | 25.48 | A | C |
| ATOM | 5742 | O | PHE | A | 102 | −6.423 | 0.765 | 32.358 | 1.00 | 25.08 | A | O |
| ATOM | 5743 | N | PRO | A | 103 | −4.773 | −0.471 | 33.259 | 1.00 | 27.90 | A | N |
| ATOM | 5744 | CD | PRO | A | 103 | −3.398 | −0.682 | 33.750 | 1.00 | 27.31 | A | C |
| ATOM | 5745 | CA | PRO | A | 103 | −5.466 | −1.751 | 33.090 | 1.00 | 29.68 | A | C |
| ATOM | 5746 | CB | PRO | A | 103 | −4.323 | −2.753 | 33.124 | 1.00 | 28.70 | A | C |
| ATOM | 5747 | CG | PRO | A | 103 | −3.410 | −2.145 | 34.142 | 1.00 | 28.84 | A | C |
| ATOM | 5748 | C | PRO | A | 103 | −6.471 | −1.975 | 34.220 | 1.00 | 31.64 | A | C |
| ATOM | 5749 | O | PRO | A | 103 | −6.208 | −2.740 | 35.150 | 1.00 | 32.46 | A | O |
| ATOM | 5750 | N | TRP | A | 104 | −7.619 | −1.308 | 34.132 | 1.00 | 33.14 | A | N |
| ATOM | 5751 | CA | TRP | A | 104 | −8.652 | −1.416 | 35.157 | 1.00 | 34.92 | A | C |
| ATOM | 5752 | CB | TRP | A | 104 | −9.740 | −0.360 | 34.936 | 1.00 | 34.59 | A | C |
| ATOM | 5753 | CG | TRP | A | 104 | −9.223 | −1.041 | 34.784 | 1.00 | 33.67 | A | C |
| ATOM | 5754 | CD2 | TRP | A | 104 | −8.909 | 1.959 | 35.838 | 1.00 | 32.46 | A | C |
| ATOM | 5755 | CE2 | TRP | A | 104 | −8.451 | 3.149 | 35.233 | 1.00 | 33.36 | A | C |
| ATOM | 5756 | CE3 | TRP | A | 104 | −8.970 | 1.891 | 37.237 | 1.00 | 32.51 | A | C |
| ATOM | 5757 | CD1 | TRP | A | 104 | −8.949 | 1.692 | 33.615 | 1.00 | 33.31 | A | C |
| ATOM | 5758 | NE1 | TRP | A | 104 | −8.486 | 2.960 | 33.876 | 1.00 | 33.69 | A | N |
| ATOM | 5759 | CZ2 | TRP | A | 104 | −8.057 | 4.265 | 35.980 | 1.00 | 33.19 | A | C |
| ATOM | 5760 | CZ3 | TRP | A | 104 | −8.577 | 3.002 | 37.979 | 1.00 | 31.26 | A | C |
| ATOM | 5761 | CH2 | TRP | A | 104 | −8.127 | 4.171 | 37.347 | 1.00 | 32.36 | A | C |
| ATOM | 5762 | C | TRP | A | 104 | −9.314 | −2.787 | 35.225 | 1.00 | 36.55 | A | C |
| ATOM | 5763 | O | TRP | A | 104 | −9.542 | −3.317 | 36.312 | 1.00 | 36.03 | A | O |
| ATOM | 5764 | N | ALA | A | 105 | −9.629 | −3.353 | 34.064 | 1.00 | 39.05 | A | N |
| ATOM | 5765 | CA | ALA | A | 105 | −10.285 | −4.657 | 34.001 | 1.00 | 41.04 | A | C |
| ATOM | 5766 | CB | ALA | A | 105 | −11.224 | −4.709 | 32.801 | 1.00 | 41.47 | A | C |
| ATOM | 5767 | C | ALA | A | 105 | −9.293 | −5.812 | 33.936 | 1.00 | 42.49 | A | C |
| ATOM | 5768 | O | ALA | A | 105 | −9.615 | −6.891 | 33.436 | 1.00 | 43.00 | A | O |
| ATOM | 5769 | N | GLU | A | 106 | −8.087 | −5.583 | 34.443 | 1.00 | 43.51 | A | N |
| ATOM | 5770 | CA | GLU | A | 106 | −7.055 | −6.610 | 34.442 | 1.00 | 44.47 | A | C |
| ATOM | 5771 | CB | GLU | A | 106 | −5.669 | −5.960 | 34.381 | 1.00 | 44.70 | A | C |
| ATOM | 5772 | CG | GLU | A | 106 | −4.502 | −6.940 | 34.373 | 1.00 | 45.21 | A | C |
| ATOM | 5773 | CD | GLU | A | 106 | −4.626 | −7.993 | 33.289 | 1.00 | 46.80 | A | C |
| ATOM | 5774 | OE1 | GLU | A | 106 | −5.375 | −8.974 | 33.490 | 1.00 | 47.31 | A | O |
| ATOM | 5775 | OE2 | GLU | A | 106 | −3.982 | −7.837 | 32.230 | 1.00 | 46.33 | A | O |
| ATOM | 5776 |  | GLU | A | 106 | −7.170 | −7.483 | 35.688 | 1.00 | 44.69 | A | C |
| ATOM | 5777 | O | GLU | A | 106 | −7.174 | −6.980 | 36.812 | 1.00 | 43.85 | A | O |
| ATOM | 5778 | N | LYS | A | 107 | −7.275 | −8.791 | 35.477 | 1.00 | 46.22 | A | N |
| ATOM | 5779 | CA | LYS | A | 107 | −7.386 | −9.744 | 36.576 | 1.00 | 47.90 | A | C |
| ATOM | 5780 | CB | LYS | A | 107 | −8.160 | −10.985 | 36.124 | 1.00 | 48.02 | A | C |
| ATOM | 5781 | CG | LYS | A | 107 | −9.649 | −10.743 | 35.925 | 1.00 | 48.88 | A | C |
| ATOM | 5782 | CD | LYS | A | 107 | −10.315 | −10.333 | 37.233 | 1.00 | 49.71 | A | C |
| ATOM | 5783 | CE | LYS | A | 107 | −11.799 | −10.060 | 37.043 | 1.00 | 50.86 | A | C |
| ATOM | 5784 | NZ | LYS | A | 107 | −12.534 | −11.251 | 36.534 | 1.00 | 51.17 | A | N |
| ATOM | 5785 | C | LYS | A | 107 | −6.010 | −10.148 | 37.096 | 1.00 | 48.88 | A | C |
| ATOM | 5786 | O | LYS | A | 107 | −5.847 | −10.426 | 38.284 | 1.00 | 49.63 | A | O |
| ATOM | 5787 | N | LYS | A | 108 | −5.025 | −10.179 | 36.204 | 1.00 | 49.39 | A | N |
| ATOM | 5788 | CA | LYS | A | 108 | −3.662 | −10.534 | 36.584 | 1.00 | 50.95 | A | C |
| ATOM | 5789 | CB | LYS | A | 108 | −2.780 | −10.649 | 35.338 | 1.00 | 50.92 | A | C |
| ATOM | 5790 | CG | LYS | A | 108 | −3.244 | −11.706 | 34.349 | 1.00 | 51.30 | A | C |
| ATOM | 5791 | CD | LYS | A | 108 | −2.370 | −11.744 | 33.100 | 1.00 | 51.21 | A | C |
| ATOM | 5792 | CE | LYS | A | 108 | −2.474 | −10.450 | 32.306 | 1.00 | 51.88 | A | C |
| ATOM | 5793 | NZ | LYS | A | 108 | −1.733 | −10.517 | 31.015 | 1.00 | 51.47 | A | N |
| ATOM | 5794 | C | LYS | A | 108 | −3.115 | −9.452 | 37.514 | 1.00 | 51.93 | A | C |
| ATOM | 5795 | O | LYS | A | 108 | −2.605 | −8.428 | 37.057 | 1.00 | 52.21 | A | O |
| ATOM | 5796 | N | GLN | A | 109 | −3.228 | −9.687 | 38.818 | 1.00 | 53.19 | A | N |
| ATOM | 5797 | CA | GLN | A | 109 | −2.770 | −8.734 | 39.827 | 1.00 | 54.34 | A | C |
| ATOM | 5798 | CB | GLN | A | 109 | −3.029 | −9.293 | 41.229 | 1.00 | 55.53 | A | C |
| ATOM | 5799 | CG | GLN | A | 109 | −2.808 | −8.292 | 42.359 | 1.00 | 57.97 | A | C |
| ATOM | 5800 | CD | GLN | A | 109 | −3.896 | −7.230 | 42.433 | 1.00 | 59.38 | A | C |
| ATOM | 5801 | OE1 | GLN | A | 109 | −3.833 | −6.318 | 43.260 | 1.00 | 60.01 | A | O |
| ATOM | 5802 | NE2 | GLN | A | 109 | −4.903 | −7.349 | 41.572 | 1.00 | 59.24 | A | N |
| ATOM | 5803 | C | GLN | A | 109 | −1.291 | −8.372 | 39.689 | 1.00 | 53.97 | A | C |
| ATOM | 5804 | O | GLN | A | 109 | −0.900 | −7.231 | 39.939 | 1.00 | 54.03 | A | O |

TABLE 6-continued

Three-dimensional structural coordinate of the complex of
human hematopoietic PGDS (SEQ ID NO: 1) with magnesium, glutathione and
9,11-dideoxy-9α,11α-epoxymethanoprostaglandine $F_{2\alpha}$ (U44)

| ATOM | 5805 | N   | ASP | A | 110 | −0.473  | −9.344  | 39.296 | 1.00 | 53.79 | A | N |
|------|------|-----|-----|---|-----|---------|---------|--------|------|-------|---|---|
| ATOM | 5806 | CA  | ASP | A | 110 | 0.961   | −9.120  | 39.136 | 1.00 | 53.28 | A | C |
| ATOM | 5807 | CB  | ASP | A | 110 | 1.687   | −10.460 | 38.967 | 1.00 | 54.50 | A | C |
| ATOM | 5808 | CG  | ASP | A | 110 | 1.180   | −11.256 | 37.777 | 1.00 | 56.41 | A | C |
| ATOM | 5809 | OD1 | ASP | A | 110 | −0.040  | −11.516 | 37.708 | 1.00 | 57.39 | A | O |
| ATOM | 5810 | OD2 | ASP | A | 110 | 2.005   | −11.626 | 36.913 | 1.00 | 57.49 | A | O |
| ATOM | 5811 | C   | ASP | A | 110 | 1.276   | −8.203  | 37.956 | 1.00 | 52.12 | A | C |
| ATOM | 5812 | O   | ASP | A | 110 | 2.309   | −7.532  | 37.939 | 1.00 | 52.35 | A | O |
| ATOM | 5813 | N   | VAL | A | 111 | 0.381   | −8.173  | 36.975 | 1.00 | 50.53 | A | N |
| ATOM | 5814 | CA  | VAL | A | 111 | 0.565   | −7.340  | 35.792 | 1.00 | 48.09 | A | C |
| ATOM | 5815 | CB  | VAL | A | 111 | −0.020  | −8.032  | 34.541 | 1.00 | 47.90 | A | C |
| ATOM | 5816 | CG1 | VAL | A | 111 | 0.175   | −7.153  | 33.313 | 1.00 | 47.07 | A | C |
| ATOM | 5817 | CG2 | VAL | A | 111 | 0.649   | −9.382  | 34.343 | 1.00 | 46.18 | A | C |
| ATOM | 5818 | C   | VAL | A | 111 | −0.106  | −5.980  | 35.973 | 1.00 | 47.23 | A | C |
| ATOM | 5819 | O   | VAL | A | 111 | 0.392   | −4.959  | 35.497 | 1.00 | 46.02 | A | O |
| ATOM | 5820 | N   | LYS | A | 112 | −1.237  | −5.974  | 36.670 | 1.00 | 46.23 | A | N |
| ATOM | 5821 | CA  | LYS | A | 112 | −1.981  | −4.746  | 36.918 | 1.00 | 45.70 | A | C |
| ATOM | 5822 | CB  | LYS | A | 112 | −3.328  | −5.076  | 37.563 | 1.00 | 45.91 | A | C |
| ATOM | 5823 | CG  | LYS | A | 112 | −4.205  | −3.866  | 37.828 | 1.00 | 47.00 | A | C |
| ATOM | 5824 | CD  | LYS | A | 112 | −5.587  | −4.288  | 38.294 | 1.00 | 46.65 | A | C |
| ATOM | 5825 | CE  | LYS | A | 112 | −6.505  | −3.093  | 38.472 | 1.00 | 47.06 | A | C |
| ATOM | 5826 | NZ  | LYS | A | 112 | −7.882  | −3.530  | 38.822 | 1.00 | 47.01 | A | N |
| ATOM | 5827 | C   | LYS | A | 112 | −1.197  | −3.793  | 37.815 | 1.00 | 45.36 | A | C |
| ATOM | 5828 | O   | LYS | A | 112 | −1.044  | −2.611  | 37.499 | 1.00 | 43.76 | A | O |
| ATOM | 5829 | N   | GLU | A | 113 | −0.700  | −4.316  | 38.931 | 1.00 | 45.30 | A | N |
| ATOM | 5830 | CA  | GLU | A | 113 | 0.065   | −3.520  | 39.885 | 1.00 | 45.81 | A | C |
| ATOM | 5831 | CB  | GLU | A | 113 | 0.434   | −4.377  | 41.100 | 1.00 | 46.58 | A | C |
| ATOM | 5832 | CG  | GLU | A | 113 | 0.985   | −3.602  | 42.292 | 1.00 | 46.95 | A | C |
| ATOM | 5833 | CD  | GLU | A | 113 | −0.079  | −2.797  | 43.024 | 1.00 | 47.25 | A | C |
| ATOM | 5834 | OE1 | GLU | A | 113 | 0.232   | −2.252  | 44.104 | 1.00 | 47.79 | A | O |
| ATOM | 5835 | OE2 | GLU | A | 113 | −1.222  | −2.708  | 42.526 | 1.00 | 46.47 | A | O |
| ATOM | 5836 | C   | GLU | A | 113 | 1.335   | −2.963  | 39.244 | 1.00 | 45.70 | A | C |
| ATOM | 5837 | O   | GLU | A | 113 | 1.734   | −1.832  | 39.520 | 1.00 | 45.29 | A | O |
| ATOM | 5838 | N   | GLN | A | 114 | 1.961   | −3.764  | 38.386 | 1.00 | 45.03 | A | N |
| ATOM | 5839 | CA  | GLN | A | 114 | 3.188   | −3.364  | 37.703 | 1.00 | 44.59 | A | C |
| ATOM | 5840 | CB  | GLN | A | 114 | 3.757   | −4.554  | 36.919 | 1.00 | 46.95 | A | C |
| ATOM | 5841 | CG  | GLN | A | 114 | 5.090   | −4.301  | 36.224 | 1.00 | 49.65 | A | C |
| ATOM | 5842 | CD  | GLN | A | 114 | 4.949   | −3.515  | 34.933 | 1.00 | 51.80 | A | C |
| ATOM | 5843 | OE1 | GLN | A | 114 | 4.223   | −3.920  | 34.024 | 1.00 | 54.22 | A | O |
| ATOM | 5844 | NE2 | GLN | A | 114 | 5.650   | −2.389  | 34.842 | 1.00 | 52.38 | A | N |
| ATOM | 5845 | C   | GLN | A | 114 | 2.956   | −2.179  | 36.767 | 1.00 | 43.31 | A | C |
| ATOM | 5846 | O   | GLN | A | 114 | 3.720   | −1.214  | 36.778 | 1.00 | 43.59 | A | O |
| ATOM | 5847 | N   | MET | A | 115 | 1.902   | −2.252  | 35.960 | 1.00 | 40.98 | A | N |
| ATOM | 5848 | CA  | MET | A | 115 | 1.586   | −1.175  | 35.026 | 1.00 | 38.92 | A | C |
| ATOM | 5849 | CB  | MET | A | 115 | 0.543   | −1.646  | 34.006 | 1.00 | 40.82 | A | C |
| ATOM | 5850 | CG  | MET | A | 115 | 0.066   | −0.553  | 33.052 | 1.00 | 43.23 | A | C |
| ATOM | 5851 | SD  | MET | A | 115 | 1.400   | 0.229   | 32.107 | 1.00 | 46.86 | A | S |
| ATOM | 5852 | CE  | MET | A | 115 | 0.903   | −0.150  | 30.414 | 1.00 | 46.99 | A | C |
| ATOM | 5853 | C   | MET | A | 115 | 1.080   | 0.073   | 35.750 | 1.00 | 36.12 | A | C |
| ATOM | 5854 | O   | MET | A | 115 | 1.414   | 1.195   | 35.366 | 1.00 | 34.59 | A | O |
| ATOM | 5855 | N   | PHE | A | 116 | 0.277   | −0.124  | 36.793 | 1.00 | 33.79 | A | N |
| ATOM | 5856 | CA  | PHE | A | 116 | −0.260  | 0.997   | 37.563 | 1.00 | 31.55 | A | C |
| ATOM | 5857 | CB  | PHE | A | 116 | −1.101  | 0.496   | 38.740 | 1.00 | 29.74 | A | C |
| ATOM | 5858 | CG  | PHE | A | 116 | −2.580  | 0.648   | 38.544 | 1.00 | 26.92 | A | C |
| ATOM | 5859 | CD1 | PHE | A | 116 | −3.277  | −0.205  | 37.697 | 1.00 | 26.13 | A | C |
| ATOM | 5860 | CD2 | PHE | A | 116 | −3.280  | 1.647   | 39.214 | 1.00 | 25.49 | A | C |
| ATOM | 5861 | CE1 | PHE | A | 116 | −4.652  | −0.069  | 37.520 | 1.00 | 25.62 | A | C |
| ATOM | 5862 | CE2 | PHE | A | 116 | −4.655  | 1.795   | 39.045 | 1.00 | 24.62 | A | C |
| ATOM | 5863 | CZ  | PHE | A | 116 | −5.343  | 0.935   | 38.196 | 1.00 | 25.52 | A | C |
| ATOM | 5864 | C   | PHE | A | 116 | 0.852   | 1.885   | 38.108 | 1.00 | 31.56 | A | C |
| ATOM | 5865 | O   | PHE | A | 116 | 0.850   | 3.100   | 37.905 | 1.00 | 29.53 | A | O |
| ATOM | 6152 | N   | TYR | A | 152 | −13.728 | 17.655  | 33.722 | 1.00 | 8.61  | A | N |
| ATOM | 6153 | CA  | TYR | A | 152 | −13.021 | 16.402  | 33.504 | 1.00 | 9.79  | A | C |
| ATOM | 6154 | CB  | TYR | A | 152 | −12.841 | 16.120  | 32.003 | 1.00 | 7.44  | A | C |
| ATOM | 6155 | CG  | TYR | A | 152 | −12.799 | 14.634  | 31.704 | 1.00 | 8.27  | A | C |
| ATOM | 6156 | CD1 | TYR | A | 152 | −13.773 | 13.778  | 32.225 | 1.00 | 8.38  | A | C |
| ATOM | 6157 | CE1 | TYR | A | 152 | −13.742 | 12.403  | 31.973 | 1.00 | 10.32 | A | C |
| ATOM | 6158 | CD2 | TYR | A | 152 | −11.791 | 14.080  | 30.919 | 1.00 | 5.95  | A | C |
| ATOM | 6159 | CE2 | TYR | A | 152 | −11.751 | 12.704  | 30.659 | 1.00 | 8.41  | A | C |
| ATOM | 6160 | CZ  | TYR | A | 152 | −12.729 | 11.873  | 31.191 | 1.00 | 8.47  | A | C |
| ATOM | 6161 | OH  | TYR | A | 152 | −12.695 | 10.517  | 30.951 | 1.00 | 9.30  | A | O |
| ATOM | 6162 | C   | TYR | A | 152 | −11.671 | 16.387  | 34.209 | 1.00 | 10.81 | A | C |
| ATOM | 6163 | O   | TYR | A | 152 | −11.237 | 15.344  | 34.695 | 1.00 | 13.37 | A | O |
| ATOM | 6164 | N   | TRP | A | 153 | −11.002 | 17.536  | 34.274 | 1.00 | 11.77 | A | N |
| ATOM | 6165 | CA  | TRP | A | 153 | −9.715  | 17.589  | 34.964 | 1.00 | 12.66 | A | C |

TABLE 6-continued

Three-dimensional structural coordinate of the complex of
human hematopoietic PGDS (SEQ ID NO: 1) with magnesium, glutathione and
9,11-dideoxy-9α,11α-epoxymethanoprostaglandine F$_{2\alpha}$ (U44)

| ATOM | 6166 | CB  | TRP | A | 153 | −9.082  | 18.981 | 34.855 | 1.00 | 13.54 | A | C |
|------|------|-----|-----|---|-----|---------|--------|--------|------|-------|---|---|
| ATOM | 6167 | CG  | TRP | A | 153 | −8.073  | 19.251 | 35.950 | 1.00 | 13.64 | A | C |
| ATOM | 6168 | CD2 | TRP | A | 153 | −6.880  | 18.503 | 36.230 | 1.00 | 12.79 | A | C |
| ATOM | 6169 | CE2 | TRP | A | 153 | −6.280  | 19.084 | 37.372 | 1.00 | 13.87 | A | C |
| ATOM | 6170 | CE3 | TRP | A | 153 | −6.260  | 17.400 | 35.629 | 1.00 | 14.97 | A | C |
| ATOM | 6171 | CD1 | TRP | A | 153 | −8.143  | 20.228 | 36.906 | 1.00 | 14.04 | A | C |
| ATOM | 6172 | NE1 | TRP | A | 153 | −7.071  | 20.132 | 37.763 | 1.00 | 14.10 | A | N |
| ATOM | 6173 | CZ2 | TRP | A | 153 | −5.088  | 18.596 | 37.927 | 1.00 | 12.50 | A | C |
| ATOM | 6174 | CZ3 | TRP | A | 153 | −5.072  | 16.914 | 36.183 | 1.00 | 14.36 | A | C |
| ATOM | 6175 | CH2 | TRP | A | 153 | −4.502  | 17.516 | 37.321 | 1.00 | 14.19 | A | C |
| ATOM | 6176 | C   | TRP | A | 153 | −9.878  | 17.232 | 36.441 | 1.00 | 11.85 | A | C |
| ATOM | 6177 | O   | TRP | A | 153 | −9.107  | 16.434 | 36.981 | 1.00 | 12.51 | A | O |
| ATOM | 6178 | N   | GLU | A | 154 | −10.883 | 17.817 | 37.089 | 1.00 | 11.73 | A | N |
| ATOM | 6179 | CA  | GLU | A | 154 | −11.134 | 17.564 | 38.512 | 1.00 | 10.94 | A | C |
| ATOM | 6180 | CB  | GLU | A | 154 | −12.231 | 18.510 | 39.027 | 1.00 | 11.59 | A | C |
| ATOM | 6181 | CG  | GLU | A | 154 | −12.404 | 18.521 | 40.546 | 1.00 | 11.01 | A | C |
| ATOM | 6182 | CD  | GLU | A | 154 | −13.332 | 17.431 | 41.059 | 1.00 | 16.21 | A | C |
| ATOM | 6183 | OE1 | GLU | A | 154 | −13.328 | 17.170 | 42.284 | 1.00 | 14.24 | A | O |
| ATOM | 6184 | OE2 | GLU | A | 154 | −14.078 | 16.842 | 40.248 | 1.00 | 16.08 | A | O |
| ATOM | 6185 | C   | GLU | A | 154 | −11.536 | 16.108 | 38.739 | 1.00 | 11.33 | A | C |
| ATOM | 6186 | O   | GLU | A | 154 | −11.134 | 15.477 | 39.725 | 1.00 | 11.71 | A | O |
| ATOM | 6187 | N   | ILE | A | 155 | −12.327 | 15.580 | 37.815 | 1.00 | 10.60 | A | N |
| ATOM | 6188 | CA  | ILE | A | 155 | −12.790 | 14.200 | 37.880 | 1.00 | 10.68 | A | C |
| ATOM | 6189 | CB  | ILE | A | 155 | −13.847 | 13.951 | 36.774 | 1.00 | 10.77 | A | C |
| ATOM | 6190 | CG2 | ILE | A | 155 | −14.071 | 12.459 | 36.564 | 1.00 | 11.39 | A | C |
| ATOM | 6191 | CG1 | ILE | A | 155 | −15.148 | 14.671 | 37.154 | 1.00 | 12.20 | A | C |
| ATOM | 6192 | CD1 | ILE | A | 155 | −16.192 | 14.711 | 36.048 | 1.00 | 9.68  | A | C |
| ATOM | 6193 | C   | ILE | A | 155 | −11.630 | 13.210 | 37.750 | 1.00 | 11.46 | A | C |
| ATOM | 6194 | O   | ILE | A | 155 | −11.493 | 12.292 | 38.567 | 1.00 | 12.61 | A | O |
| ATOM | 6195 | N   | CYS | A | 156 | −10.789 | 13.402 | 36.735 | 1.00 | 10.83 | A | N |
| ATOM | 6196 | CA  | CYS | A | 156 | −9.642  | 12.524 | 36.514 | 1.00 | 10.78 | A | C |
| ATOM | 6197 | CB  | CYS | A | 156 | −8.964  | 12.856 | 35.179 | 1.00 | 12.57 | A | C |
| ATOM | 6198 | SG  | CYS | A | 156 | −9.924  | 12.424 | 33.698 | 1.00 | 11.44 | A | S |
| ATOM | 6199 | C   | CYS | A | 156 | −8.610  | 12.617 | 37.642 | 1.00 | 11.39 | A | C |
| ATOM | 6200 | O   | CYS | A | 156 | −8.078  | 11.600 | 38.090 | 1.00 | 10.94 | A | O |
| ATOM | 6201 | N   | SER | A | 157 | −8.327  | 13.836 | 38.096 | 1.00 | 10.71 | A | N |
| ATOM | 6202 | CA  | SER | A | 157 | −7.348  | 14.035 | 39.160 | 1.00 | 11.64 | A | C |
| ATOM | 6203 | CB  | SER | A | 157 | −7.005  | 15.526 | 39.312 | 1.00 | 8.14  | A | C |
| ATOM | 6204 | OG  | SER | A | 157 | −8.149  | 16.309 | 39.581 | 1.00 | 8.71  | A | O |
| ATOM | 6205 | C   | SER | A | 157 | −7.815  | 13.463 | 40.493 | 1.00 | 11.79 | A | C |
| ATOM | 6206 | O   | SER | A | 157 | −7.000  | 12.976 | 41.280 | 1.00 | 12.03 | A | O |
| ATOM | 6207 | N   | THR | A | 158 | −9.119  | 13.521 | 40.750 | 1.00 | 10.51 | A | N |
| ATOM | 6208 | CA  | THR | A | 158 | −9.650  | 12.979 | 41.996 | 1.00 | 12.25 | A | C |
| ATOM | 6209 | CB  | THR | A | 158 | −11.188 | 13.142 | 42.086 | 1.00 | 12.13 | A | C |
| ATOM | 6210 | OG1 | THR | A | 158 | −11.512 | 14.507 | 42.379 | 1.00 | 11.92 | A | O |
| ATOM | 6211 | CG2 | THR | A | 158 | −11.758 | 12.251 | 43.180 | 1.00 | 12.89 | A | C |
| ATOM | 6212 | C   | THR | A | 158 | −9.303  | 11.497 | 42.089 | 1.00 | 12.30 | A | C |
| ATOM | 6213 | O   | THR | A | 158 | −8.873  | 11.015 | 43.135 | 1.00 | 13.28 | A | O |
| ATOM | 6214 | N   | THR | A | 159 | −9.484  | 10.778 | 40.986 | 1.00 | 11.79 | A | N |
| ATOM | 6215 | CA  | THR | A | 159 | −9.189  | 9.352  | 40.949 | 1.00 | 12.60 | A | C |
| ATOM | 6216 | CB  | THR | A | 159 | −9.777  | 8.713  | 39.671 | 1.00 | 12.94 | A | C |
| ATOM | 6217 | OG1 | THR | A | 159 | −11.207 | 8.818  | 39.711 | 1.00 | 13.88 | A | O |
| ATOM | 6218 | CG2 | THR | A | 159 | −9.383  | 7.243  | 39.570 | 1.00 | 13.31 | A | C |
| ATOM | 6219 | C   | THR | A | 159 | −7.683  | 9.073  | 41.028 | 1.00 | 12.97 | A | C |
| ATOM | 6220 | O   | THR | A | 159 | −7.242  | 8.210  | 41.792 | 1.00 | 13.33 | A | O |
| ATOM | 6221 | N   | LEU | A | 160 | −6.891  | 9.801  | 40.247 | 1.00 | 11.91 | A | N |
| ATOM | 6222 | CA  | LEU | A | 160 | −5.449  | 9.602  | 40.272 | 1.00 | 11.99 | A | C |
| ATOM | 6223 | CB  | LEU | A | 160 | −4.767  | 10.506 | 39.243 | 1.00 | 11.62 | A | C |
| ATOM | 6224 | CG  | LEU | A | 160 | −5.052  | 10.201 | 37.764 | 1.00 | 10.47 | A | C |
| ATOM | 6225 | CD1 | LEU | A | 160 | −4.377  | 11.244 | 36.896 | 1.00 | 11.07 | A | C |
| ATOM | 6226 | CD2 | LEU | A | 160 | −4.547  | 8.806  | 37.399 | 1.00 | 9.49  | A | C |
| ATOM | 6227 | C   | LEU | A | 160 | −4.869  | 9.862  | 41.667 | 1.00 | 13.79 | A | C |
| ATOM | 6228 | O   | LEU | A | 160 | −3.954  | 9.157  | 42.101 | 1.00 | 12.53 | A | O |
| ATOM | 6229 | N   | LEU | A | 161 | −5.408  | 10.863 | 42.364 | 1.00 | 13.03 | A | N |
| ATOM | 6230 | CA  | LEU | A | 161 | −4.938  | 11.210 | 43.703 | 1.00 | 13.25 | A | C |
| ATOM | 6231 | CB  | LEU | A | 161 | −5.638  | 12.476 | 44.209 | 1.00 | 13.43 | A | C |
| ATOM | 6232 | CG  | LEU | A | 161 | −5.137  | 13.820 | 43.672 | 1.00 | 14.45 | A | C |
| ATOM | 6233 | CD1 | LEU | A | 161 | −6.127  | 14.924 | 44.045 | 1.00 | 11.48 | A | C |
| ATOM | 6234 | CD2 | LEU | A | 161 | −3.751  | 14.118 | 44.237 | 1.00 | 13.53 | A | C |
| ATOM | 6235 | C   | LEU | A | 161 | −5.145  | 10.080 | 44.704 | 1.00 | 15.09 | A | C |
| ATOM | 6236 | O   | LEU | A | 161 | −4.415  | 9.979  | 45.691 | 1.00 | 16.09 | A | O |
| ATOM | 6237 | N   | VAL | A | 162 | −6.143  | 9.238  | 44.459 | 1.00 | 14.39 | A | N |
| ATOM | 6238 | CA  | VAL | A | 162 | −6.411  | 8.116  | 45.344 | 1.00 | 14.43 | A | C |
| ATOM | 6239 | CB  | VAL | A | 162 | −7.700  | 7.366  | 44.938 | 1.00 | 15.83 | A | C |
| ATOM | 6240 | CG1 | VAL | A | 162 | −7.769  | 6.019  | 45.655 | 1.00 | 11.08 | A | C |

TABLE 6-continued

Three-dimensional structural coordinate of the complex of human hematopoietic PGDS (SEQ ID NO: 1) with magnesium, glutathione and 9,11-dideoxy-9α,11α-epoxymethanoprostaglandine $F_{2\alpha}$ (U44)

| ATOM | 6241 | CG2 | VAL | A | 162 | −8.925 | 8.207 | 45.287 | 1.00 | 14.62 | A | C |
|---|---|---|---|---|---|---|---|---|---|---|---|---|
| ATOM | 6242 | C | VAL | A | 162 | −5.242 | 7.140 | 45.304 | 1.00 | 15.52 | A | C |
| ATOM | 6243 | O | VAL | A | 162 | −4.861 | 6.579 | 46.329 | 1.00 | 16.41 | A | O |
| ATOM | 6244 | N | PHE | A | 163 | −4.667 | 6.951 | 44.119 | 1.00 | 14.68 | A | N |
| ATOM | 6245 | CA | PHE | A | 163 | −3.543 | 6.036 | 43.955 | 1.00 | 15.48 | A | C |
| ATOM | 6246 | CB | PHE | A | 163 | −3.660 | 5.286 | 42.624 | 1.00 | 16.17 | A | C |
| ATOM | 6247 | CG | PHE | A | 163 | −4.915 | 4.476 | 42.498 | 1.00 | 17.77 | A | C |
| ATOM | 6248 | CD1 | PHE | A | 163 | −6.066 | 5.026 | 41.934 | 1.00 | 18.11 | A | C |
| ATOM | 6249 | CD2 | PHE | A | 163 | −4.962 | 3.172 | 42.978 | 1.00 | 17.18 | A | C |
| ATOM | 6250 | CE1 | PHE | A | 163 | −7.243 | 4.284 | 41.852 | 1.00 | 18.08 | A | C |
| ATOM | 6251 | CE2 | PHE | A | 163 | −6.134 | 2.422 | 42.901 | 1.00 | 17.00 | A | C |
| ATOM | 6252 | CZ | PHE | A | 163 | −7.277 | 2.981 | 42.338 | 1.00 | 18.37 | A | C |
| ATOM | 6253 | C | PHE | A | 163 | −2.179 | 6.714 | 44.041 | 1.00 | 15.57 | A | C |
| ATOM | 6254 | O | PHE | A | 163 | −1.164 | 6.044 | 44.214 | 1.00 | 16.24 | A | O |
| ATOM | 6528 | N | THR | A | 197 | −17.099 | 5.832 | 46.606 | 1.00 | 22.13 | A | N |
| ATOM | 6529 | CA | THR | A | 197 | −16.501 | 4.631 | 46.037 | 1.00 | 20.93 | A | C |
| ATOM | 6530 | CB | THR | A | 197 | −17.228 | 4.228 | 44.740 | 1.00 | 20.53 | A | C |
| ATOM | 6531 | OG1 | THR | A | 197 | −17.165 | 5.313 | 43.801 | 1.00 | 19.47 | A | O |
| ATOM | 6532 | CG2 | THR | A | 197 | −18.687 | 3.904 | 45.031 | 1.00 | 19.28 | A | C |
| ATOM | 6533 | C | THR | A | 197 | −15.022 | 4.835 | 45.726 | 1.00 | 19.70 | A | C |
| ATOM | 6534 | O | THR | A | 197 | −14.532 | 5.964 | 45.709 | 1.00 | 19.73 | A | O |
| ATOM | 6535 | N | LYS | A | 198 | −14.320 | 3.734 | 45.480 | 1.00 | 18.70 | A | N |
| ATOM | 6536 | CA | LYS | A | 198 | −12.895 | 3.773 | 45.164 | 1.00 | 20.70 | A | C |
| ATOM | 6537 | CB | LYS | A | 198 | −12.321 | 2.354 | 45.158 | 1.00 | 20.27 | A | C |
| ATOM | 6538 | CG | LYS | A | 198 | −10.822 | 2.287 | 44.939 | 1.00 | 21.83 | A | C |
| ATOM | 6539 | CD | LYS | A | 198 | −10.393 | 0.877 | 44.552 | 1.00 | 24.28 | A | C |
| ATOM | 6540 | CE | LYS | A | 198 | −8.880 | 0.756 | 44.464 | 1.00 | 25.89 | A | C |
| ATOM | 6541 | NZ | LYS | A | 198 | −8.481 | −0.584 | 43.937 | 1.00 | 28.24 | A | N |
| ATOM | 6542 | C | LYS | A | 198 | −12.646 | 4.419 | 43.800 | 1.00 | 21.33 | A | C |
| ATOM | 6543 | O | LYS | A | 198 | −11.809 | 5.317 | 43.664 | 1.00 | 20.34 | A | O |
| ATOM | 6544 | N | LEU | A | 199 | −13.377 | 3.949 | 42.793 | 1.00 | 21.84 | A | N |
| ATOM | 6545 | CA | LEU | A | 199 | −13.245 | 4.469 | 41.436 | 1.00 | 21.69 | A | C |
| ATOM | 6546 | CB | LEU | A | 199 | −12.977 | 3.321 | 40.459 | 1.00 | 23.94 | A | C |
| ATOM | 6547 | CG | LEU | A | 199 | −11.787 | 2.419 | 40.793 | 1.00 | 25.29 | A | C |
| ATOM | 6548 | CD1 | LEU | A | 199 | −11.612 | 1.374 | 39.698 | 1.00 | 25.62 | A | C |
| ATOM | 6549 | CD2 | LEU | A | 199 | −10.528 | 3.263 | 40.927 | 1.00 | 25.82 | A | C |
| ATOM | 6550 | C | LEU | A | 199 | −14.497 | 5.220 | 41.004 | 1.00 | 21.61 | A | C |
| ATOM | 6551 | OT1 | LEU | A | 199 | −15.506 | 5.171 | 41.740 | 1.00 | 20.08 | A | O |
| ATOM | 6552 | OT2 | LEU | A | 199 | −14.454 | 5.846 | 39.923 | 1.00 | 21.69 | A | O |
| ATOM | 6613 | N1 | GSH | H | 200 | −14.550 | 5.015 | 25.946 | 1.00 | 13.63 | H | N |
| ATOM | 6614 | CA1 | GSH | H | 200 | −15.807 | 4.471 | 26.450 | 1.00 | 13.25 | H | C |
| ATOM | 6615 | C1 | GSH | H | 200 | −16.630 | 5.539 | 27.221 | 1.00 | 12.75 | H | C |
| ATOM | 6616 | O11 | GSH | H | 200 | −16.085 | 6.603 | 27.529 | 1.00 | 12.96 | H | O |
| ATOM | 6617 | O12 | GSH | H | 200 | −17.891 | 5.250 | 27.492 | 1.00 | 15.28 | H | O |
| ATOM | 6618 | CB1 | GSH | H | 200 | −15.460 | 3.288 | 27.375 | 1.00 | 13.02 | H | C |
| ATOM | 6619 | CG1 | GSH | H | 200 | −16.582 | 2.234 | 27.492 | 1.00 | 13.79 | H | C |
| ATOM | 6620 | CD1 | GSH | H | 200 | −16.071 | 1.156 | 28.480 | 1.00 | 15.77 | H | C |
| ATOM | 6621 | OE1 | GSH | H | 200 | −15.102 | 0.436 | 28.187 | 1.00 | 15.88 | H | O |
| ATOM | 6622 | N2 | GSH | H | 200 | −16.842 | 0.986 | 29.567 | 1.00 | 14.96 | H | N |
| ATOM | 6623 | CA2 | GSH | H | 200 | −16.537 | −0.058 | 30.558 | 1.00 | 16.29 | H | C |
| ATOM | 6624 | C2 | GSH | H | 200 | −17.470 | −1.253 | 30.341 | 1.00 | 17.28 | H | C |
| ATOM | 6625 | O2 | GSH | H | 200 | −18.558 | −1.130 | 29.767 | 1.00 | 15.17 | H | O |
| ATOM | 6626 | CB2 | GSH | H | 200 | −16.864 | 0.452 | 31.977 | 1.00 | 16.12 | H | C |
| ATOM | 6627 | SG2 | GSH | H | 200 | −15.601 | 1.558 | 32.669 | 1.00 | 16.79 | H | S |
| ATOM | 6628 | N3 | GSH | H | 200 | −16.899 | −2.457 | 30.507 | 1.00 | 19.59 | H | N |
| ATOM | 6629 | CA3 | GSH | H | 200 | −17.689 | −3.694 | 30.640 | 1.00 | 20.55 | H | C |
| ATOM | 6630 | C3 | GSH | H | 200 | −17.281 | −4.655 | 29.543 | 1.00 | 22.53 | H | C |
| ATOM | 6631 | O31 | GSH | H | 200 | −17.861 | −5.761 | 29.526 | 1.00 | 20.65 | H | O |
| ATOM | 6632 | O32 | GSH | H | 200 | −16.398 | −4.285 | 28.728 | 1.00 | 22.35 | H | O |
| ATOM | 6708 | C1 | U44 | X | 201 | −13.533 | −1.851 | 34.292 | 1.00 | 70.39 | X | C |
| ATOM | 6709 | C2 | U44 | X | 201 | −13.257 | −2.563 | 35.604 | 1.00 | 70.70 | X | C |
| ATOM | 6710 | C3 | U44 | X | 201 | −12.903 | −1.371 | 36.540 | 1.00 | 70.14 | X | C |
| ATOM | 6711 | C4 | U44 | X | 201 | −13.965 | −0.313 | 36.092 | 1.00 | 69.11 | X | C |
| ATOM | 6712 | C5 | U44 | X | 201 | −14.677 | −1.086 | 34.944 | 1.00 | 69.81 | X | C |
| ATOM | 6713 | C7 | U44 | X | 201 | −15.544 | −2.216 | 35.493 | 1.00 | 70.48 | X | C |
| ATOM | 6714 | O6 | U44 | X | 201 | −14.532 | −3.138 | 35.915 | 1.00 | 70.45 | X | O |
| ATOM | 6715 | C14 | U44 | X | 201 | −13.413 | 1.005 | 35.576 | 1.00 | 66.59 | X | C |
| ATOM | 6716 | C16 | U44 | X | 201 | −13.394 | 2.213 | 36.191 | 1.00 | 62.13 | X | C |
| ATOM | 6717 | C18 | U44 | X | 201 | −12.818 | 3.501 | 35.639 | 1.00 | 58.63 | X | C |
| ATOM | 6718 | C20 | U44 | X | 201 | −12.819 | 3.574 | 34.090 | 1.00 | 55.24 | X | C |
| ATOM | 6719 | C21 | U44 | X | 201 | −11.964 | 4.730 | 33.525 | 1.00 | 50.86 | X | C |
| ATOM | 6720 | C24 | U44 | X | 201 | −12.612 | 6.108 | 33.730 | 1.00 | 48.35 | X | C |
| ATOM | 6721 | C27 | U44 | X | 201 | −11.669 | 7.268 | 33.392 | 1.00 | 45.75 | X | C |
| ATOM | 6722 | C30 | U44 | X | 201 | −12.193 | 8.608 | 33.921 | 1.00 | 40.82 | X | C |
| ATOM | 6723 | O36 | U44 | X | 201 | −11.498 | 3.620 | 36.106 | 1.00 | 60.26 | X | O |

TABLE 6-continued

Three-dimensional structural coordinate of the complex of human hematopoietic PGDS (SEQ ID NO: 1) with magnesium, glutathione and 9,11-dideoxy-9α,11α-epoxymethanoprostaglandine F$_{2α}$ (U44)

| ATOM | 6724 | C39 | U44 | X | 201 | −12.884 | −1.741 | 38.072 | 1.00 | 70.91 | X | C |
|---|---|---|---|---|---|---|---|---|---|---|---|---|
| ATOM | 6725 | C41 | U44 | X | 201 | −14.205 | −1.601 | 38.816 | 1.00 | 72.25 | X | C |
| ATOM | 6726 | C44 | U44 | X | 201 | −14.430 | −1.700 | 40.146 | 1.00 | 73.15 | X | C |
| ATOM | 6727 | C46 | U44 | X | 201 | −13.410 | −1.976 | 41.224 | 1.00 | 73.77 | X | C |
| ATOM | 6728 | C48 | U44 | X | 201 | −13.173 | −3.470 | 41.449 | 1.00 | 74.30 | X | C |
| ATOM | 6729 | C51 | U44 | X | 201 | −11.671 | −3.799 | 41.522 | 1.00 | 74.31 | X | C |
| ATOM | 6730 | C54 | U44 | X | 201 | −11.421 | −5.228 | 42.015 | 1.00 | 74.04 | X | C |
| ATOM | 6731 | O57 | U44 | X | 201 | −10.109 | −5.499 | 42.071 | 1.00 | 74.59 | X | O |
| ATOM | 6732 | O58 | U44 | X | 201 | −12.270 | −6.010 | 42.314 | 1.00 | 73.77 | X | O |
| ATOM | 6734 | MG + 2 | MG2 | M | 902 | −10.576 | 8.691 | 23.110 | 1.00 | 14.30 | M | MG + 2 |
| ATOM | 6741 | OH2 | WAT | S | 7 | −12.220 | 10.128 | 23.608 | 1.00 | 19.80 | S | O |
| ATOM | 6742 | OH2 | WAT | S | 8 | −9.999 | 7.991 | 24.913 | 1.00 | 16.06 | S | O |
| ATOM | 6743 | OH2 | WAT | S | 9 | −9.577 | 7.058 | 22.052 | 1.00 | 9.47 | S | O |
| ATOM | 6744 | OH2 | WAT | S | 10 | −11.304 | 9.428 | 21.145 | 1.00 | 20.89 | S | O |
| ATOM | 6745 | OH2 | WAT | S | 11 | −8.905 | 9.998 | 22.706 | 1.00 | 6.56 | S | O |
| ATOM | 6746 | OH2 | WAT | S | 12 | −12.342 | 7.553 | 23.132 | 1.00 | 5.11 | S | O |
| ATOM | 6755 | OH2 | WAT | S | 21 | −16.321 | 10.562 | 33.715 | 1.00 | 12.00 | S | O |
| ATOM | 6760 | OH2 | WAT | S | 26 | −22.235 | 0.646 | 24.380 | 1.00 | 8.59 | S | O |
| ATOM | 6790 | OH2 | WAT | S | 56 | −19.949 | 3.890 | 26.386 | 1.00 | 14.06 | S | O |
| ATOM | 6822 | OH2 | WAT | S | 88 | −15.088 | 1.355 | 23.422 | 1.00 | 11.11 | S | O |
| ATOM | 6845 | OH2 | WAT | S | 112 | −14.218 | 9.379 | 37.460 | 1.00 | 10.60 | S | O |
| ATOM | 6848 | OH2 | WAT | S | 115 | −30.009 | 4.031 | 30.556 | 1.00 | 20.47 | S | O |
| ATOM | 6856 | OH2 | WAT | S | 123 | −21.028 | 9.378 | 41.645 | 1.00 | 13.15 | S | O |
| ATOM | 6857 | OH2 | WAT | S | 124 | −17.894 | 1.227 | 22.644 | 1.00 | 11.10 | S | O |
| ATOM | 6869 | OH2 | WAT | S | 136 | −13.700 | 11.068 | 39.668 | 1.00 | 12.06 | S | O |
| ATOM | 6873 | OH2 | WAT | S | 140 | −16.131 | 8.790 | 24.586 | 1.00 | 10.01 | S | O |
| ATOM | 6881 | OH2 | WAT | S | 148 | −14.575 | −2.288 | 28.277 | 1.00 | 24.82 | S | O |
| ATOM | 6908 | OH2 | WAT | S | 177 | −20.137 | 2.340 | 24.117 | 1.00 | 8.16 | S | O |
| ATOM | 6925 | OH2 | WAT | S | 195 | −14.246 | −0.057 | 25.568 | 1.00 | 26.38 | S | O |
| ATOM | 6936 | OH2 | WAT | S | 206 | −14.383 | −0.255 | 21.039 | 1.00 | 21.10 | S | O |
| ATOM | 7014 | OH2 | WAT | S | 294 | −25.323 | 5.733 | 36.748 | 1.00 | 14.27 | S | O |
| ATOM | 7015 | OH2 | WAT | S | 295 | −5.015 | 5.528 | 25.654 | 1.00 | 25.26 | S | O |
| ATOM | 7026 | OH2 | WAT | S | 306 | −12.125 | −1.788 | 22.440 | 1.00 | 16.05 | S | O |
| ATOM | 7091 | OH2 | WAT | S | 374 | −19.550 | 6.899 | 43.308 | 1.00 | 15.60 | S | O |
| ATOM | 7153 | OH2 | WAT | S | 445 | −10.080 | −6.158 | 38.144 | 1.00 | 40.05 | S | O |
| ATOM | 7166 | OH2 | WAT | S | 461 | −11.181 | −0.389 | 24.993 | 1.00 | 32.17 | S | O |
| ATOM | 7189 | OH2 | WAT | S | 489 | −11.757 | 5.269 | 27.058 | 1.00 | 17.40 | S | O |
| ATOM | 7201 | OH2 | WAT | S | 504 | −21.955 | −1.663 | 40.073 | 1.00 | 22.05 | S | O |
| ATOM | 7212 | OH2 | WAT | S | 521 | −17.307 | −1.765 | 21.966 | 1.00 | 22.00 | S | O |
| ATOM | 7233 | OH2 | WAT | S | 545 | −7.572 | −3.899 | 31.498 | 1.00 | 31.88 | S | O |
| ATOM | 7238 | OH2 | WAT | S | 550 | −16.631 | −4.218 | 44.114 | 1.00 | 28.79 | S | O |
| ATOM | 7255 | OH2 | WAT | S | 571 | −16.386 | −5.314 | 21.770 | 1.00 | 19.46 | S | O |
| ATOM | 7274 | OH2 | WAT | S | 595 | −17.930 | −3.842 | 20.217 | 1.00 | 18.12 | S | O |
| ATOM | 7276 | OH2 | WAT | S | 597 | −13.769 | 7.885 | 25.487 | 1.00 | 10.50 | S | O |
| ATOM | 7288 | OH2 | WAT | S | 616 | −12.729 | 7.435 | 38.117 | 1.00 | 23.58 | S | O |
| ATOM | 7322 | OH2 | WAT | S | 668 | −8.910 | 2.771 | 24.376 | 1.00 | 47.74 | S | O |
| ATOM | 7353 | OH2 | WAT | S | 728 | −24.717 | 0.462 | 23.216 | 1.00 | 26.35 | S | O |
| ATOM | 7375 | OH2 | WAT | S | 764 | −15.374 | 9.583 | 31.111 | 1.00 | 11.02 | S | O |
| ATOM | 7389 | OH2 | WAT | S | 820 | −9.060 | −6.376 | 26.123 | 1.00 | 42.71 | S | O |
| ATOM | 7396 | OH2 | WAT | S | 831 | −23.318 | −6.716 | 23.568 | 1.00 | 37.58 | S | O |
| ATOM | 7426 | OH2 | WAT | S | 901 | −21.607 | −1.120 | 45.347 | 1.00 | 32.16 | S | O |
| ATOM | 7495 | H2 | WAT | S | 1295 | −10.054 | 5.104 | 25.040 | 1.00 | 30.17 | S | O |
| ATOM | 7535 | OH2 | WAT | S | 1341 | −11.308 | −8.312 | 40.840 | 1.00 | 33.98 | S | O |
| ATOM | 7536 | OH2 | WAT | S | 1342 | −18.306 | −0.785 | 45.664 | 1.00 | 23.47 | S | O |
| ATOM | 7548 | OH2 | WAT | S | 1355 | −11.195 | 6.225 | 36.412 | 1.00 | 22.59 | S | O |
| ATOM | 7552 | OH2 | WAT | S | 1361 | −19.290 | −9.723 | 41.426 | 1.00 | 33.42 | S | O |
| ATOM | 7553 | OH2 | WAT | S | 1362 | −20.599 | −6.591 | 22.350 | 1.00 | 29.05 | S | O |
| ATOM | 7559 | OH2 | WAT | S | 1368 | −9.450 | 1.544 | 29.448 | 1.00 | 32.22 | S | O |
| ATOM | 7560 | OH2 | WAT | S | 1369 | −6.410 | −0.567 | 29.306 | 1.00 | 38.08 | S | O |
| ATOM | 7566 | OH2 | WAT | S | 1376 | −14.934 | 13.298 | 41.070 | 1.00 | 13.87 | S | O |
| ATOM | 7569 | OH2 | WAT | S | 1380 | −17.170 | 8.649 | 45.004 | 1.00 | 13.87 | S | O |
| ATOM | 7585 | OH2 | WAT | S | 1398 | −13.501 | 6.967 | 29.029 | 1.00 | 12.91 | S | O |
| ATOM | 7586 | OH2 | WAT | S | 1399 | −11.476 | −0.026 | 31.088 | 1.00 | 30.86 | S | O |
| ATOM | 7591 | OH2 | WAT | S | 1407 | −15.761 | −4.514 | 39.356 | 1.00 | 51.81 | S | O |
| ATOM | 7592 | OH2 | WAT | S | 1408 | −15.589 | −5.579 | 35.465 | 1.00 | 42.90 | S | O |
| ATOM | 7593 | OH2 | WAT | S | 1409 | −7.748 | −3.886 | 41.337 | 1.00 | 28.05 | S | O |
| ATOM | 7681 | OH2 | WAT | S | 1560 | −14.609 | 1.320 | 43.058 | 1.00 | 31.74 | S | O |
| ATOM | 7688 | OH2 | WAT | S | 1571 | −18.720 | −5.226 | 24.140 | 1.00 | 37.27 | S | O |
| ATOM | 7724 | OH2 | WAT | S | 1614 | −7.499 | 6.183 | 23.535 | 1.00 | 42.36 | S | O |
| ATOM | 7745 | OH2 | WAT | S | 1636 | −9.600 | −1.548 | 39.202 | 1.00 | 43.85 | S | O |

TABLE 7

Three-dimensional structural coordinate of the complex of human hematopoietic PGDS (SEQ ID NO: 1) with calcium, glutathione and Cibacron Blue

| ATOM | 1690 | N | TYR | A | 8 | −2.882 | −27.583 | 10.962 | 1.00 | 8.07 | A |
|---|---|---|---|---|---|---|---|---|---|---|---|
| ATOM | 1691 | CA | TYR | A | 8 | −2.803 | −26.193 | 11.399 | 1.00 | 8.37 | A |
| ATOM | 1692 | CB | TYR | A | 8 | −1.457 | −25.586 | 10.986 | 1.00 | 8.12 | A |
| ATOM | 1693 | CG | TYR | A | 8 | −1.151 | −24.248 | 11.627 | 1.00 | 8.19 | A |
| ATOM | 1694 | CD1 | TYR | A | 8 | −1.019 | −24.131 | 13.013 | 1.00 | 7.49 | A |
| ATOM | 1695 | CE1 | TYR | A | 8 | −0.726 | −22.906 | 13.605 | 1.00 | 7.97 | A |
| ATOM | 1696 | CD2 | TYR | A | 8 | −0.983 | −23.099 | 10.850 | 1.00 | 8.28 | A |
| ATOM | 1697 | CE2 | TYR | A | 8 | −0.688 | −21.869 | 11.438 | 1.00 | 7.81 | A |
| ATOM | 1698 | CZ | TYR | A | 8 | −0.562 | −21.783 | 12.811 | 1.00 | 8.21 | A |
| ATOM | 1699 | OH | TYR | A | 8 | −0.268 | −20.575 | 13.381 | 1.00 | 8.12 | A |
| ATOM | 1700 | C | TYR | A | 8 | −3.932 | −25.418 | 10.728 | 1.00 | 8.79 | A |
| ATOM | 1701 | O | TYR | A | 8 | −4.689 | −25.979 | 9.943 | 1.00 | 8.57 | A |
| ATOM | 1702 | N | PHE | A | 9 | −4.047 | −24.134 | 11.051 | 1.00 | 9.51 | A |
| ATOM | 1703 | CA | PHE | A | 9 | −5.069 | −23.291 | 10.446 | 1.00 | 10.44 | A |
| ATOM | 1704 | CB | PHE | A | 9 | −5.179 | −21.963 | 11.191 | 1.00 | 10.48 | A |
| ATOM | 1705 | CG | PHE | A | 9 | −5.739 | −22.092 | 12.572 | 1.00 | 11.15 | A |
| ATOM | 1706 | CD1 | PHE | A | 9 | −5.022 | −21.633 | 13.672 | 1.00 | 11.38 | A |
| ATOM | 1707 | CD2 | PHE | A | 9 | −6.976 | −22.684 | 12.776 | 1.00 | 10.92 | A |
| ATOM | 1708 | CE1 | PHE | A | 9 | −5.539 | −21.768 | 14.960 | 1.00 | 11.88 | A |
| ATOM | 1709 | CE2 | PHE | A | 9 | −7.497 | −22.823 | 14.052 | 1.00 | 11.75 | A |
| ATOM | 1710 | CZ | PHE | A | 9 | −6.778 | −22.364 | 15.148 | 1.00 | 11.23 | A |
| ATOM | 1711 | C | PHE | A | 9 | −4.654 | −23.010 | 9.011 | 1.00 | 11.01 | A |
| ATOM | 1712 | O | PHE | A | 9 | −3.567 | −23.405 | 8.584 | 1.00 | 10.55 | A |
| ATOM | 1713 | N | ASN | A | 10 | −5.518 | −22.325 | 8.269 | 1.00 | 11.11 | A |
| ATOM | 1714 | CA | ASN | A | 10 | −5.204 | −21.977 | 6.887 | 1.00 | 11.58 | A |
| ATOM | 1715 | CB | ASN | A | 10 | −6.481 | −21.836 | 6.048 | 1.00 | 11.02 | A |
| ATOM | 1716 | CG | ASN | A | 10 | −6.192 | −21.414 | 4.615 | 1.00 | 12.05 | A |
| ATOM | 1717 | OD1 | ASN | A | 10 | −5.142 | −21.747 | 4.049 | 1.00 | 11.74 | A |
| ATOM | 1718 | ND2 | ASN | A | 10 | −7.130 | −20.690 | 4.012 | 1.00 | 12.36 | A |
| ATOM | 1719 | C | ASN | A | 10 | −4.439 | −20.655 | 6.889 | 1.00 | 11.87 | A |
| ATOM | 1720 | O | ASN | A | 10 | −4.998 | −19.591 | 6.618 | 1.00 | 11.89 | A |
| ATOM | 1721 | N | MET | A | 11 | −3.163 | −20.732 | 7.252 | 1.00 | 12.14 | A |
| ATOM | 1722 | CA | MET | A | 11 | −2.281 | −19.570 | 7.276 | 1.00 | 12.22 | A |
| ATOM | 1723 | CB | MET | A | 11 | −2.681 | −18.571 | 8.391 | 1.00 | 13.94 | A |
| ATOM | 1724 | CG | MET | A | 11 | −2.627 | −19.064 | 9.826 | 1.00 | 16.67 | A |
| ATOM | 1725 | SD | MET | A | 11 | −3.026 | −17.743 | 11.102 | 1.00 | 19.82 | A |
| ATOM | 1726 | CE | MET | A | 11 | −4.782 | −17.673 | 10.947 | 1.00 | 19.20 | A |
| ATOM | 1727 | C | NET | A | 11 | −0.849 | −20.065 | 7.455 | 1.00 | 11.51 | A |
| ATOM | 1728 | O | MET | A | 11 | −0.619 | −21.250 | 7.759 | 1.00 | 10.85 | A |
| ATOM | 1729 | N | ARG | A | 12 | 0.109 | −19.180 | 7.208 | 1.00 | 9.73 | A |
| ATOM | 1730 | CA | ARG | A | 12 | 1.508 | −19.544 | 7.373 | 1.00 | 9.30 | A |
| ATOM | 1731 | CB | ARG | A | 12 | 2.419 | −18.405 | 6.880 | 1.00 | 9.27 | A |
| ATOM | 1732 | CG | ARG | A | 12 | 2.249 | −18.071 | 5.381 | 1.00 | 9.28 | A |
| ATOM | 1733 | CD | ARG | A | 12 | 3.317 | −17.072 | 4.886 | 1.00 | 9.18 | A |
| ATOM | 1734 | NE | ARG | A | 12 | 3.265 | −15.815 | 5.625 | 1.00 | 9.17 | A |
| ATOM | 1735 | CZ | ARG | A | 12 | 2.303 | −14.905 | 5.491 | 1.00 | 9.26 | A |
| ATOM | 1736 | NH1 | ARG | A | 12 | 1.311 | −15.106 | 4.633 | 1.00 | 9.26 | A |
| ATOM | 1737 | NH2 | ARG | A | 12 | 2.320 | −13.806 | 6.230 | 1.00 | 7.97 | A |
| ATOM | 1738 | C | ARG | A | 12 | 1.692 | −19.802 | 8.868 | 1.00 | 8.69 | A |
| ATOM | 1739 | O | ARG | A | 12 | 1.922 | −20.936 | 9.294 | 1.00 | 7.11 | A |
| ATOM | 1740 | N | GLY | A | 13 | 1.568 | −18.742 | 9.660 | 1.00 | 8.23 | A |
| ATOM | 1741 | CA | GLY | A | 13 | 1.686 | −18.879 | 11.102 | 1.00 | 8.26 | A |
| ATOM | 1742 | C | GLY | A | 13 | 2.843 | −19.731 | 11.591 | 1.00 | 7.95 | A |
| ATOM | 1743 | O | GLY | A | 13 | 3.942 | −19.685 | 11.038 | 1.00 | 8.28 | A |
| ATOM | 1744 | N | ARG | A | 14 | 2.587 | −20.533 | 12.620 | 1.00 | 8.33 | A |
| ATOM | 1745 | CA | ARG | A | 14 | 3.623 | −21.374 | 13.210 | 1.00 | 8.64 | A |
| ATOM | 1746 | CB | ARG | A | 14 | 3.284 | −21.628 | 14.676 | 1.00 | 10.55 | A |
| ATOM | 1747 | CG | ARG | A | 14 | 3.169 | −20.337 | 15.470 | 1.00 | 14.00 | A |
| ATOM | 1748 | CD | ARG | A | 14 | 2.974 | −20.601 | 16.955 | 1.00 | 16.89 | A |
| ATOM | 1749 | NE | ARG | A | 14 | 4.069 | −20.046 | 17.745 | 1.00 | 20.03 | A |
| ATOM | 1750 | CZ | ARG | A | 14 | 5.312 | −20.519 | 17.739 | 1.00 | 20.80 | A |
| ATOM | 1751 | NH1 | ARG | A | 14 | 5.629 | −21.561 | 16.988 | 1.00 | 22.98 | A |
| ATOM | 1752 | NH2 | ARG | A | 14 | 6.242 | −19.951 | 18.482 | 1.00 | 21.79 | A |
| ATOM | 1753 | C | ARG | A | 14 | 3.894 | −22.686 | 12.500 | 1.00 | 8.02 | A |
| ATOM | 1754 | O | ARG | A | 14 | 4.787 | −23.438 | 12.888 | 1.00 | 7.13 | A |
| ATOM | 1755 | N | ALA | A | 15 | 3.136 | −22.958 | 11.445 | 1.00 | 7.13 | A |
| ATOM | 1756 | CA | ALA | A | 15 | 3.330 | −24.197 | 10.706 | 1.00 | 6.67 | A |
| ATOM | 1757 | CB | ALA | A | 15 | 1.987 | −24.747 | 10.262 | 1.00 | 6.00 | A |
| ATOM | 1758 | C | ALA | A | 15 | 4.221 | −23.975 | 9.497 | 1.00 | 6.29 | A |
| ATOM | 1759 | O | ALA | A | 15 | 4.765 | −24.925 | 8.934 | 1.00 | 6.25 | A |
| ATOM | 1760 | N | GLU | A | 16 | 4.383 | −22.714 | 9.106 | 1.00 | 6.29 | A |
| ATOM | 1761 | CA | GLU | A | 16 | 5.176 | −22.402 | 7.915 | 1.00 | 5.84 | A |
| ATOM | 1762 | CB | GLU | A | 16 | 5.209 | −20.890 | 7.678 | 1.00 | 4.97 | A |
| ATOM | 1763 | CG | GLU | A | 16 | 5.524 | −20.485 | 6.235 | 1.00 | 5.83 | A |
| ATOM | 1764 | CD | GLU | A | 16 | 4.520 | −21.037 | 5.205 | 1.00 | 6.62 | A |

TABLE 7-continued

Three-dimensional structural coordinate of the complex of
human hematopoietic PGDS (SEQ ID NO: 1) with calcium, glutathione and
Cibacron Blue

| ATOM | 1765 | OE1 | GLU | A | 16 | 3.472 | −21.597 | 5.601 | 1.00 | 6.92 | A |
|---|---|---|---|---|---|---|---|---|---|---|---|
| ATOM | 1766 | OE2 | GLU | A | 16 | 4.782 | −20.883 | 3.984 | 1.00 | 6.47 | A |
| ATOM | 1767 | C | GLU | A | 16 | 6.597 | −22.952 | 7.940 | 1.00 | 5.58 | A |
| ATOM | 1768 | O | GLU | A | 16 | 7.085 | −23.435 | 6.912 | 1.00 | 6.05 | A |
| ATOM | 1769 | N | ILE | A | 17 | 7.260 | −22.890 | 9.095 | 1.00 | 5.19 | A |
| ATOM | 1770 | CA | ILE | A | 17 | 8.631 | −23.382 | 9.203 | 1.00 | 5.07 | A |
| ATOM | 1771 | CB | ILE | A | 17 | 9.222 | −23.154 | 10.658 | 1.00 | 4.92 | A |
| ATOM | 1772 | CG2 | ILE | A | 17 | 8.396 | −23.885 | 11.716 | 1.00 | 4.41 | A |
| ATOM | 1773 | CG1 | ILE | A | 17 | 10.668 | −23.634 | 10.717 | 1.00 | 4.64 | A |
| ATOM | 1774 | CD1 | ILE | A | 17 | 11.531 | −23.053 | 9.616 | 1.00 | 5.86 | A |
| ATOM | 1775 | C | ILE | A | 17 | 8.676 | −24.858 | 8.805 | 1.00 | 4.81 | A |
| ATOM | 1776 | O | ILE | A | 17 | 9.588 | −25.305 | 8.103 | 1.00 | 4.95 | A |
| ATOM | 1966 | N | TRP | A | 39 | −11.923 | −26.095 | 14.978 | 1.00 | 32.28 | A |
| ATOM | 1967 | CA | TRP | A | 39 | −10.853 | −26.045 | 15.967 | 1.00 | 32.36 | A |
| ATOM | 1968 | CB | TRP | A | 39 | −10.353 | −24.604 | 16.130 | 1.00 | 32.57 | A |
| ATOM | 1969 | CG | TRP | A | 39 | −9.352 | −24.410 | 17.236 | 1.00 | 32.92 | A |
| ATOM | 1970 | CD2 | TRP | A | 39 | −8.212 | −25.232 | 17.526 | 1.00 | 33.08 | A |
| ATOM | 1971 | CE2 | TRP | A | 39 | −7.565 | −24.666 | 18.648 | 1.00 | 33.25 | A |
| ATOM | 1972 | CE3 | TRP | A | 39 | −7.676 | −26.392 | 16.950 | 1.00 | 33.06 | A |
| ATOM | 1973 | CD1 | TRP | A | 39 | −9.345 | −23.408 | 18.164 | 1.00 | 33.31 | A |
| ATOM | 1974 | NE1 | TRP | A | 39 | −8.277 | −23.554 | 19.015 | 1.00 | 32.95 | A |
| ATOM | 1975 | CZ2 | TRP | A | 39 | −6.407 | −25.220 | 19.208 | 1.00 | 33.30 | A |
| ATOM | 1976 | CZ3 | TRP | A | 39 | −6.522 | −26.944 | 17.508 | 1.00 | 33.28 | A |
| ATOM | 1977 | CH2 | TRP | A | 39 | −5.902 | −26.353 | 18.627 | 1.00 | 33.07 | A |
| ATOM | 1978 | C | TRP | A | 39 | −11.305 | −26.596 | 17.323 | 1.00 | 32.24 | A |
| ATOM | 1979 | O | TRP | A | 39 | −10.653 | −27.471 | 17.891 | 1.00 | 31.88 | A |
| ATOM | 1980 | N | PRO | A | 40 | −12.437 | −26.098 | 17.850 | 1.00 | 32.29 | A |
| ATOM | 1981 | CD | PRO | A | 40 | −13.335 | −25.084 | 17.264 | 1.00 | 32.39 | A |
| ATOM | 1982 | CA | PRO | A | 40 | −12.953 | −26.557 | 19.147 | 1.00 | 32.22 | A |
| ATOM | 1983 | CB | PRO | A | 40 | −14.347 | −25.943 | 19.198 | 1.00 | 32.41 | A |
| ATOM | 1984 | CG | PRO | A | 40 | −14.155 | −24.651 | 18.462 | 1.00 | 32.95 | A |
| ATOM | 1985 | C | PRO | A | 40 | −12.975 | −28.077 | 19.343 | 1.00 | 31.96 | A |
| ATOM | 1986 | O | PRO | A | 40 | −12.489 | −28.579 | 20.355 | 1.00 | 31.96 | A |
| ATOM | 1987 | N | GLU | A | 41 | −13.527 | −28.810 | 18.382 | 1.00 | 31.78 | A |
| ATOM | 1988 | CA | GLU | A | 41 | −13.599 | −30.263 | 18.503 | 1.00 | 31.71 | A |
| ATOM | 1989 | CB | GLU | A | 41 | −14.590 | −30.831 | 17.477 | 1.00 | 32.59 | A |
| ATOM | 1990 | CG | GLU | A | 41 | −16.039 | −30.398 | 17.728 | 1.00 | 34.12 | A |
| ATOM | 1991 | CD | GLU | A | 41 | −17.008 | −30.864 | 16.651 | 1.00 | 34.74 | A |
| ATOM | 1992 | OE1 | GLU | A | 41 | −18.136 | −30.324 | 16.602 | 1.00 | 35.16 | A |
| ATOM | 1993 | OE2 | GLU | A | 41 | −16.650 | −31.762 | 15.859 | 1.00 | 35.71 | A |
| ATOM | 1994 | C | GLU | A | 41 | −12.248 | −30.965 | 18.374 | 1.00 | 31.20 | A |
| ATOM | 1995 | O | GLU | A | 41 | −12.026 | −32.006 | 18.994 | 1.00 | 31.36 | A |
| ATOM | 1996 | N | ILE | A | 42 | −11.341 | −30.402 | 17.581 | 1.00 | 30.36 | A |
| ATOM | 1997 | CA | ILE | A | 42 | −10.024 | −31.008 | 17.404 | 1.00 | 29.44 | A |
| ATOM | 1998 | CB | ILE | A | 42 | −9.329 | −30.477 | 16.132 | 1.00 | 29.45 | A |
| ATOM | 1999 | CG2 | ILE | A | 42 | −7.893 | −30.971 | 16.070 | 1.00 | 29.10 | A |
| ATOM | 2000 | CG1 | ILE | A | 42 | −10.098 | −30.946 | 14.896 | 1.00 | 29.17 | A |
| ATOM | 2001 | CD1 | ILE | A | 42 | −9.533 | −30.435 | 13.587 | 1.00 | 29.41 | A |
| ATOM | 2002 | C | ILE | A | 42 | −9.133 | −30.743 | 18.614 | 1.00 | 29.13 | A |
| ATOM | 2003 | O | ILE | A | 42 | −8.395 | −31.621 | 19.064 | 1.00 | 28.94 | A |
| ATOM | 2004 | N | LYS | A | 43 | −9.215 | −29.527 | 19.140 | 1.00 | 28.55 | A |
| ATOM | 2005 | CA | LYS | A | 43 | −8.427 | −29.129 | 20.294 | 1.00 | 28.30 | A |
| ATOM | 2006 | CB | LYS | A | 43 | −8.860 | −27.739 | 20.757 | 1.00 | 28.78 | A |
| ATOM | 2007 | CG | LYS | A | 43 | −8.047 | −27.185 | 21.911 | 1.00 | 29.29 | A |
| ATOM | 2008 | CD | LYS | A | 43 | −8.485 | −25.778 | 22.266 | 1.00 | 29.95 | A |
| ATOM | 2009 | CE | LYS | A | 43 | −7.585 | −25.184 | 23.332 | 1.00 | 30.31 | A |
| ATOM | 2010 | NZ | LYS | A | 43 | −7.992 | −23.795 | 23.662 | 1.00 | 31.39 | A |
| ATOM | 2011 | C | LYS | A | 43 | −8.554 | −30.120 | 21.452 | 1.00 | 27.83 | A |
| ATOM | 2012 | O | LYS | A | 43 | −7.565 | −30.471 | 22.088 | 1.00 | 27.33 | A |
| ATOM | 2052 | N | GLY | A | 49 | −3.879 | −29.189 | 23.684 | 1.00 | 18.08 | A |
| ATOM | 2053 | CA | GLY | A | 49 | −4.819 | −28.316 | 23.011 | 1.00 | 17.77 | A |
| ATOM | 2054 | C | GLY | A | 49 | −4.205 | −27.233 | 22.144 | 1.00 | 17.36 | A |
| ATOM | 2055 | O | GLY | A | 49 | −4.742 | −26.134 | 22.055 | 1.00 | 17.62 | A |
| ATOM | 2056 | N | LYS | A | 50 | −3.087 | −27.533 | 21.492 | 1.00 | 16.57 | A |
| ATOM | 2057 | CA | LYS | A | 50 | −2.444 | −26.544 | 20.635 | 1.00 | 15.44 | A |
| ATOM | 2058 | CB | LYS | A | 50 | −1.252 | −25.901 | 21.357 | 1.00 | 16.66 | A |
| ATOM | 2059 | CG | LYS | A | 50 | −1.576 | −25.229 | 22.697 | 1.00 | 19.15 | A |
| ATOM | 2060 | CD | LYS | A | 50 | −2.571 | −24.078 | 22.546 | 1.00 | 20.62 | A |
| ATOM | 2061 | CE | LYS | A | 50 | −2.752 | −23.310 | 23.863 | 1.00 | 22.03 | A |
| ATOM | 2062 | NZ | LYS | A | 50 | −1.454 | −22.751 | 24.383 | 1.00 | 23.09 | A |
| ATOM | 2063 | C | LYS | A | 50 | −1.962 | −27.136 | 19.308 | 1.00 | 14.12 | A |
| ATOM | 2064 | O | LYS | A | 50 | −1.634 | −28.319 | 19.214 | 1.00 | 12.86 | A |
| ATOM | 2065 | N | ILE | A | 51 | −1.935 | −26.300 | 18.280 | 1.00 | 12.71 | A |
| ATOM | 2066 | CA | ILE | A | 51 | −1.442 | −26.709 | 16.976 | 1.00 | 11.10 | A |
| ATOM | 2067 | CB | ILE | A | 51 | −2.556 | −26.696 | 15.904 | 1.00 | 11.18 | A |

TABLE 7-continued

Three-dimensional structural coordinate of the complex of
human hematopoietic PGDS (SEQ ID NO: 1) with calcium, glutathione and
Cibacron Blue

| ATOM | 2068 | CG2 | ILE | A | 51 | −3.365 | −27.995 | 15.981 | 1.00 | 9.64 | A |
|---|---|---|---|---|---|---|---|---|---|---|---|
| ATOM | 2069 | CG1 | ILE | A | 51 | −3.448 | −25.464 | 16.085 | 1.00 | 11.01 | A |
| ATOM | 2070 | CD1 | ILE | A | 51 | −4.506 | −25.325 | 15.031 | 1.00 | 11.08 | A |
| ATOM | 2071 | C | ILE | A | 51 | −0.361 | −25.690 | 16.641 | 1.00 | 11.44 | A |
| ATOM | 2072 | O | ILE | A | 51 | −0.312 | −24.616 | 17.240 | 1.00 | 11.87 | A |
| ATOM | 2073 | N | PRO | A | 52 | 0.490 | −25.983 | 15.651 | 1.00 | 10.86 | A |
| ATOM | 2074 | CD | PRO | A | 52 | 1.653 | −25.134 | 15.342 | 1.00 | 10.26 | A |
| ATOM | 2075 | CA | PRO | A | 52 | 0.506 | −27.193 | 14.826 | 1.00 | 9.60 | A |
| ATOM | 2076 | CB | PRO | A | 52 | 1.479 | −26.827 | 13.715 | 1.00 | 10.27 | A |
| ATOM | 2077 | CG | PRO | A | 52 | 2.505 | −26.052 | 14.470 | 1.00 | 10.74 | A |
| ATOM | 2078 | C | PRO | A | 52 | 0.917 | −28.512 | 15.473 | 1.00 | 9.74 | A |
| ATOM | 2079 | O | PRO | A | 52 | 1.654 | −28.551 | 16.457 | 1.00 | 9.94 | A |
| ATOM | 2080 | N | ILE | A | 53 | 0.429 | −29.595 | 14.890 | 1.00 | 9.16 | A |
| ATOM | 2081 | CA | ILE | A | 53 | 0.802 | −30.928 | 15.316 | 1.00 | 9.11 | A |
| ATOM | 2082 | CB | ILE | A | 53 | −0.356 | −31.724 | 15.961 | 1.00 | 9.49 | A |
| ATOM | 2083 | CG2 | ILE | A | 53 | −0.587 | −31.248 | 17.399 | 1.00 | 9.33 | A |
| ATOM | 2084 | CG1 | ILE | A | 53 | −1.625 | −31.588 | 15.116 | 1.00 | 10.59 | A |
| ATOM | 2085 | CD1 | ILE | A | 53 | −2.661 | −32.627 | 15.451 | 1.00 | 10.74 | A |
| ATOM | 2086 | C | ILE | A | 53 | 1.209 | −31.624 | 14.028 | 1.00 | 8.87 | A |
| ATOM | 2087 | O | ILE | A | 53 | 0.795 | −31.217 | 12.937 | 1.00 | 8.80 | A |
| ATOM | 2147 | N | HIS | A | 62 | 4.066 | −32.477 | 18.677 | 1.00 | 7.17 | A |
| ATOM | 2148 | CA | HIS | A | 62 | 3.585 | −31.113 | 18.831 | 1.00 | 7.13 | A |
| ATOM | 2149 | CB | HIS | A | 62 | 2.587 | −30.991 | 20.005 | 1.00 | 6.95 | A |
| ATOM | 2150 | CG | HIS | A | 62 | 3.182 | −31.270 | 21.350 | 1.00 | 7.27 | A |
| ATOM | 2151 | CD2 | HIS | A | 62 | 3.456 | −30.449 | 22.392 | 1.00 | 6.74 | A |
| ATOM | 2152 | ND1 | HIS | A | 62 | 3.557 | −32.535 | 21.750 | 1.00 | 7.14 | A |
| ATOM | 2153 | CE1 | HIS | A | 62 | 4.030 | −32.482 | 22.982 | 1.00 | 7.45 | A |
| ATOM | 2154 | NE2 | HIS | A | 62 | 3.981 | −31.228 | 23.394 | 1.00 | 7.97 | A |
| ATOM | 2155 | C | HIS | A | 62 | 4.749 | −30.134 | 19.018 | 1.00 | 6.81 | A |
| ATOM | 2156 | O | HIS | A | 62 | 5.903 | −30.550 | 19.138 | 1.00 | 6.11 | A |
| ATOM | 2157 | N | GLN | A | 63 | 4.416 | −28.840 | 19.036 | 1.00 | 6.34 | A |
| ATOM | 2158 | CA | GLN | A | 63 | 5.371 | −27.738 | 19.167 | 1.00 | 6.36 | A |
| ATOM | 2159 | CB | GLN | A | 63 | 6.378 | −27.990 | 20.295 | 1.00 | 6.62 | A |
| ATOM | 2160 | CG | GLN | A | 63 | 5.846 | −27.668 | 21.677 | 1.00 | 6.95 | A |
| ATOM | 2161 | CD | GLN | A | 63 | 5.456 | −26.197 | 21.848 | 1.00 | 7.39 | A |
| ATOM | 2162 | OE1 | GLN | A | 63 | 5.840 | −25.338 | 21.058 | 1.00 | 7.03 | A |
| ATOM | 2163 | NE2 | GLN | A | 63 | 4.702 | −25.909 | 22.906 | 1.00 | 7.11 | A |
| ATOM | 2164 | C | GLN | A | 63 | 6.108 | −27.532 | 17.848 | 1.00 | 6.58 | A |
| ATOM | 2165 | O | GLN | A | 63 | 6.976 | −28.325 | 17.460 | 1.00 | 5.65 | A |
| ATOM | 2166 | N | SER | A | 64 | 5.756 | −26.451 | 17.163 | 1.00 | 7.01 | A |
| ATOM | 2167 | CA | SER | A | 64 | 6.327 | −26.156 | 15.858 | 1.00 | 7.60 | A |
| ATOM | 2168 | CB | SER | A | 64 | 5.830 | −24.788 | 15.369 | 1.00 | 7.93 | A |
| ATOM | 2169 | OG | SER | A | 64 | 6.500 | −23.724 | 16.016 | 1.00 | 10.49 | A |
| ATOM | 2170 | C | SER | A | 64 | 7.853 | −26.230 | 15.726 | 1.00 | 7.47 | A |
| ATOM | 2171 | O | SER | A | 64 | 8.355 | −26.838 | 14.778 | 1.00 | 8.15 | A |
| ATOM | 2172 | N | LEU | A | 65 | 8.590 | −25.625 | 16.659 | 1.00 | 7.41 | A |
| ATOM | 2173 | CA | LEU | A | 65 | 10.057 | −25.630 | 16.588 | 1.00 | 6.62 | A |
| ATOM | 2174 | CB | LEU | A | 65 | 10.635 | −24.537 | 17.507 | 1.00 | 6.26 | A |
| ATOM | 2175 | CG | LEU | A | 65 | 10.102 | −23.122 | 17.220 | 1.00 | 6.77 | A |
| ATOM | 2176 | CD1 | LEU | A | 65 | 10.889 | −22.083 | 18.008 | 1.00 | 7.45 | A |
| ATOM | 2177 | CD2 | LEU | A | 65 | 10.218 | −22.826 | 15.727 | 1.00 | 6.34 | A |
| ATOM | 2178 | C | LEU | A | 65 | 10.650 | −26.997 | 16.928 | 1.00 | 6.30 | A |
| ATOM | 2179 | O | LEU | A | 65 | 11.690 | −27.382 | 16.393 | 1.00 | 5.38 | A |
| ATOM | 2386 | N | ASP | A | 93 | 15.188 | −19.341 | 18.472 | 1.00 | 6.02 | A |
| ATOM | 2387 | CA | ASP | A | 93 | 14.502 | −18.945 | 19.704 | 1.00 | 6.44 | A |
| ATOM | 2388 | CB | ASP | A | 93 | 15.115 | −19.629 | 20.926 | 1.00 | 6.17 | A |
| ATOM | 2389 | CG | ASP | A | 93 | 14.656 | −21.070 | 21.084 | 1.00 | 6.96 | A |
| ATOM | 2390 | OD1 | ASP | A | 93 | 15.143 | −21.748 | 22.016 | 1.00 | 8.03 | A |
| ATOM | 2391 | OD2 | ASP | A | 93 | 13.816 | −21.527 | 20.286 | 1.00 | 7.18 | A |
| ATOM | 2392 | C | ASP | A | 93 | 14.500 | −17.427 | 19.910 | 1.00 | 6.65 | A |
| ATOM | 2393 | O | ASP | A | 93 | 13.550 | −16.869 | 20.470 | 1.00 | 6.96 | A |
| ATOM | 2394 | N | THR | A | 94 | 15.558 | −16.761 | 19.467 | 1.00 | 6.46 | A |
| ATOM | 2395 | CA | THR | A | 94 | 15.605 | −15.312 | 19.606 | 1.00 | 7.09 | A |
| ATOM | 2396 | CB | THR | A | 94 | 16.967 | −14.767 | 19.156 | 1.00 | 7.44 | A |
| ATOM | 2397 | OG1 | THR | A | 94 | 17.958 | −15.187 | 20.105 | 1.00 | 8.81 | A |
| ATOM | 2398 | CG2 | THR | A | 94 | 16.960 | −13.229 | 19.084 | 1.00 | 8.28 | A |
| ATOM | 2399 | C | THR | A | 94 | 14.457 | −14.732 | 18.760 | 1.00 | 6.91 | A |
| ATOM | 2400 | O | THR | A | 94 | 13.724 | −13.845 | 19.206 | 1.00 | 7.60 | A |
| ATOM | 2401 | N | LEU | A | 95 | 14.271 | −15.265 | 17.559 | 1.00 | 6.06 | A |
| ATOM | 2402 | CA | LEU | A | 95 | 13.195 | −14.795 | 16.687 | 1.00 | 6.05 | A |
| ATOM | 2403 | CB | LEU | A | 95 | 13.322 | −15.419 | 15.294 | 1.00 | 5.72 | A |
| ATOM | 2404 | CG | LEU | A | 95 | 14.587 | −15.000 | 14.533 | 1.00 | 6.19 | A |
| ATOM | 2405 | CD1 | LEU | A | 95 | 14.726 | −15.828 | 13.269 | 1.00 | 5.14 | A |
| ATOM | 2406 | CD2 | LEU | A | 95 | 14.531 | −13.509 | 14.208 | 1.00 | 6.20 | A |
| ATOM | 2407 | C | LEU | A | 95 | 11.835 | −15.144 | 17.289 | 1.00 | 6.40 | A |

TABLE 7-continued

Three-dimensional structural coordinate of the complex of human hematopoietic PGDS (SEQ ID NO: 1) with calcium, glutathione and Cibacron Blue

| ATOM | 2408 | O   | LEU | A | 95  | 10.930 | −14.310 | 17.332 | 1.00 | 6.49  | A |
|------|------|-----|-----|---|-----|--------|---------|--------|------|-------|---|
| ATOM | 2409 | N   | ASP | A | 96  | 11.705 | −16.367 | 17.788 | 1.00 | 6.39  | A |
| ATOM | 2410 | CA  | ASP | A | 96  | 10.448 | −16.806 | 18.378 | 1.00 | 7.84  | A |
| ATOM | 2411 | CB  | ASP | A | 96  | 10.531 | −18.280 | 18.762 | 1.00 | 7.75  | A |
| ATOM | 2412 | CG  | ASP | A | 96  | 9.190  | −18.956 | 18.699 | 1.00 | 7.99  | A |
| ATOM | 2413 | OD1 | ASP | A | 96  | 8.526  | −18.824 | 17.650 | 1.00 | 8.64  | A |
| ATOM | 2414 | OD2 | ASP | A | 96  | 8.805  | −19.612 | 19.685 | 1.00 | 7.98  | A |
| ATOM | 2415 | C   | ASP | A | 96  | 10.059 | −15.970 | 19.601 | 1.00 | 8.25  | A |
| ATOM | 2416 | O   | ASP | A | 96  | 8.886  | −15.648 | 19.787 | 1.00 | 8.44  | A |
| ATOM | 2417 | N   | ASP | A | 97  | 11.049 | −15.622 | 20.422 | 1.00 | 8.47  | A |
| ATOM | 2418 | CA  | ASP | A | 97  | 10.810 | −14.799 | 21.601 | 1.00 | 9.21  | A |
| ATOM | 2419 | CB  | ASP | A | 97  | 12.129 | −14.473 | 22.322 | 1.00 | 9.43  | A |
| ATOM | 2420 | CG  | ASP | A | 97  | 12.692 | −15.652 | 23.121 | 1.00 | 10.37 | A |
| ATOM | 2421 | OD1 | ASP | A | 97  | 13.867 | −15.570 | 23.540 | 1.00 | 10.72 | A |
| ATOM | 2422 | OD2 | ASP | A | 97  | 11.974 | −16.651 | 23.342 | 1.00 | 11.19 | A |
| ATOM | 2423 | C   | ASP | A | 97  | 10.145 | −13.487 | 21.161 | 1.00 | 9.58  | A |
| ATOM | 2424 | O   | ASP | A | 97  | 9.120  | −13.097 | 21.709 | 1.00 | 9.77  | A |
| ATOM | 2425 | N   | PHE | A | 98  | 10.726 | −12.812 | 20.172 | 1.00 | 9.72  | A |
| ATOM | 2426 | CA  | PHE | A | 98  | 10.162 | −11.551 | 19.712 | 1.00 | 9.93  | A |
| ATOM | 2427 | CB  | PHE | A | 98  | 11.082 | −10.888 | 18.683 | 1.00 | 10.00 | A |
| ATOM | 2428 | CG  | PHE | A | 98  | 10.641 | −9.507  | 18.285 | 1.00 | 10.18 | A |
| ATOM | 2429 | CD1 | PHE | A | 98  | 10.605 | −8.476  | 19.222 | 1.00 | 10.49 | A |
| ATOM | 2430 | CD2 | PHE | A | 98  | 10.236 | −9.246  | 16.979 | 1.00 | 10.06 | A |
| ATOM | 2431 | CE1 | PHE | A | 98  | 10.164 | −7.197  | 18.861 | 1.00 | 10.61 | A |
| ATOM | 2432 | CE2 | PHE | A | 98  | 9.798  | −7.979  | 16.612 | 1.00 | 10.38 | A |
| ATOM | 2433 | CZ  | PHE | A | 98  | 9.762  | −6.954  | 17.551 | 1.00 | 10.19 | A |
| ATOM | 2434 | C   | PHE | A | 98  | 8.754  | −11.721 | 19.126 | 1.00 | 10.12 | A |
| ATOM | 2435 | O   | PHE | A | 98  | 7.838  | −10.967 | 19.459 | 1.00 | 9.57  | A |
| ATOM | 2436 | N   | MET | A | 99  | 8.572  | −12.723 | 18.273 | 1.00 | 10.66 | A |
| ATOM | 2437 | CA  | MET | A | 99  | 7.266  | −12.956 | 17.675 | 1.00 | 11.35 | A |
| ATOM | 2438 | CB  | MET | A | 99  | 7.319  | −14.137 | 16.697 | 1.00 | 11.47 | A |
| ATOM | 2439 | CG  | MET | A | 99  | 8.239  | −13.935 | 15.491 | 1.00 | 11.14 | A |
| ATOM | 2440 | SD  | MET | A | 99  | 7.912  | −12.430 | 14.557 | 1.00 | 11.29 | A |
| ATOM | 2441 | CE  | MET | A | 99  | 6.373  | −12.849 | 13.740 | 1.00 | 10.00 | A |
| ATOM | 2442 | C   | MET | A | 99  | 6.198  | −13.223 | 18.745 | 1.00 | 12.00 | A |
| ATOM | 2443 | O   | MET | A | 99  | 5.052  | −12.804 | 18.596 | 1.00 | 12.28 | A |
| ATOM | 2444 | N   | SER | A | 100 | 6.562  | −13.909 | 19.823 | 1.00 | 12.46 | A |
| ATOM | 2445 | CA  | SER | A | 100 | 5.579  | −14.189 | 20.865 | 1.00 | 13.62 | A |
| ATOM | 2446 | CB  | SER | A | 100 | 6.092  | −15.288 | 21.808 | 1.00 | 13.99 | A |
| ATOM | 2447 | OG  | SER | A | 100 | 6.241  | −16.513 | 21.108 | 1.00 | 15.53 | A |
| ATOM | 2448 | C   | SER | A | 100 | 5.181  | −12.942 | 21.666 | 1.00 | 13.94 | A |
| ATOM | 2449 | O   | SER | A | 100 | 4.196  | −12.971 | 22.400 | 1.00 | 14.47 | A |
| ATOM | 2450 | N   | CYS | A | 101 | 5.935  | −11.853 | 21.520 | 1.00 | 14.58 | A |
| ATOM | 2451 | CA  | CYS | A | 101 | 5.634  | −10.596 | 22.222 | 1.00 | 15.68 | A |
| ATOM | 2452 | CB  | CYS | A | 101 | 6.759  | −9.571  | 22.047 | 1.00 | 16.12 | A |
| ATOM | 2453 | SG  | CYS | A | 101 | 8.291  | −9.874  | 22.933 | 1.00 | 20.40 | A |
| ATOM | 2454 | C   | CYS | A | 101 | 4.362  | −9.950  | 21.693 | 1.00 | 15.48 | A |
| ATOM | 2455 | O   | CYS | A | 101 | 3.715  | −9.184  | 22.404 | 1.00 | 15.75 | A |
| ATOM | 2456 | N   | PHE | A | 102 | 4.012  | −10.245 | 20.445 | 1.00 | 15.64 | A |
| ATOM | 2457 | CA  | PHE | A | 102 | 2.825  | −9.646  | 19.849 | 1.00 | 15.94 | A |
| ATOM | 2458 | CB  | PHE | A | 102 | 2.898  | −9.712  | 18.321 | 1.00 | 14.57 | A |
| ATOM | 2459 | CG  | PHE | A | 102 | 4.035  | −8.929  | 17.734 | 1.00 | 13.99 | A |
| ATOM | 2460 | CD1 | PHE | A | 102 | 5.336  | −9.428  | 17.770 | 1.00 | 12.96 | A |
| ATOM | 2461 | CD2 | PHE | A | 102 | 3.812  | −7.684  | 17.158 | 1.00 | 13.28 | A |
| ATOM | 2462 | CE1 | PHE | A | 102 | 6.393  | −8.701  | 17.243 | 1.00 | 12.46 | A |
| ATOM | 2463 | CE2 | PHE | A | 102 | 4.865  | −6.949  | 16.628 | 1.00 | 13.41 | A |
| ATOM | 2464 | CZ  | PHE | A | 102 | 6.159  | −7.459  | 16.671 | 1.00 | 12.82 | A |
| ATOM | 2465 | C   | PHE | A | 102 | 1.529  | −10.290 | 20.321 | 1.00 | 16.74 | A |
| ATOM | 2466 | O   | PHE | A | 102 | 1.422  | −11.517 | 20.399 | 1.00 | 16.41 | A |
| ATOM | 2467 | N   | PRO | A | 103 | 0.523  | −9.460  | 20.642 | 1.00 | 17.53 | A |
| ATOM | 2468 | CD  | PRO | A | 103 | 0.599  | −7.989  | 20.671 | 1.00 | 17.55 | A |
| ATOM | 2469 | CA  | PRO | A | 103 | −0.791 | −9.916  | 21.112 | 1.00 | 18.81 | A |
| ATOM | 2470 | CB  | PRO | A | 103 | −1.372 | −8.658  | 21.748 | 1.00 | 18.35 | A |
| ATOM | 2471 | CG  | PRO | A | 103 | −0.855 | −7.591  | 20.841 | 1.00 | 17.64 | A |
| ATOM | 2472 | C   | PRO | A | 103 | −1.646 | −10.424 | 19.954 | 1.00 | 19.69 | A |
| ATOM | 2473 | O   | PRO | A | 103 | −2.663 | −9.827  | 19.613 | 1.00 | 20.09 | A |
| ATOM | 2474 | N   | TRP | A | 104 | −1.221 | −11.527 | 19.353 | 1.00 | 21.16 | A |
| ATOM | 2475 | CA  | TRP | A | 104 | −1.925 | −12.097 | 18.215 | 1.00 | 22.57 | A |
| ATOM | 2476 | CB  | TRP | A | 104 | −1.215 | −13.364 | 17.740 | 1.00 | 22.05 | A |
| ATOM | 2477 | CG  | TRP | A | 104 | 0.208  | −13.135 | 17.325 | 1.00 | 22.03 | A |
| ATOM | 2478 | CD2 | TRP | A | 104 | 0.666  | −12.577 | 16.085 | 1.00 | 22.05 | A |
| ATOM | 2479 | CE2 | TRP | A | 104 | 2.076  | −12.530 | 16.144 | 1.00 | 22.03 | A |
| ATOM | 2480 | CE3 | TRP | A | 104 | 0.022  | −12.110 | 14.931 | 1.00 | 21.92 | A |
| ATOM | 2481 | CD1 | TRP | A | 104 | 1.324  | −13.393 | 18.060 | 1.00 | 21.72 | A |
| ATOM | 2482 | NE1 | TRP | A | 104 | 2.449  | −13.036 | 17.360 | 1.00 | 21.99 | A |

TABLE 7-continued

Three-dimensional structural coordinate of the complex of
human hematopoietic PGDS (SEQ ID NO: 1) with calcium, glutathione and
Cibacron Blue

| ATOM | 2483 | CZ2 | TRP | A | 104 | 2.856 | −12.037 | 15.092 | 1.00 | 22.09 | A |
|---|---|---|---|---|---|---|---|---|---|---|---|
| ATOM | 2484 | CZ3 | TRP | A | 104 | 0.799 | −11.618 | 13.883 | 1.00 | 22.10 | A |
| ATOM | 2485 | CH2 | TRP | A | 104 | 2.199 | −11.587 | 13.973 | 1.00 | 22.21 | A |
| ATOM | 2486 | C | TRP | A | 104 | −3.398 | −12.404 | 18.462 | 1.00 | 23.87 | A |
| ATOM | 2487 | O | TRP | A | 104 | −4.227 | −12.208 | 17.580 | 1.00 | 23.92 | A |
| ATOM | 2488 | N | ALA | A | 105 | −3.725 | −12.880 | 19.658 | 1.00 | 25.71 | A |
| ATOM | 2489 | CA | ALA | A | 105 | −5.110 | −13.223 | 19.973 | 1.00 | 27.71 | A |
| ATOM | 2490 | CB | ALA | A | 105 | −5.161 | −14.573 | 20.686 | 1.00 | 27.28 | A |
| ATOM | 2491 | C | ALA | A | 105 | −5.827 | −12.168 | 20.814 | 1.00 | 28.94 | A |
| ATOM | 2492 | O | ALA | A | 105 | −6.594 | −12.503 | 21.714 | 1.00 | 29.77 | A |
| ATOM | 2493 | N | GLU | A | 106 | −5.580 | −10.897 | 20.527 | 1.00 | 30.28 | A |
| ATOM | 2494 | CA | GLU | A | 106 | −6.227 | −9.825 | 21.272 | 1.00 | 31.40 | A |
| ATOM | 2495 | CB | GLU | A | 106 | −5.290 | −8.622 | 21.389 | 1.00 | 31.69 | A |
| ATOM | 2496 | CG | GLU | A | 106 | −5.919 | −7.415 | 22.061 | 1.00 | 32.04 | A |
| ATOM | 2497 | CD | GLU | A | 106 | −6.531 | −7.755 | 23.407 | 1.00 | 32.68 | A |
| ATOM | 2498 | OE1 | GLU | A | 106 | −5.780 | −8.147 | 24.328 | 1.00 | 33.12 | A |
| ATOM | 2499 | OE2 | GLU | A | 106 | −7.767 | −7.636 | 23.540 | 1.00 | 32.39 | A |
| ATOM | 2500 | C | GLU | A | 106 | −7.529 | −9.410 | 20.589 | 1.00 | 32.24 | A |
| ATOM | 2501 | O | GLU | A | 106 | −7.526 | −8.979 | 19.433 | 1.00 | 31.93 | A |
| ATOM | 2502 | N | LYS | A | 107 | −8.640 | −9.545 | 21.309 | 1.00 | 33.40 | A |
| ATOM | 2503 | CA | LYS | A | 107 | −9.951 | −9.194 | 20.768 | 1.00 | 34.44 | A |
| ATOM | 2504 | CB | LYS | A | 107 | −11.064 | −9.645 | 21.726 | 1.00 | 35.12 | A |
| ATOM | 2505 | CG | LYS | A | 107 | −11.028 | −11.140 | 22.042 | 1.00 | 36.21 | A |
| ATOM | 2506 | CD | LYS | A | 107 | −12.355 | −11.678 | 22.594 | 1.00 | 36.94 | A |
| ATOM | 2507 | CE | LYS | A | 107 | −12.840 | −10.921 | 23.833 | 1.00 | 37.48 | A |
| ATOM | 2508 | NZ | LYS | A | 107 | −13.493 | −9.618 | 23.499 | 1.00 | 37.90 | A |
| ATOM | 2509 | C | LYS | A | 107 | −10.082 | −7.702 | 20.472 | 1.00 | 34.49 | A |
| ATOM | 2510 | O | LYS | A | 107 | −10.542 | −7.319 | 19.396 | 1.00 | 34.58 | A |
| ATOM | 2511 | N | LYS | A | 108 | −9.683 | −6.860 | 21.421 | 1.00 | 34.77 | A |
| ATOM | 2512 | CA | LYS | A | 108 | −9.755 | −5.416 | 21.208 | 1.00 | 34.85 | A |
| ATOM | 2513 | CB | LYS | A | 108 | −9.397 | −4.654 | 22.488 | 1.00 | 35.43 | A |
| ATOM | 2514 | CG | LYS | A | 108 | −10.511 | −4.602 | 23.526 | 1.00 | 36.43 | A |
| ATOM | 2515 | CD | LYS | A | 108 | −10.639 | −5.902 | 24.298 | 1.00 | 37.04 | A |
| ATOM | 2516 | CE | LYS | A | 108 | −9.476 | −6.082 | 25.262 | 1.00 | 37.43 | A |
| ATOM | 2517 | NZ | LYS | A | 108 | −9.527 | −7.411 | 25.947 | 1.00 | 37.89 | A |
| ATOM | 2518 | C | LYS | A | 108 | −8.796 | −5.016 | 20.088 | 1.00 | 34.70 | A |
| ATOM | 2519 | O | LYS | A | 108 | −7.578 | −5.103 | 20.239 | 1.00 | 34.50 | A |
| ATOM | 2520 | N | GLN | A | 109 | −9.359 | −4.575 | 18.968 | 1.00 | 34.41 | A |
| ATOM | 2521 | CA | GLN | A | 109 | −8.575 | −4.174 | 17.806 | 1.00 | 34.31 | A |
| ATOM | 2522 | CB | GLN | A | 109 | −9.511 | −3.809 | 16.651 | 1.00 | 35.11 | A |
| ATOM | 2523 | CG | GLN | A | 109 | −8.806 | −3.584 | 15.327 | 1.00 | 36.38 | A |
| ATOM | 2524 | CD | GLN | A | 109 | −8.007 | −4.800 | 14.893 | 1.00 | 37.34 | A |
| ATOM | 2525 | OE1 | GLN | A | 109 | −8.525 | −5.922 | 14.858 | 1.00 | 37.88 | A |
| ATOM | 2526 | NE2 | GLN | A | 109 | −6.737 | −4.586 | 14.560 | 1.00 | 37.71 | A |
| ATOM | 2527 | C | GLN | A | 109 | −7.632 | −3.006 | 18.082 | 1.00 | 33.82 | A |
| ATOM | 2528 | O | GLN | A | 109 | −6.437 | −3.086 | 17.802 | 1.00 | 33.77 | A |
| ATOM | 2529 | N | ASP | A | 110 | −8.178 | −1.921 | 18.621 | 1.00 | 33.24 | A |
| ATOM | 2530 | CA | ASP | A | 110 | −7.393 | −0.731 | 18.926 | 1.00 | 32.17 | A |
| ATOM | 2531 | CB | ASP | A | 110 | −8.290 | −0.339 | 19.561 | 1.00 | 33.29 | A |
| ATOM | 2532 | CG | ASP | A | 110 | −9.147 | −0.208 | 20.689 | 1.00 | 34.12 | A |
| ATOM | 2533 | OD1 | ASP | A | 110 | −8.607 | −0.469 | 21.785 | 1.00 | 34.82 | A |
| ATOM | 2534 | OD2 | ASP | A | 110 | −10.365 | −0.383 | 20.474 | 1.00 | 35.05 | A |
| ATOM | 2535 | C | ASP | A | 110 | −6.217 | −1.045 | 19.845 | 1.00 | 30.99 | A |
| ATOM | 2536 | O | ASP | A | 110 | −5.103 | −0.561 | 19.626 | 1.00 | 30.41 | A |
| ATOM | 2537 | N | VAL | A | 111 | −6.469 | −1.852 | 20.870 | 1.00 | 29.43 | A |
| ATOM | 2538 | CA | VAL | A | 111 | −5.430 | −2.236 | 21.815 | 1.00 | 28.27 | A |
| ATOM | 2539 | CB | VAL | A | 111 | −6.010 | −3.086 | 22.964 | 1.00 | 28.68 | A |
| ATOM | 2540 | CG1 | VAL | A | 111 | −4.891 | −3.532 | 23.899 | 1.00 | 28.43 | A |
| ATOM | 2541 | CG2 | VAL | A | 111 | −7.061 | −2.285 | 23.718 | 1.00 | 28.82 | A |
| ATOM | 2542 | C | VAL | A | 111 | −4.373 | −3.061 | 21.089 | 1.00 | 27.11 | A |
| ATOM | 2543 | O | VAL | A | 111 | −3.176 | −2.848 | 21.258 | 1.00 | 26.42 | A |
| ATOM | 2544 | N | LYS | A | 112 | −4.832 | −4.005 | 20.276 | 1.00 | 26.09 | A |
| ATOM | 2545 | CA | LYS | A | 112 | −3.936 | −4.866 | 19.518 | 1.00 | 25.03 | A |
| ATOM | 2546 | CB | LYS | A | 112 | −4.754 | −5.880 | 18.717 | 1.00 | 25.17 | A |
| ATOM | 2547 | CG | LYS | A | 112 | −3.932 | −6.879 | 17.927 | 1.00 | 25.45 | A |
| ATOM | 2548 | CD | LYS | A | 112 | −4.832 | −7.932 | 17.297 | 1.00 | 25.91 | A |
| ATOM | 2549 | CE | LYS | A | 112 | −4.021 | −8.973 | 16.535 | 1.00 | 26.40 | A |
| ATOM | 2550 | NZ | LYS | A | 112 | −4.889 | −10.025 | 15.934 | 1.00 | 26.69 | A |
| ATOM | 2551 | C | LYS | A | 112 | −3.055 | −4.044 | 18.580 | 1.00 | 24.09 | A |
| ATOM | 2552 | O | LYS | A | 112 | −1.832 | −4.200 | 18.567 | 1.00 | 23.73 | A |
| ATOM | 2553 | N | GLU | A | 113 | −3.685 | −3.161 | 17.810 | 1.00 | 22.88 | A |
| ATOM | 2554 | CA | GLU | A | 113 | −2.980 | −2.314 | 16.853 | 1.00 | 22.08 | A |
| ATOM | 2555 | CB | GLU | A | 113 | −3.993 | −1.498 | 16.036 | 1.00 | 23.03 | A |
| ATOM | 2556 | CG | GLU | A | 113 | −3.394 | −0.676 | 14.915 | 1.00 | 24.94 | A |
| ATOM | 2557 | CD | GLU | A | 113 | −4.453 | −0.101 | 13.976 | 1.00 | 26.15 | A |

TABLE 7-continued

Three-dimensional structural coordinate of the complex of
human hematopoietic PGDS (SEQ ID NO: 1) with calcium, glutathione and
Cibacron Blue

| ATOM | 2558 | OE1 | GLU | A | 113 | −5.181 | −0.894 | 13.332 | 1.00 | 26.50 | A |
|---|---|---|---|---|---|---|---|---|---|---|---|
| ATOM | 2559 | OE2 | GLU | A | 113 | −4.556 | 1.142 | 13.881 | 1.00 | 27.05 | A |
| ATOM | 2560 | C | GLU | A | 113 | −1.973 | −1.383 | 17.532 | 1.00 | 20.78 | A |
| ATOM | 2561 | O | GLU | A | 113 | −0.874 | −1.162 | 17.022 | 1.00 | 19.80 | A |
| ATOM | 2562 | N | GLN | A | 114 | −2.345 | −0.839 | 18.684 | 1.00 | 19.79 | A |
| ATOM | 2563 | CA | GLN | A | 114 | −1.450 | 0.047 | 19.406 | 1.00 | 19.27 | A |
| ATOM | 2564 | CB | GLN | A | 114 | −2.154 | 0.632 | 20.634 | 1.00 | 20.01 | A |
| ATOM | 2565 | CG | GLN | A | 114 | −1.301 | 1.615 | 21.423 | 1.00 | 21.19 | A |
| ATOM | 2566 | CD | GLN | A | 114 | −0.997 | 2.890 | 20.650 | 1.00 | 22.15 | A |
| ATOM | 2567 | OE1 | GLN | A | 114 | −0.144 | 3.681 | 21.059 | 1.00 | 23.10 | A |
| ATOM | 2568 | NE2 | GLN | A | 114 | −1.699 | 3.102 | 19.536 | 1.00 | 21.70 | A |
| ATOM | 2569 | C | GLN | A | 114 | −0.188 | −0.709 | 19.838 | 1.00 | 18.22 | A |
| ATOM | 2570 | O | GLN | A | 114 | 0.927 | −0.242 | 19.604 | 1.00 | 17.80 | A |
| ATOM | 2571 | N | MET | A | 115 | −0.365 | −1.877 | 20.452 | 1.00 | 17.56 | A |
| ATOM | 2572 | CA | MET | A | 115 | 0.769 | −2.676 | 20.908 | 1.00 | 17.24 | A |
| ATOM | 2573 | CB | MET | A | 115 | 0.290 | −3.905 | 21.693 | 1.00 | 19.31 | A |
| ATOM | 2574 | CG | MET | A | 115 | 1.431 | −4.735 | 22.269 | 1.00 | 21.86 | A |
| ATOM | 2575 | SD | MET | A | 115 | 0.923 | −5.795 | 23.655 | 1.00 | 26.35 | A |
| ATOM | 2576 | CE | MET | A | 115 | 0.941 | −4.589 | 25.027 | 1.00 | 25.28 | A |
| ATOM | 2577 | C | MET | A | 115 | 1.655 | −3.122 | 19.744 | 1.00 | 15.84 | A |
| ATOM | 2578 | O | MET | A | 115 | 2.882 | −3.125 | 19.860 | 1.00 | 15.55 | A |
| ATOM | 2579 | N | PHE | A | 116 | 1.035 | −3.509 | 18.632 | 1.00 | 14.07 | A |
| ATOM | 2580 | CA | PHE | A | 116 | 1.786 | −3.928 | 17.452 | 1.00 | 13.26 | A |
| ATOM | 2581 | CB | PHE | A | 116 | 0.845 | −4.301 | 16.300 | 1.00 | 12.53 | A |
| ATOM | 2582 | CG | PHE | A | 116 | 0.588 | −5.775 | 16.176 | 1.00 | 12.20 | A |
| ATOM | 2583 | CD1 | PHE | A | 116 | −0.130 | −6.453 | 17.154 | 1.00 | 12.43 | A |
| ATOM | 2584 | CD2 | PHE | A | 116 | 1.076 | −6.489 | 15.089 | 1.00 | 12.72 | A |
| ATOM | 2585 | CE1 | PHE | A | 116 | −0.360 | −7.817 | 17.052 | 1.00 | 12.44 | A |
| ATOM | 2586 | CE2 | PHE | A | 116 | 0.851 | −7.864 | 14.974 | 1.00 | 12.31 | A |
| ATOM | 2587 | CZ | PHE | A | 116 | 0.131 | −8.526 | 15.960 | 1.00 | 12.74 | A |
| ATOM | 2588 | C | PHE | A | 116 | 2.677 | −2.775 | 17.002 | 1.00 | 12.47 | A |
| ATOM | 2589 | O | PHE | A | 116 | 3.870 | −2.948 | 16.773 | 1.00 | 12.52 | A |
| ATOM | 2876 | N | TYR | A | 152 | 13.612 | −19.507 | 9.014 | 1.00 | 7.45 | A |
| ATOM | 2877 | CA | TYR | A | 152 | 12.780 | −18.882 | 10.032 | 1.00 | 7.80 | A |
| ATOM | 2878 | CB | TYR | A | 152 | 13.127 | −19.416 | 11.419 | 1.00 | 7.71 | A |
| ATOM | 2879 | CG | TYR | A | 152 | 11.963 | −19.316 | 12.386 | 1.00 | 8.94 | A |
| ATOM | 2880 | CD1 | TYR | A | 152 | 10.717 | −19.858 | 12.063 | 1.00 | 9.56 | A |
| ATOM | 2881 | CE1 | TYR | A | 152 | 9.649 | −19.802 | 12.961 | 1.00 | 9.81 | A |
| ATOM | 2882 | CD2 | TYR | A | 152 | 12.110 | −18.706 | 13.630 | 1.00 | 9.51 | A |
| ATOM | 2883 | CE2 | TYR | A | 152 | 11.050 | −18.642 | 14.534 | 1.00 | 9.37 | A |
| ATOM | 2884 | CZ | TYR | A | 152 | 9.828 | −19.197 | 14.191 | 1.00 | 10.01 | A |
| ATOM | 2885 | OH | TYR | A | 152 | 8.787 | −19.193 | 15.101 | 1.00 | 10.22 | A |
| ATOM | 2886 | C | TYR | A | 152 | 12.871 | −17.368 | 10.032 | 1.00 | 7.80 | A |
| ATOM | 2887 | O | TYR | A | 152 | 11.906 | −16.685 | 10.363 | 1.00 | 7.64 | A |
| ATOM | 2888 | N | TRP | A | 153 | 14.037 | −16.848 | 9.671 | 1.00 | 7.83 | A |
| ATOM | 2889 | CA | TRP | A | 153 | 14.217 | −15.409 | 9.615 | 1.00 | 8.29 | A |
| ATOM | 2890 | CB | TRP | A | 153 | 15.675 | −15.058 | 9.323 | 1.00 | 8.19 | A |
| ATOM | 2891 | CG | TRP | A | 153 | 15.826 | −13.715 | 8.694 | 1.00 | 8.54 | A |
| ATOM | 2892 | CD2 | TRP | A | 153 | 15.414 | −12.464 | 9.247 | 1.00 | 8.88 | A |
| ATOM | 2893 | CE2 | TRP | A | 153 | 15.716 | −11.467 | 8.299 | 1.00 | 8.91 | A |
| ATOM | 2894 | CE3 | TRP | A | 153 | 14.816 | −12.087 | 10.458 | 1.00 | 9.75 | A |
| ATOM | 2895 | CD1 | TRP | A | 153 | 16.348 | −13.438 | 7.466 | 1.00 | 8.71 | A |
| ATOM | 2896 | NE1 | TRP | A | 153 | 16.285 | −12.087 | 7.219 | 1.00 | 9.04 | A |
| ATOM | 2897 | CZ2 | TRP | A | 153 | 15.440 | −10.111 | 8.519 | 1.00 | 9.95 | A |
| ATOM | 2898 | CZ3 | TRP | A | 153 | 14.541 | −10.734 | 10.676 | 1.00 | 9.92 | A |
| ATOM | 2899 | CH2 | TRP | A | 153 | 14.855 | −9.766 | 9.708 | 1.00 | 9.14 | A |
| ATOM | 2900 | C | TRP | A | 153 | 13.336 | −14.871 | 8.493 | 1.00 | 8.23 | A |
| ATOM | 2901 | O | TRP | A | 153 | 12.676 | −13.852 | 8.647 | 1.00 | 8.77 | A |
| ATOM | 2902 | N | GLU | A | 154 | 13.336 | −15.572 | 7.364 | 1.00 | 8.71 | A |
| ATOM | 2903 | CA | GLU | A | 154 | 12.547 | −15.159 | 6.204 | 1.00 | 8.50 | A |
| ATOM | 2904 | CB | GLU | A | 154 | 12.862 | −16.034 | 4.995 | 1.00 | 8.57 | A |
| ATOM | 2905 | CG | GLU | A | 154 | 12.336 | −15.455 | 3.679 | 1.00 | 9.53 | A |
| ATOM | 2906 | CD | GLU | A | 154 | 10.920 | −15.883 | 3.350 | 1.00 | 8.58 | A |
| ATOM | 2907 | OE1 | GLU | A | 154 | 10.337 | −15.318 | 2.400 | 1.00 | 9.21 | A |
| ATOM | 2908 | OE2 | GLU | A | 154 | 10.397 | −16.785 | 4.019 | 1.00 | 8.79 | A |
| ATOM | 2909 | C | GLU | A | 154 | 11.064 | −15.205 | 6.496 | 1.00 | 8.22 | A |
| ATOM | 2910 | O | GLU | A | 154 | 10.310 | −14.309 | 6.102 | 1.00 | 8.84 | A |
| ATOM | 2911 | N | ILE | A | 155 | 10.650 | −16.258 | 7.191 | 1.00 | 7.89 | A |
| ATOM | 2912 | CA | ILE | A | 155 | 9.254 | −16.444 | 7.547 | 1.00 | 6.85 | A |
| ATOM | 2913 | CB | ILE | A | 155 | 9.041 | −17.887 | 8.105 | 1.00 | 7.23 | A |
| ATOM | 2914 | CG2 | ILE | A | 155 | 7.742 | −17.975 | 8.898 | 1.00 | 6.59 | A |
| ATOM | 2915 | CG1 | ILE | A | 155 | 9.067 | −18.893 | 6.939 | 1.00 | 7.31 | A |
| ATOM | 2916 | CD1 | ILE | A | 155 | 9.155 | −20.382 | 7.343 | 1.00 | 5.54 | A |
| ATOM | 2917 | C | ILE | A | 155 | 8.816 | −15.378 | 8.568 | 1.00 | 7.33 | A |
| ATOM | 2918 | O | ILE | A | 155 | 7.801 | −14.702 | 8.375 | 1.00 | 6.57 | A |

TABLE 7-continued

Three-dimensional structural coordinate of the complex of
human hematopoietic PGDS (SEQ ID NO: 1) with calcium, glutathione and
Cibacron Blue

| ATOM | 2919 | N | CYS | A | 156 | 9.601 | −15.196 | 9.628 | 1.00 | 7.49 | A |
|---|---|---|---|---|---|---|---|---|---|---|---|
| ATOM | 2920 | CA | CYS | A | 156 | 9.245 | −14.209 | 10.638 | 1.00 | 7.46 | A |
| ATOM | 2921 | CB | CYS | A | 156 | 10.227 | −14.252 | 11.818 | 1.00 | 7.91 | A |
| ATOM | 2922 | SG | CYS | A | 156 | 10.226 | −15.769 | 12.755 | 1.00 | 8.41 | A |
| ATOM | 2923 | C | CYS | A | 156 | 9.230 | −12.799 | 10.029 | 1.00 | 7.56 | A |
| ATOM | 2924 | O | CYS | A | 156 | 8.238 | −12.075 | 10.148 | 1.00 | 7.15 | A |
| ATOM | 2925 | N | SER | A | 157 | 10.296 | −12.427 | 9.319 | 1.00 | 7.31 | A |
| ATOM | 2926 | CA | SER | A | 157 | 10.345 | −11.095 | 8.733 | 1.00 | 7.15 | A |
| ATOM | 2927 | CB | SER | A | 157 | 11.739 | −10.802 | 8.137 | 1.00 | 6.90 | A |
| ATOM | 2928 | OG | SER | A | 157 | 12.045 | −11.626 | 7.027 | 1.00 | 5.72 | A |
| ATOM | 2929 | C | SER | A | 157 | 9.226 | −10.893 | 7.706 | 1.00 | 7.42 | A |
| ATOM | 2930 | O | SER | A | 157 | 8.700 | −9.793 | 7.591 | 1.00 | 7.72 | A |
| ATOM | 2931 | N | THR | A | 158 | 8.831 | −11.938 | 6.980 | 1.00 | 7.58 | A |
| ATOM | 2932 | CA | THR | A | 158 | 7.744 | −11.762 | 6.012 | 1.00 | 8.17 | A |
| ATOM | 2933 | CB | THR | A | 158 | 7.434 | −13.070 | 5.248 | 1.00 | 8.62 | A |
| ATOM | 2934 | OG1 | THR | A | 158 | 8.325 | −13.172 | 4.128 | 1.00 | 9.05 | A |
| ATOM | 2935 | CG2 | THR | A | 158 | 5.989 | −13.090 | 4.742 | 1.00 | 8.43 | A |
| ATOM | 2936 | C | THR | A | 158 | 6.491 | −11.257 | 6.733 | 1.00 | 8.44 | A |
| ATOM | 2937 | O | THR | A | 158 | 5.843 | −10.317 | 6.278 | 1.00 | 7.98 | A |
| ATOM | 2938 | N | THR | A | 159 | 6.178 | −11.848 | 7.881 | 1.00 | 8.66 | A |
| ATOM | 2939 | CA | THR | A | 159 | 5.008 | −11.421 | 8.630 | 1.00 | 9.74 | A |
| ATOM | 2940 | CB | THR | A | 159 | 4.661 | −12.441 | 9.728 | 1.00 | 11.00 | A |
| ATOM | 2941 | OG1 | THR | A | 159 | 4.147 | −13.633 | 9.113 | 1.00 | 11.94 | A |
| ATOM | 2942 | CG2 | THR | A | 159 | 3.603 | −11.874 | 10.663 | 1.00 | 11.12 | A |
| ATOM | 2943 | C | THR | A | 159 | 5.136 | −10.016 | 9.248 | 1.00 | 9.29 | A |
| ATOM | 2944 | O | THR | A | 159 | 4.201 | −9.222 | 9.163 | 1.00 | 9.32 | A |
| ATOM | 2945 | N | LEU | A | 160 | 6.287 | −9.707 | 9.850 | 1.00 | 9.10 | A |
| ATOM | 2946 | CA | LEU | A | 160 | 6.509 | −8.394 | 10.464 | 1.00 | 8.76 | A |
| ATOM | 2947 | CB | LEU | A | 160 | 7.887 | −8.342 | 11.143 | 1.00 | 8.08 | A |
| ATOM | 2948 | CG | LEU | A | 160 | 8.152 | −9.296 | 12.318 | 1.00 | 8.40 | A |
| ATOM | 2949 | CD1 | LEU | A | 160 | 9.616 | −9.250 | 12.706 | 1.00 | 7.66 | A |
| ATOM | 2950 | CD2 | LEU | A | 160 | 7.259 | −8.925 | 13.491 | 1.00 | 7.69 | A |
| ATOM | 2951 | C | LEU | A | 160 | 6.424 | −7.279 | 9.417 | 1.00 | 8.80 | A |
| ATOM | 2952 | O | LEU | A | 160 | 5.912 | −6.192 | 9.691 | 1.00 | 8.81 | A |
| ATOM | 2953 | N | LEU | A | 161 | 6.946 | −7.553 | 8.226 | 1.00 | 9.13 | A |
| ATOM | 2954 | CA | LEU | A | 161 | 6.921 | −6.586 | 7.131 | 1.00 | 9.84 | A |
| ATOM | 2955 | CB | LEU | A | 161 | 7.637 | −7.159 | 5.905 | 1.00 | 9.15 | A |
| ATOM | 2956 | CG | LEU | A | 161 | 9.144 | −6.881 | 5.882 | 1.00 | 9.55 | A |
| ATOM | 2957 | CD1 | LEU | A | 161 | 9.822 | −7.612 | 4.700 | 1.00 | 9.05 | A |
| ATOM | 2958 | CD2 | LEU | A | 161 | 9.351 | −5.388 | 5.757 | 1.00 | 8.83 | A |
| ATOM | 2959 | C | LEU | A | 161 | 5.495 | −6.184 | 6.768 | 1.00 | 10.43 | A |
| ATOM | 2960 | O | LEU | A | 161 | 5.262 | −5.090 | 6.249 | 1.00 | 10.78 | A |
| ATOM | 2961 | N | VAL | A | 162 | 4.542 | −7.068 | 7.055 | 1.00 | 10.57 | A |
| ATOM | 2962 | CA | VAL | A | 162 | 3.137 | −6.794 | 6.776 | 1.00 | 11.31 | A |
| ATOM | 2963 | CB | VAL | A | 162 | 2.244 | −8.045 | 7.041 | 1.00 | 11.09 | A |
| ATOM | 2964 | CG1 | VAL | A | 162 | 0.770 | −7.682 | 6.916 | 1.00 | 12.11 | A |
| ATOM | 2965 | CG2 | VAL | A | 162 | 2.585 | −9.147 | 6.047 | 1.00 | 11.31 | A |
| ATOM | 2966 | C | VAL | A | 162 | 2.660 | −5.648 | 7.662 | 1.00 | 11.94 | A |
| ATOM | 2967 | O | VAL | A | 162 | 1.909 | −4.789 | 7.214 | 1.00 | 12.85 | A |
| ATOM | 2968 | N | PHE | A | 163 | 3.104 | −5.622 | 8.916 | 1.00 | 12.19 | A |
| ATOM | 2969 | CA | PHE | A | 163 | 2.681 | −4.561 | 9.825 | 1.00 | 12.54 | A |
| ATOM | 2970 | CB | PHE | A | 163 | 2.500 | −5.112 | 11.239 | 1.00 | 13.07 | A |
| ATOM | 2971 | CG | PHE | A | 163 | 1.527 | −6.248 | 11.321 | 1.00 | 14.49 | A |
| ATOM | 2972 | CD1 | PHE | A | 163 | 1.959 | −7.555 | 11.156 | 1.00 | 14.30 | A |
| ATOM | 2973 | CD2 | PHE | A | 163 | 0.168 | −6.007 | 11.532 | 1.00 | 14.47 | A |
| ATOM | 2974 | CE1 | PHE | A | 163 | 1.058 | −8.618 | 11.197 | 1.00 | 15.26 | A |
| ATOM | 2975 | CE2 | PHE | A | 163 | −0.743 | −7.061 | 11.574 | 1.00 | 15.43 | A |
| ATOM | 2976 | CZ | PHE | A | 163 | −0.297 | −8.371 | 11.406 | 1.00 | 14.83 | A |
| ATOM | 2977 | C | PHE | A | 163 | 3.625 | −3.362 | 9.868 | 1.00 | 12.48 | A |
| ATOM | 2978 | O | PHE | A | 163 | 3.233 | −2.280 | 10.305 | 1.00 | 12.19 | A |
| ATOM | 3252 | N | THR | A | 197 | −2.372 | −16.130 | 2.207 | 1.00 | 8.89 | A |
| ATOM | 3253 | CA | THR | A | 197 | −3.090 | −15.716 | 3.399 | 1.00 | 9.12 | A |
| ATOM | 3254 | CB | THR | A | 197 | −3.159 | −16.854 | 4.438 | 1.00 | 8.54 | A |
| ATOM | 3255 | OG1 | THR | A | 197 | −1.826 | −17.241 | 4.803 | 1.00 | 7.22 | A |
| ATOM | 3256 | CG2 | THR | A | 197 | −3.891 | −18.055 | 3.859 | 1.00 | 8.20 | A |
| ATOM | 3257 | C | THR | A | 197 | −2.349 | −14.557 | 4.045 | 1.00 | 10.07 | A |
| ATOM | 3258 | O | THR | A | 197 | −1.153 | −14.380 | 3.829 | 1.00 | 9.98 | A |
| ATOM | 3259 | N | LYS | A | 198 | −3.063 | −13.756 | 4.821 | 1.00 | 11.83 | A |
| ATOM | 3260 | CA | LYS | A | 198 | −2.431 | −12.648 | 5.525 | 1.00 | 14.16 | A |
| ATOM | 3261 | CB | LYS | A | 198 | −3.407 | −11.497 | 5.746 | 1.00 | 14.77 | A |
| ATOM | 3262 | CG | LYS | A | 198 | −2.803 | −10.367 | 6.571 | 1.00 | 16.50 | A |
| ATOM | 3263 | CD | LYS | A | 198 | −3.868 | −9.483 | 7.196 | 1.00 | 17.64 | A |
| ATOM | 3264 | CE | LYS | A | 198 | −3.217 | −8.361 | 8.008 | 1.00 | 18.15 | A |
| ATOM | 3265 | NZ | LYS | A | 198 | −4.215 | −7.462 | 8.646 | 1.00 | 18.92 | A |
| ATOM | 3266 | C | LYS | A | 198 | −2.042 | −13.213 | 6.882 | 1.00 | 15.13 | A |

TABLE 7-continued

Three-dimensional structural coordinate of the complex of
human hematopoietic PGDS (SEQ ID NO: 1) with calcium, glutathione and
Cibacron Blue

| ATOM | 3267 | O | LYS | A | 198 | −2.869 | −13.236 | 7.788 | 1.00 | 17.31 | A |
|---|---|---|---|---|---|---|---|---|---|---|---|
| ATOM | 3268 | N | LEU | A | 199 | −0.803 | −13.670 | 7.005 | 1.00 | 14.65 | A |
| ATOM | 3269 | CA | LEU | A | 199 | −0.257 | −14.254 | 8.234 | 1.00 | 13.81 | A |
| ATOM | 3270 | CB | LEU | A | 199 | −1.137 | −13.966 | 9.468 | 1.00 | 15.00 | A |
| ATOM | 3271 | CG | LEU | A | 199 | −1.354 | −12.517 | 9.953 | 1.00 | 15.52 | A |
| ATOM | 3272 | CD1 | LEU | A | 199 | −2.352 | −12.514 | 11.110 | 1.00 | 15.65 | A |
| ATOM | 3273 | CD2 | LEU | A | 199 | −0.032 | −11.901 | 10.400 | 1.00 | 16.55 | A |
| ATOM | 3274 | C | LEU | A | 199 | −0.078 | −15.770 | 8.070 | 1.00 | 13.40 | A |
| ATOM | 3275 | O | LEU | A | 199 | 0.673 | −16.360 | 8.862 | 1.00 | 12.28 | A |
| ATOM | 3276 | OXT | LEU | A | 199 | −0.695 | −16.347 | 7.147 | 1.00 | 12.25 | A |
| ATOM | 6573 | N1 | GSH | F | 200 | 4.240 | −22.620 | 20.817 | 1.00 | 44.60 | F |
| ATOM | 6574 | CA1 | GSH | F | 200 | 3.413 | −23.575 | 20.073 | 1.00 | 44.99 | F |
| ATOM | 6575 | C1 | GSH | F | 200 | 4.146 | −24.142 | 18.822 | 1.00 | 44.16 | F |
| ATOM | 6576 | O11 | GSH | F | 200 | 5.277 | −23.724 | 18.545 | 1.00 | 44.01 | F |
| ATOM | 6577 | O12 | GSH | F | 200 | 3.502 | −25.050 | 18.113 | 1.00 | 43.49 | F |
| ATOM | 6578 | CB1 | GSH | F | 200 | 2.101 | −22.895 | 19.661 | 1.00 | 45.74 | F |
| ATOM | 6579 | CG1 | GSH | F | 200 | 1.180 | −22.538 | 20.853 | 1.00 | 46.69 | F |
| ATOM | 6580 | CD1 | GSH | F | 200 | 0.010 | −21.712 | 20.254 | 1.00 | 47.11 | F |
| ATOM | 6581 | OE1 | GSH | F | 200 | −0.142 | −20.530 | 20.586 | 1.00 | 47.97 | F |
| ATOM | 6582 | N2 | GSH | F | 200 | −0.754 | −22.340 | 19.334 | 1.00 | 47.00 | F |
| ATOM | 6583 | CA2 | GSH | F | 200 | −1.817 | −21.594 | 18.641 | 1.00 | 46.63 | F |
| ATOM | 6584 | C2 | GSH | F | 200 | −3.172 | −22.214 | 18.985 | 1.00 | 46.78 | F |
| ATOM | 6585 | O2 | GSH | F | 200 | −3.381 | −23.428 | 18.891 | 1.00 | 46.26 | F |
| ATOM | 6586 | CB2 | GSH | F | 200 | −1.659 | −21.704 | 17.108 | 1.00 | 46.61 | F |
| ATOM | 6587 | SG2 | GSH | F | 200 | −0.726 | −20.334 | 16.354 | 1.00 | 45.55 | F |
| ATOM | 6588 | N3 | GSH | F | 200 | −4.138 | −21.341 | 19.347 | 1.00 | 47.03 | F |
| ATOM | 6589 | CA3 | GSH | F | 200 | −5.549 | −21.727 | 19.555 | 1.00 | 47.63 | F |
| ATOM | 6590 | C3 | GSH | F | 200 | −5.805 | −21.983 | 21.029 | 1.00 | 47.96 | F |
| ATOM | 6591 | O31 | GSH | F | 200 | −6.963 | −22.325 | 21.339 | 1.00 | 48.33 | F |
| ATOM | 6592 | O32 | GSH | F | 200 | −4.849 | −21.855 | 21.833 | 1.00 | 48.13 | F |
| ATOM | 6684 | C1 | CBD | V | 201 | 1.320 | −16.944 | 18.446 | 1.00 | 55.65 | V |
| ATOM | 6685 | SA | CBD | V | 201 | 0.790 | −17.122 | 20.115 | 1.00 | 56.02 | V |
| ATOM | 6686 | O1A | CBD | V | 201 | 1.575 | −18.205 | 20.799 | 1.00 | 55.76 | V |
| ATOM | 6687 | O2A | CBD | V | 201 | −0.636 | −17.464 | 19.966 | 1.00 | 55.91 | V |
| ATOM | 6688 | O3A | CBD | V | 201 | 1.221 | −15.829 | 20.717 | 1.00 | 55.92 | V |
| ATOM | 6689 | C2 | CBD | V | 201 | 2.711 | −17.027 | 18.129 | 1.00 | 55.38 | V |
| ATOM | 6690 | N2 | CBD | V | 201 | 3.702 | −17.265 | 19.274 | 1.00 | 55.19 | V |
| ATOM | 6691 | C3 | CBD | V | 201 | 3.112 | −16.894 | 16.760 | 1.00 | 55.20 | V |
| ATOM | 6692 | C4 | CBD | V | 201 | 4.532 | −16.974 | 16.323 | 1.00 | 54.93 | V |
| ATOM | 6693 | O4 | CBD | V | 201 | 5.374 | −17.167 | 17.212 | 1.00 | 55.39 | V |
| ATOM | 6694 | C5 | CBD | V | 201 | 5.017 | −16.849 | 14.925 | 1.00 | 54.45 | V |
| ATOM | 6695 | C6 | CBD | V | 201 | 6.495 | −16.945 | 14.509 | 1.00 | 54.14 | V |
| ATOM | 6696 | C7 | CBD | V | 201 | 6.812 | −16.806 | 13.140 | 1.00 | 53.94 | V |
| ATOM | 6697 | C8 | CBD | V | 201 | 5.803 | −16.585 | 12.172 | 1.00 | 53.98 | V |
| ATOM | 6698 | C9 | CBD | V | 201 | 4.432 | −16.493 | 12.529 | 1.00 | 54.22 | V |
| ATOM | 6699 | C10 | CBD | V | 201 | 4.023 | −16.624 | 13.897 | 1.00 | 54.48 | V |
| ATOM | 6700 | C11 | CBD | V | 201 | 2.621 | −16.543 | 14.333 | 1.00 | 54.89 | V |
| ATOM | 6701 | O11 | CBD | V | 201 | 1.771 | −16.353 | 13.468 | 1.00 | 54.55 | V |
| ATOM | 6702 | C12 | CBD | V | 201 | 2.094 | −16.666 | 15.725 | 1.00 | 55.45 | V |
| ATOM | 6703 | C13 | CBD | V | 201 | 0.676 | −16.584 | 16.095 | 1.00 | 56.18 | V |
| ATOM | 6704 | C14 | CBD | V | 201 | 0.298 | −16.725 | 17.474 | 1.00 | 55.98 | V |
| ATOM | 6705 | NB | CBD | V | 201 | −0.387 | −16.360 | 15.063 | 1.00 | 57.55 | V |
| ATOM | 6706 | CB1 | CBD | V | 201 | −4.096 | −17.069 | 15.898 | 1.00 | 61.45 | V |
| ATOM | 6707 | SB | CBD | V | 201 | −5.117 | −18.384 | 16.588 | 1.00 | 62.03 | V |
| ATOM | 6708 | O1B | CBD | V | 201 | −5.591 | −17.837 | 17.918 | 1.00 | 62.06 | V |
| ATOM | 6709 | O2B | CBD | V | 201 | −4.217 | −19.550 | 16.781 | 1.00 | 62.13 | V |
| ATOM | 6710 | O3B | CBD | V | 201 | −6.221 | −18.727 | 15.629 | 1.00 | 61.84 | V |
| ATOM | 6711 | CB2 | CBD | V | 201 | −4.648 | −15.806 | 15.457 | 1.00 | 61.61 | V |
| ATOM | 6712 | CB3 | CBD | V | 201 | −3.798 | −14.783 | 14.909 | 1.00 | 60.85 | V |
| ATOM | 6713 | CB4 | CBD | V | 201 | −2.415 | −14.973 | 14.785 | 1.00 | 59.79 | V |
| ATOM | 6714 | CB5 | CBD | V | 201 | −1.838 | −16.208 | 15.214 | 1.00 | 59.24 | V |
| ATOM | 6715 | CB6 | CBD | V | 201 | −2.667 | −17.266 | 15.769 | 1.00 | 60.28 | V |
| ATOM | 6716 | NC | CBD | V | 201 | −6.100 | −15.699 | 15.626 | 1.00 | 62.61 | V |
| ATOM | 6717 | NC1 | CBD | V | 201 | −7.272 | −13.869 | 16.843 | 1.00 | 64.01 | V |
| ATOM | 6718 | CC2 | CBD | V | 201 | −7.958 | −12.677 | 16.830 | 1.00 | 64.30 | V |
| ATOM | 6719 | XCL | CBD | V | 201 | −8.536 | −11.955 | 18.433 | 1.00 | 64.97 | V |
| ATOM | 6720 | NC3 | CBD | V | 201 | −8.179 | −12.086 | 15.587 | 1.00 | 64.60 | V |
| ATOM | 6721 | CC4 | CBD | V | 201 | −7.742 | −12.647 | 14.411 | 1.00 | 64.72 | V |
| ATOM | 6722 | NC5 | CBD | V | 201 | −7.067 | −13.826 | 14.459 | 1.00 | 64.27 | V |
| ATOM | 6723 | CC6 | CBD | V | 201 | −6.835 | −14.427 | 15.666 | 1.00 | 63.60 | V |
| ATOM | 6724 | ND | CBD | V | 201 | −7.999 | −11.990 | 13.118 | 1.00 | 65.16 | V |
| ATOM | 6725 | CD1 | CBD | V | 201 | −6.460 | −11.914 | 11.166 | 1.00 | 65.80 | V |
| ATOM | 6726 | SD | CBD | V | 201 | −5.663 | −10.543 | 12.000 | 1.00 | 66.14 | V |
| ATOM | 6727 | O1D | CBD | V | 201 | −4.963 | −11.035 | 13.249 | 1.00 | 66.20 | V |
| ATOM | 6728 | O2D | CBD | V | 201 | −6.740 | −9.533 | 12.229 | 1.00 | 66.14 | V |

TABLE 7-continued

Three-dimensional structural coordinate of the complex of
human hematopoietic PGDS (SEQ ID NO: 1) with calcium, glutathione and
Cibacron Blue

| ATOM | 6729 | O3D | CBD | V | 201 | −4.469 | −9.967 | 11.283 | 1.00 | 66.06 | V |
|---|---|---|---|---|---|---|---|---|---|---|---|
| ATOM | 6730 | CD2 | CBD | V | 201 | −7.612 | −12.553 | 11.819 | 1.00 | 65.58 | V |
| ATOM | 6731 | CD3 | CBD | V | 201 | −8.282 | −13.667 | 11.168 | 1.00 | 65.50 | V |
| ATOM | 6732 | CD4 | CBD | V | 201 | −7.820 | −14.138 | 9.898 | 1.00 | 65.62 | V |
| ATOM | 6733 | CD5 | CBD | V | 201 | −6.689 | −13.516 | 9.253 | 1.00 | 65.58 | V |
| ATOM | 6734 | CD6 | CBD | V | 201 | −6.009 | −12.418 | 9.867 | 1.00 | 65.66 | V |
| ATOM | 6736 | CA + 2 | CA2 | M | 902 | 10.668 | −20.783 | 23.896 | 1.00 | 51.04 | M |
| ATOM | 6737 | OH2 | WAT | S | 1 | 1.351 | −21.691 | 3.667 | 1.00 | 7.98 | S |
| ATOM | 6739 | OH2 | WAT | S | 3 | −1.239 | −27.422 | 7.740 | 1.00 | 3.33 | S |
| ATOM | 6740 | OH2 | WAT | S | 4 | 8.134 | −25.070 | 19.531 | 1.00 | 9.51 | S |
| ATOM | 6743 | OH2 | WAT | S | 7 | 6.599 | −20.828 | 11.162 | 1.00 | 4.11 | S |
| ATOM | 6747 | OH2 | WAT | S | 11 | 5.286 | −16.048 | 7.235 | 1.00 | 3.73 | S |
| ATOM | 6751 | OH2 | WAT | S | 15 | 6.780 | −21.479 | 14.227 | 1.00 | 6.02 | S |
| ATOM | 6758 | OH2 | WAT | S | 22 | 0.702 | −16.833 | 2.360 | 1.00 | 8.75 | S |
| ATOM | 6760 | OH2 | WAT | S | 24 | 7.629 | −15.477 | 2.582 | 1.00 | 9.74 | S |
| ATOM | 6761 | OH2 | WAT | S | 25 | −2.129 | −33.873 | 12.001 | 1.00 | 6.94 | S |
| ATOM | 6772 | OH2 | WAT | S | 36 | 0.027 | −13.756 | 1.035 | 1.00 | 15.53 | S |
| ATOM | 6773 | OH2 | WAT | S | 37 | 2.414 | −15.170 | 10.370 | 1.00 | 10.38 | S |
| ATOM | 6777 | OH2 | WAT | S | 42 | 9.861 | −20.611 | 21.788 | 1.00 | 19.36 | S |
| ATOM | 6782 | OH2 | WAT | S | 47 | −0.738 | −19.696 | 3.763 | 1.00 | 7.26 | S |
| ATOM | 6786 | OH2 | WAT | S | 51 | −8.079 | −21.562 | 9.291 | 1.00 | 11.54 | S |
| ATOM | 6798 | OH2 | WAT | S | 63 | 11.971 | −27.063 | 20.805 | 1.00 | 13.89 | S |
| ATOM | 6799 | OH2 | WAT | S | 64 | −6.746 | −29.289 | 4.136 | 1.00 | 17.17 | S |
| ATOM | 6806 | OH2 | WAT | S | 71 | 2.082 | −27.303 | 18.951 | 1.00 | 6.50 | S |
| ATOM | 6808 | OH2 | WAT | S | 73 | 6.370 | −34.029 | 20.049 | 1.00 | 7.66 | S |
| ATOM | 6833 | OH2 | WAT | S | 98 | −0.925 | −29.526 | 21.487 | 1.00 | 8.88 | S |
| ATOM | 6873 | OH2 | WAT | S | 138 | 12.612 | −27.001 | 23.449 | 1.00 | 21.34 | S |
| ATOM | 6881 | OH2 | WAT | S | 146 | 1.862 | −24.047 | 27.300 | 1.00 | 13.69 | S |
| ATOM | 6900 | OH2 | WAT | S | 165 | 8.353 | −19.515 | 24.914 | 1.00 | 21.77 | S |
| ATOM | 6940 | OH2 | WAT | S | 205 | −5.859 | −14.566 | 5.222 | 1.00 | 13.11 | S |
| ATOM | 6972 | OH2 | WAT | S | 237 | −2.575 | −19.558 | 21.111 | 1.00 | 44.73 | S |
| ATOM | 6992 | OH2 | WAT | S | 257 | −8.895 | −24.364 | 5.325 | 1.00 | 26.95 | S |
| ATOM | 6996 | OH2 | WAT | S | 261 | 4.413 | −17.589 | 25.511 | 1.00 | 30.40 | S |
| ATOM | 7000 | OH2 | WAT | S | 265 | −5.639 | −28.605 | 26.537 | 1.00 | 35.00 | S |
| ATOM | 7015 | OH2 | WAT | S | 280 | −6.647 | −16.720 | 1.613 | 1.00 | 29.73 | S |
| ATOM | 7031 | OH2 | WAT | S | 296 | 13.593 | −19.947 | 25.168 | 1.00 | 25.03 | S |
| ATOM | 7053 | OH2 | WAT | S | 318 | 6.658 | −19.330 | 21.220 | 1.00 | 29.42 | S |
| ATOM | 7057 | OH2 | WAT | S | 322 | 7.702 | −22.083 | 20.657 | 1.00 | 26.23 | S |
| ATOM | 7060 | OH2 | WAT | S | 325 | 13.812 | −24.922 | 22.589 | 1.00 | 25.62 | S |
| ATOM | 7066 | OH2 | WAT | S | 331 | −3.023 | −35.741 | 20.966 | 1.00 | 51.90 | S |
| ATOM | 7071 | OH2 | WAT | S | 336 | 8.646 | −22.439 | 23.070 | 1.00 | 32.36 | S |
| ATOM | 7117 | OH2 | WAT | S | 383 | −7.864 | −19.607 | 18.001 | 1.00 | 49.01 | S |
| ATOM | 7119 | OH2 | WAT | S | 385 | 12.122 | −19.312 | 22.304 | 1.00 | 36.04 | S |
| ATOM | 7149 | OH2 | WAT | S | 415 | 4.500 | −17.354 | 9.500 | 1.00 | 17.11 | S |
| ATOM | 7151 | OH2 | WAT | S | 417 | 3.003 | −10.979 | 2.789 | 1.00 | 8.57 | S |
| ATOM | 7161 | OH2 | WAT | S | 427 | 1.666 | −28.319 | 21.869 | 1.00 | 9.23 | s |
| ATOM | 7173 | OH2 | WAT | S | 439 | 1.707 | −26.590 | 23.994 | 1.00 | 20.49 | S |
| ATOM | 7175 | OH2 | WAT | S | 441 | −7.142 | −12.553 | 6.181 | 1.00 | 27.77 | S |
| ATOM | 7217 | OH2 | WAT | S | 483 | −1.287 | −25.245 | 26.731 | 1.00 | 38.16 | S |
| ATOM | 7239 | OH2 | WAT | S | 505 | 8.962 | −18.324 | 22.747 | 1.00 | 40.69 | S |
| ATOM | 7269 | OH2 | WAT | S | 535 | −8.231 | −19.382 | 10.779 | 1.00 | 39.27 | S |
| ATOM | 7291 | OH2 | WAT | S | 557 | −7.790 | −15.423 | 3.534 | 1.00 | 48.88 | S |
| ATOM | 7294 | OH2 | WAT | S | 560 | −6.131 | −17.042 | 6.655 | 1.00 | 28.01 | S |
| ATOM | 7305 | OH2 | WAT | S | 571 | −5.344 | −20.658 | 29.405 | 1.00 | 33.64 | S |
| ATOM | 7319 | OH2 | WAT | S | 585 | −8.529 | −10.641 | 23.648 | 1.00 | 36.23 | S |
| ATOM | 7335 | OH2 | WAT | S | 601 | 13.245 | −24.342 | 20.045 | 1.00 | 20.43 | S |
| ATOM | 7341 | OH2 | WAT | S | 607 | 15.091 | −23.061 | 18.509 | 1.00 | 28.00 | S |
| ATOM | 7342 | OH2 | WAT | S | 608 | 2.114 | −23.889 | 24.521 | 1.00 | 24.13 | S |
| ATOM | 7354 | OH2 | WAT | S | 620 | −5.822 | −33.782 | 12.796 | 1.00 | 39.40 | S |
| ATOM | 7412 | OH2 | WAT | S | 679 | −4.210 | −15.053 | 7.903 | 1.00 | 7.85 | S |
| ATOM | 7416 | OH2 | WAT | S | 683 | −11.812 | −20.860 | 17.588 | 1.00 | 35.78 | S |
| ATOM | 7418 | OH2 | WAT | S | 685 | −5.319 | −36.445 | 17.400 | 1.00 | 36.65 | S |
| ATOM | 7432 | OH2 | WAT | S | 701 | 0.414 | −10.954 | 3.856 | 1.00 | 3.57 | S |
| ATOM | 7433 | OH2 | WAT | S | 702 | 3.171 | −13.470 | 2.015 | 1.00 | 31.21 | S |
| ATOM | 7518 | OH2 | WAT | S | 792 | −6.880 | −19.345 | 1.064 | 1.00 | 28.83 | S |
| ATOM | 7544 | OH2 | WAT | S | 818 | −14.589 | −21.459 | 10.093 | 1.00 | 28.52 | S |
| ATOM | 7546 | OH2 | WAT | S | 820 | −15.291 | −27.899 | 16.026 | 1.00 | 38.45 | S |
| ATOM | 7576 | OH2 | WAT | S | 850 | 4.135 | −19.875 | 21.107 | 1.00 | 51.02 | S |
| ATOM | 7581 | OH2 | WAT | S | 855 | 5.075 | −11.173 | 29.078 | 1.00 | 44.63 | S |
| ATOM | 7582 | OH2 | WAT | S | 856 | −1.969 | −27.093 | 28.386 | 1.00 | 36.21 | S |
| ATOM | 7590 | OH2 | WAT | S | 864 | 1.742 | −9.916 | 24.316 | 1.00 | 49.81 | S |
| ATOM | 7591 | OH2 | WAT | S | 865 | 6.598 | −16.698 | 4.969 | 1.00 | 27.41 | S |

TABLE 8

Three-dimensional structural coordinate of the complex of human hematopoietic PGDS (SEQ ID NO: 1) with magnesium, glutathione and 4-benzhydryloxy-1-{3-(1H-tetrazol-5-yl)-propyl}piperidine (HQL-79)

| ATOM | 4966 | N   | TYR | A | 8  | 17.463 | −2.741 | 10.967 | 1.00 | 2.30  | A |
|------|------|-----|-----|---|----|--------|--------|--------|------|-------|---|
| ATOM | 4967 | CA  | TYR | A | 8  | 16.069 | −2.648 | 11.384 | 1.00 | 2.27  | A |
| ATOM | 4968 | CB  | TYR | A | 8  | 15.463 | −1.311 | 10.947 | 1.00 | 1.93  | A |
| ATOM | 4969 | CG  | TYR | A | 8  | 14.123 | −1.007 | 11.579 | 1.00 | 1.75  | A |
| ATOM | 4970 | CD1 | TYR | A | 8  | 13.996 | −0.888 | 12.962 | 1.00 | 1.76  | A |
| ATOM | 4971 | CE1 | TYR | A | 8  | 12.771 | −0.568 | 13.551 | 1.00 | 1.82  | A |
| ATOM | 4972 | CD2 | TYR | A | 8  | 12.987 | −0.803 | 10.792 | 1.00 | 1.81  | A |
| ATOM | 4973 | CE2 | TYR | A | 8  | 11.762 | −0.479 | 11.366 | 1.00 | 2.19  | A |
| ATOM | 4974 | CZ  | TYR | A | 8  | 11.658 | −0.360 | 12.748 | 1.00 | 1.84  | A |
| ATOM | 4975 | OH  | TYR | A | 8  | 10.456 | −0.003 | 13.318 | 1.00 | 2.39  | A |
| ATOM | 4976 | C   | TYR | A | 8  | 15.320 | −3.786 | 10.709 | 1.00 | 2.74  | A |
| ATOM | 4977 | O   | TYR | A | 8  | 15.902 | −4.543 | 9.939  | 1.00 | 2.59  | A |
| ATOM | 4978 | N   | PHE | A | 9  | 14.033 | −3.916 | 11.011 | 1.00 | 3.54  | A |
| ATOM | 4979 | CA  | PHE | A | 9  | 13.216 | −4.945 | 10.378 | 1.00 | 4.12  | A |
| ATOM | 4980 | CB  | PHE | A | 9  | 11.873 | −5.079 | 11.102 | 1.00 | 4.53  | A |
| ATOM | 4981 | CG  | PHE | A | 9  | 11.981 | −5.579 | 12.511 | 1.00 | 4.71  | A |
| ATOM | 4982 | CD1 | PHE | A | 9  | 11.552 | −4.791 | 13.577 | 1.00 | 5.32  | A |
| ATOM | 4983 | CD2 | PHE | A | 9  | 12.499 | −6.844 | 12.777 | 1.00 | 5.02  | A |
| ATOM | 4984 | CE1 | PHE | A | 9  | 11.639 | −5.256 | 14.889 | 1.00 | 5.60  | A |
| ATOM | 4985 | CE2 | PHE | A | 9  | 12.589 | −7.316 | 14.085 | 1.00 | 5.47  | A |
| ATOM | 4986 | CZ  | PHE | A | 9  | 12.158 | −6.521 | 15.142 | 1.00 | 5.95  | A |
| ATOM | 4987 | C   | PHE | A | 9  | 12.946 | −4.517 | 8.936  | 1.00 | 4.36  | A |
| ATOM | 4988 | O   | PHE | A | 9  | 13.277 | −3.398 | 8.532  | 1.00 | 4.11  | A |
| ATOM | 4989 | N   | ASN | A | 10 | 12.354 | −5.405 | 8.146  | 1.00 | 4.68  | A |
| ATOM | 4990 | CA  | ASN | A | 10 | 12.026 | −5.046 | 6.778  | 1.00 | 5.42  | A |
| ATOM | 4991 | CB  | ASN | A | 10 | 11.933 | −6.278 | 5.880  | 1.00 | 5.82  | A |
| ATOM | 4992 | CG  | ASN | A | 10 | 11.502 | −5.933 | 4.465  | 1.00 | 6.24  | A |
| ATOM | 4993 | OD1 | ASN | A | 10 | 11.787 | −4.841 | 3.954  | 1.00 | 6.66  | A |
| ATOM | 4994 | ND2 | ASN | A | 10 | 10.822 | −6.869 | 3.814  | 1.00 | 7.65  | A |
| ATOM | 4995 | C   | ASN | A | 10 | 10.694 | −4.319 | 6.813  | 1.00 | 5.70  | A |
| ATOM | 4996 | O   | ASN | A | 10 | 9.636  | −4.892 | 6.537  | 1.00 | 5.50  | A |
| ATOM | 4997 | N   | MET | A | 11 | 10.763 | −3.054 | 7.208  | 1.00 | 6.01  | A |
| ATOM | 4998 | CA  | MET | A | 11 | 9.597  | −2.189 | 7.287  | 1.00 | 6.18  | A |
| ATOM | 4999 | CB  | MET | A | 11 | 8.725  | −2.548 | 8.500  | 1.00 | 9.09  | A |
| ATOM | 5000 | CG  | MET | A | 11 | 9.416  | −2.585 | 9.840  | 1.00 | 11.64 | A |
| ATOM | 5001 | SD  | MET | A | 11 | 8.242  | −3.077 | 11.159 | 1.00 | 15.13 | A |
| ATOM | 5002 | CE  | MET | A | 11 | 8.390  | −4.861 | 11.133 | 1.00 | 14.75 | A |
| ATOM | 5003 | C   | MET | A | 11 | 10.072 | −0.749 | 7.378  | 1.00 | 5.10  | A |
| ATOM | 5004 | O   | MET | A | 11 | 11.250 | −0.502 | 7.633  | 1.00 | 4.65  | A |
| ATOM | 5005 | N   | ARG | A | 12 | 9.168  | 0.193  | 7.132  | 1.00 | 4.17  | A |
| ATOM | 5006 | CA  | ARG | A | 12 | 9.518  | 1.607  | 7.220  | 1.00 | 3.48  | A |
| ATOM | 5007 | CB  | ARG | A | 12 | 8.395  | 2.484  | 6.640  | 1.00 | 3.58  | A |
| ATOM | 5008 | CG  | ARG | A | 12 | 8.129  | 2.254  | 5.147  | 1.00 | 4.20  | A |
| ATOM | 5009 | CD  | ARG | A | 12 | 7.130  | 3.273  | 4.574  | 1.00 | 4.87  | A |
| ATOM | 5010 | NE  | ARG | A | 12 | 5.888  | 3.302  | 5.344  | 1.00 | 5.23  | A |
| ATOM | 5011 | CZ  | ARG | A | 12 | 4.941  | 2.372  | 5.278  | 1.00 | 5.80  | A |
| ATOM | 5012 | NH1 | ARG | A | 12 | 5.080  | 1.336  | 4.466  | 1.00 | 5.95  | A |
| ATOM | 5013 | NH2 | ARG | A | 12 | 3.865  | 2.465  | 6.052  | 1.00 | 5.74  | A |
| ATOM | 5014 | C   | ARG | A | 12 | 9.725  | 1.891  | 8.704  | 1.00 | 2.96  | A |
| ATOM | 5015 | O   | ARG | A | 12 | 10.844 | 2.170  | 9.144  | 1.00 | 2.74  | A |
| ATOM | 5016 | N   | GLY | A | 13 | 8.639  | 1.808  | 9.466  | 1.00 | 2.56  | A |
| ATOM | 5017 | CA  | GLY | A | 13 | 8.697  | 2.009  | 10.904 | 1.00 | 2.19  | A |
| ATOM | 5018 | C   | GLY | A | 13 | 9.591  | 3.120  | 11.415 | 1.00 | 2.22  | A |
| ATOM | 5019 | O   | GLY | A | 13 | 9.625  | 4.212  | 10.850 | 1.00 | 2.01  | A |
| ATOM | 5020 | N   | ARG | A | 14 | 10.321 | 2.833  | 12.489 | 1.00 | 2.32  | A |
| ATOM | 5021 | CA  | ARG | A | 14 | 11.192 | 3.823  | 13.108 | 1.00 | 2.60  | A |
| ATOM | 5022 | CB  | ARG | A | 14 | 11.457 | 3.436  | 14.570 | 1.00 | 2.99  | A |
| ATOM | 5023 | CG  | ARG | A | 14 | 10.223 | 3.584  | 15.442 | 1.00 | 4.04  | A |
| ATOM | 5024 | CD  | ARG | A | 14 | 10.492 | 3.265  | 16.906 | 1.00 | 5.12  | A |
| ATOM | 5025 | NE  | ARG | A | 14 | 9.320  | 3.584  | 17.718 | 1.00 | 6.44  | A |
| ATOM | 5026 | CZ  | ARG | A | 14 | 8.960  | 4.815  | 18.073 | 1.00 | 7.09  | A |
| ATOM | 5027 | NH1 | ARG | A | 14 | 9.688  | 5.867  | 17.709 | 1.00 | 7.50  | A |
| ATOM | 5028 | NH2 | ARG | A | 14 | 7.841  | 4.998  | 18.765 | 1.00 | 7.96  | A |
| ATOM | 5029 | C   | ARG | A | 14 | 12.510 | 4.077  | 12.392 | 1.00 | 2.41  | A |
| ATOM | 5030 | O   | ARG | A | 14 | 13.238 | 4.997  | 12.750 | 1.00 | 2.83  | A |
| ATOM | 5031 | N   | ALA | A | 15 | 12.822 | 3.277  | 11.378 | 1.00 | 2.21  | A |
| ATOM | 5032 | CA  | ALA | A | 15 | 14.068 | 3.484  | 10.648 | 1.00 | 1.80  | A |
| ATOM | 5033 | CB  | ALA | A | 15 | 14.627 | 2.144  | 10.156 | 1.00 | 2.27  | A |
| ATOM | 5034 | C   | ALA | A | 15 | 13.858 | 4.405  | 9.458  | 1.00 | 1.82  | A |
| ATOM | 5035 | O   | ALA | A | 15 | 14.815 | 4.976  | 8.938  | 1.00 | 1.57  | A |
| ATOM | 5036 | N   | GLU | A | 16 | 12.610 | 4.575  | 9.033  | 1.00 | 1.93  | A |
| ATOM | 5037 | CA  | GLU | A | 16 | 12.359 | 5.372  | 7.840  | 1.00 | 1.94  | A |
| ATOM | 5038 | CB  | GLU | A | 16 | 10.870 | 5.346  | 7.482  | 1.00 | 2.14  | A |
| ATOM | 5039 | CG  | GLU | A | 16 | 10.579 | 5.687  | 6.016  | 1.00 | 2.49  | A |
| ATOM | 5040 | CD  | GLU | A | 16 | 11.126 | 4.665  | 5.011  | 1.00 | 3.04  | A |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 5041 | OE1 | GLU | A | 16 | 11.667 | 3.615 | 5.422 | 1.00 | 3.42 | A |
|---|---|---|---|---|---|---|---|---|---|---|---|
| ATOM | 5042 | OE2 | GLU | A | 16 | 11.008 | 4.916 | 3.793 | 1.00 | 3.55 | A |
| ATOM | 5043 | C | GLU | A | 16 | 12.875 | 6.801 | 7.878 | 1.00 | 1.89 | A |
| ATOM | 5044 | O | GLU | A | 16 | 13.356 | 7.302 | 6.866 | 1.00 | 1.73 | A |
| ATOM | 5045 | N | ILE | A | 17 | 12.807 | 7.460 | 9.030 | 1.00 | 1.19 | A |
| ATOM | 5046 | CA | ILE | A | 17 | 13.306 | 8.825 | 9.107 | 1.00 | 1.35 | A |
| ATOM | 5047 | CB | ILE | A | 17 | 13.031 | 9.454 | 10.510 | 1.00 | 1.50 | A |
| ATOM | 5048 | CG2 | ILE | A | 17 | 13.702 | 8.649 | 11.614 | 1.00 | 1.52 | A |
| ATOM | 5049 | CG1 | ILE | A | 17 | 13.514 | 10.909 | 10.532 | 1.00 | 1.26 | A |
| ATOM | 5050 | CD1 | ILE | A | 17 | 12.833 | 11.795 | 9.501 | 1.00 | 1.74 | A |
| ATOM | 5051 | C | ILE | A | 17 | 14.807 | 8.856 | 8.760 | 1.00 | 1.44 | A |
| ATOM | 5052 | O | ILE | A | 17 | 15.275 | 9.775 | 8.079 | 1.00 | 2.26 | A |
| ATOM | 5242 | N | TRP | A | 39 | 16.279 | −11.644 | 14.583 | 1.00 | 11.83 | A |
| ATOM | 5243 | CA | TRP | A | 39 | 16.330 | −10.580 | 15.586 | 1.00 | 11.41 | A |
| ATOM | 5244 | CB | TRP | A | 39 | 14.938 | −9.947 | 15.714 | 1.00 | 10.48 | A |
| ATOM | 5245 | CG | TRP | A | 39 | 14.752 | −8.981 | 16.856 | 1.00 | 9.62 | A |
| ATOM | 5246 | CD2 | TRP | A | 39 | 15.630 | −7.913 | 17.256 | 1.00 | 9.22 | A |
| ATOM | 5247 | CE2 | TRP | A | 39 | 15.022 | −7.269 | 18.356 | 1.00 | 9.06 | A |
| ATOM | 5248 | CE3 | TRP | A | 39 | 16.865 | −7.439 | 16.793 | 1.00 | 8.94 | A |
| ATOM | 5249 | CD1 | TRP | A | 39 | 13.687 | −8.935 | 17.705 | 1.00 | 9.52 | A |
| ATOM | 5250 | NE1 | TRP | A | 39 | 13.842 | −7.915 | 18.607 | 1.00 | 9.30 | A |
| ATOM | 5251 | CZ2 | TRP | A | 39 | 15.608 | −6.173 | 19.005 | 1.00 | 8.71 | A |
| ATOM | 5252 | CZ3 | TRP | A | 39 | 17.450 | −6.345 | 17.442 | 1.00 | 8.93 | A |
| ATOM | 5253 | CH2 | TRP | A | 39 | 16.817 | −5.729 | 18.536 | 1.00 | 8.40 | A |
| ATOM | 5254 | C | TRP | A | 39 | 16.848 | −11.032 | 16.960 | 1.00 | 11.66 | A |
| ATOM | 5255 | O | TRP | A | 39 | 17.710 | −10.382 | 17.547 | 1.00 | 11.72 | A |
| ATOM | 5256 | N | PRO | A | 40 | 16.337 | −12.156 | 17.487 | 1.00 | 12.01 | A |
| ATOM | 5257 | CD | PRO | A | 40 | 15.261 | −13.023 | 16.971 | 1.00 | 12.11 | A |
| ATOM | 5258 | CA | PRO | A | 40 | 16.795 | −12.629 | 18.799 | 1.00 | 12.31 | A |
| ATOM | 5259 | CB | PRO | A | 40 | 16.171 | −14.016 | 18.894 | 1.00 | 12.32 | A |
| ATOM | 5260 | CG | PRO | A | 40 | 14.862 | −13.816 | 18.203 | 1.00 | 12.38 | A |
| ATOM | 5261 | C | PRO | A | 40 | 18.308 | −12.656 | 19.023 | 1.00 | 12.59 | A |
| ATOM | 5262 | O | PRO | A | 40 | 18.799 | −12.163 | 20.042 | 1.00 | 12.72 | A |
| ATOM | 5263 | N | GLU | A | 41 | 19.053 | −13.223 | 18.081 | 1.00 | 12.84 | A |
| ATOM | 5264 | CA | GLU | A | 41 | 20.500 | −13.309 | 18.231 | 1.00 | 13.09 | A |
| ATOM | 5265 | CB | GLU | A | 41 | 21.054 | −14.364 | 17.270 | 1.00 | 14.07 | A |
| ATOM | 5266 | CG | GLU | A | 41 | 20.459 | −15.745 | 17.544 | 1.00 | 15.68 | A |
| ATOM | 5267 | CD | GLU | A | 41 | 20.995 | −16.831 | 16.634 | 1.00 | 16.54 | A |
| ATOM | 5268 | OE1 | GLU | A | 41 | 20.297 | −17.854 | 16.473 | 1.00 | 17.39 | A |
| ATOM | 5269 | OE2 | GLU | A | 41 | 22.109 | −16.677 | 16.088 | 1.00 | 17.54 | A |
| ATOM | 5270 | C | GLU | A | 41 | 21.229 | −11.972 | 18.074 | 1.00 | 12.61 | A |
| ATOM | 5271 | O | GLU | A | 41 | 22.373 | −11.827 | 18.506 | 1.00 | 12.75 | A |
| ATOM | 5272 | N | ILE | A | 42 | 20.566 | −10.995 | 17.467 | 1.00 | 11.99 | A |
| ATOM | 5273 | CA | ILE | A | 42 | 21.160 | −9.673 | 17.307 | 1.00 | 11.37 | A |
| ATOM | 5274 | CB | ILE | A | 42 | 20.596 | −8.939 | 16.065 | 1.00 | 11.34 | A |
| ATOM | 5275 | CG2 | ILE | A | 42 | 20.978 | −7.464 | 16.105 | 1.00 | 11.36 | A |
| ATOM | 5276 | CG1 | ILE | A | 42 | 21.128 | −9.596 | 14.788 | 1.00 | 11.71 | A |
| ATOM | 5277 | CD1 | ILE | A | 42 | 20.546 | −9.013 | 13.510 | 1.00 | 11.80 | A |
| ATOM | 5278 | C | ILE | A | 42 | 20.819 | −8.870 | 18.561 | 1.00 | 11.10 | A |
| ATOM | 5279 | O | ILE | A | 42 | 21.665 | −8.178 | 19.123 | 1.00 | 10.73 | A |
| ATOM | 5280 | N | LYS | A | 43 | 19.571 | −8.996 | 19.000 | 1.00 | 10.69 | A |
| ATOM | 5281 | CA | LYS | A | 43 | 19.075 | −8.292 | 20.176 | 1.00 | 11.07 | A |
| ATOM | 5282 | CB | LYS | A | 43 | 17.665 | −8.788 | 20.506 | 1.00 | 10.56 | A |
| ATOM | 5283 | CG | LYS | A | 43 | 17.027 | −8.164 | 21.737 | 1.00 | 10.22 | A |
| ATOM | 5284 | CD | LYS | A | 43 | 15.654 | −8.770 | 21.969 | 1.00 | 10.10 | A |
| ATOM | 5285 | CE | LYS | A | 43 | 14.982 | −8.200 | 23.204 | 1.00 | 9.67 | A |
| ATOM | 5286 | NZ | LYS | A | 43 | 14.601 | −6.767 | 23.037 | 1.00 | 9.62 | A |
| ATOM | 5287 | C | LYS | A | 43 | 19.986 | −8.462 | 21.391 | 1.00 | 11.41 | A |
| ATOM | 5288 | O | LYS | A | 43 | 20.292 | −7.495 | 22.089 | 1.00 | 11.31 | A |
| ATOM | 5328 | N | GLY | A | 49 | 18.949 | −3.542 | 23.669 | 1.00 | 8.96 | A |
| ATOM | 5329 | CA | GLY | A | 49 | 18.093 | −4.495 | 22.982 | 1.00 | 8.21 | A |
| ATOM | 5330 | C | GLY | A | 49 | 16.991 | −3.983 | 22.078 | 1.00 | 7.54 | A |
| ATOM | 5331 | O | GLY | A | 49 | 15.959 | −4.642 | 21.937 | 1.00 | 7.64 | A |
| ATOM | 5332 | N | LYS | A | 50 | 17.203 | −2.832 | 21.444 | 1.00 | 6.95 | A |
| ATOM | 5333 | CA | LYS | A | 50 | 16.197 | −2.263 | 20.554 | 1.00 | 6.45 | A |
| ATOM | 5334 | CB | LYS | A | 50 | 15.528 | −1.042 | 21.199 | 1.00 | 7.37 | A |
| ATOM | 5335 | CG | LYS | A | 50 | 14.831 | −1.283 | 22.528 | 1.00 | 9.43 | A |
| ATOM | 5336 | CD | LYS | A | 50 | 13.634 | −2.197 | 22.385 | 1.00 | 10.69 | A |
| ATOM | 5337 | CE | LYS | A | 50 | 12.660 | −2.004 | 23.550 | 1.00 | 11.86 | A |
| ATOM | 5338 | NZ | LYS | A | 50 | 13.354 | −1.838 | 24.858 | 1.00 | 12.34 | A |
| ATOM | 5339 | C | LYS | A | 50 | 16.803 | −1.810 | 19.233 | 1.00 | 5.62 | A |
| ATOM | 5340 | O | LYS | A | 50 | 17.999 | −1.515 | 19.152 | 1.00 | 4.99 | A |
| ATOM | 5341 | N | ILE | A | 51 | 15.968 | −1.766 | 18.198 | 1.00 | 4.81 | A |
| ATOM | 5342 | CA | ILE | A | 51 | 16.386 | −1.277 | 16.892 | 1.00 | 4.23 | A |
| ATOM | 5343 | CB | ILE | A | 51 | 16.427 | −2.400 | 15.821 | 1.00 | 4.50 | A |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 5344 | CG2 | ILE | A | 51 | 17.736 | −3.173 | 15.951 | 1.00 | 4.04 | A |
|------|------|-----|-----|---|----|--------|--------|--------|------|------|---|
| ATOM | 5345 | CG1 | ILE | A | 51 | 15.214 | −3.320 | 15.954 | 1.00 | 4.67 | A |
| ATOM | 5346 | CD1 | ILE | A | 51 | 15.125 | −4.353 | 14.851 | 1.00 | 5.01 | A |
| ATOM | 5347 | C   | ILE | A | 51 | 15.403 | −0.173 | 16.503 | 1.00 | 3.91 | A |
| ATOM | 5348 | O   | ILE | A | 51 | 14.295 | −0.096 | 17.037 | 1.00 | 3.85 | A |
| ATOM | 5349 | N   | PRO | A | 52 | 15.769 | 0.677  | 15.540 | 1.00 | 3.47 | A |
| ATOM | 5350 | CD  | PRO | A | 52 | 14.929 | 1.849  | 15.221 | 1.00 | 3.53 | A |
| ATOM | 5351 | CA  | PRO | A | 52 | 17.011 | 0.704  | 14.767 | 1.00 | 3.15 | A |
| ATOM | 5352 | CB  | PRO | A | 52 | 16.712 | 1.735  | 13.687 | 1.00 | 3.26 | A |
| ATOM | 5353 | CG  | PRO | A | 52 | 15.878 | 2.741  | 14.442 | 1.00 | 3.38 | A |
| ATOM | 5354 | C   | PRO | A | 52 | 18.294 | 1.063  | 15.490 | 1.00 | 3.11 | A |
| ATOM | 5355 | O   | PRO | A | 52 | 18.288 | 1.690  | 16.547 | 1.00 | 3.03 | A |
| ATOM | 5356 | N   | ILE | A | 53 | 19.394 | 0.632  | 14.887 | 1.00 | 3.27 | A |
| ATOM | 5357 | CA  | ILE | A | 53 | 20.723 | 0.974  | 15.351 | 1.00 | 3.18 | A |
| ATOM | 5358 | CB  | ILE | A | 53 | 21.495 | −0.199 | 16.021 | 1.00 | 3.72 | A |
| ATOM | 5359 | CG2 | ILE | A | 53 | 20.858 | −0.553 | 17.356 | 1.00 | 4.09 | A |
| ATOM | 5360 | CG1 | ILE | A | 53 | 21.596 | −1.386 | 15.064 | 1.00 | 4.16 | A |
| ATOM | 5361 | CD1 | ILE | A | 53 | 22.466 | −2.510 | 15.594 | 1.00 | 5.20 | A |
| ATOM | 5362 | C   | ILE | A | 53 | 21.453 | 1.369  | 14.074 | 1.00 | 3.15 | A |
| ATOM | 5363 | O   | ILE | A | 53 | 21.090 | 0.928  | 12.978 | 1.00 | 2.64 | A |
| ATOM | 5423 | N   | HIS | A | 62 | 22.206 | 4.210  | 18.799 | 1.00 | 3.50 | A |
| ATOM | 5424 | CA  | HIS | A | 62 | 20.835 | 3.722  | 18.927 | 1.00 | 2.95 | A |
| ATOM | 5425 | CB  | HIS | A | 62 | 20.705 | 2.722  | 20.090 | 1.00 | 3.26 | A |
| ATOM | 5426 | CG  | HIS | A | 62 | 20.931 | 3.318  | 21.445 | 1.00 | 3.82 | A |
| ATOM | 5427 | CD2 | HIS | A | 62 | 22.047 | 3.813  | 22.031 | 1.00 | 3.92 | A |
| ATOM | 5428 | ND1 | HIS | A | 62 | 19.923 | 3.438  | 22.376 | 1.00 | 4.07 | A |
| ATOM | 5429 | CE1 | HIS | A | 62 | 20.406 | 3.984  | 23.478 | 1.00 | 3.93 | A |
| ATOM | 5430 | NE2 | HIS | A | 62 | 21.692 | 4.222  | 23.295 | 1.00 | 4.38 | A |
| ATOM | 5431 | C   | HIS | A | 62 | 19.890 | 4.910  | 19.100 | 1.00 | 2.81 | A |
| ATOM | 5432 | O   | HIS | A | 62 | 20.342 | 6.050  | 19.215 | 1.00 | 2.85 | A |
| ATOM | 5433 | N   | GLN | A | 63 | 18.586 | 4.624  | 19.094 | 1.00 | 2.56 | A |
| ATOM | 5434 | CA  | GLN | A | 63 | 17.501 | 5.612  | 19.201 | 1.00 | 2.38 | A |
| ATOM | 5435 | CB  | GLN | A | 63 | 17.730 | 6.586  | 20.366 | 1.00 | 2.32 | A |
| ATOM | 5436 | CG  | GLN | A | 63 | 17.350 | 6.000  | 21.730 | 1.00 | 2.96 | A |
| ATOM | 5437 | CD  | GLN | A | 63 | 15.851 | 5.823  | 21.898 | 1.00 | 3.14 | A |
| ATOM | 5438 | OE1 | GLN | A | 63 | 15.063 | 6.295  | 21.081 | 1.00 | 3.72 | A |
| ATOM | 5439 | NE2 | GLN | A | 63 | 15.449 | 5.151  | 22.971 | 1.00 | 3.70 | A |
| ATOM | 5440 | C   | GLN | A | 63 | 17.348 | 6.359  | 17.878 | 1.00 | 2.37 | A |
| ATOM | 5441 | O   | GLN | A | 63 | 18.164 | 7.212  | 17.516 | 1.00 | 2.00 | A |
| ATOM | 5442 | N   | SER | A | 64 | 16.279 | 6.028  | 17.160 | 1.00 | 2.43 | A |
| ATOM | 5443 | CA  | SER | A | 64 | 16.037 | 6.600  | 15.841 | 1.00 | 2.49 | A |
| ATOM | 5444 | CB  | SER | A | 64 | 14.678 | 6.132  | 15.296 | 1.00 | 2.81 | A |
| ATOM | 5445 | OG  | SER | A | 64 | 13.591 | 6.666  | 16.036 | 1.00 | 3.28 | A |
| ATOM | 5446 | C   | SER | A | 64 | 16.138 | 8.113  | 15.705 | 1.00 | 2.23 | A |
| ATOM | 5447 | O   | SER | A | 64 | 16.742 | 8.603  | 14.750 | 1.00 | 2.28 | A |
| ATOM | 5448 | N   | LEU | A | 65 | 15.553 | 8.854  | 16.639 | 1.00 | 2.47 | A |
| ATOM | 5449 | CA  | LEU | A | 65 | 15.581 | 10.307 | 16.548 | 1.00 | 2.69 | A |
| ATOM | 5450 | CB  | LEU | A | 65 | 14.465 | 10.899 | 17.409 | 1.00 | 3.06 | A |
| ATOM | 5451 | CG  | LEU | A | 65 | 13.100 | 10.321 | 17.010 | 1.00 | 3.16 | A |
| ATOM | 5452 | CD1 | LEU | A | 65 | 11.993 | 10.980 | 17.835 | 1.00 | 4.12 | A |
| ATOM | 5453 | CD2 | LEU | A | 65 | 12.854 | 10.538 | 15.522 | 1.00 | 3.74 | A |
| ATOM | 5454 | C   | LEU | A | 65 | 16.935 | 10.886 | 16.925 | 1.00 | 2.92 | A |
| ATOM | 5455 | O   | LEU | A | 65 | 17.330 | 11.935 | 16.411 | 1.00 | 3.32 | A |
| ATOM | 5662 | N   | ASP | A | 93 | 9.345  | 15.416 | 18.542 | 1.00 | 3.67 | A |
| ATOM | 5663 | CA  | ASP | A | 93 | 8.972  | 14.730 | 19.781 | 1.00 | 3.91 | A |
| ATOM | 5664 | CB  | ASP | A | 93 | 9.654  | 15.361 | 20.997 | 1.00 | 5.09 | A |
| ATOM | 5665 | CG  | ASP | A | 93 | 11.041 | 14.797 | 21.243 | 1.00 | 6.18 | A |
| ATOM | 5666 | OD1 | ASP | A | 93 | 11.674 | 15.203 | 22.246 | 1.00 | 7.93 | A |
| ATOM | 5667 | OD2 | ASP | A | 93 | 11.495 | 13.945 | 20.442 | 1.00 | 7.01 | A |
| ATOM | 5668 | C   | ASP | A | 93 | 7.462  | 14.714 | 19.985 | 1.00 | 3.61 | A |
| ATOM | 5669 | O   | ASP | A | 93 | 6.926  | 13.766 | 20.539 | 1.00 | 3.01 | A |
| ATOM | 5670 | N   | THR | A | 94 | 6.776  | 15.762 | 19.540 | 1.00 | 3.46 | A |
| ATOM | 5671 | CA  | THR | A | 94 | 5.325  | 15.808 | 19.676 | 1.00 | 3.57 | A |
| ATOM | 5672 | CB  | THR | A | 94 | 4.792  | 17.195 | 19.258 | 1.00 | 3.73 | A |
| ATOM | 5673 | OG1 | THR | A | 94 | 5.167  | 18.152 | 20.257 | 1.00 | 4.06 | A |
| ATOM | 5674 | CG2 | THR | A | 94 | 3.273  | 17.186 | 19.101 | 1.00 | 3.88 | A |
| ATOM | 5675 | C   | THR | A | 94 | 4.721  | 14.702 | 18.811 | 1.00 | 3.74 | A |
| ATOM | 5676 | O   | THR | A | 94 | 3.789  | 14.001 | 19.223 | 1.00 | 3.84 | A |
| ATOM | 5677 | N   | LEU | A | 95 | 5.268  | 14.520 | 17.618 | 1.00 | 3.30 | A |
| ATOM | 5678 | CA  | LEU | A | 95 | 4.766  | 13.475 | 16.740 | 1.00 | 3.42 | A |
| ATOM | 5679 | CB  | LEU | A | 95 | 5.377  | 13.609 | 15.346 | 1.00 | 3.94 | A |
| ATOM | 5680 | CG  | LEU | A | 95 | 4.919  | 14.812 | 14.518 | 1.00 | 4.38 | A |
| ATOM | 5681 | CD1 | LEU | A | 95 | 5.763  | 14.924 | 13.245 | 1.00 | 4.83 | A |
| ATOM | 5682 | CD2 | LEU | A | 95 | 3.444  | 14.650 | 14.184 | 1.00 | 5.05 | A |
| ATOM | 5683 | C   | LEU | A | 95 | 5.117  | 12.113 | 17.323 | 1.00 | 3.25 | A |

TABLE 8-continued

Three-dimensional structural coordinate of the complex of human hematopoietic PGDS (SEQ ID NO: 1) with magnesium, glutathione and 4-benzhydryloxy-1-{3-(1H-tetrazol-5-yl)-propyl}piperidine (HQL-79)

| ATOM | 5684 | O | LEU | A | 95 | 4.275 | 11.217 | 17.397 | 1.00 | 3.09 | A |
|---|---|---|---|---|---|---|---|---|---|---|---|
| ATOM | 5685 | N | ASP | A | 96 | 6.364 | 11.960 | 17.756 | 1.00 | 3.25 | A |
| ATOM | 5686 | CA | ASP | A | 96 | 6.796 | 10.687 | 18.305 | 1.00 | 3.69 | A |
| ATOM | 5687 | CB | ASP | A | 96 | 8.301 | 10.702 | 18.585 | 1.00 | 4.27 | A |
| ATOM | 5688 | CG | ASP | A | 96 | 8.891 | 9.305 | 18.644 | 1.00 | 4.99 | A |
| ATOM | 5689 | OD1 | ASP | A | 96 | 8.774 | 8.574 | 17.637 | 1.00 | 6.02 | A |
| ATOM | 5690 | OD2 | ASP | A | 96 | 9.478 | 8.933 | 19.684 | 1.00 | 6.06 | A |
| ATOM | 5691 | C | ASP | A | 96 | 6.038 | 10.316 | 19.573 | 1.00 | 3.81 | A |
| ATOM | 5692 | O | ASP | A | 96 | 5.791 | 9.137 | 19.819 | 1.00 | 3.60 | A |
| ATOM | 5693 | N | ASP | A | 97 | 5.677 | 11.315 | 20.377 | 1.00 | 3.85 | A |
| ATOM | 5694 | CA | ASP | A | 97 | 4.924 | 11.062 | 21.608 | 1.00 | 4.32 | A |
| ATOM | 5695 | CB | ASP | A | 97 | 4.600 | 12.377 | 22.332 | 1.00 | 5.15 | A |
| ATOM | 5696 | CG | ASP | A | 97 | 5.754 | 12.898 | 23.172 | 1.00 | 5.96 | A |
| ATOM | 5697 | OD1 | ASP | A | 97 | 5.657 | 14.053 | 23.647 | 1.00 | 6.78 | A |
| ATOM | 5698 | OD2 | ASP | A | 97 | 6.748 | 12.163 | 23.377 | 1.00 | 6.61 | A |
| ATOM | 5699 | C | ASP | A | 97 | 3.614 | 10.355 | 21.261 | 1.00 | 4.57 | A |
| ATOM | 5700 | O | ASP | A | 97 | 3.214 | 9.403 | 21.931 | 1.00 | 4.45 | A |
| ATOM | 5701 | N | PHE | A | 98 | 2.947 | 10.823 | 20.210 | 1.00 | 4.32 | A |
| ATOM | 5702 | CA | PHE | A | 98 | 1.680 | 10.219 | 19.809 | 1.00 | 4.70 | A |
| ATOM | 5703 | CB | PHE | A | 98 | 0.956 | 11.086 | 18.778 | 1.00 | 5.18 | A |
| ATOM | 5704 | CG | PHE | A | 98 | −0.415 | 10.574 | 18.423 | 1.00 | 5.70 | A |
| ATOM | 5705 | CD1 | PHE | A | 98 | −1.420 | 10.518 | 19.385 | 1.00 | 6.58 | A |
| ATOM | 5706 | CD2 | PHE | A | 98 | −0.690 | 10.107 | 17.144 | 1.00 | 6.14 | A |
| ATOM | 5707 | CE1 | PHE | A | 98 | −2.681 | 10.001 | 19.077 | 1.00 | 6.93 | A |
| ATOM | 5708 | CE2 | PHE | A | 98 | −1.950 | 9.587 | 16.825 | 1.00 | 6.50 | A |
| ATOM | 5709 | CZ | PHE | A | 98 | −2.945 | 9.534 | 17.798 | 1.00 | 6.64 | A |
| ATOM | 5710 | C | PHE | A | 98 | 1.876 | 8.825 | 19.232 | 1.00 | 4.66 | A |
| ATOM | 5711 | O | PHE | A | 98 | 1.147 | 7.896 | 19.574 | 1.00 | 4.59 | A |
| ATOM | 5712 | N | MET | A | 99 | 2.857 | 8.678 | 18.352 | 1.00 | 4.84 | A |
| ATOM | 5713 | CA | MET | A | 99 | 3.117 | 7.377 | 17.749 | 1.00 | 5.40 | A |
| ATOM | 5714 | CB | MET | A | 99 | 4.299 | 7.464 | 16.777 | 1.00 | 5.46 | A |
| ATOM | 5715 | CG | MET | A | 99 | 4.123 | 8.469 | 15.638 | 1.00 | 5.83 | A |
| ATOM | 5716 | SD | MET | A | 99 | 2.682 | 8.141 | 14.594 | 1.00 | 6.06 | A |
| ATOM | 5717 | CE | MET | A | 99 | 3.312 | 6.790 | 13.572 | 1.00 | 6.22 | A |
| ATOM | 5718 | C | MET | A | 99 | 3.420 | 6.339 | 18.832 | 1.00 | 6.00 | A |
| ATOM | 5719 | O | MET | A | 99 | 2.994 | 5.188 | 18.739 | 1.00 | 6.05 | A |
| ATOM | 5720 | N | SER | A | 100 | 4.143 | 6.759 | 19.866 | 1.00 | 6.83 | A |
| ATOM | 5721 | CA | SER | A | 100 | 4.523 | 5.860 | 20.951 | 1.00 | 8.20 | A |
| ATOM | 5722 | CB | SER | A | 100 | 5.628 | 6.516 | 21.790 | 1.00 | 7.84 | A |
| ATOM | 5723 | OG | SER | A | 100 | 6.767 | 6.802 | 20.987 | 1.00 | 8.21 | A |
| ATOM | 5724 | C | SER | A | 100 | 3.367 | 5.412 | 21.854 | 1.00 | 9.33 | A |
| ATOM | 5725 | O | SER | A | 100 | 3.524 | 4.476 | 22.646 | 1.00 | 9.63 | A |
| ATOM | 5726 | N | CYS | A | 101 | 2.211 | 6.062 | 21.721 | 1.00 | 10.45 | A |
| ATOM | 5727 | CA | CYS | A | 101 | 1.029 | 5.738 | 22.528 | 1.00 | 12.16 | A |
| ATOM | 5728 | CB | CYS | A | 101 | −0.005 | 6.870 | 22.455 | 1.00 | 12.99 | A |
| ATOM | 5729 | SG | CYS | A | 101 | 0.391 | 8.383 | 23.352 | 1.00 | 16.33 | A |
| ATOM | 5730 | C | CYS | A | 101 | 0.334 | 4.450 | 22.106 | 1.00 | 12.31 | A |
| ATOM | 5731 | O | CYS | A | 101 | −0.382 | 3.836 | 22.900 | 1.00 | 12.62 | A |
| ATOM | 5732 | N | PHE | A | 102 | 0.526 | 4.044 | 20.857 | 1.00 | 12.65 | A |
| ATOM | 5733 | CA | PHE | A | 102 | −0.137 | 2.843 | 20.368 | 1.00 | 13.00 | A |
| ATOM | 5734 | CB | PHE | A | 102 | −0.054 | 2.787 | 18.844 | 1.00 | 12.20 | A |
| ATOM | 5735 | CG | PHE | A | 102 | −0.888 | 3.838 | 18.165 | 1.00 | 11.64 | A |
| ATOM | 5736 | CD1 | PHE | A | 102 | −0.514 | 5.179 | 18.211 | 1.00 | 11.24 | A |
| ATOM | 5737 | CD2 | PHE | A | 102 | −2.065 | 3.493 | 17.507 | 1.00 | 11.38 | A |
| ATOM | 5738 | CE1 | PHE | A | 102 | −1.297 | 6.164 | 17.610 | 1.00 | 11.11 | A |
| ATOM | 5739 | CE2 | PHE | A | 102 | −2.858 | 4.468 | 16.902 | 1.00 | 11.06 | A |
| ATOM | 5740 | CZ | PHE | A | 102 | −2.474 | 5.809 | 16.953 | 1.00 | 10.93 | A |
| ATOM | 5741 | C | PHE | A | 102 | 0.382 | 1.557 | 20.998 | 1.00 | 13.83 | A |
| ATOM | 5742 | O | PHE | A | 102 | 1.580 | 1.275 | 20.975 | 1.00 | 13.59 | A |
| ATOM | 5743 | N | PRO | A | 103 | −0.537 | 0.762 | 21.579 | 1.00 | 14.74 | A |
| ATOM | 5744 | CD | PRO | A | 103 | −1.976 | 1.093 | 21.609 | 1.00 | 14.92 | A |
| ATOM | 5745 | CA | PRO | A | 103 | −0.297 | −0.516 | 22.259 | 1.00 | 15.72 | A |
| ATOM | 5746 | CB | PRO | A | 103 | −1.578 | −0.707 | 23.061 | 1.00 | 15.57 | A |
| ATOM | 5747 | CG | PRO | A | 103 | −2.608 | −0.199 | 22.114 | 1.00 | 15.22 | A |
| ATOM | 5748 | C | PRO | A | 103 | −0.008 | −1.711 | 21.354 | 1.00 | 16.75 | A |
| ATOM | 5749 | O | PRO | A | 103 | −0.814 | −2.639 | 21.265 | 1.00 | 16.71 | A |
| ATOM | 5750 | N | TRP | A | 104 | 1.146 | −1.693 | 20.697 | 1.00 | 17.88 | A |
| ATOM | 5751 | CA | TRP | A | 104 | 1.527 | −2.786 | 19.812 | 1.00 | 19.32 | A |
| ATOM | 5752 | CB | TRP | A | 104 | 2.792 | −2.423 | 19.032 | 1.00 | 18.89 | A |
| ATOM | 5753 | CG | TRP | A | 104 | 2.548 | −1.458 | 17.925 | 1.00 | 18.58 | A |
| ATOM | 5754 | CD2 | TRP | A | 104 | 2.010 | −1.762 | 16.635 | 1.00 | 18.48 | A |
| ATOM | 5755 | CE2 | TRP | A | 104 | 1.931 | −0.548 | 15.918 | 1.00 | 18.52 | A |
| ATOM | 5756 | CE3 | TRP | A | 104 | 1.584 | −2.944 | 16.015 | 1.00 | 18.55 | A |
| ATOM | 5757 | CD1 | TRP | A | 104 | 2.767 | −0.110 | 17.942 | 1.00 | 18.43 | A |
| ATOM | 5758 | NE1 | TRP | A | 104 | 2.400 | 0.444 | 16.739 | 1.00 | 18.43 | A |

TABLE 8-continued

Three-dimensional structural coordinate of the complex of human hematopoietic PGDS (SEQ ID NO: 1) with magnesium, glutathione and 4-benzhydryloxy-1-{3-(1H-tetrazol-5-yl)-propyl}piperidine (HQL-79)

| ATOM | 5759 | CZ2 | TRP | A | 104 | 1.443 | −0.481 | 14.610 | 1.00 | 18.51 | A |
|---|---|---|---|---|---|---|---|---|---|---|---|
| ATOM | 5760 | CZ3 | TRP | A | 104 | 1.099 | −2.877 | 14.712 | 1.00 | 18.61 | A |
| ATOM | 5761 | CH2 | TRP | A | 104 | 1.033 | −1.651 | 14.026 | 1.00 | 18.57 | A |
| ATOM | 5762 | C | TRP | A | 104 | 1.756 | −4.094 | 20.562 | 1.00 | 20.48 | A |
| ATOM | 5763 | O | TRP | A | 104 | 1.734 | −5.170 | 19.964 | 1.00 | 20.69 | A |
| ATOM | 5764 | N | ALA | A | 105 | 1.965 | −4.000 | 21.870 | 1.00 | 21.92 | A |
| ATOM | 5765 | CA | ALA | A | 105 | 2.214 | −5.182 | 22.688 | 1.00 | 23.42 | A |
| ATOM | 5766 | CB | ALA | A | 105 | 3.036 | −4.796 | 23.914 | 1.00 | 23.28 | A |
| ATOM | 5767 | C | ALA | A | 105 | 0.943 | −5.910 | 23.120 | 1.00 | 24.45 | A |
| ATOM | 5768 | O | ALA | A | 105 | 1.013 | −6.976 | 23.732 | 1.00 | 24.65 | A |
| ATOM | 5769 | N | GLU | A | 106 | −0.217 | −5.342 | 22.802 | 1.00 | 25.65 | A |
| ATOM | 5770 | CA | GLU | A | 106 | −1.485 | −5.962 | 23.174 | 1.00 | 26.85 | A |
| ATOM | 5771 | CB | GLU | A | 106 | −2.660 | −5.132 | 22.655 | 1.00 | 27.04 | A |
| ATOM | 5772 | CG | GLU | A | 106 | −4.013 | −5.813 | 22.819 | 1.00 | 27.53 | A |
| ATOM | 5773 | CD | GLU | A | 106 | −4.291 | −6.224 | 24.252 | 1.00 | 27.76 | A |
| ATOM | 5774 | OE1 | GLU | A | 106 | −4.226 | −5.354 | 25.146 | 1.00 | 27.91 | A |
| ATOM | 5775 | OE2 | GLU | A | 106 | −4.580 | −7.417 | 24.484 | 1.00 | 28.01 | A |
| ATOM | 5776 | C | GLU | A | 106 | −1.599 | −7.391 | 22.649 | 1.00 | 27.52 | A |
| ATOM | 5777 | O | GLU | A | 106 | −1.223 | −7.680 | 21.512 | 1.00 | 27.83 | A |
| ATOM | 5778 | N | LYS | A | 107 | −2.130 | −8.275 | 23.487 | 1.00 | 28.30 | A |
| ATOM | 5779 | CA | LYS | A | 107 | −2.300 | −9.682 | 23.139 | 1.00 | 28.87 | A |
| ATOM | 5780 | CB | LYS | A | 107 | −2.444 | −10.514 | 24.414 | 1.00 | 29.16 | A |
| ATOM | 5781 | CG | LYS | A | 107 | −1.271 | −10.395 | 25.373 | 1.00 | 29.57 | A |
| ATOM | 5782 | CD | LYS | A | 107 | 0.009 | −10.925 | 24.750 | 1.00 | 29.90 | A |
| ATOM | 5783 | CE | LYS | A | 107 | 1.156 | −10.889 | 25.748 | 1.00 | 30.13 | A |
| ATOM | 5784 | NZ | LYS | A | 107 | 0.857 | −11.708 | 26.956 | 1.00 | 30.43 | A |
| ATOM | 5785 | C | LYS | A | 107 | −3.509 | −9.927 | 22.241 | 1.00 | 29.12 | A |
| ATOM | 5786 | O | LYS | A | 107 | −3.376 | −10.446 | 21.132 | 1.00 | 29.28 | A |
| ATOM | 5787 | N | LYS | A | 108 | −4.689 | −9.560 | 22.729 | 1.00 | 29.38 | A |
| ATOM | 5788 | CA | LYS | A | 108 | −5.921 | −9.745 | 21.972 | 1.00 | 29.63 | A |
| ATOM | 5789 | CB | LYS | A | 108 | −7.134 | −9.496 | 22.872 | 1.00 | 30.00 | A |
| ATOM | 5790 | CG | LYS | A | 108 | −7.169 | −10.367 | 24.123 | 1.00 | 30.56 | A |
| ATOM | 5791 | CD | LYS | A | 108 | −8.456 | −10.178 | 24.922 | 1.00 | 30.98 | A |
| ATOM | 5792 | CE | LYS | A | 108 | −9.673 | −10.768 | 24.211 | 1.00 | 31.33 | A |
| ATOM | 5793 | NZ | LYS | A | 108 | −9.995 | −10.085 | 22.924 | 1.00 | 31.67 | A |
| ATOM | 5794 | C | LYS | A | 108 | −5.969 | −8.806 | 20.773 | 1.00 | 29.56 | A |
| ATOM | 5795 | O | LYS | A | 108 | −6.053 | −7.588 | 20.929 | 1.00 | 29.53 | A |
| ATOM | 5796 | N | GLN | A | 109 | −5.912 | −9.380 | 19.575 | 1.00 | 29.46 | A |
| ATOM | 5797 | CA | GLN | A | 109 | −5.950 | −8.594 | 18.348 | 1.00 | 29.31 | A |
| ATOM | 5798 | CB | GLN | A | 109 | −5.908 | −9.519 | 17.130 | 1.00 | 29.60 | A |
| ATOM | 5799 | CG | GLN | A | 109 | −5.886 | −8.795 | 15.788 | 1.00 | 30.07 | A |
| ATOM | 5800 | CD | GLN | A | 109 | −4.671 | −7.898 | 15.624 | 1.00 | 30.20 | A |
| ATOM | 5801 | OE1 | GLN | A | 109 | −3.531 | −8.347 | 15.745 | 1.00 | 30.51 | A |
| ATOM | 5802 | NE2 | GLN | A | 109 | −4.911 | −6.623 | 15.341 | 1.00 | 30.44 | A |
| ATOM | 5803 | C | GLN | A | 109 | −7.213 | −7.740 | 18.306 | 1.00 | 29.07 | A |
| ATOM | 5804 | O | GLN | A | 109 | −7.197 | −6.614 | 17.808 | 1.00 | 29.12 | A |
| ATOM | 5805 | N | ASP | A | 110 | −8.304 | −8.281 | 18.838 | 1.00 | 28.67 | A |
| ATOM | 5806 | CA | ASP | A | 110 | −9.582 | −7.576 | 18.871 | 1.00 | 28.20 | A |
| ATOM | 5807 | CB | ASP | A | 110 | −10.662 | −8.464 | 19.494 | 1.00 | 28.84 | A |
| ATOM | 5808 | CG | ASP | A | 110 | −10.698 | −9.855 | 18.892 | 1.00 | 29.35 | A |
| ATOM | 5809 | OD1 | ASP | A | 110 | −11.510 | −10.681 | 19.362 | 1.00 | 29.82 | A |
| ATOM | 5810 | OD2 | ASP | A | 110 | −9.918 | −10.126 | 17.954 | 1.00 | 29.79 | A |
| ATOM | 5811 | C | ASP | A | 110 | −9.450 | −6.303 | 19.700 | 1.00 | 27.49 | A |
| ATOM | 5812 | O | ASP | A | 110 | −9.794 | −5.210 | 19.248 | 1.00 | 27.41 | A |
| ATOM | 5813 | N | VAL | A | 111 | −8.952 | −6.466 | 20.921 | 1.00 | 26.54 | A |
| ATOM | 5814 | CA | VAL | A | 111 | −8.765 | −5.352 | 21.844 | 1.00 | 25.62 | A |
| ATOM | 5815 | CB | VAL | A | 111 | −8.261 | −5.852 | 23.214 | 1.00 | 25.70 | A |
| ATOM | 5816 | CG1 | VAL | A | 111 | −8.118 | −4.687 | 24.176 | 1.00 | 25.75 | A |
| ATOM | 5817 | CG2 | VAL | A | 111 | −9.220 | −6.892 | 23.769 | 1.00 | 25.72 | A |
| ATOM | 5818 | C | VAL | A | 111 | −7.751 | −4.361 | 21.288 | 1.00 | 24.87 | A |
| ATOM | 5819 | O | VAL | A | 111 | −7.890 | −3.150 | 21.457 | 1.00 | 24.76 | A |
| ATOM | 5820 | N | LYS | A | 112 | −6.733 | −4.893 | 20.623 | 1.00 | 23.93 | A |
| ATOM | 5821 | CA | LYS | A | 112 | −5.679 | −4.082 | 20.034 | 1.00 | 22.97 | A |
| ATOM | 5822 | CB | LYS | A | 112 | −4.645 | −4.995 | 19.376 | 1.00 | 23.32 | A |
| ATOM | 5823 | CG | LYS | A | 112 | −3.397 | −4.302 | 18.873 | 1.00 | 23.86 | A |
| ATOM | 5824 | CD | LYS | A | 112 | −2.432 | −5.333 | 18.305 | 1.00 | 24.32 | A |
| ATOM | 5825 | CE | LYS | A | 112 | −1.157 | −4.697 | 17.788 | 1.00 | 24.73 | A |
| ATOM | 5826 | NZ | LYS | A | 112 | −0.215 | −5.733 | 17.271 | 1.00 | 25.05 | A |
| ATOM | 5827 | C | LYS | A | 112 | −6.259 | −3.114 | 19.007 | 1.00 | 22.11 | A |
| ATOM | 5828 | O | LYS | A | 112 | −5.962 | −1.920 | 19.031 | 1.00 | 21.79 | A |
| ATOM | 5829 | N | GLU | A | 113 | −7.092 | −3.636 | 18.111 | 1.00 | 21.14 | A |
| ATOM | 5830 | CA | GLU | A | 113 | −7.715 | −2.815 | 17.079 | 1.00 | 20.14 | A |
| ATOM | 5831 | CB | GLU | A | 113 | −8.529 | −3.690 | 16.119 | 1.00 | 20.72 | A |
| ATOM | 5832 | CG | GLU | A | 113 | −7.713 | −4.763 | 15.412 | 1.00 | 21.85 | A |
| ATOM | 5833 | CD | GLU | A | 113 | −8.491 | −5.456 | 14.303 | 1.00 | 22.40 | A |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 5834 | OE1 | GLU | A | 113 | −7.956 | −6.422 | 13.717 | 1.00 | 22.88 | A |
|------|------|-----|-----|---|-----|--------|--------|--------|------|-------|---|
| ATOM | 5835 | OE2 | GLU | A | 113 | −9.632 | −5.032 | 14.010 | 1.00 | 23.04 | A |
| ATOM | 5836 | C | GLU | A | 113 | −8.623 | −1.766 | 17.712 | 1.00 | 19.20 | A |
| ATOM | 5837 | O | GLU | A | 113 | −8.699 | −0.632 | 17.240 | 1.00 | 18.59 | A |
| ATOM | 5838 | N | GLN | A | 114 | −9.313 | −2.157 | 18.780 | 1.00 | 18.24 | A |
| ATOM | 5839 | CA | GLN | A | 114 | −10.211 | −1.252 | 19.492 | 1.00 | 17.58 | A |
| ATOM | 5840 | CB | GLN | A | 114 | −10.867 | −1.989 | 20.665 | 1.00 | 18.40 | A |
| ATOM | 5841 | CG | GLN | A | 114 | −11.701 | −1.110 | 21.590 | 1.00 | 19.72 | A |
| ATOM | 5842 | CD | GLN | A | 114 | −12.983 | −0.617 | 20.951 | 1.00 | 20.35 | A |
| ATOM | 5843 | OE1 | GLN | A | 114 | −13.741 | −0.141 | 21.560 | 1.00 | 21.36 | A |
| ATOM | 5844 | NE2 | GLN | A | 114 | −13.238 | −1.045 | 19.721 | 1.00 | 21.11 | A |
| ATOM | 5845 | C | GLN | A | 114 | −9.433 | −0.044 | 20.011 | 1.00 | 16.47 | A |
| ATOM | 5846 | O | GLN | A | 114 | −9.841 | 1.101 | 19.822 | 1.00 | 15.90 | A |
| ATOM | 5847 | N | MET | A | 115 | −8.306 | −0.308 | 20.664 | 1.00 | 15.39 | A |
| ATOM | 5848 | CA | MET | A | 115 | −7.469 | 0.754 | 21.215 | 1.00 | 14.42 | A |
| ATOM | 5849 | CB | MET | A | 115 | −6.325 | 0.146 | 22.022 | 1.00 | 15.54 | A |
| ATOM | 5850 | CG | MET | A | 115 | −6.800 | −0.675 | 23.205 | 1.00 | 16.96 | A |
| ATOM | 5851 | SD | MET | A | 115 | −5.448 | −1.470 | 24.079 | 1.00 | 18.84 | A |
| ATOM | 5852 | CE | MET | A | 115 | −5.262 | −2.923 | 23.139 | 1.00 | 18.77 | A |
| ATOM | 5853 | C | MET | A | 115 | −6.912 | 1.655 | 20.117 | 1.00 | 13.19 | A |
| ATOM | 5854 | O | MET | A | 115 | −6.872 | 2.877 | 20.267 | 1.00 | 12.74 | A |
| ATOM | 5855 | N | PHE | A | 116 | −6.476 | 1.050 | 19.017 | 1.00 | 11.78 | A |
| ATOM | 5856 | CA | PHE | A | 116 | −5.947 | 1.813 | 17.890 | 1.00 | 10.59 | A |
| ATOM | 5857 | CB | PHE | A | 116 | −5.490 | 0.870 | 16.773 | 1.00 | 10.36 | A |
| ATOM | 5858 | CG | PHE | A | 116 | −4.061 | 0.413 | 16.901 | 1.00 | 10.46 | A |
| ATOM | 5859 | CD1 | PHE | A | 116 | −3.595 | −0.162 | 18.081 | 1.00 | 10.57 | A |
| ATOM | 5860 | CD2 | PHE | A | 116 | −3.180 | 0.559 | 15.836 | 1.00 | 10.60 | A |
| ATOM | 5861 | CE1 | PHE | A | 116 | −2.264 | −0.584 | 18.196 | 1.00 | 10.91 | A |
| ATOM | 5862 | CE2 | PHE | A | 116 | −1.850 | 0.140 | 15.940 | 1.00 | 10.80 | A |
| ATOM | 5863 | CZ | PHE | A | 116 | −1.395 | −0.431 | 17.123 | 1.00 | 10.66 | A |
| ATOM | 5864 | C | PHE | A | 116 | −7.028 | 2.746 | 17.352 | 1.00 | 9.91 | A |
| ATOM | 5865 | O | PHE | A | 116 | −6.784 | 3.926 | 17.107 | 1.00 | 9.44 | A |
| ATOM | 6152 | N | TYR | A | 152 | 9.540 | 13.762 | 9.073 | 1.00 | 2.77 | A |
| ATOM | 6153 | CA | TYR | A | 152 | 8.881 | 12.942 | 10.085 | 1.00 | 2.75 | A |
| ATOM | 6154 | CB | TYR | A | 152 | 9.375 | 13.285 | 11.493 | 1.00 | 2.46 | A |
| ATOM | 6155 | CG | TYR | A | 152 | 9.275 | 12.107 | 12.439 | 1.00 | 2.52 | A |
| ATOM | 6156 | CD1 | TYR | A | 152 | 9.745 | 10.850 | 12.057 | 1.00 | 2.65 | A |
| ATOM | 6157 | CE1 | TYR | A | 152 | 9.704 | 9.767 | 12.931 | 1.00 | 2.76 | A |
| ATOM | 6158 | CD2 | TYR | A | 152 | 8.749 | 12.251 | 13.727 | 1.00 | 2.68 | A |
| ATOM | 6159 | CE2 | TYR | A | 152 | 8.700 | 11.166 | 14.614 | 1.00 | 2.62 | A |
| ATOM | 6160 | CZ | TYR | A | 152 | 9.187 | 9.928 | 14.206 | 1.00 | 2.82 | A |
| ATOM | 6161 | OH | TYR | A | 152 | 9.200 | 8.848 | 15.069 | 1.00 | 3.50 | A |
| ATOM | 6162 | C | TYR | A | 152 | 7.367 | 13.051 | 10.016 | 1.00 | 2.91 | A |
| ATOM | 6163 | O | TYR | A | 152 | 6.660 | 12.070 | 10.255 | 1.00 | 2.96 | A |
| ATOM | 6164 | N | TRP | A | 153 | 6.863 | 14.237 | 9.696 | 1.00 | 3.18 | A |
| ATOM | 6165 | CA | TRP | A | 153 | 5.424 | 14.392 | 9.562 | 1.00 | 3.43 | A |
| ATOM | 6166 | CB | TRP | A | 153 | 5.044 | 15.839 | 9.240 | 1.00 | 3.92 | A |
| ATOM | 6167 | CG | TRP | A | 153 | 3.631 | 15.957 | 8.702 | 1.00 | 4.79 | A |
| ATOM | 6168 | CD2 | TRP | A | 153 | 2.425 | 15.511 | 9.340 | 1.00 | 5.21 | A |
| ATOM | 6169 | CE2 | TRP | A | 153 | 1.359 | 15.767 | 8.446 | 1.00 | 5.55 | A |
| ATOM | 6170 | CE3 | TRP | A | 153 | 2.141 | 14.917 | 10.578 | 1.00 | 5.42 | A |
| ATOM | 6171 | CD1 | TRP | A | 153 | 3.256 | 16.454 | 7.485 | 1.00 | 5.26 | A |
| ATOM | 6172 | NE1 | TRP | A | 153 | 1.894 | 16.341 | 7.324 | 1.00 | 5.61 | A |
| ATOM | 6173 | CZ2 | TRP | A | 153 | 0.029 | 15.449 | 8.749 | 1.00 | 5.49 | A |
| ATOM | 6174 | CZ3 | TRP | A | 153 | 0.812 | 14.599 | 10.880 | 1.00 | 5.68 | A |
| ATOM | 6175 | CH2 | TRP | A | 153 | −0.223 | 14.868 | 9.967 | 1.00 | 5.61 | A |
| ATOM | 6176 | C | TRP | A | 153 | 4.929 | 13.497 | 8.428 | 1.00 | 3.45 | A |
| ATOM | 6177 | O | TRP | A | 153 | 3.935 | 12.797 | 8.576 | 1.00 | 3.37 | A |
| ATOM | 6178 | N | GLU | A | 154 | 5.618 | 13.518 | 7.291 | 1.00 | 3.56 | A |
| ATOM | 6179 | CA | GLU | A | 154 | 5.176 | 12.711 | 6.162 | 1.00 | 3.71 | A |
| ATOM | 6180 | CB | GLU | A | 154 | 5.999 | 13.035 | 4.908 | 1.00 | 4.32 | A |
| ATOM | 6181 | CG | GLU | A | 154 | 5.412 | 12.438 | 3.622 | 1.00 | 5.29 | A |
| ATOM | 6182 | CD | GLU | A | 154 | 5.831 | 11.001 | 3.395 | 1.00 | 6.03 | A |
| ATOM | 6183 | OE1 | GLU | A | 154 | 5.164 | 10.291 | 2.610 | 1.00 | 7.04 | A |
| ATOM | 6184 | OE2 | GLU | A | 154 | 6.840 | 10.587 | 3.991 | 1.00 | 6.58 | A |
| ATOM | 6185 | C | GLU | A | 154 | 5.242 | 11.218 | 6.467 | 1.00 | 3.29 | A |
| ATOM | 6186 | O | GLU | A | 154 | 4.349 | 10.463 | 6.092 | 1.00 | 3.50 | A |
| ATOM | 6187 | N | ILE | A | 155 | 6.290 | 10.801 | 7.166 | 1.00 | 3.02 | A |
| ATOM | 6188 | CA | ILE | A | 155 | 6.466 | 9.397 | 7.520 | 1.00 | 3.13 | A |
| ATOM | 6189 | CB | ILE | A | 155 | 7.888 | 9.182 | 8.105 | 1.00 | 2.70 | A |
| ATOM | 6190 | CG2 | ILE | A | 155 | 7.991 | 7.836 | 8.827 | 1.00 | 2.70 | A |
| ATOM | 6191 | CG1 | ILE | A | 155 | 8.912 | 9.275 | 6.974 | 1.00 | 2.60 | A |
| ATOM | 6192 | CD1 | ILE | A | 155 | 10.341 | 9.455 | 7.455 | 1.00 | 2.55 | A |
| ATOM | 6193 | C | ILE | A | 155 | 5.393 | 8.931 | 8.509 | 1.00 | 3.34 | A |
| ATOM | 6194 | O | ILE | A | 155 | 4.757 | 7.888 | 8.304 | 1.00 | 3.01 | A |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 6195 | N | CYS | A | 156 | 5.178 | 9.708 | 9.570 | 1.00 | 3.50 | A |
|------|------|------|-----|---|-----|--------|--------|--------|------|-------|---|
| ATOM | 6196 | CA | CYS | A | 156 | 4.176 | 9.345 | 10.570 | 1.00 | 4.03 | A |
| ATOM | 6197 | CB | CYS | A | 156 | 4.227 | 10.298 | 11.771 | 1.00 | 4.29 | A |
| ATOM | 6198 | SG | CYS | A | 156 | 5.678 | 10.099 | 12.840 | 1.00 | 5.23 | A |
| ATOM | 6199 | C | CYS | A | 156 | 2.767 | 9.339 | 9.989 | 1.00 | 4.27 | A |
| ATOM | 6200 | O | CYS | A | 156 | 2.009 | 8.390 | 10.199 | 1.00 | 4.23 | A |
| ATOM | 6201 | N | SER | A | 157 | 2.419 | 10.391 | 9.254 | 1.00 | 4.32 | A |
| ATOM | 6202 | CA | SER | A | 157 | 1.085 | 10.469 | 8.668 | 1.00 | 4.75 | A |
| ATOM | 6203 | CB | SER | A | 157 | 0.838 | 11.865 | 8.072 | 1.00 | 5.10 | A |
| ATOM | 6204 | OG | SER | A | 157 | 1.761 | 12.194 | 7.047 | 1.00 | 5.43 | A |
| ATOM | 6205 | C | SER | A | 157 | 0.852 | 9.369 | 7.631 | 1.00 | 4.95 | A |
| ATOM | 6206 | O | SER | A | 157 | −0.264 | 8.874 | 7.487 | 1.00 | 4.57 | A |
| ATOM | 6207 | N | THR | A | 158 | 1.898 | 8.963 | 6.920 | 1.00 | 5.02 | A |
| ATOM | 6208 | CA | THR | A | 158 | 1.731 | 7.901 | 5.937 | 1.00 | 5.46 | A |
| ATOM | 6209 | CB | THR | A | 158 | 3.044 | 7.623 | 5.168 | 1.00 | 5.08 | A |
| ATOM | 6210 | OG1 | THR | A | 158 | 3.223 | 8.638 | 4.175 | 1.00 | 6.03 | A |
| ATOM | 6211 | CG2 | THR | A | 158 | 3.002 | 6.255 | 4.484 | 1.00 | 5.35 | A |
| ATOM | 6212 | C | THR | A | 158 | 1.257 | 6.624 | 6.623 | 1.00 | 5.78 | A |
| ATOM | 6213 | O | THR | A | 158 | 0.330 | 5.963 | 6.153 | 1.00 | 6.22 | A |
| ATOM | 6214 | N | THR | A | 159 | 1.868 | 6.273 | 7.749 | 1.00 | 6.08 | A |
| ATOM | 6215 | CA | THR | A | 159 | 1.439 | 5.056 | 8.416 | 1.00 | 6.86 | A |
| ATOM | 6216 | CB | THR | A | 159 | 2.511 | 4.534 | 9.380 | 1.00 | 7.60 | A |
| ATOM | 6217 | OG1 | THR | A | 159 | 3.698 | 4.230 | 8.633 | 1.00 | 8.88 | A |
| ATOM | 6218 | CG2 | THR | A | 159 | 2.029 | 3.261 | 10.065 | 1.00 | 8.45 | A |
| ATOM | 6219 | C | THR | A | 159 | 0.102 | 5.219 | 9.141 | 1.00 | 6.36 | A |
| ATOM | 6220 | O | THR | A | 159 | −0.716 | 4.304 | 9.136 | 1.00 | 6.28 | A |
| ATOM | 6221 | N | LEU | A | 160 | −0.139 | 6.378 | 9.749 | 1.00 | 6.36 | A |
| ATOM | 6222 | CA | LEU | A | 160 | −1.416 | 6.583 | 10.433 | 1.00 | 6.28 | A |
| ATOM | 6223 | CB | LEU | A | 160 | −1.442 | 7.938 | 11.145 | 1.00 | 6.43 | A |
| ATOM | 6224 | CG | LEU | A | 160 | −0.494 | 8.064 | 12.344 | 1.00 | 6.55 | A |
| ATOM | 6225 | CD1 | LEU | A | 160 | −0.635 | 9.446 | 12.969 | 1.00 | 6.99 | A |
| ATOM | 6226 | CD2 | LEU | A | 160 | −0.815 | 6.977 | 13.369 | 1.00 | 6.80 | A |
| ATOM | 6227 | C | LEU | A | 160 | −2.567 | 6.505 | 9.428 | 1.00 | 6.52 | A |
| ATOM | 6228 | O | LEU | A | 160 | −3.635 | 5.979 | 9.744 | 1.00 | 6.37 | A |
| ATOM | 6229 | N | LEU | A | 161 | −2.344 | 7.026 | 8.224 | 1.00 | 6.39 | A |
| ATOM | 6230 | CA | LEU | A | 161 | −3.369 | 7.006 | 7.178 | 1.00 | 6.80 | A |
| ATOM | 6231 | CB | LEU | A | 161 | −2.881 | 7.764 | 5.941 | 1.00 | 6.77 | A |
| ATOM | 6232 | CG | LEU | A | 161 | −2.994 | 9.287 | 6.026 | 1.00 | 6.85 | A |
| ATOM | 6233 | CD1 | LEU | A | 161 | −2.211 | 9.934 | 4.893 | 1.00 | 6.96 | A |
| ATOM | 6234 | CD2 | LEU | A | 161 | −4.468 | 9.686 | 5.967 | 1.00 | 6.94 | A |
| ATOM | 6235 | C | LEU | A | 161 | −3.770 | 5.589 | 6.785 | 1.00 | 6.97 | A |
| ATOM | 6236 | O | LEU | A | 161 | −4.869 | 5.370 | 6.272 | 1.00 | 7.11 | A |
| ATOM | 6237 | N | VAL | A | 162 | −2.884 | 4.627 | 7.015 | 1.00 | 7.20 | A |
| ATOM | 6238 | CA | VAL | A | 162 | −3.199 | 3.240 | 6.692 | 1.00 | 7.82 | A |
| ATOM | 6239 | CB | VAL | A | 162 | −1.963 | 2.317 | 6.867 | 1.00 | 7.65 | A |
| ATOM | 6240 | CG1 | VAL | A | 162 | −2.372 | 0.853 | 6.720 | 1.00 | 8.05 | A |
| ATOM | 6241 | CG2 | VAL | A | 162 | −0.905 | 2.673 | 5.830 | 1.00 | 7.94 | A |
| ATOM | 6242 | C | VAL | A | 162 | −4.308 | 2.760 | 7.620 | 1.00 | 8.18 | A |
| ATOM | 6243 | O | VAL | A | 162 | −5.197 | 2.014 | 7.205 | 1.00 | 8.53 | A |
| ATOM | 6244 | N | PHE | A | 163 | −4.257 | 3.204 | 8.875 | 1.00 | 8.35 | A |
| ATOM | 6245 | CA | PHE | A | 163 | −5.251 | 2.813 | 9.871 | 1.00 | 8.79 | A |
| ATOM | 6246 | CB | PHE | A | 163 | −4.612 | 2.753 | 11.263 | 1.00 | 9.22 | A |
| ATOM | 6247 | CG | PHE | A | 163 | −3.511 | 1.746 | 11.376 | 1.00 | 10.12 | A |
| ATOM | 6248 | CD1 | PHE | A | 163 | −2.201 | 2.083 | 11.058 | 1.00 | 10.55 | A |
| ATOM | 6249 | CD2 | PHE | A | 163 | −3.792 | 0.440 | 11.773 | 1.00 | 10.59 | A |
| ATOM | 6250 | CE1 | PHE | A | 163 | −1.186 | 1.129 | 11.135 | 1.00 | 10.94 | A |
| ATOM | 6251 | CE2 | PHE | A | 163 | −2.787 | −0.515 | 11.850 | 1.00 | 11.22 | A |
| ATOM | 6252 | CZ | PHE | A | 163 | −1.481 | −0.169 | 11.530 | 1.00 | 11.03 | A |
| ATOM | 6253 | C | PHE | A | 163 | −6.454 | 3.745 | 9.920 | 1.00 | 8.73 | A |
| ATOM | 6254 | O | PHE | A | 163 | −7.541 | 3.341 | 10.333 | 1.00 | 9.27 | A |
| ATOM | 6528 | N | THR | A | 197 | 6.261 | −2.354 | 2.065 | 1.00 | 5.54 | A |
| ATOM | 6529 | CA | THR | A | 197 | 5.873 | −3.026 | 3.294 | 1.00 | 6.03 | A |
| ATOM | 6530 | CB | THR | A | 197 | 7.027 | −2.988 | 4.330 | 1.00 | 6.06 | A |
| ATOM | 6531 | OG1 | THR | A | 197 | 7.395 | −1.626 | 4.585 | 1.00 | 6.14 | A |
| ATOM | 6532 | CG2 | THR | A | 197 | 8.251 | −3.733 | 3.796 | 1.00 | 6.10 | A |
| ATOM | 6533 | C | THR | A | 197 | 4.634 | −2.343 | 3.865 | 1.00 | 6.45 | A |
| ATOM | 6534 | O | THR | A | 197 | 4.355 | −1.181 | 3.559 | 1.00 | 6.41 | A |
| ATOM | 6535 | N | LYS | A | 198 | 3.889 | −3.065 | 4.691 | 1.00 | 7.24 | A |
| ATOM | 6536 | CA | LYS | A | 198 | 2.679 | −2.512 | 5.272 | 1.00 | 7.84 | A |
| ATOM | 6537 | CB | LYS | A | 198 | 1.929 | −3.596 | 6.046 | 1.00 | 8.50 | A |
| ATOM | 6538 | CG | LYS | A | 198 | 0.529 | −3.190 | 6.464 | 1.00 | 9.42 | A |
| ATOM | 6539 | CD | LYS | A | 198 | −0.346 | −3.015 | 5.237 | 1.00 | 10.37 | A |
| ATOM | 6540 | CE | LYS | A | 198 | −1.794 | −2.809 | 5.616 | 1.00 | 10.74 | A |
| ATOM | 6541 | NZ | LYS | A | 198 | −2.644 | −2.633 | 4.407 | 1.00 | 11.54 | A |
| ATOM | 6542 | C | LYS | A | 198 | 2.996 | −1.350 | 6.203 | 1.00 | 7.94 | A |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 6543 | O | LYS | A | 198 | 2.420 | −0.263 | 6.082 | 1.00 | 8.01 | A |
|------|------|-----|-----|---|-----|--------|--------|--------|------|-------|---|
| ATOM | 6544 | N | LEU | A | 199 | 3.929 | −1.589 | 7.119 | 1.00 | 8.20 | A |
| ATOM | 6545 | CA | LEU | A | 199 | 4.335 | −0.592 | 8.101 | 1.00 | 8.16 | A |
| ATOM | 6546 | CB | LEU | A | 199 | 4.199 | −1.180 | 9.510 | 1.00 | 8.84 | A |
| ATOM | 6547 | CG | LEU | A | 199 | 2.859 | −1.852 | 9.827 | 1.00 | 9.23 | A |
| ATOM | 6548 | CD1 | LEU | A | 199 | 2.923 | −2.499 | 11.203 | 1.00 | 9.71 | A |
| ATOM | 6549 | CD2 | LEU | A | 199 | 1.739 | −0.827 | 9.745 | 1.00 | 9.80 | A |
| ATOM | 6550 | C | LEU | A | 199 | 5.775 | −0.130 | 7.882 | 1.00 | 8.13 | A |
| ATOM | 6551 | OT1 | LEU | A | 199 | 6.440 | −0.652 | 6.959 | 1.00 | 7.55 | A |
| ATOM | 6552 | OT2 | LEU | A | 199 | 6.216 | 0.753 | 8.649 | 1.00 | 8.21 | A |
| ATOM | 6613 | N1 | GSH | H | 4 | 12.088 | 5.233 | 20.820 | 1.00 | 7.13 | H |
| ATOM | 6614 | CA1 | GSH | H | 4 | 12.962 | 4.197 | 20.254 | 1.00 | 7.03 | H |
| ATOM | 6615 | C1 | GSH | H | 4 | 13.457 | 4.588 | 18.834 | 1.00 | 6.55 | H |
| ATOM | 6616 | O11 | GSH | H | 4 | 12.879 | 5.504 | 18.242 | 1.00 | 6.42 | H |
| ATOM | 6617 | O12 | GSH | H | 4 | 14.524 | 3.959 | 18.368 | 1.00 | 5.57 | H |
| ATOM | 6618 | CB1 | GSH | H | 4 | 12.145 | 2.885 | 20.215 | 1.00 | 7.92 | H |
| ATOM | 6619 | CG1 | GSH | H | 4 | 13.006 | 1.603 | 20.044 | 1.00 | 8.47 | H |
| ATOM | 6620 | CD1 | GSH | H | 4 | 12.022 | 0.396 | 19.925 | 1.00 | 9.25 | H |
| ATOM | 6621 | OE1 | GSH | H | 4 | 11.170 | 0.182 | 20.803 | 1.00 | 9.64 | H |
| ATOM | 6622 | N2 | GSH | H | 4 | 12.250 | −0.419 | 18.881 | 1.00 | 9.52 | H |
| ATOM | 6623 | CA2 | GSH | H | 4 | 11.428 | −1.623 | 18.662 | 1.00 | 10.30 | H |
| ATOM | 6624 | C2 | GSH | H | 4 | 12.205 | −2.870 | 19.063 | 1.00 | 10.93 | H |
| ATOM | 6625 | O2 | GSH | H | 4 | 13.436 | −2.897 | 19.121 | 1.00 | 9.41 | H |
| ATOM | 6626 | CB2 | GSH | H | 4 | 11.161 | −1.836 | 17.165 | 1.00 | 10.45 | H |
| ATOM | 6627 | SG2 | GSH | H | 4 | 10.101 | −0.583 | 16.421 | 1.00 | 11.44 | H |
| ATOM | 6628 | N3 | GSH | H | 4 | 11.453 | −3.878 | 19.521 | 1.00 | 12.52 | H |
| ATOM | 6629 | CA3 | GSH | H | 4 | 11.906 | −5.282 | 19.488 | 1.00 | 13.88 | H |
| ATOM | 6630 | C3 | GSH | H | 4 | 12.200 | −5.722 | 20.899 | 1.00 | 14.49 | H |
| ATOM | 6631 | O31 | GSH | H | 4 | 12.672 | −6.865 | 21.036 | 1.00 | 15.15 | H |
| ATOM | 6632 | O32 | GSH | H | 4 | 12.014 | −4.897 | 21.826 | 1.00 | 15.40 | H |
| ATOM | 6675 | MG + 2 | MG2 | M | 901 | 10.564 | 10.708 | 23.002 | 1.00 | 6.47 | M |
| ATOM | 6761 | C1 | HQL | X | 201 | 0.783 | 3.731 | 14.700 | 1.00 | 14.62 | X |
| ATOM | 6762 | C2 | HQL | X | 201 | 1.692 | 4.118 | 15.845 | 1.00 | 14.59 | X |
| ATOM | 6763 | C3 | HQL | X | 201 | 3.106 | 3.797 | 15.836 | 1.00 | 14.55 | X |
| ATOM | 6764 | C4 | HQL | X | 201 | 3.711 | 3.097 | 14.685 | 1.00 | 14.90 | X |
| ATOM | 6765 | C5 | HQL | X | 201 | 5.187 | 2.827 | 14.734 | 1.00 | 15.13 | X |
| ATOM | 6766 | O1 | HQL | X | 201 | 5.430 | 1.582 | 13.989 | 1.00 | 16.49 | X |
| ATOM | 6767 | C6 | HQL | X | 201 | 6.385 | 0.713 | 14.568 | 1.00 | 18.14 | X |
| ATOM | 6768 | C7 | HQL | X | 201 | 5.869 | 0.071 | 16.022 | 1.00 | 18.91 | X |
| ATOM | 6769 | C8 | HQL | X | 201 | 5.795 | −1.443 | 16.083 | 1.00 | 19.93 | X |
| ATOM | 6770 | N1 | HQL | X | 201 | 5.334 | −2.091 | 14.799 | 1.00 | 20.61 | X |
| ATOM | 6771 | C9 | HQL | X | 201 | 5.405 | −3.554 | 15.187 | 1.00 | 21.81 | X |
| ATOM | 6772 | C10 | HQL | X | 201 | 5.034 | −4.554 | 14.080 | 1.00 | 23.26 | X |
| ATOM | 6773 | C11 | HQL | X | 201 | 5.181 | −5.967 | 14.572 | 1.00 | 24.56 | X |
| ATOM | 6774 | C12 | HQL | X | 201 | 4.877 | −6.836 | 13.391 | 1.00 | 25.39 | X |
| ATOM | 6775 | N2 | HQL | X | 201 | 3.772 | −6.819 | 12.624 | 1.00 | 25.84 | X |
| ATOM | 6776 | N3 | HQL | X | 201 | 3.922 | −7.729 | 11.695 | 1.00 | 26.13 | X |
| ATOM | 6777 | N4 | HQL | X | 201 | 5.093 | −8.318 | 11.859 | 1.00 | 26.09 | X |
| ATOM | 6778 | N5 | HQL | X | 201 | 5.695 | −7.787 | 12.893 | 1.00 | 25.73 | X |
| ATOM | 6779 | C13 | HQL | X | 201 | 6.228 | −1.740 | 13.566 | 1.00 | 19.90 | X |
| ATOM | 6780 | C14 | HQL | X | 201 | 6.591 | −0.245 | 13.299 | 1.00 | 18.75 | X |
| ATOM | 6781 | C15 | HQL | X | 201 | 5.994 | 4.025 | 14.243 | 1.00 | 14.57 | X |
| ATOM | 6782 | C16 | HQL | X | 201 | 6.642 | 4.886 | 15.312 | 1.00 | 14.43 | X |
| ATOM | 6783 | C17 | HQL | X | 201 | 7.411 | 6.102 | 14.925 | 1.00 | 14.09 | X |
| ATOM | 6784 | C18 | HQL | X | 201 | 7.560 | 6.480 | 13.475 | 1.00 | 14.22 | X |
| ATOM | 6785 | C19 | HQL | X | 201 | 6.931 | 5.623 | 12.396 | 1.00 | 14.18 | X |
| ATOM | 6786 | C20 | HQL | X | 201 | 6.151 | 4.410 | 12.778 | 1.00 | 14.33 | X |
| ATOM | 6787 | C21 | HQL | X | 201 | 2.813 | 2.674 | 13.498 | 1.00 | 14.91 | X |
| ATOM | 6788 | C22 | HQL | X | 201 | 1.353 | 2.988 | 13.530 | 1.00 | 14.88 | X |
| ATOM | 6790 | OH2 | WAT | S | 2 | 14.771 | 8.489 | 19.484 | 1.00 | 5.47 | S |
| ATOM | 6791 | OH2 | WAT | S | 3 | 11.680 | 1.507 | 3.580 | 1.00 | 5.07 | S |
| ATOM | 6794 | OH2 | WAT | S | 6 | 16.764 | 2.346 | 18.953 | 1.00 | 6.31 | S |
| ATOM | 6797 | OH2 | WAT | S | 9 | 10.902 | 6.761 | 11.193 | 1.00 | 3.72 | S |
| ATOM | 6802 | OH2 | WAT | S | 14 | 17.269 | −1.249 | 7.632 | 1.00 | 5.08 | S |
| ATOM | 6804 | OH2 | WAT | S | 16 | 19.130 | −0.458 | 21.382 | 1.00 | 6.03 | S |
| ATOM | 6807 | OH2 | WAT | S | 19 | 9.886 | −0.690 | 3.622 | 1.00 | 4.46 | S |
| ATOM | 6809 | OH2 | WAT | S | 21 | 11.248 | 7.004 | 14.090 | 1.00 | 4.99 | S |
| ATOM | 6814 | OH2 | WAT | S | 26 | 23.738 | −1.909 | 12.157 | 1.00 | 5.26 | S |
| ATOM | 6818 | OH2 | WAT | S | 30 | 17.625 | 1.909 | 21.799 | 1.00 | 6.78 | S |
| ATOM | 6824 | OH2 | WAT | S | 36 | 16.161 | 2.164 | 24.178 | 1.00 | 8.59 | S |
| ATOM | 6825 | OH2 | WAT | S | 37 | 6.016 | 5.686 | 6.917 | 1.00 | 8.02 | S |
| ATOM | 6834 | OH2 | WAT | S | 46 | 6.979 | 0.708 | 2.055 | 1.00 | 6.31 | S |
| ATOM | 6838 | OH2 | WAT | S | 50 | 12.098 | 8.108 | 20.192 | 1.00 | 7.43 | S |
| ATOM | 6851 | OH2 | WAT | S | 63 | 5.327 | 2.748 | 9.978 | 1.00 | 10.75 | S |
| ATOM | 6862 | OH2 | WAT | S | 74 | 7.157 | 4.594 | 9.351 | 1.00 | 8.69 | S |

TABLE 8-continued

Three-dimensional structural coordinate of the complex of
human hematopoietic PGDS (SEQ ID NO: 1) with magnesium, glutathione and 4-
benzhydryloxy-1-{3-(1H-tetrazol-5-yl)-propyl}piperidine (HQL-79)

| ATOM | 6875 | OH2 | WAT | S | 87 | 13.436 | 2.712 | 24.346 | 1.00 | 11.43 | S |
|---|---|---|---|---|---|---|---|---|---|---|---|
| ATOM | 6881 | OH2 | WAT | S | 93 | 13.465 | 2.511 | 27.281 | 1.00 | 8.49 | S |
| ATOM | 6917 | OH2 | WAT | S | 129 | 4.790 | −5.831 | 4.947 | 1.00 | 16.22 | S |
| ATOM | 6923 | OH2 | WAT | S | 135 | 11.522 | −7.922 | 8.942 | 1.00 | 14.58 | S |
| ATOM | 6927 | OH2 | WAT | S | 139 | 7.332 | 5.571 | 25.452 | 1.00 | 13.15 | S |
| ATOM | 6931 | OH2 | WAT | S | 144 | 4.347 | 8.725 | 24.399 | 1.00 | 18.59 | S |
| ATOM | 6936 | OH2 | WAT | S | 149 | 21.684 | −0.730 | 22.365 | 1.00 | 19.24 | S |
| ATOM | 6940 | OH2 | WAT | S | 153 | 6.829 | 6.961 | 4.592 | 1.00 | 11.46 | S |
| ATOM | 6994 | OH2 | WAT | S | 207 | 9.472 | 5.801 | 21.506 | 1.00 | 15.51 | S |
| ATOM | 6997 | OH2 | WAT | S | 210 | 5.042 | −4.149 | 7.833 | 1.00 | 13.78 | S |
| ATOM | 7091 | OH2 | WAT | S | 304 | 3.700 | 2.599 | 19.458 | 1.00 | 18.38 | S |
| ATOM | 7143 | OH2 | WAT | S | 356 | 4.462 | 6.079 | 25.441 | 1.00 | 21.81 | S |
| ATOM | 7153 | OH2 | WAT | S | 366 | 14.674 | −8.789 | 5.088 | 1.00 | 25.86 | S |
| ATOM | 7162 | OH2 | WAT | S | 375 | 14.316 | 13.133 | 20.343 | 1.00 | 19.71 | S |
| ATOM | 7174 | OH2 | WAT | S | 387 | 8.250 | 1.189 | 18.665 | 1.00 | 24.62 | S |
| ATOM | 7183 | OH2 | WAT | S | 396 | 20.328 | −6.928 | 24.875 | 1.00 | 32.42 | S |
| ATOM | 7223 | OH2 | WAT | S | 436 | 22.932 | −6.039 | 12.661 | 1.00 | 30.30 | S |
| ATOM | 7226 | OH2 | WAT | S | 439 | 10.226 | −11.668 | 9.025 | 1.00 | 26.07 | S |
| ATOM | 7227 | OH2 | WAT | S | 440 | 10.828 | 1.782 | 27.468 | 1.00 | 17.99 | S |
| ATOM | 7231 | OH2 | WAT | S | 444 | 11.916 | −14.217 | 16.326 | 1.00 | 26.35 | S |
| ATOM | 7244 | OH2 | WAT | S | 457 | 16.265 | −1.371 | 28.167 | 1.00 | 34.60 | S |
| ATOM | 7281 | OH2 | WAT | S | 494 | 7.021 | −5.903 | 6.732 | 1.00 | 25.70 | S |
| ATOM | 7290 | OH2 | WAT | S | 503 | 11.401 | 0.940 | 23.577 | 1.00 | 22.25 | S |
| ATOM | 7313 | OH2 | WAT | S | 526 | 15.359 | 0.458 | 26.169 | 1.00 | 23.29 | S |
| ATOM | 7325 | OH2 | WAT | S | 538 | 11.588 | −8.884 | 22.349 | 1.00 | 25.83 | S |
| ATOM | 7341 | OH2 | WAT | S | 554 | 10.740 | −8.906 | 19.123 | 1.00 | 36.43 | S |
| ATOM | 7365 | OH2 | WAT | S | 578 | 9.748 | −2.511 | 21.886 | 1.00 | 32.74 | S |
| ATOM | 7428 | OH2 | WAT | S | 641 | 9.454 | 12.503 | 23.240 | 1.00 | 7.54 | S |
| ATOM | 7429 | OH2 | WAT | S | 642 | 9.887 | 9.966 | 24.786 | 1.00 | 10.81 | S |
| ATOM | 7430 | OH2 | WAT | S | 643 | 12.091 | 11.779 | 23.976 | 1.00 | 13.97 | S |
| ATOM | 7431 | OH2 | WAT | S | 644 | 11.037 | 11.297 | 21.097 | 1.00 | 12.32 | S |
| ATOM | 7432 | OH2 | WAT | S | 645 | 8.928 | 9.669 | 22.178 | 1.00 | 9.54 | S |
| ATOM | 7433 | OH2 | WAT | S | 646 | 11.790 | 9.079 | 22.827 | 1.00 | 8.22 | S |
| ATOM | 7445 | OH2 | WAT | S | 658 | 8.377 | 3.747 | 23.391 | 1.00 | 28.44 | S |
| ATOM | 7448 | OH2 | WAT | S | 661 | 10.331 | −0.751 | 28.752 | 1.00 | 36.87 | S |
| ATOM | 7449 | OH2 | WAT | S | 662 | 11.270 | −5.110 | 29.771 | 1.00 | 27.40 | S |
| ATOM | 7473 | OH2 | WAT | S | 686 | 6.297 | −7.443 | 3.798 | 1.00 | 34.15 | S |
| ATOM | 7482 | OH2 | WAT | S | 695 | 2.766 | −7.409 | 6.323 | 1.00 | 31.70 | S |
| ATOM | 7483 | OH2 | WAT | S | 696 | 3.236 | −5.622 | 9.446 | 1.00 | 30.92 | S |
| ATOM | 7490 | OH2 | WAT | S | 703 | 7.547 | 8.295 | 24.274 | 1.00 | 13.98 | S |
| ATOM | 7498 | OH2 | WAT | S | 711 | 23.720 | 0.535 | 21.093 | 1.00 | 33.19 | S |
| ATOM | 7518 | OH2 | WAT | S | 731 | 11.607 | −11.967 | 17.559 | 1.00 | 29.38 | S |
| ATOM | 7606 | OH2 | WAT | S | 819 | 13.230 | −5.747 | 25.483 | 1.00 | 31.58 | S |
| ATOM | 7607 | OH2 | WAT | S | 820 | 15.415 | −8.549 | 26.956 | 1.00 | 34.91 | S |
| ATOM | 7646 | OH2 | WAT | S | 859 | 19.195 | −6.110 | 26.916 | 1.00 | 43.51 | S |
| ATOM | 7663 | OH2 | WAT | S | 876 | 9.450 | −8.128 | 10.745 | 1.00 | 28.17 | S |
| ATOM | 7664 | OH2 | WAT | S | 877 | 6.964 | −8.045 | 9.036 | 1.00 | 32.76 | S |
| ATOM | 7677 | OH2 | WAT | S | 890 | −4.103 | −2.947 | 14.907 | 1.00 | 31.94 | S |
| ATOM | 7685 | OH2 | WAT | S | 898 | 0.382 | −6.331 | 13.311 | 1.00 | 40.22 | S |
| ATOM | 7703 | OH2 | WAT | S | 916 | 12.503 | −10.886 | 20.792 | 1.00 | 32.79 | S |
| ATOM | 7726 | OH2 | WAT | S | 939 | 9.361 | 1.904 | 25.025 | 1.00 | 24.74 | S |
| ATOM | 7733 | OH2 | WAT | S | 946 | 6.220 | 10.170 | 25.032 | 1.00 | 33.80 | S |
| ATOM | 7801 | OH2 | WAT | S | 1014 | 9.686 | −9.232 | 5.261 | 1.00 | 31.69 | S |
| ATOM | 7802 | OH2 | WAT | S | 1015 | 3.009 | −1.511 | 23.142 | 1.00 | 36.99 | S |
| ATOM | 7825 | OH2 | WAT | S | 1038 | 12.443 | −8.837 | 27.155 | 1.00 | 37.43 | S |
| ATOM | 7836 | OH2 | WAT | S | 1049 | 2.595 | 0.473 | 29.257 | 1.00 | 34.46 | S |
| ATOM | 7879 | OH2 | WAT | S | 1092 | 8.471 | −3.139 | 15.245 | 1.00 | 24.42 | S |
| ATOM | 7889 | OH2 | WAT | S | 1102 | 8.537 | −5.669 | 15.531 | 1.00 | 33.36 | S |
| ATOM | 7890 | OH2 | WAT | S | 1103 | 9.120 | −7.616 | 16.968 | 1.00 | 37.15 | S |
| ATOM | 7932 | OH2 | WAT | S | 1147 | 2.722 | 0.246 | 25.232 | 1.00 | 38.87 | S |
| ATOM | 7933 | OH2 | WAT | S | 1148 | 1.715 | 2.322 | 24.218 | 1.00 | 34.69 | S |
| ATOM | 7946 | OH2 | WAT | S | 1161 | 12.929 | −1.852 | 29.410 | 1.00 | 40.70 | S |
| ATOM | 8049 | OH2 | WAT | S | 1264 | 5.506 | −4.229 | 21.028 | 1.00 | 36.38 | S |
| ATOM | 8050 | OH2 | WAT | S | 1265 | 7.355 | −0.482 | 24.373 | 1.00 | 39.74 | S |
| ATOM | 8051 | OH2 | WAT | S | 1266 | 5.564 | −1.958 | 27.066 | 1.00 | 38.45 | S |
| ATOM | 8054 | OH2 | WAT | S | 1269 | 1.047 | −2.647 | 28.146 | 1.00 | 39.12 | S |

What is claimed is:

1. An isolated non-crystalline complex consisting of human hematopoietic prostaglandin D synthase (PGDS) consisting of the amino acid sequence of SEQ ID NO: 1, glutathione and magnesium in a molar ratio of 2:2:1, which has the three dimensional structure shown by the structural coordinates in Table 2.

* * * * *

SEQUENCE LISTING

<160> NUMBER OF SEQ ID NOS: 1

<210> SEQ ID NO 1
<211> LENGTH: 198
<212> TYPE: PRT
<213> ORGANISM: Homo sapiens

<400> SEQUENCE: 1

```
Pro Asn Tyr Lys Leu Thr Tyr Phe Asn Met Arg Gly Arg Ala Glu Ile
                5                   10                  15

Ile Arg Tyr Ile Phe Ala Tyr Leu Asp Ile Gln Tyr Glu Asp His Arg
            20                  25                  30

Ile Glu Gln Ala Asp Trp Pro Glu Ile Lys Ser Thr Leu Pro Phe Gly
        35                  40                  45

Lys Ile Pro Ile Leu Glu Val Asp Gly Leu Thr Leu His Gln Ser Leu
    50                  55                  60

Ala Ile Ala Arg Tyr Leu Thr Lys Asn Thr Asp Leu Ala Gly Asn Thr
65                  70                  75                  80

Glu Met Glu Gln Cys His Val Asp Ala Ile Val Asp Thr Leu Asp Asp
                85                  90                  95

Phe Met Ser Cys Phe Pro Trp Ala Glu Lys Lys Gln Asp Val Lys Glu
            100                 105                 110

Gln Met Phe Asn Glu Leu Leu Thr Tyr Asn Ala Pro His Leu Met Gln
        115                 120                 125

Asp Leu Asp Thr Tyr Leu Gly Gly Arg Glu Trp Leu Ile Gly Met Ser
    130                 135                 140

Val Thr Trp Ala Asp Phe Tyr Trp Glu Ile Cys Ser Thr Thr Leu Leu
145                 150                 155                 160

Val Phe Lys Pro Asp Leu Leu Asp Asn His Pro Arg Leu Val Thr Leu
                165                 170                 175

Arg Lys Lys Val Gln Ala Ile Pro Ala Val Ala Asn Trp Ile Lys Arg
            180                 185                 190

Arg Pro Gln Thr Lys Leu
            195
```